US010563259B2

(12) United States Patent
Wolfgang et al.

(10) Patent No.: US 10,563,259 B2
(45) Date of Patent: Feb. 18, 2020

(54) METHOD OF TREATMENT BASED ON POLYMORPHISMS OF THE KCNQ1 GENE

(71) Applicant: Vanda Pharmaceuticals, Inc., Washington, DC (US)

(72) Inventors: Curt D. Wolfgang, Germantown, MD (US); Mihael H. Polymeropoulos, Potomac, MD (US)

(73) Assignee: VANDA PHARMECEUTICALS, INC., Washington, DC (US)

( * ) Notice: Subject to any disclaimer, the term of this patent is extended or adjusted under 35 U.S.C. 154(b) by 110 days.

(21) Appl. No.: 15/705,048

(22) Filed: Sep. 14, 2017

(65) Prior Publication Data

US 2018/0002756 A1 Jan. 4, 2018

Related U.S. Application Data

(60) Continuation of application No. 14/841,884, filed on Sep. 1, 2015, now abandoned, which is a division of application No. 14/632,914, filed on Feb. 26, 2015, now Pat. No. 9,157,121, which is a division of application No. 13/263,074, filed as application No. PCT/US2010/029921 on Apr. 5, 2010, now Pat. No. 8,999,638.

(60) Provisional application No. 61/167,136, filed on Apr. 6, 2009.

(51) Int. Cl.

| | |
|---|---|
| ***C12Q 1/68*** | (2018.01) |
| ***C12Q 1/6883*** | (2018.01) |
| ***A61K 31/519*** | (2006.01) |
| ***A61K 31/454*** | (2006.01) |
| ***A61K 31/496*** | (2006.01) |

(52) U.S. Cl.

CPC .......... *C12Q 1/6883* (2013.01); *A61K 31/454* (2013.01); *A61K 31/496* (2013.01); *A61K 31/519* (2013.01); *C12Q 2600/106* (2013.01); *C12Q 2600/118* (2013.01); *C12Q 2600/156* (2013.01)

(58) Field of Classification Search

None

See application file for complete search history.

(56) References Cited

U.S. PATENT DOCUMENTS

| | | | |
|---|---|---|---|
| 5,364,866 | A | 11/1994 | Strupczewski et al. |
| 5,658,911 | A | 8/1997 | Strupczewski et al. |
| 6,140,345 | A | 10/2000 | Strupczewski et al. |
| 2006/0073506 | A1 | 4/2006 | Christians et al. |
| 2011/0077539 | A1 | 3/2011 | George et al. |

FOREIGN PATENT DOCUMENTS

| | | | |
|---|---|---|---|
| WO | 9309276 | A1 | 5/1993 |
| WO | 9511680 | A1 | 5/1995 |
| WO | 0124681 | A1 | 4/2001 |
| WO | 0124681 | A2 | 4/2001 |
| WO | 0179554 | A1 | 10/2001 |
| WO | 03016504 | A1 | 2/2003 |
| WO | 03016504 | A2 | 2/2003 |
| WO | 03020707 | A1 | 3/2003 |
| WO | 03062791 | A1 | 7/2003 |
| WO | 03062791 | A2 | 7/2003 |
| WO | 2004057030 | A1 | 7/2004 |
| WO | 2004057030 | A2 | 7/2004 |
| WO | 2006039663 | A2 | 4/2006 |
| WO | 2006039663 | A3 | 11/2006 |
| WO | 2006124646 | A2 | 11/2006 |
| WO | 2006131528 | A2 | 12/2006 |
| WO | 2006131528 | A3 | 3/2007 |
| WO | 2006124646 | A3 | 8/2007 |

OTHER PUBLICATIONS

Genbank Accession No. AJ006345.1 (NCBI, NLM, 2006).*
Juppner, "Functional Properties of the PTH/PTHrP Receptor," 1995, pp. 39S-42S, Bone, vol. 17, No. 2.
Levine et al., "Iloperidone: A novel atypical antipsychotic for the treatment of schizophrenia," 2008, pp. 1-7, Formulary Journal.
Lucentini, "Gene Association Studies Typically Wrong," 2004, p. 20, The Scientist, vol. 24.
Hegele, "SNP Judgments and Freedom of Association," 2003, pp. 1058-1061, Arteriosclerosis, Thrombosis, and Vascular Biology, vol. 22.
Volpi et al., "Pharmacogenomic analysis shows differences between markers associated with responses of two atypical antipsychotics, iloperidone and ziprasidone, in the treatment of patients with schizophrenia," 2007, Abstsract, 57 Annual Meeting of the American Society of Human Genetics.
Ss66324480, rs3775378, dbSNP Short Genetic Variations, NCBI, NLM, 2006, 5 pages.
Ss66391863, rs7067971, dbSNP Short Genetic Variations, NCBI, NLM, 2006, 3 pages.
Ss66046634, rs1083338, dbSNP Short Genetic Variations, NCBI, NLM, 2007, 5 pages.
Sitton, Office Action Communication for U.S. Appl. No. 13/263,075 dated Oct. 8, 2013, 23 pages.
Sitton, Office Action Communication for U.S. Appl. No. 13/263,076 dated Nov. 29, 2013, 24 pages.
Sitton, Office Action Communication for U.S. Appl. No. 13/263,077 dated Nov. 7, 2013, 25 pages.
Sitton, Office Action Communication for U.S. Appl. No. 13/263,075 dated Mar. 20, 2014, 11 pages.
Sitton, Office Action Communication for U.S. Appl. No. 13/263,076 dated Mar. 27, 2014, 11 pages.
Sitton, Office Action Communication for U.S. Appl. No. 13/263,077 dated Mar. 27, 2014, 11 pages.
Albers et al., "Iloperidone: a new benzisoxazole atypical antipsychotic drug. Is it novel enough to impact the crowded atypical antipsychotic market?" Expert Opin Investig Drugs. 17(1):61-75 (2008).

(Continued)

*Primary Examiner* — Jehanne S Sitton
(74) *Attorney, Agent, or Firm* — Hoffman Warnick LLC

(57) ABSTRACT

The invention provides methods for the administration of compounds capable of prolonging a QTc interval and methods for predicting whether an individual is predisposed to such QTc prolongation.

11 Claims, No Drawings

Specification includes a Sequence Listing.

(56) References Cited

OTHER PUBLICATIONS

Sitton, Office Action Communication for U.S. Appl. No. 13/263,074, dated Oct. 2, 2014, 18 pages.
Sitton, Office Action Communication for U.S. Appl. No. 13/263,075, dated Oct. 3, 2014, 19 pages.
Sitton, Office Action Communication for U.S. Appl. No. 13/263,076, dated Oct. 3, 2014, 19 pages.
Sitton, Office Action Communication for U.S. Appl. No. 13/263,077, dated Oct. 3, 2014, 19 pages.
Sitton, Notice of Allowance and Fee(s) Due for U.S. Appl. No. 13/263,074, dated Feb. 11, 2015, 15 pages.
Sitton, Notice of Allowance and Fee(s) Due for U.S. Appl. No. 13/263,075, dated Mar. 6, 2015, 7 pages.
Sitton, Notice of Allowance and Fee(s) Due for U.S. Appl. No. 13/263,076, dated Mar. 10, 2015, 11 pages.
Sitton, Notice of Allowance and Fee(s) Due for U.S. Appl. No. 13/263,077, dated Mar. 13, 2015, 7 pages.
Cascorbi, "Role of Pharmacogenetics of ATP-Binding Cassette Transporters in the Pharmacokinetis of Drugs," Nov. 2006, pp. 457-473, Pharmacology & Therapeutics, Science Direct, vol. 112, No. 2.
Chiang et al., "The Long QT Syndromes: Genetic Basis and Clinical Implications," Jul. 2000, pp. 1-12, Journal of American College of Cardiology, vol. 36, Nol 1 (XP002590440).
Cohen et al., "Cloning and Characterization of FAM13A1—A Gene Near a Milk Protein QTL on BTA6: Evidence for Population-Wide Linkage Disequilibrium in Israeli Holsteins," Aug. 2004, pp. 374-383, Genomics 84, Academic Press, available online at: www.sciencedirect.com.
Derosse et al., "The Genetics of Symptom-Based Phenotypes: Toward a Molecular Classification of Schizophrenia," Jul. 2008, pp. 1047-1043, Schizophrenia Bulletin, vol. 34, No. 6 (XP007913527).
Donger et al., "KVLQT1 C-Terminal Missense Mutation Causes a Forme Fruste Long-QT Syndrome," Nov. 1997, pp. 2778-2781, American Heart Association, vol. 96, No. 9 (XP002922668).
Fujita et al., "Association of ATP-Binding Cassette, Sub-Family C, No. 2 (ABCC2) Genotype with Pharmacokinetics of Irinotecan in Japanese Patients with Metastatic Colorectal Cancer Treated with Irinotecan Plus Infusional 5-Fluorouracil/Leucovorin (FOLFIRI)," Nov. 2008, pp. 2137-2142, Biological & Pharmaceutical Bulletin, vol. 31, No. 11 (XP007913544).
Liu et al., "KCNQ1 and KCNH2 Mutations Associated with Long QT Syndrome in a Chinese Population," Nov. 2002, pp. 1-7, Human Mutation, Mutation in Brief, vol. 20, No. 6 (XP002590441).
Volpi et al., "Pharmacogenomic analysis shows differences between markers associated with responses of two atypical antipsychotics, iloperidone and ziprasidone, in the treatment of patients with schizophrenia," 2007, Abstract, 57 Annual Meeting of the American Society of Human Genetics.
Volpi et al., "Whole Genome Association Study Identifies Polymorphisms Associated with QT Prolongation During Iloperidone Treatment of Schizophrenia," Jun. 2008, pp. 1024-1031, Molecular Psychiatry, vol. 14, No. 11 (XP002590482).
Yang et al., "Allelic Variants in Long-QT Disease Genes in Patients With Drug-Associated Torsades de Pointes," Apr. 2002, pp. 1943-1948, Circulation downloaded from: circ.ahajournals.org at the European Patent Office.
Patent Cooperation Treaty, PCT Notification of Transmittal of The International Search Report and The Written Opinion of the International Searching Authority, or the Declaration for PCT/US2010/029921 dated Aug. 19, 2010, 15 pages.
Patent Cooperation Treaty, PCT Notification of Transmittal of The International Search Report and The Written Opinion of the International Searching Authority, or the Declaration for PCT/US2010/029931 dated May 27, 2010, 13 pages.
Patent Cooperation Treaty, PCT Notification of Transmittal of The International Search Report and The Written Opinion of the International Searching Authority, or the Declaration for PCT/US2010/029943 dated Jul. 5, 2010, 14 pages.
Patent Cooperation Treaty, PCT Notification of Transmittal of The International Search Report and The Written Opinion of the International Searching Authority, or the Declaration for PCT/US2010/029945 dated Jul. 7, 2010, 13 pages.
Cussac, International Application No. PCT / US2010 / 029931, PCT International Preliminary Report on Patentability, dated Apr. 6, 2009, 7 pages.
Nickitas-Etienne, International Application No. PCT / US2010 / 029945, PCT International Preliminary Report on Patentability, dated Apr. 6, 2009, 7 pages.
Nickitas-Etienne, International Application No. PCT / US2010 / 029943, PCT International Preliminary Report on Patentability, dated Apr. 6, 2009, 7 pages.
Lindner, International Application No. PCT / US2010 / 029921, PCT International Preliminary Report on Patentability, dated Apr. 6, 2009, 7 pages.
Mueller, Frank, Patent Application No. 10713287.0 Office Action dated Jun. 11, 2014, 4 pages.
Office Action for U.S. Appl. No. 14/694,135, dated Jun. 9, 2015, 28 pages.
Office Action for U.S. Appl. No. 14/694,141, dated Jun. 9, 2015, 27 pages.
Office Action for U.S. Appl. No. 14/694,142, dated Jun. 18, 2015, 28 pages.
U.S. Appl. No. 14/694,135, Final Office Action 1 dated Oct. 8, 2015, 14 pages.
U.S. Appl. No. 14/694,141, Final Office Action 1 dated Oct. 8, 2015, 14 pages.
U.S. Appl. No. 14/694,142, Final Office Action 1 dated Oct. 8, 2015, 14 pages.
U.S. Appl. No. 14/694,141, Final Office Action 2 dated Aug. 24, 2016, 26 pages.
Terwilliger, et al., "An utter refutation of the 'Fundamental Theorem of the HapMap,'" European Journal of Human Genetics, (14): pp. 426-437 (2006).
Sotos, et al., "The Transitivity Misconception of Pearson's Correlation Coefficient," Statistics Education Research Journal, 8(2): pp. 33-55 (2009).
Wall, et al. "Haplotype Blocks and Linkage Disequilibrium in the Human Genome," Nature Reviews-Genetics, (4): pp. 587-597 (2003).
Mueller, Frank, Patent Application No. 10713287.0 Office Action dated Jun. 11, 2014, 6 pages.
Volpi et al., "Whole Genome Association Study Identities Polymorphisms Associated with QT Prolongation During Iloperidone Treatment of Schizophrenia," Jun. 2008, pp. 1024-1031, Molecular Psychiatry, vol. 14, No. 11 (XP002590482).

* cited by examiner

METHOD OF TREATMENT BASED ON POLYMORPHISMS OF THE KCNQ1 GENE

CROSS-REFERENCE TO RELATED APPLICATIONS

This patent application is a continuation of co-pending application Ser. No. 14/841,884, which was filed 1 Sep. 2015, which is a divisional of application Ser. No. 14/632,914 (U.S. Pat. No. 9,157,121) filed 26 Feb. 2015, which is a divisional of application Ser. No. 13/263,074 (U.S. Pat. No. 8,999,638) filed 5 Oct. 2011, which is a National Stage Entry under 35 USC 371 of International Patent Application No. PCT/US2010/029921 filed 5 Apr. 2010, which in turn claims the benefit of U.S. Provisional Patent Application No. 61/167,136, filed 6 Apr. 2009. Each of the foregoing applications is incorporated by reference as though fully set forth herein.

SEQUENCE LISTING

The sequence listing contained in the electronic file entitled "VAND-0039-US-DIV2-CON_PatentIn_Seq_ST25," created Oct. 21, 2019, comprising 513 KB, is hereby incorporated by reference herein.

BACKGROUND OF THE INVENTION

1. Technical Field

The invention relates generally to the administration of antipsychotics, and more particularly, to the administration of antipsychotics based on an individual's KCNQ1 genotype.

2. Background

Prolongation of the electrocardiographic QT interval (the time between the start of the Q wave and the end of the T wave) is referred to as long QT syndrome (LQTS). LQTS may comprise a genetic component. In some patients with LQTS, QT prolongation can be a chronic condition. In some persons, LQTS may be induced by the administration of an active pharmaceutical ingredient that prolongs the QT interval.

An area of focus in the evaluation of drug safety is the effect of non-cardiac medications on the QT interval. It is thought that the primary mechanism of action by which non-cardiac medications prolong the duration of the QT interval is through inhibition of the Human Ether-a-go-go related Gene (HERG) channel, a potassium channel directly involved in ventricular repolarization. QT prolongation and its relationship to torsades de pointes arrhythmia has received increased attention from regulatory authorities, resulting in warnings on the labels of some antipsychotics.

Since the QT interval changes with changes in heart rate, the QT interval is often measured as a corrected QT (QTc) interval. Any number of formulas may be employed to calculate the QTc, including, for example, the Fridericia formula (QTcF), the Bazett formula (QTcB), and the Rautaharju formula (QTp), among others.

DNA variants in potassium voltage-gated channels, such as KCNQ1, have been identified to predispose patients to drug-associated "acquired" LQTS and are considered congenital LQTS genes.

The KCNQ1 gene encodes a protein for a voltage-gated potassium channel required for the repolarization phase of the cardiac action potential. The gene product can form heteromultimers with two other potassium channel proteins, KCNE1 and KCNE3. Mutations in the KCNQ1 gene are associated with hereditary LQTS, Romano-Ward syndrome, Jervell and Lange-Nielsen syndrome, and familial atrial fibrillation. The gene is located in a region of chromosome 11 that contains a large number of contiguous genes that are abnormally imprinted in cancer and the Beckwith-Wiedemann syndrome.

KCNQ1 alpha-subunits coassemble with KCNE1 beta-subunits to form channels that conduct the slow delayed rectifier K+ current (IKs) important for repolarization of the cardiac action potential. Mutations in KCNQ1 reduce IKs and cause LQTS.

Antipsychotics, both typical and atypical, have been associated with an increase in the duration of the QTc interval. A study comparing the effect of several antipsychotics on the QTc duration showed thioridazine to be associated with the highest degree of QTc prolongation, followed by ziprasidone. Quetiapine, risperidone, olanzapine, and haloperidol were also associated with a prolongation of the QTc interval. In this study, minimum increase in QTc was observed when metabolic inhibitors of the CYP450 isoenzyme responsible for the metabolism of each respective drug, except for haloperidol, which resulted in a doubling of QTc with metabolic inhibition.

As has been seen with other antipsychotics, iloperidone has been observed to have some effects on QTc duration. Iloperidone is metabolized by CYP2D6. Metabolic inhibition by adding an inhibitor of CYP2D6 increases the effect of iloperidone on the QTcF duration. Methods for the administration of iloperidone based on an individual's CYP2D6 genotype are described in International Patent Application Publication No. WO2006039663, which is incorporated herein.

In addition to iloperidone, a number of other compounds are believed to be capable of causing QT prolongation. These include amiodarone, arsenic trioxide, bepridil, chloroquine, chlorpromazine, cisapride, clarithromycin, disopyramide, dofetilide, domperidone, droperidol, erythromycin, halofantrine, haloperidol, ibutilide, levomethadyl, mesoridazine, methadone, pentamidine, pimozide, procainamide, quinidine, sotalol, sparfloxacin, and thioridazine.

Other compounds, in addition to ziprasidone, are suspected of being capable of prolonging the QT interval, although such prolongation has not been definitively established. These include alfuzosin, amantadine, azithromycin, chloral hydrate, clozapine, dolasetron, felbamate, flecainide, foscarnet, fosphenytoin, gatifloxacin, gemifloxacin, granisetron, indapamide, isradipine, levofloxacin, lithium, moexipril, moxifloxacin, nicardipine, octreotide, ofloxacin, ondansetron, quetiapine, ranolazine, risperidone, roxithromycin, tacrolimus, tamoxifen, telithromycin, tizanidine, vardenafil, venlafaxine, and voriconazole.

Individuals at risk of suffering LQTS are advised not to use still other compounds, due to the possibility that they may prolong the QT interval. These include albuterol, amitriptyline, amoxapine, amphetamine, dextroamphetamine, atomoxetine, chloroquine, ciprofloxacin, citalopram, clomipramine, cocaine, desipramine, dexmethylphenidate, dobutamine, dopamine, doxepin, ephedrine, epinephrine, fenfluramine, fluconazole, fluoxetine, galantamine, imipramine, isoproterenol, itraconazole, ketoconazole, levalbuterol, metaproterenol, methylphenidate, mexiletine, midodrine, norepinephrine, nortriptyline, paroxetine, phentermine, phenylephrine, phenylpropanolamine, protriptyline, pseudoephedrine, ritodrine, salmeterol, sertraline, sibutramine, solifenacin, terbutaline, tolterodine, trimethoprim-sulfa, and trimipramine.

SUMMARY OF THE INVENTION

The invention provides methods for the administration of compounds capable of prolonging a QTc interval and methods for predicting whether an individual is predisposed to such QTc prolongation.

A first aspect of the invention provides a method of treating a patient with a compound capable of prolonging the QT interval, the method comprising: determining at least a portion of the patient's KCNQ1 gene sequence; and administering to the patient a quantity of the compound based on the patient's KCNQ1 gene sequence. In some embodiments, the method further includes determining at least a portion of the patient's CYP2D6 gene sequence.

A second aspect of the invention provides a method of determining whether an individual is predisposed to prolongation of the QTc interval, the method comprising: determining at least a portion of an individual's KCNQ1 gene sequence.

A third aspect of the invention provides a method of treating a patient with a compound capable of prolonging the QT interval, the method comprising:

characterizing an expression product of the patient's KCNQ1 gene; and administering to the patient a quantity of the compound based on the characterized expression product.

A fourth aspect of the invention provides a method of determining whether an individual is predisposed to prolongation of the QTc interval, the method comprising: characterizing an expression product of an individual's KCNQ1 gene.

The illustrative aspects of the present invention are designed to solve the problems herein described and other problems not discussed, which are discoverable by a skilled artisan.

DETAILED DESCRIPTION

As indicated above, the invention provides methods for the administration of antipsychotics based on an individual's KCNQ1 genotype. The sequence of wild type KCNQ1 (GenBank Accession No. AJ006345.1) is provided herein as SEQ ID NO. 1.

As noted above, a large number of compounds are known or suspected to be capable of inducing QT prolongation in some individuals, including individuals not suffering from LQTS. Such compounds may include compounds of Formula (1):

(1)

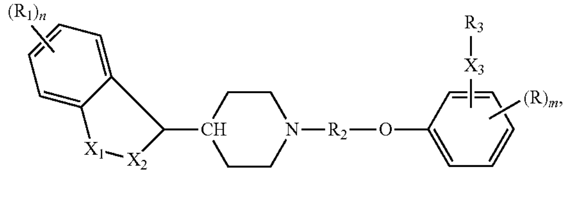

wherein:

R is, independently, hydrogen, lower alkyl, lower alkoxy, hydroxyl, carboxyl, lower hydroxyketone, lower alkanol, hydroxyl acetic acid, pyruvic acid, ethanediol, chlorine, fluorine, bromine, iodine, amino, lower mono or dialkylamino, nitro, lower alkyl thio, trifluoromethoxy, cyano, acylamino, trifluoromethyl, trifluoroacetyl, aminocarbonyl, monoaklylaminocarbonyl, dialkylaminocarbonyl, formyl,

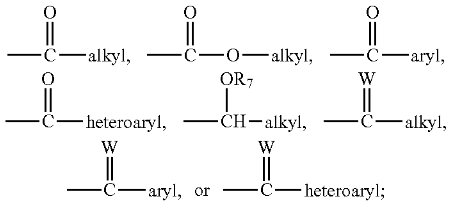

alkyl is lower alkyl, branched or straight and saturated or unsaturated;

acyl is lower alkyl or lower alkyloxy bonded through a carbonyl;

aryl is phenyl or phenyl substituted with at least one group, $R_5$, wherein each $R_5$ is, independently, hydrogen, lower alkyl, lower alkoxy, hydroxy, chlorine, fluorine, bromine, iodine, lower monoalkylamino, lower dialkylamino, nitro, cyano, trifluoromethyl, or trifluoromethoxy;

heteroaryl is is a five- or six-membered aryl ring having at least one heteroatom, $Q_3$, wherein each $Q_3$ is, independently, —O—, —S—, —N(H)—, or —C(H)═N—

W is $CH_2$ or $CHR_8$ or N—$R_9$;

$R_1$ is —H, lower alkyl, —OH, halo, lower alkoxy, trifluormethyl, nitro, or amino;

$R_2$ is $C_2$-$C_5$ alkylene, alkenylene (cis or trans), or alkynylene, optionally substituted by at least one $C_1$-$C_6$ linear alkyl group, phenyl group or

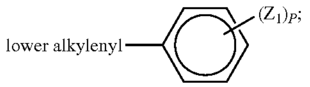

where $Z_1$ is lower alkyl, —OH, lower alkoxy, —$CF_3$, —$NO_2$, —$NH_2$, or halogen;

$R_3$ is lower alkyl or hydrogen;

$R_7$ is hydrogen, lower alkyl, or acyl;

$R_8$ is lower alkyl;

$R_9$ is hydroxy, lower alkoxy, or —$NHR_{10}$;

$R_{10}$ is hydrogen, lower alkyl, $C_1$-$C_3$ acyl, aryl,

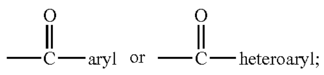

$X_1$, $X_2$, and $X_3$ are, independently, —O—, —S—, ═N—, or —N($R_3$)—, or $X_1$ and $X_2$ are not covalently bound to each other and are, independently, —OH, ═O, —$R_3$, or ═$NR_3$;

lower is 1-4 carbon atoms;

m is 1, 2, or 3; and n is 1 or 2.

The compound may further include a compound of Formula (1) wherein:

R is —C(O)$CH_2$OH, —CH(OH)C(O)$CH_2$OH, —C(O)OH, CH(OH)$CH_3$, or C(O)$CH_3$;

$R_1$ is halo;

$X_1$ and $X_2$ are different and are ═O, —OH, ═N—, or —O—;

$R_2$ is $C_2$-$C_4$ alkylene or alkenylene;

$R_3$ is hydrogen, methyl, or ethyl;

$X_3$ is —O—; and

R is substituted as shown in Formula 1A (1A)

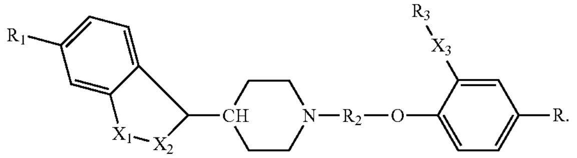

In a further embodiment, the compound may be iloperidone, which is also referred to as 1-[4-3-[4-(6-fluoro-1,2-benzisoxazol-3-yl)-1-piperidinyl]propoxy]-3-methoxyphenyl]ethanone, as shown in Formula 1B:

(1B)

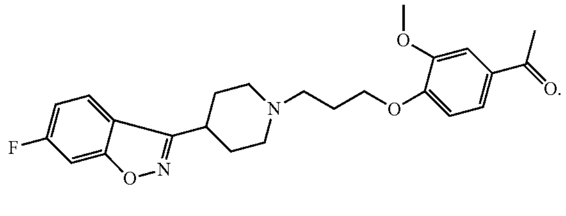

Iloperidone is disclosed in U.S. Pat. Nos. 5,364,866, 5,658,911, and 6,140,345, each of which is incorporated herein by reference. Metabolites of iloperidone may also be capable of prolonging a QT interval. Metabolites of Iloperidone, e.g., 1-[4-[3-[4-(6-Fluoro-1,2-benzisoxazol-3-yl)-1-piperidinyl] propoxy]-3-methoxyphenyl]ethanol, as shown in Formula 10:

(1C)

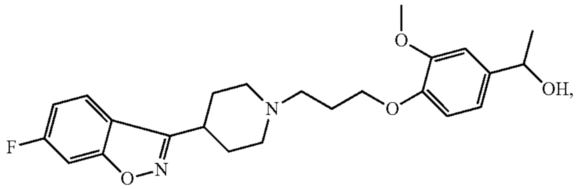

are described in International Patent Application Publication No. WO03020707, which is also incorporated herein by reference. Other iloperidone metabolites include: 1-[4-[3-[4-(6-Fluoro-1,2-benzisoxazol-3-yl)-1-piperidinyl]propoxy]-3-hydroxyphenyl]ethanone; 1-[4-[3-[4-(6-Fluoro-1,2-benzisoxazol-3-yl)-1-piperidinyl]propoxy]-3-methoxyphenyl]-2-hydroxyethanone; 4-[3-[4-(6-Fluoro-1,2-benzisoxazol-3-yl)-1-piperidinyl]propoxy]-3-hydroxy-α-methylbenzene methanol; 4-[3-[4-(6-Fluoro-1,2-benzisoxazol-3-yl)-1-piperidinyl]propoxyl-2-hydroxy-5-methoxy-α-methylbenzenemethanol; 1-[4-[3-[4-(6-Fluoro-1,2-benzisoxazol-3-yl)-1-piperidinyl]propoxy]-2-hydroxy-5-methoxyphenyl] ethanone; and 1-[4-[3-[4-(6-Fluoro-1,2-benzisoxazol-3-yl)-1-piperidinyl]propoxy]-2,5-dihydroxyphenyl]ethanone. See U.S. Pat. No. 5,364,866 and International Patent Application Publication Nos. WO9309276 and WO9511680, which are incorporated herein by reference.

The DNA variants in KCNQ1 noted above were examined for correlation with iloperidone-induced QT prolongation. These single nucleotide polymorphisms (SNPs) are shown in Table 1, below.

TABLE 1

KCNQ1 SNPs Linked to Acquired LQTS

| Genbank Accession No. | Position | Mutation |
|---|---|---|
| AJ006345.1 | 79764 | C to G |
| AJ006345.1 | 286414 | G to A |
| AJ006345.1 | 78927 | A to C |

Individuals from an earlier study of CYP2D6 genotypes and a predisposition to QT prolongation were genotyped at each of the KCNQ1 SNPs above. 22 individuals had been given a dose of 8 mg of iloperidone b.i.d., 30 had been given 12 mg b.i.d., and 22 had been given 24 mg q.d.

Results for the position 79764 SNP are shown below in Tables 2 and 3. As can be seen, individuals homozygous for the C>G polymorphism showed a significantly greater increase in QTc interval following the administration of iloperidone. In fact, the average QTc change in individuals with the GG genotype was more than twice the change in individuals with a non-GG genotype.

TABLE 2

79764 SNP Genotype and QTcF Change Following Iloperidone Administration

| Genotype | n | QTcF change (msec) |
|---|---|---|
| CC | 13 | 10.38 |
| CG | 32 | 6.80 |
| GG | 26 | 17.58 |

TABLE 3

79764 SNP Genotype and QTcF Change Following Iloperidone Administration

| Genotype | n | QTcF change (msec) | P value |
|---|---|---|---|
| Non-GG | 45 | 7.83 | 0.0008 |
| GG | 26 | 17.58 | |

The results were similar when ziprasidone was administered at a dosage of 80 mg b.i.d. The QTc changes for each genotype are shown below in Tables 4 and 5.

TABLE 4

79764 SNP Genotype and QTcF Change Following Ziprasidone Administration

| Genotype | n | QTcF change (msec) |
|---|---|---|
| CC | 5 | 8.30 |
| CG | 14 | 6.19 |
| GG | 6 | 15.32 |

TABLE 5

79764 SNP Genotype and QTcF Change Following Ziprasidone Administration

| Genotype | n | QTcF change (msec) | P value |
|---|---|---|---|
| Non-GG | 19 | 6.75 | 0.084 |
| GG | 6 | 15.32 | |

Similar results were observed for the 286414 position SNP, the results of which are shown below in Tables 6 and 7. Individuals homozygous for the G>A polymorphism experienced average QTc increases more than double those experienced by individuals with a non-AA genotype.

TABLE 6

286414 position SNP Genotype and QTcF Change Following Iloperidone Administration

| Genotype | n | QTcF change (msec) |
|---|---|---|
| AA | 32 | 12.50 |
| AG | 18 | 3.15 |
| GG | 7 | 10.34 |

TABLE 7

286414 position SNP Genotype and QTcF Change Following Iloperidone Administration

| Genotype | n | QTcF change (msec) | P value |
|---|---|---|---|
| AA | 32 | 12.51 | 0.0268 |
| Non-AA | 25 | 5.16 | |

The 78927 position SNP also yielded similar results, shown below in Tables 8 and 9. Again, individuals homozygous for the A>C polymorphism experienced average QTc increases more than double those experienced by individuals with a non-CC genotype.

TABLE 8

78927 position SNP Genotype and QTcF Change Following Iloperidone Administration

| Genotype | n | QTcF change (msec) |
|---|---|---|
| AA | 10 | 7.21 |
| AC | 31 | 9.19 |
| CC | 33 | 14.08 |

TABLE 9

78927 position SNP Genotype and QTcF Change Following Iloperidone Administration

| Genotype | n | QTcF change (msec) | P value |
|---|---|---|---|
| Non-CC | 41 | 6.46 | 0.057 |
| CC | 33 | 14.08 | |

As noted above, and as described in International Patent Application Publication No. WO2006/039663, an individual's ability to metabolize iloperidone may be predicted based on his/her CYP2D6 genotype. The CYP2D6 gene is highly polymorphic, with more than 70 allelic variants described so far (see http://www.cypalleles.ki.se/).

The two most common polymorphisms within the CYP2D6 gene in Caucasian populations, CYP2D6G1846A and CYP2D6C100T, result in a "poor metabolizer" phenotype and thus higher circulating drug levels in the blood. The CYP2D6G1846A polymorphism represents a G to A transition at the junction between intron 3 and exon 4, shifting the splice junction by one base pair, resulting in frameshift and premature termination of the protein. The CYP2D6C100T polymorphism, also known as CYP2D6P34S, represents a C to T change that results in the substitution of a proline at position 34 by serine. Both of these polymorphisms have been associated with reduced enzymatic activity for different substrates.

Interestingly, a relationship was found between the KCNQ1 polymorphisms above and an individual's metabolizer status (i.e., "extensive," "intermediate," or "poor"), as predicted by whether the individual has one or both of the CYP2D6G1846A and CYP2D6$C_{100}$T polymorphisms.

Tables 10 and 11 below show CYP2D6 metabolizer status against QTcFmax change from baseline for individuals having GG and non-GG genotypes, respectively, at the KCNQ1 79764 position SNP.

TABLE 10

QTcF Change in Individuals Having KCNQ1 79764 Position SNP Genotype GG and Varying CYP2D6 Metabolizer Status

| CYP2D6 Metabolizer Status | n (%) | QTcFmax Change (msec) |
|---|---|---|
| Extensive | 17 (65%) | 16.4 |
| Intermediate | 8 (31%) | 18.1 |
| Poor | 1 (4%) | 33.6 |

TABLE 11

QTcF Change in Individuals Having KCNQ1 79764 Position SNP Genotype Non-GG and Varying CYP2D6 Metabolizer Status

| CYP2D6 Metabolizer Status | n (%) | QTcFmax Change (msec) |
|---|---|---|
| Extensive | 37 (82%) | 8.3 |
| Intermediate | 7 (16%) | 3.1 |
| Poor | 1 (2%) | 24.6 |

As can be seen, individuals who are GG at the 79764 SNP experience greater QTc prolongation than do individuals who are non-GG. In addition, within each group, and particularly among GG individuals, CYP2D6 metabolizer status is highly predictive of the relative degree of QTc prolongation an individual will experience. Thus, an individual who is GG at the KCNQ1 79764 SNP and a CYP2D6 poor metabolizer may be administered a lower dose of iloperidone or other QT-prolonging compound, due to the individual's greater likelihood of experiencing more severe QT prolongation. Alternatively, the individual may instead be administered a compound not known or suspected of causing QT prolongation.

In order to assess the CYP2D6 component to such prolongation, QTc change was separately compared to the CYP2D6G1846A and CYP2D6$C_{100}$T polymorphisms. These results are shown below in Tables 12 and 13. As can be seen, individuals homozygous for the wild-type allele (G for CYP2D6G1846A and C for CYP2D6$C_{100}$T) experienced less QT prolongation than did individuals having one or two mutant alleles (A for CYP2D6G1846A and T for CYP2D6$C_{100}$T).

TABLE 12

| CYP2D6G1846A Polymorphism Compared to QTc Change Following Iloperidone Administration | | | |
|---|---|---|---|
| Genotype | n | QTcF change (msec) | P value |
| GG | 52 | 11.1 | |
| AG | 14 | 15.9 | |
| AA | 2 | 41.6 | |
| GG | 52 | 11.1 | 0.0594 |
| Non-GG | 16 | 18.5 | |

TABLE 13

| CYP2D6C100T Polymorphism Compared to QTc Change Following Iloperidone Administration | | | |
|---|---|---|---|
| Genotype | n | QTcF change (msec) | P value |
| CC | 54 | 10.8 | |
| CT | 14 | 16.9 | |
| TT | 3 | 31.3 | |
| CC | 54 | 10.8 | 0.0281 |
| Non-CC | 17 | 19.2 | |

Tables 14 and 15 below show QTc changes in individuals grouped according to their KCNQ1 79764, CYP2D6G1846A, and CYP2D6$C_{100}$T genotypes. This shows that individuals who were non-GG at KCNQ1 79764 and were homozygous for the wild-type allele at the CYP2D6 loci (i.e., GG for CYP2D6G1846A and CC for CYP2D6$C_{100}$T) experienced the least QT prolongation. Similarly, individuals who were GG at KCNQ1 79764 and had one or two mutant alleles at the CYP2D6 loci (i.e., AG or AA at CYP2D6G1846A and CT or TT at CYP2D6$C_{100}$T) experienced the greatest QT prolongation.

This may make it possible, for example, to manage the risk associated with the administration of compounds capable of prolonging the QTc interval. Individuals possessing only the wild-type alleles at the KCNQ1 and CYP2D6 loci may reasonably be expected to experience relatively little QTc prolongation while individuals possessing one or more mutant alleles may be expected to experience greater QTc prolongation, with the extent of prolongation increasing with an increasing number of mutant alleles. Individuals would then be administered a dosage of the compound based on his/her KCNQ1 and/or CYP2D6 genotypes or may be administered another compound instead that is not known or suspected of prolonging the QTc interval.

The data in Tables 14 and 15 also suggest that KCNQ1 polymorphisms have a greater impact on QTc prolongation than do the CYP2D6 polymorphisms. This may provide greater detail in the risk management, testing, and treatment methods above.

TABLE 14

| QTcF Change Compared to KCNQ1 79764 and CYP2D6G1846A Genotypes Following Iloperidone Administration | | |
|---|---|---|
| | QTcF change (msec) | |
| KCNQ1 79764 non-GG | 7.6 (n = 34) | 9.6 (n = 6) |
| KCNQ1 79764 GG | 19.5 (n = 15) | 25.5 (n = 10) |
| | CYP2D6G1846A GG | CYP2D6G1846A non-GG |

TABLE 15

| QTcF Change Compared to KCNQ1 79764 and CYP2D6C100T Genotypes Following Iloperidone Administration | | |
|---|---|---|
| | QTcF change (msec) | |
| KCNQ1 79764 non-GG | 7.4 (n = 35) | 12.6 (n = 7) |
| KCNQ1 79764 GG | 19.2 (n = 15) | 23.5 (n = 10) |
| | CYP2D6C100T CC | CYP2D6C100T non-CC |

Additional KCNQ1 SNPs were examined for any correlation to a predisposition to QTc prolongation. Those SNPs are shown below in Table 16. SNPs useful in the practice of the invention include those listed above and in Table 16 below, and can be used singly or in any combination of two or more.

TABLE 16

| KCNQ1 SNP Genotypes and QT Prolongation Following Administration of Iloperidone | | | | | | |
|---|---|---|---|---|---|---|
| Affymetrix SNP No. | rs_number[1] | Position[2] | Lowest QTc change | P value[3] | Allele A | Allele B |
| SNP_A-1861793 | rs234873 | 2764098 | nonAA | 0.110421 | C | T |
| SNP_A-1905847 | rs233446 | 2794201 | nonAA | 0.12044 | A | C |
| SNP_A-1905948 | rs179428 | 2507085 | nonAA | 0.548076 | A | G |
| SNP_A-2063010 | rs10832134 | 2459062 | AA | 0.613499 | C | T |
| SNP_A-2070173 | rs10832405 | 2605095 | nonAA | 0.421724 | G | T |
| SNP_A-2128672 | rs10798 | 2826741 | nonAA | 0.149325 | C | T |
| SNP_A-2138827 | rs548566 | 2739224 | AA | 0.533236 | A | G |
| SNP_A-2155585 | rs231915 | 2705591 | nonAB | 0.811901 | A | G |
| SNP_A-2170993 | rs170786 | 2707279 | BB | 0.609952 | C | T |
| SNP_A-2176134 | rs10766379 | 2782775 | BB | 0.149903 | A | G |
| SNP_A-2203798 | rs8181588 | 2788117 | nonBB | 0.486341 | A | G |
| SNP_A-2217853 | rs179429 | 2507306 | BB | 0.323283 | C | T |
| SNP_A-2244304 | rs7128926 | 2653320 | AB | 0.074244 | C | T |
| SNP_A-2264175 | rs6578283 | 2630151 | BB | 0.385571 | A | G |
| SNP_A-2299737 | rs163177 | 2794989 | AA | 0.03059 | A | G |
| SNP_A-2301145 | rs163166 | 2781804 | BB | 0.147875 | G | T |
| SNP_A-2305877 | rs231916 | 2704944 | nonAB | 0.033582 | A | G |
| SNP_A-4241656 | rs231907 | 2708706 | nonBB | 0.802946 | A | T |
| SNP_A-4242308 | rs2283208 | 2700435 | AA | 0.019908 | A | G |
| SNP_A-4248246 | — | 2667398 | nonAA | 0.381774 | C | T |
| SNP_A-4254887 | rs231348 | 2630257 | nonBB | 0.626472 | A | G |
| SNP_A-4257005 | rs16928297 | 2442696 | AA | 0.483607 | G | T |

TABLE 16-continued

KCNQ1 SNP Genotypes and QT Prolongation Following Administration of Iloperidone

| Affymetrix SNP No. | rs_number[1] | Position[2] | Lowest QTc change | P value[3] | Allele A | Allele B |
|---|---|---|---|---|---|---|
| SNP_A-4281714 | rs3852527 | 2783179 | nonAA | 0.197306 | A | G |
| SNP_A-4288131 | rs231890 | 2732635 | nonAB | 0.573 | C | T |
| SNP_A-4288827 | rs10766218 | 2594657 | AA | 0.357049 | A | G |
| SNP_A-4301076 | rs163171 | 2777641 | nonAB | 0.259187 | C | T |
| SNP_A-4301585 | rs9666537 | 2642440 | nonBB | 0.262343 | C | T |
| SNP_A-4302062 | rs1971929 | 2729947 | AA | 0.611517 | C | G |
| SNP_A-4302119 | rs3852528 | 2783193 | nonBB | 0.041388 | A | G |
| SNP_A-1819033 | rs151291 | 2731415 | nonAA | 0.260891 | C | T |
| SNP_A-1824380 | rs179409 | 2483882 | AA | 0.310425 | C | G |
| SNP_A-1829337 | rs231873 | 2742118 | nonAB | 0.422393 | C | G |
| SNP_A-1845199 | rs2412058 | 2597705 | AA | 0.29063 | C | T |
| SNP_A-1866128 | rs12804445 | 2834275 | BB | 0.431295 | A | C |
| SNP_A-2045452 | rs7942590 | 2590291 | AA | 0.7495 | C | G |
| SNP_A-2078818 | rs4430486 | 2741967 | BB | 0.177528 | C | G |
| SNP_A-2089816 | rs10741669 | 2600056 | nonAB | 0.154721 | C | T |
| SNP_A-2108877 | rs10766212 | 2589728 | AA | 0.181241 | A | G |
| SNP_A-2111327 | rs11517737 | 2481124 | nonAB | 0.612965 | A | G |
| SNP_A-2115624 | rs4930013 | 2818735 | AB | 0.762452 | G | T |
| SNP_A-2139714 | rs4930149 | 2692602 | AA | 0.42212 | A | C |
| SNP_A-2147212 | rs11023096 | 2484579 | BB | 0.011594 | A | G |
| SNP_A-2167641 | rs7927129 | 2672108 | nonAA | 0.905521 | A | C |
| SNP_A-2185200 | rs231901 | 2687761 | AA | 0.399107 | C | T |
| SNP_A-2188014 | rs2237866 | 2486738 | AA | 0.016676 | C | T |
| SNP_A-2199433 | rs12576156 | 2455394 | nonAA | 0.055461 | C | T |
| SNP_A-2207071 | rs163183 | 2801017 | nonBB | 0.080842 | A | G |
| SNP_A-2222217 | rs231841 | 2680180 | AB | 0.041003 | A | C |
| SNP_A-2248126 | rs3819506 | 2484900 | BB | 0.043565 | A | G |
| SNP_A-2279904 | rs16928561 | 2672031 | BB | 0.222103 | A | G |
| SNP_A-2279707 | rs179407 | 2483474 | nonBB | 0.011184 | C | T |
| SNP_A-2281097 | rs1079714 | 2717317 | nonBB | 0.583124 | C | T |
| SNP_A-2286096 | rs11023094 | 2483937 | nonAB | 0.158471 | C | T |
| SNP_A-2306355 | rs17744869 | 2780438 | nonBB | 0.236986 | C | G |

[1]Official SNP nomenclature according to NCBI db SNP version 126, May 2006.
[2]Chromosomal position based on the NCBI Build 36.1, March 2006.
[3]P value of genotype having highest QT values versus all other genotypes.

Among the SNPs shown in Table 16, a genotype of TT at SNP_A-2279707 (rs179407) was shown to accurately predict a predisposition to QTc prolongation. Therefore, an individual having a genotype of TT at SNP_A-2279707 (rs179407) may be predicted to be predisposed to QTc prolongation.

Table 17 below shows the results of a study of 174 individuals, each of whom was genotyped at the rs179407locus and their QT interval measured following the oral administration of 24 mg/day B.I.D. of iloperidone for a period of two weeks.

For example, using the lowest threshold of a change in QTc interval (between baseline and the end of the second week) greater than 5 milliseconds (normal QTc intervals are between 0.30 and 0.44 seconds for males and between 0.30 and 0.45 for females), 102 of those individuals with a SNP genotype (test is considered positive if genotype for SNP_A-2279707 (rs179407) is TT) associated with a predisposition to QT prolongation experienced QT prolongation while only 47 such individuals did not. Similarly, nearly seven times as many individuals (102) experiencing QT prolongation possessed a SNP genotype associated with a predisposition to QT prolongation as did not (15). This resulted in a sensitivity (probability that the individual will have a SNP genotype associated with a predisposition to QT prolongation, given that he/she experienced QT prolongation) of 0.87 and a

TABLE 17

QT Prolongation and Presence or Absence of a Genotype for SNP_A-2279707 (rs179407) Associated with a Predisposition to QT Prolongation

| Change Threshold | Low QT | | High QT | | Odds | | | | negative predictive | positive predictive |
|---|---|---|---|---|---|---|---|---|---|---|
| (msec) | −test | +test | −test | +test | Ratio | p value | sensitivity | specificity | value | value |
| QT > 5 | 19 | 47 | 15 | 102 | 2.748936 | 0.0091 | 0.871795 | 0.287879 | 0.558824 | 0.684564 |
| QT > 15 | 25 | 85 | 9 | 64 | 2.091503 | 0.0807 | 0.876712 | 0.227273 | 0.735294 | 0.42953 |
| QT > 30 | 32 | 123 | 2 | 26 | 3.382114 | 0.1089 | 0.928571 | 0.206452 | 0.941176 | 0.174497 |

As can be seen in Table 17, an individual's KCNQ1 sequence at the SNP_A-2279707 (rs179407) locus is highly predictive of whether the individual will experience QT prolongation following the administration of iloperidone.

specificity (probability that the individual will not have a SNP genotype associated with a predisposition to QT prolongation, given that he/she did not experience QT prolongation) of 0.29, a negative predictive value (probability that the individual will not experience QT prolongation, given that he/she does not have a SNP genotype associated with a predisposition to QT prolongation) of 0.56, and a positive predictive value (probability that the individual will experience QT prolongation, given that he/she has a SNP genotype associated with a predisposition to QT prolongation) of 0.68.

The use of higher thresholds (i.e., QTs greater than 15 and 30 milliseconds) yielded markedly increased negative predictive values (0.74 and 0.94, respectively). The associated decrease in positive predictive values, from 0.68 for QTs greater than 5 milliseconds to 0.17 for QTs greater than 30 milliseconds) suggests that additional factors affect more severe QT prolongation.

As the data in Table 17 show, an individual's KCNQ1 sequence at the SNP loci above may be used to predict whether an individual is predisposed to QT prolongation due to the administration of a compound capable of prolonging the QT interval. That is, individuals having one or more SNP genotype associated with a predisposition to QT prolongation may reliably be predicted to experience a prolonged QT interval (i.e., a QT interval prolonged by at least 5 milliseconds) following the administration of a compound capable of prolonging the QT interval. Similarly, individuals not having any of the above SNP genotypes associated with a predisposition to QT prolongation may reliably be predicted to not experience severe QT prolongation (i.e., a QT interval prolonged greater than 15 milliseconds) following the administration of a compound capable of prolonging the QT interval.

Methods according to the invention may involve direct sequencing or genotyping of an individual's KCNQ1 and/or CYP2D6 genes or the characterization of expression products of the genes. For example, as noted above, the CYP2D6G1846A polymorphism results in premature termination of the CYP2D6 protein and the CYP2D6C100T polymorphism results in the substitution of a proline at position 34 by serine. Either of these polymorphisms could be determined from the resulting proteins or RNA. Accordingly, the invention includes testing genes and/or their expression products.

Thus, in addition to other illustrative embodiments, this invention can be seen to comprise one or more of the following illustrative embodiments:

1. A method of treating a patient with a compound capable of prolonging the QT interval, the method comprising:

determining at least a portion of the patient's KCNQ1 gene sequence; and administering to the patient a quantity of the compound based on the patient's KCNQ1 gene sequence.

2. The method of embodiment 1, wherein the quantity of the compound administered is less if the patient's KCNQ1 genotype at position 79764 of reference sequence AJ006345.1 is GG than if the patient's genotype is not GG.

3. The method of embodiment 1, wherein the quantity of the compound administered is less if the patient's KCNQ1 genotype at position 286414 of reference sequence AJ006345.1 is AA than if the patient's genotype is not AA.

4. The method of embodiment 1, wherein the quantity of the compound administered is less if the patient's KCNQ1 genotype at position 78927 of reference sequence AJ006345.1 is CC than if the patient's genotype is not CC.

5. The method of embodiment 1, wherein the compound is selected from a group consisting of:

amiodarone, arsenic trioxide, bepridil, chloroquine, chlorpromazine, cisapride, clarithromycin, disopyramide, dofetilide, domperidone, droperidol, erythromycin, halofantrine, haloperidol, ibutilide, iloperidone, levomethadyl, mesoridazine, methadone, pentamidine, pimozide, procainamide, quinidine, sotalol, sparfloxacin, thioridazine;

alfuzosin, amantadine, azithromycin, chloral hydrate, clozapine, dolasetron, felbamate, flecainide, foscarnet, fosphenytoin, gatifloxacin, gemifloxacin, granisetron, indapamide, isradipine, levofloxacin, lithium, moexipril, moxifloxacin, nicardipine, octreotide, ofloxacin, ondansetron, quetiapine, ranolazine, risperidone, roxithromycin, tacrolimus, tamoxifen, telithromycin, tizanidine, vardenafil, venlafaxine, voriconazole, ziprasidone;

albuterol, amitriptyline, amoxapine, amphetamine, dextroamphetamine, atomoxetine, chloroquine, ciprofloxacin, citalopram, clomipramine, cocaine, desipramine, dexmethylphenidate, dobutamine, dopamine, doxepin, ephedrine, epinephrine, fenfluramine, fluconazole, fluoxetine, galantamine, imipramine, isoproterenol, itraconazole, ketoconazole, levalbuterol, metaproterenol, methylphenidate, mexiletine, midodrine, norepinephrine, nortriptyline, paroxetine, phentermine, phenylephrine, phenylpropanolamine, protriptyline, pseudoephedrine, ritodrine, salmeterol, sertraline, sibutramine, solifenacin, terbutaline, tolterodine, trimethoprim-sulfa, trimipramine, and metabolites, pharmaceutically-acceptable salts, and combinations thereof.

6. The method of embodiment 5, wherein the compound has the formula:

(1)

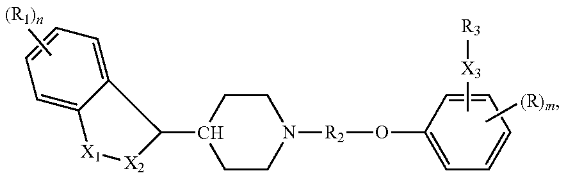

wherein:

R is, independently, hydrogen, lower alkyl, lower alkoxy, hydroxyl, carboxyl, lower hydroxyketone, lower alkanol, hydroxyl acetic acid, pyruvic acid, ethanediol, chlorine, fluorine, bromine, iodine, amino, lower mono or dialkylamino, nitro, lower alkyl thio, trifluoromethoxy, cyano, acylamino, trifluoromethyl, trifluoroacetyl, aminocarbonyl, monoaklylaminocarbonyl, dialkylaminocarbonyl, formyl,

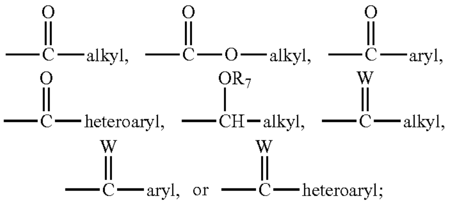

alkyl is lower alkyl, branched or straight and saturated or unsaturated;

acyl is lower alkyl or lower alkyloxy bonded through a carbonyl;

aryl is phenyl or phenyl substituted with at least one group, $R_5$, wherein each $R_5$ is, independently, hydrogen, lower alkyl, lower alkoxy, hydroxy, chlorine, fluorine, bromine, iodine, lower monoalkylamino, lower dialkylamino, nitro, cyano, trifluoromethyl, or trifluoromethoxy;

heteroaryl is is a five- or six-membered aryl ring having at least one heteroatom, $Q_3$, wherein each $Q_3$ is, independently, —O—, —S—, —N(H)—, or —C(H)═N—

W is $CH_2$ or $CHR_8$ or N—$R_9$;

$R_1$ is —H, lower alkyl, —OH, halo, lower alkoxy, trifluormethyl, nitro, or amino;

$R_2$ is $C_2$-$C_5$ alkylene, alkenylene (cis or trans), or alkynylene, optionally substituted by at least one $C_1$-$C_6$ linear alkyl group, phenyl group or

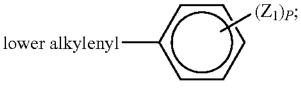

where $Z_1$ is lower alkyl, —OH, lower alkoxy, —$CF_3$, —$NO_2$, —$NH_2$, or halogen;

$R_3$ is lower alkyl or hydrogen;

$R_7$ is hydrogen, lower alkyl, or acyl;

$R_8$ is lower alkyl;

$R_9$ is hydroxy, lower alkoxy, or —$NHR_{10}$;

$R_{10}$ is hydrogen, lower alkyl, $C_1$-$C_3$ acyl, aryl,

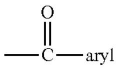 or 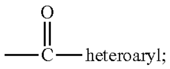

$X_1$, $X_2$, and $X_3$ are, independently, —O—, —S—, ═N—, or —N($R_3$)—, or $X_1$ and $X_2$ are not covalently bound to each other and are, independently, —OH, ═O, —$R_3$, or ═$NR_3$;

lower is 1-4 carbon atoms;

m is 1, 2, or 3; and n is 1 or 2.

7. The method of embodiment 6, wherein

R is —C(O)$CH_2$OH, —CH(OH)C(O)$CH_2$OH, —C(O)OH, CH(OH)$CH_3$, or C(O)$CH_3$;

$R_1$ is halo;

$X_1$ and $X_2$ are different and are ═O, —OH, ═N—, or —O—;

$R_2$ is $C_2$-$C_4$ alkylene or alkenylene;

$R_3$ is hydrogen, methyl, or ethyl;

$X_3$ is —O—; and

R is substituted as shown in Formula 1A (1A)

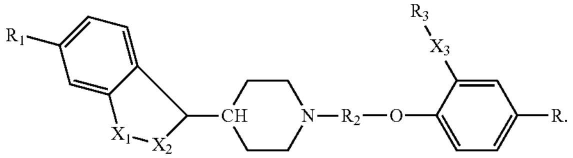

8. The method of embodiment 7, wherein the compound of Formula 1 is 1-[4-3-[4-(6-fluoro-1,2-benzisoxazol-3-yl)-1-piperidinyl]propoxy]-3-methoxyphenyl]ethanone, as shown in Formula 1B:

(1B)

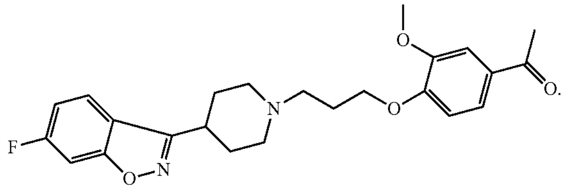

9. The method of embodiment 7, wherein the compound of Formula 1 is 1-[4-[3-[4-(6-Fluoro-1,2-benzisoxazol-3-yl)-1-piperidinyl]propoxy]-3-methoxyphenyl]ethanol, as shown in Formula 10:

(1C)

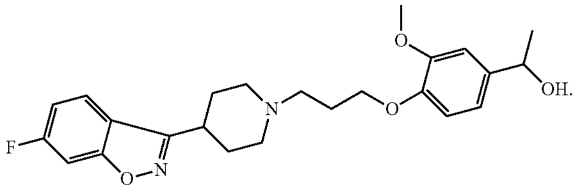

10. The method of embodiment 1, further comprising:

determining at least a portion of the patient's CYP2D6 gene sequence.

11. The method of embodiment 10, wherein the quantity of the compound administered is less if the patient's CYP2D6G1846A genotype is AA or GA than if the patient's genotype is GG.

12. The method of embodiment 10, wherein the quantity of the compound administered is less if the patient's CYP2D6C100T genotype is TT or CT than if the patient's genotype is CC.

13. The method of embodiment 1, wherein the patient is suffering from at least one condition selected from a group consisting of: schizophrenia, schizoaffective disorder, depression, bipolar mania/depression, cardiac arrythmia, Tourette's Syndrome, a psychotic disorder, a delusional disorder, and schizophreniform disorder.

14. The method of embodiment 13, wherein the patient is suffering from at least one condition selected from a group consisting of: paranoid schizophrenia, catatonic schizophrenia, disorganized schizophrenia, undifferentiated schizophrenia, and residual schizophrenia.

15. The method of embodiment 13, wherein the patient is suffering from at least one condition selected from a group consisting of: brief psychotic disorder, a psychotic disorder not otherwise specified, a psychotic disorder due to a general medical condition, and a substance-induced psychotic disorder.

16. A method of determining whether an individual is predisposed to prolongation of the QTc interval, the method comprising:

determining at least a portion of an individual's KCNQ1 gene sequence.

17. The method of embodiment 16, wherein determining includes determining the individual's genotype at at least one single nucleotide polymorphism (SNP) locus selected from a group consisting of: 79764 of reference sequence AJ006345.1, position 286414 of reference sequence AJ006345.1, and position 78927 of reference sequence AJ006345.1.

18. The method of embodiment 18, further comprising:

concluding that the individual is predisposed to prolongation of the QTc interval if the individual's KCNQ1 genotype includes any of the following:

GG at position 79764 of reference sequence AJ006345.1;

AA at position 286414 of reference sequence AJ006345.1; or

CC at position 78927 of reference sequence AJ006345.1.

19. The method of embodiment 16, further comprising:

determining at least a portion of the individual's CYP2D6 gene sequence.

20. The method of embodiment 19, wherein determining includes determining whether the individual's CYP2D6 gene sequence includes the CYP2D6G1846A polymorphism.

21. The method of embodiment 19, wherein determining includes determining whether the individual's CYP2D6 gene sequence includes the CYP2D6$C_{100}$T polymorphism.

22. A method of treating a patient with a compound capable of prolonging the QT interval, the method comprising:

characterizing an expression product of the patient's KCNQ1 gene; and administering to the patient a quantity of the compound based on the characterized expression product.

23. The method of embodiment 22, wherein the quantity of the compound is reduced if the characterized expression product corresponds to any of the following:

a GG KCNQ1 genotype at position 79764 of reference sequence AJ006345.1;

an AA KCNQ1 genotype at position 286414 of reference sequence AJ006345.1; or a CC KCNQ1 genotype at position 78927 of reference sequence AJ006345.1.

24. The method of embodiment 22, further comprising:

characterizing an expression product of the patient's CYP2D6 gene.

25. The method of embodiment 24, further comprising:

determining whether the characterized expression product corresponds to a CYP2D6 polymorphism selected from a group consisting of: CYP2D6G1846A and CYP2D6$C_{100}$T.

26. The method of embodiment 22, wherein the compound is selected from a group consisting of:

amiodarone, arsenic trioxide, bepridil, chloroquine, chlorpromazine, cisapride, clarithromycin, disopyramide, dofetilide, domperidone, droperidol, erythromycin, halofantrine, haloperidol, ibutilide, iloperidone, levomethadyl, mesoridazine, methadone, pentamidine, pimozide, procainamide, quinidine, sotalol, sparfloxacin, thioridazine;

alfuzosin, amantadine, azithromycin, chloral hydrate, clozapine, dolasetron, felbamate, flecainide, foscarnet, fosphenytoin, gatifloxacin, gemifloxacin, granisetron, indapamide, isradipine, levofloxacin, lithium, moexipril, moxifloxacin, nicardipine, octreotide, ofloxacin, ondansetron, quetiapine, ranolazine, risperidone, roxithromycin, tacrolimus, tamoxifen, telithromycin, tizanidine, vardenafil, venlafaxine, voriconazole, ziprasidone;

albuterol, amitriptyline, amoxapine, amphetamine, dextroamphetamine, atomoxetine, chloroquine, ciprofloxacin, citalopram, clomipramine, cocaine, desipramine, dexmethylphenidate, dobutamine, dopamine, doxepin, ephedrine, epinephrine, fenfluramine, fluconazole, fluoxetine, galantamine, imipramine, isoproterenol, itraconazole, ketoconazole, levalbuterol, metaproterenol, methylphenidate, mexiletine, midodrine, norepinephrine, nortriptyline, paroxetine, phentermine, phenylephrine, phenylpropanolamine, protriptyline, pseudoephedrine, ritodrine, salmeterol, sertraline, sibutramine, solifenacin, terbutaline, tolterodine, trimethoprim-sulfa, trimipramine, and metabolites, pharmaceutically-acceptable salts, and combinations thereof.

27. A method of determining whether an individual is predisposed to prolongation of the QTc interval, the method comprising:

characterizing an expression product of an individual's KCNQ1 gene.

28. The method of embodiment 27, further comprising:

determining whether the characterized expression product corresponds to any of the following:

a GG KCNQ1 genotype at position 79764 of reference sequence AJ006345.1;

an AA KCNQ1 genotype at position 286414 of reference sequence AJ006345.1; or a CC KCNQ1 genotype at position 78927 of reference sequence AJ006345.1.

29. The method of embodiment 27, further comprising:

characterizing an expression product of the individual's CYP2D6 gene.

30. The method of embodiment 29, further comprising:

determining whether the characterized expression product corresponds to a CYP2D6 polymorphism selected from a group consisting of: CYP2D6G1846A and CYP2D6$C_{100}$T.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims.

What is claimed is:

1. A method of treating a human patient with a compound that is iloperidone, a metabolite of iloperidone, or a pharmaceutically-acceptable salt of iloperidone or metabolite thereof, the method comprising:

determining the patient's KCNQ1 genotype at position 286414 of SEQ ID NO: 1; and administering to the patient a quantity of the compound based on the patient's KCNQ1 genotype at position 286414 of SEQ ID NO: 1, wherein a first quantity of the compound is administered if the patient's KCNQ1 genotype at position 286414 of SEQ ID NO: 1 is not AA and a second quantity of the compound is administered if the patient's KCNQ1 genotype at position 286414 of SEQ ID NO: 1 is AA, wherein the second quantity of the compound is less than the first quantity of the compound.

2. The method of claim 1, further comprising determining at least a portion of the patient's CYP2D6 gene sequence.

3. The method of claim 2, wherein the quantity of the compound administered is less if the patient's CYP2D6G1846A genotype is AA or GA than if the patient's genotype is GG, and is less if the patient's CYP2D6C100T genotype is TT or CT than if the patient's genotype is CC.

4. The method of claim 1, wherein the patient is suffering from at least one condition selected from a group consisting of: schizophrenia, schizoaffective disorder, depression, bipolar mania/depression, Tourette's Syndrome, a psychotic disorder, a delusional disorder, and schizophreniform disorder.

5. The method of claim 4, wherein the patient is suffering from at least one condition selected from a group consisting of: paranoid schizophrenia, catatonic schizophrenia, disorganized schizophrenia, undifferentiated schizophrenia, and residual schizophrenia.

6. The method of claim 4, wherein the patient is suffering from at least one condition selected from a group consisting of: brief psychotic disorder, a psychotic disorder not otherwise specified, a psychotic disorder due to a general medical condition, and a substance-induced psychotic disorder.

7. A method of treating a human patient with a compound that is iloperidone, a metabolite of iloperidone, or a pharmaceutically-acceptable salt of iloperidone or metabolite thereof, the method comprising:

characterizing the genotype of the expression product of the patient's KCNQ1 gene corresponding to position 286414 of SEQ ID NO: 1; and administering to the patient a quantity of the compound based on the genotype of the patient's KCNQ1 characterized expression product, wherein a first quantity of the compound is administered if the genotype of the characterized expression product is not AA at the position corresponding to position 286414 of SEQ ID NO: 1 and a second quantity of the compound is administered if the genotype of the characterized expression product is AA at the position corresponding to position 286414 of SEQ ID NO: 1, wherein the second quantity of the compound is less than the first quantity of the compound.

8. The method of claim 7, further comprising:

characterizing an expression product of the patient's CYP2D6 gene.

9. The method of claim 7, further comprising:
determining whether the characterized expression product corresponds to a CYP2D6 polymorphism selected from a group consisting of: CYP2D6G1846A and CYP2D6C100T.

10. The method of claim 1, wherein the compound is iloperidone, and the quantity for administering to the patient is 24 mg/day if the patient's genotype at the position 286414 is not AA.

11. The method of claim 7, wherein the compound is iloperidone, and the quantity for administering to the patient is 24 mg/day if the characterized expression product corresponds to a non-AA genotype at the position 286414.

* * * * *

SEQUENCE LISTING

```
<160> NUMBER OF SEQ ID NOS: 1

<210> SEQ ID NO 1
<211> LENGTH: 404123
<212> TYPE: DNA
<213> ORGANISM: Homo sapiens
<300> PUBLICATION INFORMATION:
<308> DATABASE ACCESSION NUMBER: GenBank AJ006345.1
<309> DATABASE ENTRY DATE: 2006-11-14
<313> RELEVANT RESIDUES IN SEQ ID NO: (1)..(404123)

<400> SEQUENCE: 1

cccaccccccc agcagccctg ccggctcccc acccacacag ctcccactgg gaggtacctg      60

acagtggtgg tcccatctca ccctcccggt ccaagggccc tggtgggaag cgacccgagc     120
```

-continued

```
gtattcgccg cccgcagctc gcgcgcctgg gcacccgggg gcgctcacag tgatcgcggg    180
gccagcacac cctcacccag gacatccctt tcctcccccc aaccccaact ccggagtggc    240
tcagagggag ggaaagtaga tgccggcacc ctaccccgcc cctcctgccc ccgctgtgcc    300
gttctcggtc gtggtatcgg ccaggcctta ccccttcctc cctggcgcag ctggggtcct    360
cctccgggcc aggcagagca ggcgggcatc agaagtgggg gccaagcagg tgggtgaggg    420
cagggcagga gcaagcaggg gagatgcaga cggggcgggg ccaagcaggt gggtgagggc    480
ggggccaagc aggtgggcgg ggagggggcg gggccaggcg gggtaaatgc acactggaac    540
ggggccaaac aggtgggcga ggagggggcg gggccaagcg ggatagatga cacgagcggg    600
gctaagcagg tgggctcggg cgggggtggg ggtgggggcg ggggcgcagg cgggggcggg    660
ggcgcggaca ggccaagcca gggggtgagg cggaggcagg gccaggccgg tccgtgaggg    720
agagggcggg ccaaaccggt gggcgcgggc agggacgccc tgtgcgcgcc ggaccggcgg    780
gggcggggcg tgcaggcggg ggcggggcac gccgtcccat gggaccggcc ctcggccact    840
gccccctccg gccccgcccc gagcgcccgg gctgggccgg cagcggcccc ccgcggcggg    900
gctggcagca gtggctgccc gcactgcgcc cgggcgctcg ccttcgctgc agctcccggt    960
gccgccgctc gggccggccc cccggcaggc cctcctcgtt atggccgcgg cctcctcccc   1020
gcccagggcc gaaaggaagc gctggggttg gggccgcctg ccaggcgccc ggcggggcag   1080
cgcgggcctg gccaaaaaat gccccttctc gctggaactg gcggagggcg gcccggcggg   1140
cggcgcgctc tacgcgccca tcgcgcccgg cgccccaggt cccgcgcccc atgtgtcccc   1200
ggccgcgccc gccgcgcccc cagttgcttc cgaccttggc ccgcggccgc cggtgagcct   1260
agacccgcgc gtctccatat acagcacgcg ccgcccggtg ttggcgcgaa cccacgtcca   1320
gggccgcgtc tacaacttcc tcgagcgtcc caccggctgg aaatgcttcg tttaccactt   1380
cgccgtgtga gtatcgccac cggcgacggc cggcacgaag gtgcttcctg agagctggtg   1440
tgggggagct ctgtcccagc gccacctgcc ccgtcggagc tgcgaccccg gagcagagga   1500
gggaaggaag tggggaaacg cagaaacaca aactctgcac tctcccttga agttcagagg   1560
cgctgctgtg tctgggggtg cgcatcttct cgcaggcccg gcgtggggag ggagccggct   1620
ggggagggga ccacctggag cccagaattt ggctccacac ctccgggagg gtagtccagg   1680
tgtgaatcct tctgggaaga gaagcgtgct ggggagcgca cccttgggtg cagtaagata   1740
actcctcaag gtcggctgag actcgaggct caggagcccc caagagagaa ggcccctgat   1800
gtccggtgcc gcatctcaga ccccctgagg cccaggtgga ctctggggca gggggctgtc   1860
caggatagga aggtgacggt ggcggtgctc cctgagggct cagcatgcca cgggccgtcc   1920
ccacgggccc cacattaact aattgaacca agctcatgaa aacctggctt gatgcagaga   1980
gcggagaggc acgtttgcag ctctcactaa gaggcagctg tgctcccgga gaaagcagcg   2040
ctggtagcag aggcacctgg ccccccctgtt accaggtggt tccaattccc ggtacagcgt   2100
gcctgagcag ggctgggcac tggatttctc agggacaggc ctgggaagtc acctccggga   2160
aggtccaggc tgctctcctc catgcctgcc tggggccttc ccccgctgcc ccagtggccc   2220
tacttcctgg ctgcccagcc agcggccttt tggtgtggtg ccagcctctg gcctgggagc   2280
ctctacccag acatcccatg gctgatggct gtggggctca cctgagggct gaagggtggt   2340
ctccctgagc gtcctcaggt ggaagcatct cctctgcctc gggcaggctc agtagagaac   2400
tggctggagg gcatccagag gcctgtccat gcctgctggc agctgccacc agggcctcag   2460
```

-continued

```
ggcgggtgac agcaggagcc aggccccaaa tggcttcaag catcgtctca ggtgaggggg   2520
tggggtaggg gtcgcagggc tactgccttc cttgctaaga ggtggccttc cacatcagga   2580
aggggaagtc ttacccacct ccctcctcaa agatgtggtt ggggggtgat cttggagact   2640
tttccccacc ccagctccca agcccctgtc tcctgacatg tcagtgggtg cctgagccac   2700
agccgctgct ggtctgtaag aggagctggc tctgctcgtg gctgcaacag cgggggctcg   2760
gcttggggtt tgggagatat ttgtgtgcag tgaccccagg ggaacccagt ccgatgccac   2820
tgtgcaaatg tctagcagat gccaggttca caggtgctgt gtgctggtgg ccacctgcct   2880
cccggacccc agactctctg agatgtccaa gggtgggaag acctcctcag ccagaggcca   2940
aggcaaagtg cccgcagacc ccctcaattc tcacttgtat tcaggtttgt ggacacatgc   3000
ctccgggctc actgcagcca cccgtgtgga ggaagaggag gaagagggct cgccacgccc   3060
cagaggaagt ctctgcttgc acttgtgttt tcttcctcat ttggattgtt taggtctcgg   3120
aagtttgctc agcaagagtc taccttcgcc cagcctccgc agagctggca aggcaggggt   3180
ggcttctggg gacaggggca ggatggcttc tgtgaagggg tggccaggaa agggatgctt   3240
ctgtgaagtg gccagatctg ggctggtcc tttccagttc tgggtcctgt ccttgtaaga   3300
cgtgtgcctg gccctgggaa gttgtcatga acagcctcca acccaggtac ctccatgtgg   3360
ggtgggactg gaggtggacc ctgactgggc aggacatgtg gcttggtggg ggcctgggag   3420
atgcgctccc accctcagtg ccctaggagg ttggcaggac cagtctcttg aggggagacc   3480
tggtcataga accaggatgg cagagtagct ggaggccacc tgcagcctca cgaaatcagg   3540
tccagccttg cgccagtcca gccttgtgtt gctgtaagaa gtcttggcaa tggtggcgga   3600
gacagggccc tgtccttagg tggattgtga aatgagaaat attgtggttt ctggcctgaa   3660
gacgacaagc ctggccttga agagccaggg cccaggcatg tgtgcagggg ggttgaggca   3720
ggagccggtg ttccgctgac cctacagggc tagggcgaac tctcctgtgt gcgcctgggg   3780
aagccagcca ggatatcctg tcccctcctc ggggaacccc ccctccccag gagagcagct   3840
cttcctgtgt tccttctggc ctccctgggc tggccggggt ggacacggca cctgggccac   3900
aactcttgcc cgcttaggct tcctgccccc aacaccccca gttatctgtg gttgcttgcg   3960
cccccactgg gggcagctcc catcttagct gaggggatgg gggtccatac agccctgctg   4020
cacccagcgg tcctagctcc cttgctgtga gccttagcca ggggtgtgga catccaggtg   4080
gcatctactc tggttgctga gatgcttgga gatcctggtt gtggccaagg agagggattt   4140
gagggggac ctgcagtgca tggagactgc ccctgtaggc tctcaaacct aagtctggct   4200
cagcagcccc tgttccccgc tcctacagcc ttggctttcc ctgtttccca agaactttcc   4260
aggggtgttg gcagaaccct cgcgggtgcg tgttaatcaa caatggagcc agaagcaggt   4320
cccagaggtg gatggggctg atctggctgc ctccccaaaa gacaaggcca tgcagagcca   4380
gctctcaggg tgcagcaccc aactttgtgg actccagtgc cctcctatct ccaggctctg   4440
gcattggagt ctgaagcagc tgctgggcag ttgttctgca gctgggcagg gaggccagag   4500
gccaaggcag gtggtggggc tgggcacaga ggaggacggg gctctctgag ccatcaggtc   4560
tctttctctc catcttcttt aagatctgtc cacccactcc tcagccctag attcccagga   4620
aaactgggaa ttcctttgg ggcttttccc agtgctacct tctgtggggc atgagccctt   4680
ggtctcatcc cctggctgtc tggggtcccc tcacctacat cgcagacccg gcccagtgtt   4740
tctagatccg ctcttgccaa catgtcgagt gcctaactgt ggcttcgtac tagttggggg   4800
gaacacaggc atcccttacc cctggccgtc agctggggag gggtagtcc aggtggcaag   4860
```

-continued

```
agcctagagc ctgggagaaa gggcctcccc agcctgtgtg gggacagggg atcaggaggg   4920
tggtagggac ttgggtcctt gcaggtggcc tgggcagtgc ctggtgggca tggatcaggt   4980
ggcagggctt tgtgtctggg catggccctg tggctgggct gccttggcca gggtcctggg   5040
ccttctgagt ctgcgtctca ttctctgtgg caggctcctg gtgctggcac cttcagtgca   5100
gggtgcctcg gttggaggga acattcaccc gtgcctggca ctgaagccac agctccctgt   5160
gggcatggtg cccgcagctt gagcctacaa ccctggggta ctgggggcag gagggtccct   5220
ttttgcttgg cagttgcgag gtactggaac ctttgcatat aacgtgcggg ctgcgttgtg   5280
tcacagggcc gggtctgagg gaggggcttt gcggggacac tcctgggtac cgatgggatg   5340
aacttccgct gggcctgaag gcctgggatg cttttgggcc ggccagtgcg gggtcaggtg   5400
gttggagcca gggagctggc acgtcagctg ctgctatgag ttctgccacg tgccatcctg   5460
gcatgtggca cgtcttgcag aggacaggaa gggtgaacag ctccaaaccc accctatgtg   5520
tgctccagag ctggaaacag gctgtgcgga gctgagtgcc tttgggggca gctgagatgg   5580
gcaggagcac cgtgcccacc gagggtgtca gagtgacagg ggttgccagg caactccacc   5640
cgggtggctg atgcccccgt ttttaaaggc gttgggtgcc gagaattccc ctcctgctgc   5700
taggctggtt tcaagtctgc tccttctgca cttgacgtcc ttgccagtgt gatccagagc   5760
tgctcacacg agcaagcgtc ctcgagtcct agggatgctg ttaacagggc agcgggtcca   5820
gggagctggt cctgacgcag gggtcctgat gcagcgggtc cagggagctc atgccttcca   5880
gcgatgggaa tgccaccggt ccctgtagcc aaggtgcaga tgcacacgtc ctggtcctga   5940
gcccctgctc ggccctaggc agggccccca gttccctgca ttccacccgc cttgtctggg   6000
aggtggacga gccctccgta gccctgacat tccaaactgg cttttggccc ctgcgatatc   6060
ttgctgtgat tcaagactct gtccacgggc aagaacaaca aggctgggac aatctcatct   6120
caggcatctg tgggaggaga cagctcccaa gggcggtgat gccaggagaa cattccaggc   6180
ccaggaagag ctgagagaca gcagatgccc aagacgagtt gctggtgtgt ggccagtgct   6240
gggagagcat ggtgtcggcc cggggagatg ccgcagagaa gcttccagaa gcccaacatc   6300
tgctgctgga ggggagaatg aggcaatgaa tatcaccatc ctgggccact ttgacccaga   6360
ccccaaggat ttggttacag aggggagggc ggcagcgtct ggcttcactc tcgggaggtg   6420
ccttggggct ggccagtatg ggattgctgt cactgtgggt cactccagcc ccggatgctc   6480
ctacaccatg ctctgcttgc atctggggtc cctgcgggca cgtcggtgag accgtcctgg   6540
cctccacacc ccttcctggt gggtagctgt ctctctccag cagctcctcc aaccaccatg   6600
agaaacccca gacctcacag atgcaaaatt atcgtggttg acaaagggag gcggctggtg   6660
tctctggtac tggctgggtg accacaggga tgccgcgtga ccctagtcca gggggccgct   6720
tttacacgag gcatctgacc atgtgatagg gtgtggcttc tgctgcctgg cccagccctc   6780
ttctgggagc cccacgtggg tgggtgctgg ctggggaggg gcttctctct ggggagcagg   6840
ccctggctgg aggtggggaa gatccatgat gggacccagg tgtcttccca cttctcgacc   6900
atctcctggg aagttctaat gtttggttca gggtgtgggg tccatctgag caggcatggt   6960
gcttccagaa ggatccaggt taagggtggt gggtccaagg gggtgcctga gcccttctgc   7020
agaaacaccg ttccccgtag agcagcagtc cccaaccttt ttagtaccag agacctgttt   7080
tatggaagaa agatttttcc acccgggcag tggtgatctt gggatgaaac tgttccatct   7140
cagatcatca ggtattagat tctcataaga agcgtgcaac ctagatccct tgtgtgcgca   7200
```

-continued

```
gttcacaata ggatttgtgc tcctgtgaga atctaatgcc accgctgatc caacaggagg   7260
tagagctcag gtggccgtgc acattcacct gacgctcact cactgctgtg cggcctgctc   7320
cctaacaggc cacggacccg gggttggaga accctgtctt agaggattga ggctcggggc   7380
catgggatcg gcactgtcat tgcccttgga gggttctgag cactggaagg acctggctgt   7440
ggtcccaggc actgggtgga tggaccagca gaaaggctcc caggagggtc gtggctccct   7500
catcggcacc ggactctcag gatgagccgc ctggagtctg ttggcatctg cctggccgcc   7560
tctggcagga acttctcctg atggaagagc cgggctgggg agctgactcc aggacaggcc   7620
cctgcccgct ctgggacctg gggcctgggc tctgctcccc atttcgctcc tccactcaca   7680
gatgaggaca tttgggtcgc cttacagatg agacaactag gcctggccac tttgctcatg   7740
ccacacccag aaagccctca ggacacccag aagcccttag gatgcccaga agcccttagg   7800
atgctgtggt ctcaagtgag gtggtgcact attcctggcc tcaggcccag tttgtatcca   7860
tgggcacccc cactcccacc tagcacttgc caccaggaag caccctgagg actgtcccct   7920
ttgagagttg gctctcaaag ccttggtctg tgcctgcgtc ctggcagcgg gtgagctacg   7980
gctgccctca cccagagagt gcaggttccc tgggggcggg ggctcttagc tttccctcca   8040
tatctgctaa ggtgcacacc tttctctgct gccttccaaa atcatactct ggggcgcact   8100
gaaagggtgc tctgagtagc tctccccggc tcctggctga acttgctcca ggcagagatt   8160
tgaagagatt cagaaagcag gaaccacagg cagagcagct ggacagggac ccccacccct   8220
gtactccctt cggccctgga atgctcctct gcatggagac agcccagctg cactgggacc   8280
cctcacccca ccctggggcc aggggctgtg tcctcgactt ccacgcagag cagcccgggc   8340
agcttagagg agggagcaga aggagctctg actgagaggg gtagacccct cccagaggca   8400
tccccaccct gccccaaaga ggggagcagc tggagacggg gcgggaacct cctctggcta   8460
tatctaagca gccccgggaa ccatgcgctt caagcgtttg atcttgacgg gccctgggct   8520
tggcattcta ttccgtgacg tctccagctg ttctcttgtg aagagtcacg tctgtgctct   8580
tggctaggat ggctcaaata ttataaaaca tacagctttg ctaattaaaa cagcatgaca   8640
ttgccttata ggcaggcaga tcaccaatgg aacagctttt taaaaaccgc atgtaactcc   8700
attgtatatg aagtttcgta aaagaggcag catctccaac cagtggggaa cagatgggcg   8760
gcttcatgcg tgctgcgggg tgggtgggtg gccatgtgga aagtgaccag actgcaccca   8820
cttgtcacat cacacaccag gatagactcc cagtgggtca gaaaaccact tgggtaccta   8880
aagaaagcgc ctggaattct ttaccctgag agcgaagaaa cttttctatg acttgaatgc   8940
tagatgcgtg gaggagattt atgtgtttga ccacataaga aagaagcaac cttggctggg   9000
tgcggtggct cacgcctgta atcccagcac tttgggaggc caaggcgggc ggatcacctt   9060
aggtcgggag ttcgagacca gcctgaccaa cgtggtgaaa ccctgtctct actaaaaata   9120
cagaattagc cgggcgtggt ggtgcatgcc tgtaatccca gctacttggg aggctgaggc   9180
aggagaatca cttgaacccg ggaggtggag gttgcagtga gccgagatca cgccgttgca   9240
ctccagcctg ggcaataaga gtgaaattcc atctcaggga aaaaaaaaaa tcttaatggg   9300
aaacagccaa ttgccaggct gggggaagat gtgatgtttc acgaagggtt aatctgttta   9360
ctacagaaag agtttctgaa aacagaagaa aacccacagc cagcaggaga tgtgaatacc   9420
actcacagga cagtgaccca cagggggacc ttgaacatgt gagaaggtgc cgccttcact   9480
cctggcgaga ggggtgtcga ggaaaatgtc actgaggtcc cttctggctg gcagaaatcc   9540
tttggcattt gctggtaggc atgcaagagg gtagactctg tgaggaaggg atttggcaac   9600
```

-continued atctagcaaa actgtcttca ctgacctgtg acccagcaac cccctcccca gaacctacct 9660
gaaggcactg gcaaaggcag gagaagctgc gtgtgcaggg ctgcttgtga aagtactgtt 9720
tggaaaactg caaatgccca ttgtaggaga ctggttgaat cagagatttg tggaatatta 9780
tgcagctgta aaaaaggaat gcatagatct ctcttattat gaagtgatta tcaggattta 9840
tttaattatt tttttcaggc agggtcttgc tgtgttggca agggtggtct tgaaatcttg 9900
gcctcaagca gtcctcccac ctcagcctcc caaagtgctt agattacagg tatgagccac 9960
cacacctggc gtatcaggat gctttttaag tgaaaaagca cagtgaataa aaatatagca 10020
gctattcttc atctgataaa ggggaggatg caagtctgga tgtatattaa aaacgaaagc 10080
aatggaagcc tccaaatctt aaaagtttac ctcaaaaggg tggcgggggg ggaggtggca 10140
tatggaatca agatgcctct gaatgtacct ggttttatag atttcacttt gaagccatgt 10200
aaatcaatag cttgcgtaat ttttaaaaag ctgttcgtaa tcgcttggtg aaaaatccct 10260
aaataaatct taaccagaaa aagtagtccc tcaaaattga aatgaaacaa atgagcctaa 10320
aaatgtgtgc tgaattagtg gcttaaccac ccagaaggac tgatttcagg tgacatattt 10380
ctagcgggtt actgctgaag acaaatagag ctgcatgcag tggccacata attgttgtga 10440
tactatttgt tatattattc taagagtgct gcatgggaat tgcaggttaa ggtaagtaat 10500
tgtgttggta tcaccaagaa tggaggtttt acaaaatatg attcacatgt aaacagaatt 10560
aaaaacaaaa accgtatgat catctcaata gatgtagaaa aaaacttttg ataaaattca 10620
tcatcccttc attaaaaaac cctcaacaaa aataggcatc aaaggaacat atctcaataa 10680
gagccatcta tgacaaaccc atggtaaatg tggtactgaa tgggtaaaag cgagacacat 10740
tccccttaag aataggaaca agacaaggat gcccactttc accactccta ttcaaaataa 10800
tactggaggt cctagtcaga aaaatcaggc aagagaaaga aataaaaggg gatccaaata 10860
ggaaaagagg aactcaaatc atctcccttc accgatgatg ataagattct atacctagaa 10920
aaccctaaag agtctgccaa aagccttctg gaactgtaag tgaagtctca ggatacaaaa 10980
tccatgtaca aaaatcagca gctttttttt tttttttgag atggagtctc actctgtcac 11040
ccaggctgga gtgcagtgat gagatcttgg ctcactgcaa gctctgcctc ccaggttcac 11100
accattctcc tgcctcagcc tcccaagtag ctgggacaac aggcgtctgc caccacgccc 11160
ggctaatttt ttgtattttt tagtagagac ggggtttcac cgtgttagcc aggatggtct 11220
tgatctcctg accttgtgat ccacccgcct tggcctccca aagtgctggg attcaggctt 11280
gagccaccgt gcctggccaa tcagcagcat tcttatacac caatgatgtt caaactcaga 11340
gccaaatcaa gaatgcaatt ccatttataa tagacacaaa aagaataaaa tacccaggaa 11400
tacatctaac caaggaggtg aaagatctct acacaagagt tacaaaacac tgctgaaaga 11460
aatcatagat gacagaaatg gaaaaacatt ccatgctgat gggttggaag aatcaatatt 11520
gttaaaatgg ccatacggcc caaagcaatc tacagattca atgctattcc tatcaaacta 11580
ccaatgccac ttttcataga attagaaaaa actattctaa cattcatgta gaaccaaaaa 11640
agagccgaaa tagcaaaaaa ggaactaagc cagaggcatc acattacctg acttcaaact 11700
atacttcaag gctacagtag ccaaaacagc atggtattgg tacatagaca tatagaccaa 11760
tggaacagaa tagagaactc agaaataaag ccacacacct acagccatct gatcatcaat 11820
aaaatcaaca aaaatatgcc atggggaaaa gacttcatat tcaataatgg cacagggata 11880
actggctccc catatgcaga ggaatgaagt cagactccta tctatcacca tatacaaaaa 11940

-continued

```
ttaaagacag attagacgtg gccaggcaca gtggctcatg cctgtaatcc tagcactttg  12000
ggaggccaag gtgggtggat catggggtca ggagtttgag accagcttgg ccaaggtggt  12060
gaaaccccat ctctactaaa aatacaaaaa ttagctgggt gtggtggtac gcacctgtgg  12120
tcccagctac ccgggaagct gaggcaggag attgcaccac tgcgctccag cctgggtgac  12180
aagagcaaaa ctctatctca aaacaaaaaa aaaaaaatta aaaaagatta gatgtaaaca  12240
ttagattaca aactgaaaaa atcctggaag aaaatagtct tctcaatatt ggccttggca  12300
aataatatat agctaataag tcctcaaaag caattgcaac aaaactaaaa attcacaagt  12360
gggacctaat taaagagctg ctgcacagca agagagactg ccaagggaat aaacagataa  12420
cctacagaat gggagaaaat attagcaaac tttgaactga caaaggccta atattcaaag  12480
tctacaaaga attaacaaat caacaagcaa aaaaacaacc ccattaaaaa gtgggcaaaa  12540
gggccgggcg cggtggctca cgcctgtaat cccagcacgt tgggaggcca aggtgggcag  12600
atcaccaggt caggagatcg agaccatcct ggctaacatg gtgaaaccct gtctctacta  12660
aaaatacaaa aaaaaaaaaa aaaaaaaaaa attagccggg cgtgggggtg ggcgcctgta  12720
gtcccagcta ctcgggaggc tgaggcagga gaatggcgtg aacccaggag acggagcttg  12780
cagtaagccg agatcacgcc actgcactcc agcctgggtg acagagcaag actcggtctc  12840
aaaaaaaaaa aaaaaaaaaa aaaaaaacac aaaaaaacaa aaagtgggca aaagatatgg  12900
tagacagttc ttaaaaagaa gacatacaaa cagtcaaaca catgaaaaaa tgctcatcac  12960
tgatcatcag agaaatgcaa atcaaagtca caatgagata ccatctcacg ccagtcagaa  13020
tggcctttgt ttaaaaagtc tcaaaacaac agatgctgga gaggcagtag agaaagggga  13080
acacttacac cctgttgacg ggagtgtaaa tgagtccagc caccatggaa ggcagtttgg  13140
agatttccca aagaaccaag agttgaacta ccattcgatc cagcagtccc gtgtgctgag  13200
tttataccca aagaaaaatt agtcgttcta ccaaaaagac atatgcacct aaacattcat  13260
ggcagaaaga catgagtcaa ctcaggtgcc tgtcaatggt agatcgaata aagcaaatgt  13320
gatatatata caccatggaa tactatgcag acgtgaaaat catgtccttt gcagcaacat  13380
ggatgcagct ggaggtcgtt atcctaagtg aattaatgca gaaactgaaa accaaatact  13440
gcgtggtctc atggattata agtgagggct aaacatcaaa tccatgtgga cataatgatg  13500
agaaccaaag acactgggga aaacaaaagt ggggaagggg gaaagggaac aaggttttaa  13560
aagttacctg tgggtgctgt gcgcactacg tgggaaaccg gatcgtttgg actccaaacc  13620
tcagcatcat gcaaaaaacc tttgtgacaa acctggactt ggacctcctg aacccattta  13680
aaaagttgaa taaaatggaa acttttggca tgggagaaaa aaaaaaaaaa cagatgtaag  13740
ttagaagagg ttacgcaaaa atcctccatc cctgcatttg aatgaggact atcagtatgc  13800
atccaggatg acgtttactt aaatatctct gtttcctgga aaggcccagg accaaggacc  13860
actcagcagc taagagcatc tctagacccc agactgtggc ctctaggtac catttccccc  13920
tgaaagaaac cagggcccct ggcggattcc aggtctgtgg cagaagatgt gcaagctaag  13980
cctggagtat tcatcacagc agaaggcagg gaagttatca gaggcccccct agggccatgt  14040
cactggaact tgaaggggtc cttgtcttcc cccttctccc caagctgaag atgcagtggg  14100
taagcctcac tgaaaataac agaggaagtg gatgagctgc attgatgggg ttcagatccc  14160
aagttcatcc tgatactgag gggcaaaacc agtggacttt gatttgcatt tctctaaaga  14220
tctgtggagg tcaataggga gaccgctcat gatgttgaat cctggcaagc aaacggagag  14280
aatctgacat gtgtcccagt cgtgattaac ctgtgaactg taactcgggg aaacccagta  14340
```

-continued

```
gctgatgggg ttgcgtcctt ctttgggact cccgcagatg cctgaggcgg cagtgctgct  14400
gaagtcctgc caggctccag ctcctggtga ggtcagggat tccgcatgca gcgtcacagc  14460
tgccaacctc tccaaagcag taaaggcctt cggacagtgc acagaaagtg ctcccatcca  14520
caatgcttcc ttgcctggat ggatggatgg atggatggat ggatggatgg atggatggat  14580
ggatggatcg atcgatctca ccaagcctcg tgctctaagt acaagtttac tggaaatact  14640
cgggccagag gaacgcgcta aatgatacta caggaggcca cttgcagaat cccagtggtg  14700
ggggatggct ctgtaggaca catgacctga tttcctcagt aagtcaatga ccaagaaata  14760
acggagagaa ggaggaaaga atcacctatc caccaattgt gacatatggc cttagttagg  14820
tcctcaataa atgatgacaa atattggatt aaattacttc tggtttgctg catgttccat  14880
ttttgcccat gccgcacctg ccatggtgca tttctgattc ccgtgcccag ttgggaggct  14940
ttggggttgt tgggatgctt ttgtgaatgg cttccttcct tcccaggcac aggggcttta  15000
tggggctctg gagcagacag accagagttt gcacccagct cccagctggc catgttacct  15060
caactgcaaa acgagagacg gacttccttg ggacgcggtg gtggggacac tgtggtctgt  15120
ctcctctggg cgccccgtgg cgcccggtgg tgtgaggtta ggatgtgggg cgtggtgtcc  15180
agggactgtg tggcctgcct ggagctgggc agagacaaag catgcatgtg acactccctg  15240
acttcaggcc ataacagggg caggggtggg gggcaatcag ggttcctaga ggacaacccc  15300
atgtagttcc tcactgcagg gcttggaggg agcaggtgaa ggcttacctg tcttaggtaa  15360
tgaggagctg tgcgggtctg agacagctct ggttccttta agggtatgta ggggtcactg  15420
ccagtctgta gctccctctg tgggggcagg ctgtggcact gtggcgactg gcagtactga  15480
cttcctctaa gccaaccggg cagggacaag tcagcttgtt gttccgtcca cagtagaggg  15540
cggccctggg ggtgaacggc tgaccgtgag ggcgtggtcc ctccccccag accaccccgg  15600
aggcccccctc cgccctcctg cctacaaaga gttcccccctt tgtgttgaga ggcctgggtc  15660
tcagaggtag atgaatggag tcgtgaaatc aggcagggat tcccttctgc ttaaaaccca  15720
ctctccttcc catgcagcac aggtggccaa aacctgcggc tgggtcagag gactggttta  15780
gtaagaattt tttttttttt aaatgtggtt atctgctagc cagaaaaggt gtgtggtttc  15840
gcagtctttc agacaaactg aatttaatag tagctgacgt gaacccctgt ttctcctcta  15900
ggctccagag ccgcacccca gtgcaggtgt ggaagctcag ttcctccaaa acccagacag  15960
gccttggtgt cctgactgcc acccccaggg ggcccctcac tcgagtcctt gcttgcagtg  16020
cccatgggca gcagaggtgt ccggagatgc aacagggccc agacccctac cagcctgtgg  16080
cccagctggg ggcaggactc cggggcaggg tgagtccctg cgtgacctga ttctctgtgg  16140
gcaggccggg cagggtggct gcagggcggc ggagcctgtg ctgctggcct gcatttctct  16200
ggctggacag atactgcgcc catatccctg gtctttcaaa gggctctgtg gctggtggag  16260
ggcagcaatg ccccaaggga ggagcaggtg cccaagcccc caggtggccc tccgggtaca  16320
ggtacttgtt tactctgtgg catcagtcct gcttcccagc tcaaggccct ggcctccaca  16380
ggcctcctcc ctccctccct ccctccctcc ttcccttttt tcctgtggct ccaaggccca  16440
cagtagaaag gctccagtct gtgtccatgt gttttggagg cctctcaggt acagggactg  16500
tcagcccagc tgtaagtgga ccttggaccg caaatttgca tgggcccctt tgccaaagcc  16560
ctgtgcccac tgctggggaa cgctggggac tccgctcttg tggggcagtg gggctgggtg  16620
ggagcaaccc cccatccggg tggctgtggc cgaggccctt atgagagggt ggtaggtgtg  16680
```

-continued

```
tctccacagt gggggaccag atctctctct ggccccaaag actgcttcaa gcctctggag  16740
gagcactttg ccccaggctg gggcgtgact gcttctggtt gagggttgct gcctgtgcag  16800
gtggccctct tgtcggtctt gtctgctgca tgggggtgtg gcctcctgtg gatggcccct  16860
gtcctgggtg gtactgctgc aggacctggg tttccggggg tgtccgggag tcggatgggc  16920
ctcactctcc tggcctccac tgggtccagg agtggcgatc tgtgagccaa tggccgtggc  16980
tgggggcagc ctggggtgtt gagaggccct gggcagccac cttgcctctc tgagtttgtc  17040
ctcatgtgtc tctggggctg gaactcggtg tccgacctgg tgatgggtca ggtgtgatca  17100
ggtgtgtggg gctcggtctg catgtgcagg gctgtttgaa ggcctgtggg gccatctgat  17160
gcccccccttt tcttcagcct tggagaggat ggcttctcag gccgcctcgc agcagatttg  17220
tagtctggtt gctgtcgttc ctgaaatagc ctctgaagct ctgtccggga agggaacctt  17280
gagtgtggag gagataagcc tgctgactgg gtgagccggc cggggcgggg gtggcccctc  17340
ttcccttcct cccctgcagc ttccatggcc tggggctgtg agaggcccgg gaaggcactg  17400
tctttgcgcc tgcacatgtg tgtgtctgga gtgtaggatg gcactggtgc cgggcctgga  17460
tttactcagc ccagatcacg gctgcttttg tttacgtggc ccctgctctc acccacaact  17520
ccaggtttct ggctctcggg aatttgaggc ctgtggctgc tgtggaccct gggaaagagc  17580
ctgtgcttcc tgagccagtg cggggcctgg catggagtag gtaccccggg ggtggacaga  17640
taggcagagg aagggatggg caggtggatg gggggctgaa ttgtggtcag ttatgggtgg  17700
cgggtagatg ggtggacagc tggatagatg aagtactggg tgggtggaga gagaaagggg  17760
tgggtggacg gagggatggg cagggagaga aatggatggg gcatgctgct tccagcaccc  17820
actgggtgca gctgtctgct gtctgctgtc ctgggggaag gtctggagag ggcctctcgg  17880
tgagtgtgga ctcagccagc ctagtcccaa tacagctggg atgcattgct gctccttccg  17940
ccatcccagc agctgtccag agatgagacc cagccccact gtgtctttct gggattcaca  18000
agaatccttc cctgggctga gggggcgttg ctgtgggtgt atctcatgga gagccccaag  18060
gagccaggga ggagccttct ggtggtttgg gttctggatt ggtgggtgct gggtgggtct  18120
tcatggctgt tcttggggct gccaggcctg caaggtagac aggcctctgg acttgagtgt  18180
ggctgtggac gagggcagcg tcgccatcag aggcgatgtc tagggccacc ccctctgact  18240
tgcctcctcc tccttctgac ttgcctcctc tctctgacgg gcctgctcct gagcttgaca  18300
cctgcctggg ggctcccggc gaaggccgct ggtttctaga atgcaccatc tcttcctggc  18360
atgacgggaa ccacctgtga cattgccacc acctcgctgt aatctgggca gcagctgtca  18420
tgatcccacc atgtgccccc cgtgaggccc ccacctgtta ctgagtggca gggacgtgct  18480
cccacacccc catgcgccat cctgcaggtg ctttctgctg acttctgtgt gccctggggc  18540
ctgctctctt ggtaggggtt gaccctgcct gtgacttaga cagcttggag ggccaggact  18600
gaggggaggg ggcggtggag tgaaggggag ggtgggcgct gctggcaaga accacaggca  18660
aagagggtgc cgggggcagg gaaggcctgg aggtttgagg agcagaaagt agacccttga  18720
ccctccctgg gctggtgagt cggggcccag cccagagtga cagggaccaa acctgggtcc  18780
atgtgccgtg cccagcctgg ggttcaggtt tcttccccgt gagctgagca gacagggagg  18840
gtcttggggg aaggctgtgg gcccttgggt ggaagagtct tgggtgaggc ccctgaactg  18900
gtaagcgggg cagcggcggc agggggccca gggaagtggg gccagtcggg ggtcctcagg  18960
ggtccttcag ggatatacct gctgtcaggg tgtggggagt gggaagtggg ggacggggtg  19020
gattccagga ttccgggttg tgcttggtca gagtggggaa ctggacgctc cgtccctggc  19080
```

-continued

```
tcagcctctc ccggctgtga ccttggggga ccattgactt tactgtgtgc ctggagagcc  19140
taatccctac ctgccagtgg gtgacacaga aggcaggaat gcagaaggcc tttcagaagt  19200
tctcactggc ctgcaaggta gaggctgttt tctgctgagg atacatttgc cccctctatc  19260
ccccagatcg gcggctgctc aaggagcctg gtacagctgc acggaggcgc agcacccaca  19320
ggacaagtgg tggaatgttc tggttgtcct tggtgcaggt ggcgggcggg gctgggggc  19380
tctgtagcct tcctggcttc ggtcccctgg acaggctcca cctccctctt atcgtggccc  19440
ctttggcagg ctgcctgcca cctcaaagtc acgctgccct gggcaccctg cctcttccgg  19500
ggactggggc tggggctggg gcagctgtgt ttatgggtgt actccctgtg ctgggcactg  19560
cgctgagctc aacacacagg ggctcgggga ggtctgtggg tgcccaggcc gagatgtgaa  19620
ccctgagttt gtgcaactcg agtttcagag tggcggcctc tgctcctcac aagacattgc  19680
cctgcgaggg ggtcagccct gaagccggat ggcccggccc ccgctaccac gtggaggctc  19740
cctgtaggtg cttgtgtaga tgcccccgtg cggggacttg tttggctgat ggatcagggg  19800
gaaggttctc cccacggtgt gaggcagcac cgagggctcc gtgcccagca ggctcactgt  19860
cggcagttgg gtctggtttg ataaccgtgg accggggtga caggccctga ctctgcagag  19920
caggactgtg gaaaatggac actgatgctg cccggtggat ccaggcaggg ccgggatgtt  19980
tgcaggaccc acgggacaat tagaacgact gggcctgact ggcacaggga tgtggactac  20040
ggtgcttgcc atcagcagat acaagctgta cgcagtgggc cgcaggcgct ccctgggccg  20100
gaacacatgg acgtccaggt gtggaatggc ccggacagca gataacaagc cttcgtcgtg  20160
gtcacccctg ggtgtgggct gtgggtttta atcttttcat ttttgctcat ctgaattttc  20220
taattaaaaa tatattgctt tttaaaaata ataaaagatc atttaaatta aaatatataa  20280
gtgaggagag gctggtaaga ggattctgga gtccctggag tgtcttctgg catcgcatgg  20340
atgagaactc tgaatgaatt gagtgtgatt tgacctagga gagtgccggg gtgggggcag  20400
gtgcactgtg gtcctgggtc cacatggtgc tagggtccca tgggctcctg gcccctggct  20460
gctgccccca cattgggccc tgcaccaggc atgagtccca tgtcctgtcc ttggggaggc  20520
ctgggggaca ggagttgggg gggtgggcag tgcctctgtg tggcagattc cagcttctct  20580
caggggccag gattacatgg tccgtgttgg actctgggat gctggtggga agaacagtct  20640
gggcgaggag gaaagggtgg ctctgctgac ccctcctagg tgggctgggg ctgaggcgga  20700
tcccactgtg gggagctgcc cagagatgga aggagctgga gtccacaggg cgcttctctt  20760
ctcttttcct gtgtgttaag gtagttcaaa gtcctcctgc ccgaggaagt aagacagcaa  20820
tctctggggt cctgggcacc aactctgggc actgatgggc tggtccagtg cagggagctg  20880
ccccggccgc ccccgtgggt gcaggccatg ggctcttgtt tcctttcccc catctgtaaa  20940
atgggtaacg gccgctcctt caggggctgt tagccacatg cttagaccgc accgagaaaa  21000
tgcagtccct ccagagctcc taaccttcca tgggccacag gccccttccc agaagttttt  21060
ttattttta ttttttttg aagcagggtc tcactctgtc gcctaggtta gagtgcagtg  21120
gcacagtcat cactcactgc agtgcgacct cctgggctca agctggcacc gtgacccctt  21180
ctccaaggcc tgccaggctg gcctccagtc caggtgtgag gccctgaggc cctggctgca  21240
gctggaagct cttgggcagt gcactgtccc cacagcggac tgcctcctgc agccaggtgg  21300
ccttaggtga tcctccaagg tccagccagc caggatctga gtcaggagga accacggccc  21360
ccaccagggc tgagactcct ctgagctcgt cacttgtctt ggttgggtag aggcctgaga  21420
```

-continued gggtggacac ttgcccaggg tcacacagct tgtgcgtagc agagctccct gtccggcccc 21480
tgccccgtgc tggcccctct cacaccttgc tcacgctagg tgccttgtac cagtgcctgc 21540
ttgggggtgg aattggagag gggaggggtg ggcgccgagc tctgcctccc accagcatgc 21600
ttcccagagc ttcctgggag aaggtttacg gaggagtggc cttgtctggt gtccctctgg 21660
gtagagcctg tgttccgggc aggctgggaa caatgaatgg tacagatcca cggctcccct 21720
tgggccttgg tgggctccag ccatgcctcc tggaaggcca tttggagcct ggctggcagg 21780
caggagctgt gtgctgccag gcgggtctag atgtggttgg ttcctggctg cacctgccgg 21840
gctcatgacc tgccctgtcc tttccttggg gagcttggtg acggctcagg tcgactccca 21900
ggggcccgcc cttcagggcc tgcatgagtg ttctcgggct ggctatgggg gcattgcttc 21960
ttcctgtcct agccgggacc tgcccatcca cccagggggc tcagggacgt tttgagtttt 22020
tcctgaggct ttgcctaggg agtgtcgctg aggaagctgg aacagtgacc ttcgttgttg 22080
ggggaggaga tgcaggcagg ctgtggccca gctgccccat tttgtagctg gggaaactga 22140
ggcccagagt ggagaagcga tctccaaagg ggaggtgaca catggctgag ccccgcctga 22200
tgggtgcttg ctgggggggag aagtcctggc tgggacttcc cctccccagg ctggggtttg 22260
tcccctactt tgcaggagga gggggctcc cagaagagag tgagttttga gggaacacag 22320
tgctgggggt cccctcctgg gcctggggct gtggttctta gaggggcaag gggctggccc 22380
ctgttgctgg ctgtggcagc cacagccttc tgacccttgc tggcctgtcg tggagtgggg 22440
ttcaagatgc tatcactgac atctgcccag gctcgggggc ttctgtgtgg tgccagcctt 22500
gcccgggggc acagccatca gcaggccaga agtcctcagg agagcttgct gccaggctgc 22560
tgcctggggc caggcttcag atatgctggc cagccttgtc cagggggcct cctgccaggt 22620
gggcagaggg agagggcctt cctgtcctca tgagaacagg gctgagctcc atgttcctta 22680
gcctcccttg gcctcagtca tcctatctgg aaacagggat cataatagtt ttagtttata 22740
gagagcgagg gcctggcccc tgcgctcttc ctctgtggtc tcctctgccc gctcccagaa 22800
cacctggcct cctgctctga gggccagccc tgggttgcag cagtgagcat gacctggcca 22860
cagtctaggg gctttggggt gggtttgtgg gcagctgggc tgcagggggc tgtgggagcc 22920
tgagggagtg ccttccaggg gaagcccgac agatgggggc actccaggca ggggcaggag 22980
gtgacctgga ggtcggagga gcaagctgtg gctggagagc cgggcagggt tggtcagcag 23040
gtccgagggc ctgggcctcc ctggggtgag ggccagggtg cctctgcagg ggtggaagtg 23100
ggctgtgagg gggtctgggt ttatctcccc attgcacagg gctccatggg gtgggctgag 23160
ccatgagcgc ccttcgtggc accttggtgt ccggcaggga ggcaggggcc caggaggagg 23220
gcaggactgg cttcaacggt gtcggcctct accctttttgg tcctcacgga ggaggctgct 23280
ccctcttccc tggagcagcc agggatggtg tggggccctg gtcccctggc ttgatatagg 23340
cttctgcaga ggatatggtg tggccggggg ctcagctgag aagccaccag gagacagata 23400
cagcctcagg aagtggtttt gtatctctgc tgagaaccac aatccgagtc acatgggacc 23460
attgagatca cgtcagggtg caggctgggg aaggctggga gctggggttt ggcaaaggcg 23520
ttggggtgct cttgtgctgg acaggctgct gcccaccggg cctggcccag gtgaggtgag 23580
agacacctgc cccccacgtc aatgcctggg cacacgggcc cagtgcacac agccagcagg 23640
cgtgcgtctt gcaatggggg ctgtggggac ccctttgctc ccctgatccc ttccctgcag 23700
acccaggcca ggtggattca aggtgtgggg cagggtagga gctgggcact gctggatggc 23760
atgggccacc cgcactgggg ctgctgtgac ctccgagtcc aggcactgcc ttccacctgg 23820
ttagggacag ggcagggagg ctgatgggct ggcccagcgt ggggacctgc ccagtggccc 23880
tgtgggtgca ggccatgtgc ctctgcattt cctttacccc atctgtaaaa tagggataac 23940
agcagcttct taaagggctg ttagccacgt gcttagactg tgcccggaaa atgcactgtc 24000
tctcctgggc tcccaacctt tcacaggcca caggcccatt cccagaagtt tatttttat 24060
ttttcgagac agggtctccc tctgtcactt aggctaagag tgcagtggtg tgatcttggt 24120
tcactgcagc ctcgacctcc ctggctcaag agatcctccc gcctcagcct cctgagtagc 24180
tgggactaca gatgcacacc accacgcctg gctaattttt gtatttttg tagagatggg 24240
gtcttgctat attgcccagt ctagtctcaa gctcctgagc tcaagcgatc tgcctgcctc 24300
agcctcccaa agtgctggga ttacaggcat gcactttttt tttctaagta gctttacgga 24360
ggcgtgcttg gcatacggta aactgcccca gtttaaagca gacagttcca tgagtcctga 24420
catttggagg ccctgtgaag ccagcatcag cagagtgggc acacccatca ccctcacagc 24480
gtccccctgt ccccacgacc aggccactgc tgccctacca tcaggcacga tggatgggct 24540
tgtgccttgt ggaattttat ttggatggac tctggcagcc aacgctggtt tcgtctggct 24600
tcttttattc agcgtcatga ttttgagctg tgtgtctgtt gtgtgtgtcg gcctgttgtt 24660
tgggtagagc ctactttgcc gatccatgca cctgttgatg gacatgtggg cggctgtatc 24720
ccatttgggc tctcacaaat gatactgcta ggaatagctg gagtctctgt gcgagcaaat 24780
gcttttgctt ctcttgtgca agcaagtggt tgaactgctc tgcagcccgc tgggaagtgg 24840
aacggctgtg tcatggggtg ggtgagggct tcactttcta ggacactgac aaaccgtttt 24900
ctaaagcagc aatccccttt tgcagtccag cagctccgtg cgacagctct agttcctctg 24960
tctccttgtc aacacttggt gtggtcggtc tttaatttta gccaatctaa caggtgtgtc 25020
ggggccctcc ctggcattcc tggtgactca ctgtgtgggg tcatcttttc agctgcttag 25080
ttgttgtcca catatcttct ttggtaaagt gtctgtcaaa ttgtctgtta agaaaacgtg 25140
ggtggttttt cattgaattc aagagttttt tttttttct ttattttgag agagaatctc 25200
actctccgtc tcccaggttg tagtgtggtg gcgtgatctt gcttggctca ctgcaacctc 25260
tgcctcccgg gttcaagtga ttctcctgcc tcagcctccc aagtagttgg gactacagat 25320
gcccgccacc atgactggct aatatttgta ttttagtaga gacagggttt caccacgttg 25380
gccaggctgg tctctaactc ctgacctcgt gatccacctg cctcggcctc ccaaagtgct 25440
gggattacag gcatgagcta cggctcccgg ccgagatgtt acatgtttct atattctgga 25500
ccaagtcctc tatcagatac ctgctctgtg aagccttccc ttatcccttg ctagtccttc 25560
agttctttta aacaattttt tttttctttt tttgagacgg agtctcgctc tgtcacccag 25620
gctggagtgc agtggcgcga tctcggctca ctgcaagctc cgccttccgg gttcatgcca 25680
ttctcctgcc tcagcctccc gagtagctgg gactacaggc gcccgccact gtatccagct 25740
gattttttgt atttttatag agacagggtt tcaccgtggt ctccatctcc tgacctcgtg 25800
atccgcccgc ctcagcctcc caaagtgctg ggattacagg catgagccac cacgcccggc 25860
ccttttaaac aacttgtttt tagagctgcg gtctcactct gtcgcccagg ttgaagtgct 25920
tggtgctatg acggctcact gcagttccaa ctcctgggct caagccatcc tcccgtctca 25980
gcctcctaag tagctgggac cacaggcgca tgtcaccacg cccggctgat tgttaaattt 26040
tttgtagagc tggggtctgg ctatgtcgct gacaatcaaa atgaggactt gaagcatact 26100
cctcaaatca tcgaggttta ttgagccaac gtgagggcac gcccaggaaa aactccagtc 26160

-continued

```
acagaagcat ctgtggctgc tttttccaaa gaggtgcgta ggaggtttca ttcatattta  26220
tatgttttct tgaaaagggg aggggcatca agtgagacaa atgattatat acttgcgaga  26280
ctttagttag agcccagtaa atctacattt tacagaagac gtatattgga ggaaagaggg  26340
agcatggaag cgtatatccc agggaggcgg aagaacatct cgttatctcg tctcgccttt  26400
gttctgtgcc tgggaaggaa gacaagccgg cgtcttatga aaaggctggt ttctgttcag  26460
ccctttggga agaaaaccca atgacagtta tcaagggagg gggtgtgatg atacgtatcc  26520
aaccgcacat ccatcatggc cctgaactca gcttccaggg tttctctggg gttccctcgg  26580
ccaagtgggg atccactcag ttaggtgggg gggggggtgc ttagaatttt atttttattt  26640
ctcattgccc agactggtct caaaaccctg gtctcgatca atcctcccac ctcagcctcc  26700
cattctctta atagtgccct tttagagagc aaacgttttg actttgatga agtccagttt  26760
atcaacttgt tcccttatgg attgtgtttt ttggtgctct cagaaatctt tccctaaacc  26820
aagggcacag attttctgtt ttcttccaga aattttgtag tgtcaggttt cacactgagg  26880
tggatattcc ttttgagtta atgtctgacc agctgggagg tgtcggtgga ggctcccttt  26940
ctgcccgcgg gttccagcac atttgctggg atggccctcc tccctccaca gcagagttct  27000
acccgccctc accaccctgt atcaactcat ctcatcgata tctcccaacg gctggggaac  27060
aagggctgac tcggctgcaa tcatcctgca gccagactcg gggacctagg actctgaacc  27120
tccaactggt gtggcttcag ggtccccaac ttttcagacc ccacctctgt gttgctctgc  27180
aagtggggat cagcagggct gtaccccaaa tgctgcttgc ttctcccgcc ctcctccctc  27240
tccccatctg ctcttggctg cacccccaac cctgacccaa gtgtccttca cgctcagcaa  27300
cgccacagcc tctgacactc cacggcacta aagtgtcaag agacccaggg gacctgcgag  27360
atccatctcg ccccacacac caccaggtcc ccaggacttg gaggatgctg atggcccagc  27420
tctgggtcct aagcatggca gtatcacagc ctcacaggca catgtgtatg tgtgtgtgtg  27480
cacgtgtgta tgggtgcgtg tgcacctgtg tatatgggtg tgtgcacgta tgcacggatg  27540
tgtgtacaca tgtgtatggg tgtgtgcatg ggtgtgcaca tgtgtatggg tgtgcatgtg  27600
tgtataggtg tgtgtatgtg tgcatgggcg tgtgtatgtg tgcatgggcg tgtgtgtact  27660
tgtgtatggg tgtgtgcatg tgattgggtg tgtgcatgtg tatataggtg tgtgtgcacg  27720
tgtatgggtg cgtgtgcacc tatgtgtgta taggtgtgtg tgtttatgta tgggtgtgtg  27780
tgcacatgtg tataggtgtg tgtatgcgtg cacctatgtg tgtataggcg tgtatgtgtg  27840
cgcgtgtgta ggtgtgtgtt catatatatg ggtgtgtgtg cacctatgtg tataagtgtg  27900
tgtgcacatg tgtataggtg tatgtatggt tgtgtgtgta taggtatgta tgtgtgcaca  27960
tgtgtgtagg tgtgtgtgtt catgtatata tgggtgtgtg tgcacctatg tgtataagtg  28020
tatgtgcaca tgcgtatagg tgtgtgtgtt ttatgtatgg gtgtgtgtgc acctttgtgt  28080
gtatatgtgc atgtctatgt gtgcacatgt gtgtaggtgt gtgtgttcat gtatatatgg  28140
gtgtgtgtgc acccatgtgt ataagtgtat gtgcacatgt gtataggtgt gtgttttatg  28200
tgtgggtgtg tgtgcacctt tgtgtgtata cgtgcatgtc tgtgtgtgtt tgtgggtgtg  28260
tgtgtaccta tgtctgtata ggtgtgtgtg tttgtgtctg ggtgtgtgtg cacctatggg  28320
tgtgtgtgtg tatgcatgtg tgcatgtccc tcacagggca gagctggaaa gaactggaga  28380
ggctgaggct ggtcccttca tctcagggtg aagcaccttt acccagagaa ggagggtcgt  28440
ggcctgggct actttgtggg ctggagtcct ggtctctgtc actgaaaaaa gcaaggcaga  28500
gcgtctggga ggggtgtcat gcggggcttt ctgagtcact ggctgcgtga gatgtgagta  28560
```

-continued ggtctgtggg atagggagct ggccagggac ttgagctccc tgcctgctat gacctcagtc 28620
agcccctgcc cattgtcagg ctccttccct gtctaggggt acccagtaga gctgcccagc 28680
cctgccactc cagcttgttt gaggaaaaag tgcaaccatg ctgtgggtgg aggcagatgt 28740
gattctgtcc tcagaggcat gggggtgact ccatggctct gagccaagtt gcagctctgg 28800
ggcccttctt gatactccag ggccccccat caccccagca ccgagatggg catgagcaga 28860
ggggctcatg gtgatggggt gggcgtggct gggagaagcc tgcatatgaa ggcctctgtc 28920
attggaggag actgtcccat gtccctccag atcatgtccc tgagtgggga gcgccttctg 28980
ggcagagtgg cacacagggt cccacccatc tcaagtccat gggattaact cccctgtgct 29040
ggaagctgca ggagctgctg cctgtggctg aggagaggcc aggacgggcc aaggagagca 29100
ggcaagagaa ggggtggggc tggcagggag ggggctccat taattctgat gtcatttatt 29160
gctgttccta tatttgtata ataaatggaa gaaaatagtg gttgggggct tgctggggac 29220
tcagggaggg ttggggacct ccagggcttc cattcgacct gaggcccatg gtgcagtgag 29280
tcctgcctgg agtcccgtcc agcaggaggc aggagagctg gtgtttggag atgtgagggg 29340
ctgggccctc ccaggtgagc gggttgggaa aggaaagggt ctgtgctggg aaatccaagg 29400
ggcaaggccg tttcccgtcc tggtccgtcg ttgagtcccc tgccgtggga cagcgctcag 29460
catggcacag acgctcagcc gtgtcatgtg gcttgtagag cgagggtgtg cggccggcat 29520
catcctcagg gaactctgga gggactgggc ctcagttggc ctggcctggc gcggggctgc 29580
cagccaagag ccttcctcca tcccattgag agccagggca ggtcctggag atggcagcct 29640
gcaggttgaa gcccccgaca gctgggggag gcattgctct gcacaggtag ggccatgggg 29700
cccgctggcc agggtggcca ttgctcagtg gcaccagctg ggcagacagc cgcatgcgct 29760
caccactcgc cctccacaga tgggagcctg ggagagccct gcctcccgga acggacatcc 29820
tccttcacca aatccgcaaa ataggcctga tgccaggaac ggggcactgc agggcccttg 29880
ggagggaggt aagcgggcag ccgggccaac ctgctgcttg gggaagggct gtggctggcc 29940
ccagcctcct accgctggcc cagtggtctc tccacacatc acccagtgtg gagtggtttt 30000
ttgtctttct ttcgaaacag gctttcctca ctgagggctc accatggggc tgtgctgggg 30060
acactggatg tgtccagggt ccgtcaagaa gcgttggggg tagtcagggt ctcagggacc 30120
actctgctgt cctcgagtct cctggtggtg accagtggtg actcttgtgg cgcccgggcc 30180
acagctactt tgttcacctc ctaggaggga agagggcgag ggtgagccta gggcagatgc 30240
cagggcagtg aggctcacgt gggtctcttt gcctgatgtg ccggtgtcca ggctgcagtg 30300
ggcacccgag ccctgtggga agcctcctgg gtctgcagct gagcaaaaca gcagccgcca 30360
gatgatgggc cctaagtggc tgcagatagc aggcaccatt aaatgcagag gccatctgag 30420
gctgcaggct cagcacaggt ggctttggtg cccttaggga ggggcagcgg tggagcccag 30480
gtctctgaaa catttatgac ttcatgcgtc agctggaggc tctttcaccg cccagacaaa 30540
aggcccttgc gtcagagtgt tccatgtggg gcgggagctt gggctgagag cttgggcccc 30600
tgctcccaga gaggcccaga gctggggtgg ccacacctgc tgggaatgct gctggtggga 30660
ctaggttaag gcgagaagga ggtgtccatg gccaggtgga ttagtgcaga ttgtgatggt 30720
gtggtggtgc tcacggtggg ggacttgcct atgggaacct catcacagcc ccacatcggg 30780 ccctttaca gatgggaaaa ctgaggcatg gggtgcatag ctagtgagga gcagagccag 30840
atgggaacca ggcgtcgact tcagagctga cctttgtgca tttgtgcatt gtttgtgttg 30900

-continued

```
tgattaaata cacgtaacgt aaaattgacc tttttaaccc atgtttcatg gtcttcggtt  30960
tactcgcagt gctaggcgtc cgacacgtct ttctaattcc tgaacatttc catcatccgc  31020
aagaggaaat tagcagtcac ccctttcccc catgccccca gctcctgaca accacaagcc  31080
cactttctgc ccctggattt agctattctg gatgtttcat gtgcctgaaa tcatggcaaa  31140
cgtggccctg tgtgtctggt ttccttcacc gagcgtcctg tcttcactgt ccgccgtgtt  31200
ataacacgca agggaattcc cttcctttct gagctgagta gtggtctgtg gtgtggatgg  31260
actacgtgca gctgtctctg cctttggctg ttgtggctag aggctccttc ctgaaagcct  31320
gatacttaga atggatttaa aaacaaattc aaatgtgtgt tgcttatgaa aatcacaaaa  31380
ttaagtatga tgccatcaaa atgaaaaaat ggctaaagat tttcaagcac acacacctaa  31440
agatagcaga cattccattc aacccttcatc tcaaagaatt agggcaagga gggcgattct  31500
aaatggctgg agacatagtc agctgtgaag ctgtaacttt catgaagaca gtgacgtggt  31560
ttgtcactgc ccggatctca tcttgaattc cctgtgttgt gggagggacc tggtgggggg  31620
taattgaatc acggggacga gtctttcctg tgctgttctc gtaatagtga atacgtctca  31680
taagatctga tggttttaaa aagaggcatt ccgctacaca agctctctca tgttttgcct  31740
gccaccatcc acgtaagatg ggacttggtc ctccttgcct tccgccatga ttgtgaggct  31800
tccccagcca catggaactg taagtccaat taaacctctt tcttttgtac atttgctcag  31860
tcttgggtat gtctttatca gcagtgtgaa aacggactaa tactgacaat aaattaaaaa  31920
ctatttaaaa tgcaaaggaa aatataaatt taaatcacct cttcgagtct ctggtagatc  31980
aagaaaacaa aaataatctg aattattgat atagttaaat taatagatat atcaaacttt  32040
gtaacttaaa agcaaaagat gtacctttta cagtgttcct ggaacactca caaacattga  32100
tcatatacta gactgcaaaa acttcaagac attctaaaat taagaaccta tgctggatat  32160
ctctgatttc aacgtatgtt taaaatatat gttattaatt acaagtttaa ttaatgaaag  32220
tctaaagaag aaaagtctac ttagaagtaa aaacatcagc aatattactg tgtaatagat  32280
ctgaacatta aaggggcata tatgcatatc tgtacaccga ggcaaattta tagctacagg  32340
cattttcctt ttttgaaaaa agtaaatatg taagttaaaa agttcacagt aagaaaagtg  32400
aatgtaaata agagataaga atagaaaata ataggaaaca ggaaaacaga cttgagggtt  32460
ctttttggga ggtgattctt ggttctttga ggaaaacaat atatatctta taatttcaat  32520
catggaaaaa ccccaagtat atatctaaat ttagacatga gaaggctctt tggcaatcga  32580
tttagaaaag ttttgtttgt gtttttaaga cagagtctca ctcaatcacc caggctggag  32640
tgcagtggtg caatcttggc ttacagcaac gtctacctcc cgggttcaag cgctcctccc  32700
ccctcagcct cccaagtagc tgggtttacg ggcatgtgcc accacccctg gctaactttt  32760
tgtattttta gtagagacaa aggtttcatt atgttggcca ggctggtatt gaactcctga  32820
gcacaagtga tccacccacc tcggcctccc aaagtgctgg gatcacaggc atgagccact  32880
gcacccagcc cagtttttaa tgtgacagta ctttgtaaaa ttgtactcca gtgaatttga  32940
aaaatgttgt gagatggctt attctttggg aaaaaatgtt aagtcaaaat taggaagaag  33000
tggagacaat ctcagtatgt gtgagatgaa tctgaaccct catcagaacg tccacagctg  33060
acggtgaaca cattggcagg tgagatatgt ggagacatgg cacgtggtga aaatgcttgg  33120
caaagtgttc aaggcaggat ggagataccg tatgggcatt cactggacag tgttttcatc  33180
ccgtatgttt gaacaatttt taatgtggga tcaaaggtag gaaatgctct ttacaaagtc  33240
atcaaaaagt tttttctgga aaagcctcca gcccacggtg acctaggttc ttcccaccat  33300
```

-continued

```
tgaattagga tgccgtctgc tactgagaga gccagtcatg ttagtggctc aatgggcagg  33360
gtgcccaggt tagctgtgaa caaagtgatc tctctgctgc ctcactagca gagagaaaag  33420
aaaactacag accagtgata tgtacacaga gagcaatgaa aatcctcatt atgatggcag  33480
actaaaccca tagtgtgtta aaaatgacca cacatgtagg ctaggcacag tagttcatgc  33540
ctgtaatccc accactttgg gaggctaagg tgggaggatt gcctgagctc aggagaccag  33600
cctgggtgac atagtgagac cccatctctt tttattaaaa aaaaaaaaaa gaccatacat  33660
acacacatgc acacacaaca gtggtaatgg attataattc atgaaaaaag aatctatgca  33720
tccacaggga cacacccatg tatataaaca aataagtgga agaaaggaat ccagttctca  33780
cgttagaatc aacagggctg gaaggccatc aaggaaaccc cgtggcaggg gcaggggttc  33840
aaagagctgg tggttgtagt ctcagtgtct cccaccacca cttactagtt acaaaggaaa  33900
aagaatcact ttctagaggc aaagctggcg acaccacccg agccaagtga tccaagttaa  33960
catcaccagg aatgggacag gccagcttca ccaccctccg gatggacagc ctcggtagca  34020
gaactcctgc caaagacaca gctgtccagg gtcgaatcat ccggagacac agggcaaacc  34080
cacatggagg gagacacaca cagtggcctg aatactttga aaatgccagg gccaaaaaac  34140
gtagaaggct aaataaagta ccgttcaggg tgaaggggaa ggaagaaatg tgatgcctaa  34200
gtgggagtct atgattccac tatgttatgt attagtccat tttcaaatta ctgataaaga  34260
catacctgag actggataat ttataaaggg aagaggttta attgactcac agttccacat  34320
ggctggggag gcctcacaat cacagcagaa gatgaaggaa gaacaaagga acatcttaca  34380
tgatgacagg caaagagata atgaaaactg agcacaaagg gtttcccctt ataaaaccat  34440
cagatctcgt gagacttatt cattaccatg agaacagcat ggaggaaacc acccccatga  34500
ttcaattatc tcccacgagg tccctcccat gacacgtggg aattatggga gctacaattc  34560
acgatgagat ttgggtgggg acacagccaa accatatcat tccaccccgg cccctcccta  34620
atctcatgtc ctcacatttc aaaaccaatc atgccttccc aacggtgccc caaagtctta  34680
actcatttca gcattaactc aaaaatctgc agtccaaagt ctcatctgag accaggcaag  34740
tcccttccac ctatgagcct gtaaaatcaa aagcaagtta gttaattcct agacacaatt  34800
agggtacagg ccttggataa atacacccat ttgaaatggg agtaattggc caaaacgaag  34860
gggctaaagg ccccatgcaa gttcgaaatc cagtggggca gttaaatctt aatgctccaa  34920
aatgatctcc attgactcca tgtctcacat ctaggtcatg ctgatgcaag aggtgggttc  34980
ccatagtctt gagcagctct gcccctctgg ctttgcaggg tacagcctcc ctcctggctg  35040
ctttcacagg ctggcattga gtgtctgcag cttttccagg cacatggtgc aagctgttga  35100
tggatctatc attctgggat ctggaggaca gtggccctct tctcacagct ccactaggca  35160
gtgccccagt ggggactttg catgggggct ccaaccccac ttttcccttc ctcactgccc  35220
tagcagaggt tctccatgag gaccccaccc ctgcagcaaa cttctgcctg gacatccagg  35280
catttccata catctctgaa atctaggcag agctttccat acctcaattc ttgacttctg  35340
tgcacccaca ggctcaacac cacatggaag ctaccaagag ttggggcttg caccctctga  35400
agccacagcc caagctgtac cttgacacct tttagctatg gctagagcgg ctgggacaca  35460
gggcaccaag tccctaggct gcacacagca tggaggccct gggcccagtc caggaaacca  35520
tttttgcctc ctaggcctct gggcctggga tgggaggggc tgctcctaag gtctctgaca  35580
tgccctggag acattttccc cattgtctta gtgattaaca tttggcttct tgttacttat  35640
```

gcaaatttct gcaggctgct tgactttctc ctcagaaaat gggtttttat tttctatcac 35700
attttcagac tgcaaatttt ctgaactttt atctctgttt ccctttcaaa actgaatgct 35760
tttaacaaca cccaagtcac ctcttgaaag ctttgcagct tagaaatttc ttccaccaaa 35820
taccctaaat catctccctc aagttcaaag ttccacaaat ctctagggca gtggtaaaat 35880
actgccagtc tctttgctaa aacatagcaa gagtcatctt taatccactt cccaaaaagt 35940
ttctcatctc catctgagac cacctcagcc tggatttcat tgtccatatc attatcagaa 36000
ttttggtcaa gcccttcaac aagtttctag gaagttccag actctcccac attttcttgt 36060
catcttctga gccctccaaa ctgtccaacc tctgcctctt acccagttcc aaagttgctt 36120
ccacattttt gggtatcttt acagccgcac cccactccca gtaccaattt actgtattag 36180
tccattttca tgctgctgat aaagacatac ctgagactgg gtaatttata aagggaagag 36240
gtttaattga ctcacagttc cacatggctg gggaggtctc acaatcatgg cggaagatga 36300
agaaagagca aaggcacatc ttacgtggca gctggcaaag agagaatgaa aacagagtgc 36360
aaggggttcc cccttataaa accatcagat ctcatgagac ttaattcact accacgagaa 36420
caatatggga gaaactgccc ccatggttca attatctccc actgggtccc tcccacaaca 36480
catgggaatt atgggagcta cagttcaaga tgagatttgg gtggggacac agccaaacca 36540
tatcagagtt gaatcctgtc tgggaagaga tggctgcaat agccagtgtc tgggcagctg 36600
atgatgtgag agtgtgaggt agagaactgt agtgtgcaat agagacctgt agtgtgcatg 36660
tcagtgttgt ttcccgattt tgacaacagt accacatggt tacagaagag aacaccctta 36720
ttcctaagaa atccatgagg aggcgtttag cagaaaacag gcatggtgtc tccaagggct 36780
cagaaagatt caaccaaaag agggaagtct ggagagggac aggatggagc aggacggggg 36840
cagtgtagaa accgcaggca agtctaagca gagcacgttt gggagttcct tctgctattc 36900
ttgcaacttc tctataagtt tgaaatgaaa tcatataaat cgaaagttag aagagaatta 36960
ccacatcatg ttggatttca ctcatagcca cgagaacggg tggtggtctc ttctgcagtg 37020
aactgatgcg atgtgtgatg tcactagttc tcatccaaag cagatgacaa ttccagttac 37080
tcctcaccag acataagaaa atgcttttag tagatcagtt tttctgattg taaagttcag 37140
aaatgttaat cagagaacgt gcagaaattt ttaaagaaga aaagtaaaat gactcatcgt 37200
accaaaagcc agagatgcca gcttttagtt tcctgctagt ctttttctcg gcgtgtgtgt 37260
gtgcgcgcgt gcatgcacat gtttctactt ggtctttgtg tgtgtgttaa gggcgtgtac 37320
acacacagtg cagtcaggag tgagttgcac gtctacagct aggctgcttc cccgaggctg 37380
tgtggccatc agccaggcgt ccccaacccc caggccatga agcactacca gtccatggcc 37440
tgttaggaac caggctgcac agcaggaggt gagtggcagg tgagcaagtg aagcttcatc 37500
tgtatttaca gtcactcccc atcactcgca ttaccgcgtg agctctgcct cctatcagat 37560
cagtggcggc attagattct cacaggggtg tgtaccctgt tgcaaactat gcatgtgagg 37620
gatctaggtt gcctcctctt tataagaatc taatgcctga tgatctgtca ctgtctccca 37680
tcacccccag atgggactgt ctagttgcag gaaaacaagc tcagggctct cactgattct 37740
acattatggt gagttgtata attatttaat tctatattac aatgtaataa tagtagaaat 37800
aaagtgccca atgcaagtaa tgtgcttgaa tcatcccaga accacccaca ccactggtct 37860
gtggaaaaac tgttttccat gaaaccagtc actggtccca aaaaggttgg ggaccacggc 37920
catcggctgt ttgctttatg aatttgtgcc tcagtttctt catctctgaa acgggaacga 37980
tgggagccct cacctcgtat ggtggtttga ggattgaatg aactcattgt ccagcaccct 38040

-continued

```
tagcttcttg ccagctcagg aagtgctgag cagggtaacc cctatcactg cgtgtgtgtg  38100
tgtgtatatg tgtgtgtgtg catacttgcc tatgtgtgtc tgtgcaaata cttggtaaaa  38160
ttgagagggt actagacaac tcatttgtat cttcttacct tttgacacat ggcagacatg  38220
tctcacatct gttcttcctc caaatgtgac ctttcaatgg ctgcctggca tttcccctgt  38280
gttattgaac gtaatcaact ctctattgac ggctgggtta tttcctaatt gactgctgta  38340
aatagcattg tgatgcaaat ccttgtacac tcatttttgc ctggaactca agattatttc  38400
cttgggtcac atttgcagga gaagactgac aggatcaaag ggttcctgca tttttatggc  38460
tctgacacct ttggccaaat caccttccgg gagtgttttc ctaatttagc ttcctactgt  38520
gctgctggac atcactgact ccccccgcca acccccaccc cacactgcac cacaaagctg  38580
ggtattatca taaaaacact gccattatga tgaagcaaaa atagaatatc cttcctcctc  38640
ttagtgaggg gagtatgttt atgtttgttg agctctttgt attttagcca cccattcact  38700
ggcccacctg cccctggtgc acctgcagca gcaagactgt catctaggtt gttggggaaa  38760
ccaggagtga gtggagcacg agggtcaccc tccaggaagt gacctgcaag agaatggaga  38820
gagtcatgga ccggcatggc gtggtaatgc atggtgcgtg tctcttagca gtaagacctt  38880
gagaaggagc caggcaggga ggaatgggag ggtgaaggag tgccttttgt ggaggggagt  38940
cggacacaga tgggatttca gcagagacct gatggaattg agggagtggg tggtgtgtgc  39000
ttctgcagga agagcaccca gacagagggc atggcacatg caaaggtcct gtgttgggaa  39060
cgtgcttggt gcatgtgaag aactgtgcag ggaaggtgct ggagatagga cgggagggcc  39120
acgagggtta agatcctgag agcaatgcgg ggggtgcgag tgatgaggga caacatcagt  39180
cctctcttgg cttctgtact ttaataaaat cattttgttt tgaagcaatt ttagacctac  39240
agaaaagttc cacgacagta ctgagagttc ctgtggactc ctagtattaa catcttaata  39300
acggggtgta ttgaccaaaa ccgacacctg atacattacc gtgaactcaa ctgcagatct  39360
gattcaaatc ccgcgttttt ctagcatccg gtttctgttc tgtgatcccc acgttgcttt  39420
cagctgccag gtctcctttc gtgtcctgca gcctgtgcca gctcctcagt ctctctttgt  39480
ctttcgtgac cttgatgttt tagataagta ctgggcggct gttttgtaga acgtccctcg  39540
gtttggattc tctgatatgc tctcatgatt agatcaagat tgtgcatttt tggcaagaac  39600
accgcgggag tgttgttggg tcccgaggag tccctgtggc agggctgtgt gaggtcagca  39660
tgtcttaggg cgggttcatt tgaccttgac cactcaggta ggagtgtgtc agctgggctt  39720
ctcagctgta aattaaccat tttccgcttc ataattagta aacaccttga ggaagctaca  39780
ttgagacatt gcagctgcct tttttctcct gagattttgc cccgctgatt ttagtgccca  39840
tcagctggtt ttgcttgtga caggcaaagt ctgtggtgct tgccaaatgg ggatttgttt  39900
atttcccact ttctttctat gtttgttaat ttggattctt ctccaggaag agctgtcccc  39960
tttgttctgg ttatgtatcc agtggcttat gtatatcagc atggtttcat agatacttct  40020
tttgtgttat gggctataag ccaatgctat tattatttat tttcctccat ttatttattt  40080
atttagagac ggagttttac tcttgcacag gctggagtgc agtggcatga tctcggctca  40140
ctgaaacctc tgcttccggg gttcaagtga ttctcctgcc tcagcctcct gagtagctgg  40200
gattacaggc acgtaccacc acgcccaact aatattttgt atttttagtg gagacggggt  40260
ttcatcatgt tggccaggct ggtcttgaac tcctaacctc aggtgatcca cccgccttgg  40320
cctcccaaag tgcagggatt acaggtgtga gccactgcac ccagcctcat tatttatttt  40380
```

-continued

```
cattgctcaa attgtgctgg cttttgcccc agaaacaacc ttccattcag cttccatgcc  40440
cctttggtgg gccctgtctt ttcttggaca ctgccttcct ggcaccccaa gatgctctgg  40500
gctcagcttg tatttccttg cctcagtctt gaaatcaccc acttctccaa ggagccaggg  40560
ttccttccat tggagagtgg tctttagaaa cccaggcctg ggtgcatggt gtgctcatcg  40620
ccactgtgga cctgctgctc tgcgcccact cggccgacgg agctggggaa tatgtgtatg  40680
gcacccccac gtctacgctt ctgtgttcat ctgcagatat attcatacat gagtgggctc  40740
atactgtctc caactccagt tctgccccag tggggccaat tctctctctt tgttgtaaca  40800
cctttcttca atagtgagaa acctggctct ctcaccttca cctgctcgtc caaccccagc  40860
tgcaagggaa ctggctccat acttgctgat gcgtgccccc atgagaagtg actgaccacc  40920
cagagcctgg cgcctgtgca tggcgtctgt gcacggcgcg tcttgtcttc agcctcactg  40980
cgtcccatca gtgcttttcc ccacggtgac tttgagtatt tctttacttc tgtactccct  41040
tcagtgtgat tatgtcattc atctgtgaca tgtttagatt tatctgttag gttggtattc  41100
cattttgggt gtcccccgat tctgattgtt tttagttact tatctggggg tctgtgtgaa  41160
gggaatgtaa agctgctgtg actcctggag tcagaggtgc acaaagagtg tcctcagagg  41220
agagccaggc gcccaccctg ccagcccttc cctccccact ccatccccca cccccccacc  41280
ctggacaaaa ccagctcttc agcctttcat gtctctcttg caggcctctc gcacagatga  41340
gaaaatacac gtgtgttttc ctgtatcccc tctttcttac aaaaagggaa gcacactatc  41400
aatactcttg tagatcttta attgcggtaa gatacactaa tgcaaaattt accattttaa  41460
ctatttttaa gcacacagtt cagtggcatg aagtacattg attttgttat gcaaccatca  41520
ccaccatcca tttctagaat ttctcatcc tcccaaactg aaactccatc cccattaaac  41580
accaactccc ccattctctc ttccccagcc cctggcacct accatttacc tttcgtccct  41640
atggatttga ctaatccagg aacttcataa aagtgggatc attgagtact ctatttgtct  41700
tttgtgactg gcttatttca cttgggcata atgtcctgaa agttcactca tgctgtagca  41760
tgtgtcagaa tttccttttc cttttcaagg ctgaataata ttccactgta tggatagacc  41820
acattttgct tatccattca tcttttgatg aacatttggg ttgcctccat gttttagcta  41880
ttgtgaataa tgctactatg aatatgggtg tacaaatatc ttttcaacgc cctgctttca  41940
attcttttgg gtatataccc agaagtggaa tttctggatt atatggtaat tatagtttta  42000
atttcttgag gaaccactat gccgttttcc acagtagcta ccacatcctc accaacactt  42060
gtaatttctg gggtttttta atagtagcca ttctagtggg tgtgcagtgg tatctcatta  42120
tagttttgat ttacattttc ttatgagtag tgatgttgag tatcttttca tgctcttatt  42180
agccatttgt atatcttctt tggagaatat ctcctcagct cttttgccca cttcattaaa  42240
ttgagaggtt tgtttttgct gttgagtttt agaacttctc tatatattct ggatattaat  42300
cccttatcag atataggatt tgcaaatatt ttctctcatt ctgtggggtg ccttttttact  42360
ccgttgatag tgtctttgta caaaaatttt taatgttcac gaagtccaag ttgtctactt  42420
tttgttttgt tgcctgtgcc tttggtcttt gtgttagtcc atttagcatt gctataaagg  42480
aatacctgag gctggtaatt tataaagaaa agaggtttaa ttggcttatg gttctgcagg  42540
ctgtacaaga aacatggtgc cagcacctgc ttctggcgag agcctcagga agcttccaat  42600
cacggcagaa ggtgaagcgg gagtaggtgt ctcatatgat gagacaggga gcaagagaaa  42660
ggaggttcca gtctcctttt aacaaccaga tcttgcatga actcattacc taatcatggg  42720
gaatctgccc ctatgaccca aacagcaccc accaggcccc acctccaacg ctggggatca  42780
```

-continued

```
catttcaaca tgagagttgg aggggacaaa tatctgaact ctatcaatgt tatatccaag  42840
aaatcatagc caaatccaat gtcatgaagc ttttgcccta tgttttcttc taagattttt  42900
atagttttac gttgcacatt tagatatttg atccattttg agttaatttt tgtatatggt  42960
gtgaagtaag ggtccagctt ccctcttgca tgtggatttc cagttttccc agcaccattt  43020
gttgaaaaga cagtcctttt ctcattgaat agtcttggaa ccctagtcaa aaatcattta  43080
accatttatg ccacggttta tttctgggct gtctcatgtt ccattggttt atatgtctgt  43140
ctttttgcct gtgtcacact gtcttgatta ctgtaagttt atagtaaagt tttgaaatca  43200
gaaagtgtta ggcttccagc ttggcttttc tttttcaata ttgcttttgg ctattttaag  43260
ttccttgaga ttccatatga attttaggat gggtttttct atttttgcaa aaagtgtcat  43320
tgggattttg agagggattg cactgaatct ataaatcact ttgggtagta ttgatatctc  43380
aacattgtct tctaatccat gaacatggga tatgtttcca tttatttgca tctttttaag  43440
tttctttcag taatgttttg tgggttttgc tgcagaagtc ttttacctcc ttggttaagt  43500
taattcctaa gtattctact tgatgctatt ataaattaaa ttgttttctt aatttcattt  43560
ttagattgtt cattgttagc atatagaaat gcaactgatt ttgcatgttt accttagatt  43620
ctgtaacttt gctgacttca tttattacct ctaataagtt tttggggaat ctttaggggt  43680
ttctacatat gaaattatgt aatctgtgaa tagaaatagt tttacgtctt ttttttccat  43740
tctggatgcc ttttatttct tttaattttt ttcttgccaa attgctctgg ctaaaatttt  43800
cagtccaatg ttgaatagaa gtggtgaaag tggtcaccct ggccttattc ctgaccttaa  43860
agggaaaaat ttcagtctca tcattatgat gttagctgtg gattttcaca tatggttttt  43920
attatgttaa ggtagttccc ttctattcct agtttgttga aagtttttaa taaggatgtt  43980
gaattttgtc aaatgctttt tgtatcaatt gagatcatgt gatcatgtga ctgttatttc  44040
ttcattctgt taatatgctc ttttacatgg atttattttt gtatgttgaa ccatccttgc  44100
attccaggac taaatctcac atggtcatga tatgtaatac tttaactatg tttctgaact  44160
cagtttgcta ttttgttgag aattttgcat cagttttcat aagggatatt ggtctgtagt  44220
tttcttgtag tctttgtctg gctttagtat cagagtaatg ctctcctcat agaatgagtt  44280
agaaaccttt cccctcctct ttaatttttt gggaaagatt gagaaggatg ggagtttatt  44340
ctttaaatat ttggtaggat tcattgggga agccatcagg tccaggcttt tctttgttga  44400
gagtttttttg attactgatt caatctcctc actagttata ggtccatgaa gattttgtat  44460
ttctttgtga tttagtttg gtaggtttcg tgtttctcag aatttgtcca tttcatctag  44520
gttatccaat ttgttgatac acaattgttc acaatactct cttataatcc tttttatttc  44580
tgtagaattg atagtcatgt ccctattttc acttctgatt tcagtagtct tctctctttt  44640
ttacttagtc catctagcta aaggtttgtc aattcttaaa atcttttcag agaagcaact  44700
ttgatttaat tgattttctt ctattgtttt tctattctct attttgttgg tctctgctgt  44760
ggtatttatt atcttctttc ttctgctagc tttgggttta gttcttttgc tagttcctta  44820
agtggtaaag ttaggttatt tactggagat ctttcttgtt tattaatgta acaatttata  44880
gggagggagt ggagcaagat ggccaaatag aagcctccaa ttgtcctccc caacaggaac  44940
accaaatttg agaactatct acacaaaaaa gcaccttcat aagaaccaaa attcagataa  45000
gcaatcacag tatctgcttt taactttata ttgctggaag aggcactgaa gagggcaaga  45060
gagacagtac tgaatcactg acagcactgt gcctcccatc ccccagctat gtggcatgga  45120
```

-continued

```
gagagaatct gagagcttgg gggagggaaa gtgcagtgct ttgggactgt ccatcgagct  45180
cagtgattcc ctgttgccac agaaagcaga accaggctaa attcagccca cacccagcac  45240
agagggagca tttaaaccag ccctagccag aggggaatca catatctcag gggtcagaaa  45300
ctgagttcca gaaaaccttg ccaccacggg ctaaagtgct ctggggttct aaataaactt  45360
gtaaggcagt ctaggccaca ataactgcaa ttcctaggca agtcctattg ctgagatggg  45420
ctcagagcca gtggatgtgg ggggcacaca acctagtgag acaccagcca gggtggctaa  45480
ccccaggcag cacagctcac agaaacaaaa gtgactcttt tcctctgctt aaagagagga  45540
gatggagcag taaagagaac attgtcttgc atcttggata ccagctcaac cacagtagga  45600
gaggacactg ggcagagtca atgggcacac atttcaggcc ctggctcttg gacatttcca  45660
gacacaccct gggccagaag ggaatccact gccttggagg gaaggaccta gtcttgtcag  45720
aattcatcat cagctgacta aagagccctt ggaccctgaa caaccagcag tgccaggtag  45780
tatcctgtgg gccttgaatg agattctgaa atatactggc ttcaggtacc agcttgacca  45840
cagtggggta gagcaccaaa tggctcttg gggtccctga ttccaggcct tggctcttgg  45900
acagcatttc tggacctgct ctaggccaga agggagccca ctgacctgaa aggtgagtcc  45960
acagcctaga agccttcacc acaagctgac tgaagagccc tcaggccttc agtggacaac  46020
catggtagcc tgacagtact gcctatgggc ctgtagtggt ggtggccaca gggagaggct  46080
cctttgccta tggaaaggag aaggaattct gggtatgact ttgtcttgtg ctactactga  46140
gtgccagctt agcctctgta gtataccaca ccaggtaggt ttctaaggtc tttgactaca  46200
gacccttgct cctggatggc atctctggac ccaccttgga cttgggggaa ctcaccaccc  46260
taaagtgaag gacaaaagcc tggctggctt taccatttgc taattgtaga gccctggggc  46320
tttgagtgaa cataggtggt agccaggtag tgcttacagc gggccttggg tgaaacccag  46380
tgatgtgttg gcttcaggtc tgaccagcac agtcccagtg gtggtggcca caggtaagct  46440
tgtgtcactc ctccccaagc ttcaggtggc ttagcataga gagagagtcc atttctttgg  46500
gagaaagtaa gagaagaaaa caagagtctc tgcctcgtaa tgcagagaat tcttctggat  46560
cttatctaag accaccaagg cagtattttt tttaatattt attttttgaa acagagtttc  46620
actcttgttg ccaaggctag agcgcaatgg tgtgatctca gctcaccgca acctctgtct  46680
cccgggttta agcgattctc ctgcctcagt ctcctgagta gctaggatta taggcatgtg  46740
ccatcatgcc tggctaattt ttgtttgttt gtttgtttgt ttgttttagt agagacaggg  46800
tttctccatg ttggtcaggc tggtcttgaa ctcccgacct caggtgatct gcccgcctcg  46860
gcctcccaaa gtgctgggat tacaggcgtg agccactgcg cctggcccca aggcagtatt  46920
tttatgagtc tgcaagaacc acagtgttac tgggcttggg atgctgccta atgcagatac  46980
ggcttagatc acaacaccca agtccctttg aatacctgga aagctttacc aagaaagatg  47040
ggtacaaaca agcccagact gcaaaggcta caataaatac ctaactcttt aatgcctaga  47100
caccaatgaa caagaccatc taggaaaaca tgacctgacc aaacaaacta aataaagcat  47160
cagggaccaa tcctgaagaa aagagatatg tgacctttca gagagagaat ttaaaatagc  47220
tgttatgaga aaactcaaat tcaagataac acagcgaagg aattcagaat tctatcagat  47280
aaatttaata aagagattaa aataagaatc aagcagaaat tctggagttg aaaaatgcag  47340
ctgacatatt gaagaatgta tcagaatctc ttgataacag cattgatcaa gaacaaaaaa  47400
gaattagtaa gcttgaagac aggatatttg taaatacaca gaggagacag aataagaacg  47460
aatgaagcat gatctagaaa atagcctcaa aagggcaaat ctaagattta ttgaccttaa  47520
```

```
agaggaggta gagaaagaga taggggtaga aagcttattc aaagggatac taacatagaa  47580
cttcccaaac ctagagaaag ataccaatat tcaaatacaa gaagattcta gaataccaag  47640
cagatttaac ccaaagaaga ctacctcaag gtatttaata gtcaaagttc caaaggtcaa  47700
ggataaagaa aggatcctaa aagcagcaag aaaaaaaaga cttataattg aactccatta  47760
tatctggcag cagagttttc aatggaaact ttatgggcca gaagagagtg gcaggacata  47820
tttaaggtgc tgaaggaaaa aaaagaaaaa aacttttgct ctagaatagt atatctggtg  47880
aaaatatcct tccaacatga aggagaaata cagaccttcc cagacaaaca aaagctgagg  47940
atgtcatcaa caccagagct gtcttacaag aaatgctaaa gggaattctt caatctgaaa  48000
gaaaagggtg ttaataagca acaagaaatg atgtgaaggt acaaaactca ctggtaatac  48060
atacacagaa atacaaatag tattataaca ctgtaattat ggtgtgtaaa ctactcatat  48120
attaagtaga aggatgaaaa gaagaactga taaataatga ctacaacaac ttttgcggta  48180
caataggcag tacaataaga tatagagaca aaaaaactta aaaagcggag agacaaaagt  48240
tgaagtgtag agatttttttg ttttacttta agttctggaa tacgtgtgct gaacgtgcag  48300
gtttgttaca tacgtataca gtgccatggt ggtttgctgc acctatcaac ccatcatcta  48360
ggttttaagc cctacatgca ttaggtattt gtcctaatgc tctccctccc cttggccccc  48420
atctccccac agatcccggt gtgtgatgtt cccctccctg tgtccgtgta ttctcattgt  48480
tcaacttcca cttatgagtg agaacatatg gtgtttggtt ttctgttcct gtgttagttt  48540
gccgagaatg gtttccagct tcatccccac aaaagacatg aactcattct tttttatgg  48600
ctgcatatta ttccatggtg tatatgtgcc acattttctt tatccagcct atcattgatg  48660
ggcatttggg ttggttccaa gtctttgcta ttgtaaatag tggtgcagta aacatatgtg  48720
tgcatgtgtc tttatagtag aatgatttat aatcctttgg gtatataccc agtaatggga  48780
ttgctgggtc aaatggtatt tctagttcta gaatctagtt ctagaatcac cacgctgtct  48840
tccacaatgg ttgaactaat ttacactccc accaacagtg taaaagcgtt cctatttctc  48900
cacatcctct ccagcatctg ttgtttcctg attttttagt gatcgccatt ctaactggca  48960
tgagatggta tctccttgtg gttttgattt gcatttctct gatgaccagt aatgattagc  49020
ttttttttcc atatgtttct tggccacata aatgtcttct tttgagaagt atctgttcgt  49080
atcctttacc cactttttga tggggttgtt tttttcttgt aaatttaagt tccttgtaga  49140
ttttggatat tagaccttgt cagatggata gattgcaaat attttctccc attctgtagg  49200
ttgcctattc actctgatgc tagcttcttt tactgtgcag aagctcttta gtttaattag  49260
atcccatttg tcaattttgg cttttgttgc aattgctctt ggtgttttag tcatgaagtc  49320
cttgcccatg cctatgtcct gaatggtatt gcctgggtat tcttctaggg tttccgtggt  49380
tttaggtttt acatttaagt ctttaatcat cttgagttaa tttttatata agttgtaagg  49440
aaggggtcca gtttctgttt tctgcatatg actagccagt tttcccagca ccatttatta  49500
aatagagaat cctttccgca ttgctttttt gtcaggttgg tcaaagatca gatgatttta  49560
ggtgagtggt gttatttctg aggtctctgt tctgttccat tggtttatat atctgtcttc  49620
ataccagtac catgctgttt tcgttactat agccttgtag tatagtttga agtcaggtag  49680
tgtgatgcct ccagctttgt tctttttact taggattgtc ttggctatat gggctctttt  49740
ttggttccat atgaaattta aagtagtttt ttctaattct gtgaagaaag tcaatgatag  49800
cttgatggga atagcattga atctataaat tactttgggc agtatggcca ttttcatgat  49860
```

-continued actgattatt cctatccatg agcatggaat ttttttccat ttgtttgtgt cctttccttt 49920
ccttcagcag tggtttgttg ttctccttga agaggtcctt cacatccctt gtaagttgta 49980
ttcctaggta ttttcttctc tttgtagcaa ttatgaatgg ggattcactc atgatttggc 50040
tctctgcttg tctatttttg gtgtatagga atgcttgtga attttgcaca ttgattttgt 50100
atcccaagac tttgctgaag ttggctatca gcttaaggag tttttgggct gagacaatgg 50160
ggttttctaa atatacaatc atgtcatctg caaacagaga aaatttgact tcctcttttc 50220
ctatttgaat actctttatt ttttcgcttg ccttattgtc ctggccagaa cttccaatac 50280
tatgttgaat gggagtggtg agagagggca tccttgtctt gtgctggttt tcaaagtgaa 50340
tgcttccagc ttttgcccgt tcagtatgat attgcctgtg ggtttgtcat aaatagctct 50400
tgttattttg agatatgttc catcaattcc tagtttattg agagtttttg gcatgaaggg 50460
atgttgaatt ttatcgaagg ctttttctgc atctattgag ataatcatgt ggtttttgtc 50520
attggttctg tttatgtgat gtttagtgat ttacatatgt tgaatcagcc ttgcatccca 50580
gggatgaagc ccacttgatc accatggata agctttttga tgtgctgctg gattcagttt 50640
gccagtattt tattgaagat ttttgcatcg gtgctcatca gggatattgg cctgaagttt 50700
tctttttttg tgtgtcgctg ccaaattttg gtatcaggat gatgctggcc tcataaaatg 50760
agttagggag gggtccctct ttttctactg tttggaatag tttcagaagg aatggtacca 50820
gctcctcttt gtgcctctgg tagaatttgg gtgtgaatcc gtctggtcct gggctttttt 50880
tggttggcag gctattaatt actgcctcaa tttcagaact tgttgttggt ctattcaggg 50940
attcgacttt ttcctggttt agtcttggag ggtgtatgtg tccaggaatt tatccatttt 51000
ttctagattt tctagtttat ttgcatggag gtgtttttag tattctctga tggtagtttg 51060
tatttctgtg ggatcagtgg tgatatcccc tttatcattt tttattgcat ctatttgatt 51120
cttctctctt ttcttctttg ttagtctggc tggcagtcta ttttgttaat cttttcaaaa 51180
aaccagctcc tggattcatt gatttttttg gaagggtttt tcatgtctct atctccttca 51240
gttctgctct gatcttagtt atttcttgtc ttctgctagc ttttgaattt gtttgctctt 51300
gcttctctag ttcttttaat tgtgatgttt gggtgtcgat ttcagatctc tctagctttc 51360
tgatatgggc atttagtgct ataaatttgc ctctaaacac tgctttagct gtgtcccaga 51420
aattctggta cgttgtctct ttgttttcat ttgtttcaaa gaatttcttt atttctgcct 51480
tgattttgtt atttactcag tagtcattca gtagcaggtt gttcaatttc catgtatctg 51540
tgtggttttt agtgagtttc ttcatcctga gttctaattt gatcgtactg tgttctgaga 51600
gactgtttgt tatgatttcc attctttggc atttgctgag gagtgtttta cttccagtta 51660
tgtggtcaat tttagaataa gtgctatgtg atgctgagaa caatgtacat tctcttgatt 51720
tggggtggaa agttctgtag atgtctatta ggtccgcttg gtccagagct gagttcaagt 51780
cctgaatatc cttgttaatt ttctgtctca ttgatctgtc taatattgac agtggagtgt 51840
taaagtctcg cactgttatt gagtaggaat ataagtctct ttgtaggtct ctaagaactt 51900
gttttatgaa tctaggtgct cctgtattgg gtgcatttat ttaggatagt tagctcttct 51960
tgttgcattg atccctttac cattatgtaa tgctcttctt tgtctttttt tatctttctt 52020
agtttgaagt ctgttttatc aaaggctagg atcttggccg ggtgcagtgg ctcatgcctg 52080
taatcccagc actttgggag gctgaggtgg ttggatcacg agatcaggag atcgagacca 52140
tcctggctaa cacgatgaaa ccccatctct actaaaaata caaaaaaatt agtcaggcat 52200
ggtggcgggc acctgtagtc ccagctactc ggcaggctga ggcaggagaa tggcgtgaac 52260
ccgggaggtg gagcttgcag cgagccaaga tagcgccact gcagtctggc ctgggcaaaa 52320
gagtgagact ccatctcagg aaaaataaaa aataaaaaat aaaattaaaa aaaatggcta 52380
ggatcacaac ccctgctttt tttttttttt tttttttttt ttgtgctttc cattgcttgg 52440
taaatattcc tccatccctt tattttgagc atatgtgtgt ctttgcacat gagatggatc 52500
tcctgaataa agcacactga tgggccttaa ctctttatcc agtttgccag tctgtgtctt 52560
ttaattgggg catttagccc atttacattt aacgttaaca ttgttatgtg tgaatttggt 52620
cctgtcgtca tgatgctagc tggttattct gcacattagt tgatgcagtt tcttcatagt 52680
gtcattggtc attattttgg tgtggttttg cagtggctga tactgctttt tcctttccat 52740
gtttagtgct tccttcagga gctcttgtaa ggcaagcctg gtggtgtcaa aatccctcag 52800
catttgcttg tttggaaagg attttattta tcctttactc atgaagctta gtttggctgg 52860
atatgaaatt ctgcttgaaa attcttttct ttatgaatgt tgaatattgg ctcccactct 52920
cttctggctt gtagggtttc tgcagagaga tttgctgtta gtctgatgca cttctctttg 52980
taggtaacct gacctttctc tctggctgcc cttaacgttt tgtccttcat ttaaaccttg 53040
gagaatctga caattatatg tcttggggtt gctcttcttg aggagtatct tagtggtgtt 53100
ctctgtattt cctgaatttg aatgctagcc tgtcttgcta ggttggggaa gttctcctgg 53160
ataatatcct gaagtgtgtt ttccaacttg gttccattct ccccgtcact ttcaggtaca 53220
gcaatcaatt gtaggtttgg tcttttcata tagtcccata tttcttggag gttttgttcg 53280
ttctttttca tcatttttc tctaatcttg tctgcatgcc ttatttcgtt aagttgatct 53340
tcaatctctg atatcctttc ttccacttga ttcattcggc tattgatact tgtgtatgca 53400
tcacaaagtt ctcatgctgt gtttttcagc tccatgaggt catttatgtt cctctctaaa 53460
ctggttattc tagttagcag ttcctgtaac cttttatcag gttcttagct tccttgcatt 53520
gggttagaac atgcttctct agctcagagg aatttgttat tacccacctt ctgaagccta 53580
cttctgtcaa ttcgtcagtc tcattctccg tccagttttg tgcccttgct ggagaggaga 53640
tgtgatcatt tggaggagaa gaggcattct ggtttttaga atgttcagca tttttgtgct 53700
ggtttttcct catctttgtg gatttatctg cctttgctct ttgaggctga tgacctttgg 53760
atggggtttt tgtgtggggg gtccctttg ttgatgttga ttttgttgct ttctgtttgc 53820
tagcttttct tctaagagtc aagcctgcag tcctgcaggt ctgctgcagt ttgctggagg 53880
tccactccag accctgtttg cctgggtatc accagtggag gctgcagaac agcaaagatt 53940
gctgcctact ccttcctctg gaagctttgt cccagaaggg caccagcctg atgccaacca 54000
gagctctcct gtttgaggtg tctgttgacc cctgttggga ggtcttgcct gctcaggagg 54060
catggggctc agggacccac ttgaggaggc agtctgtccc ttagcagagc tcatgcactg 54120
tgctgcgaga atccccttg tcaggatcag ctgctctctt cagagccagc aggcaggaga 54180
gttcaagtct gctgaagctg tgcccacagc cacccttct ccaggtgctc tgtcccaggg 54240
aaatgggagt tttatctata atcccctgac tggggctgct gcctttcttt cagagatgcc 54300
ctgcccagtg aggaggaatc tagagaagca gtctggcctc agctgctttg ctgtgctttg 54360
gtgaattctg cccagtccaa gcctcccagc ctccttagca ctatcagggg aaaaccgcct 54420
actaaagcct cagtaatacc aaatgcccct cccgccacca agcttgagca tcccaggtca 54480
acttcagact gctgtgctgg cagtgagaat ttgaagccag tggttcttag cttgctgggc 54540
tccatgggag tgggacccac tgagtgagac cacttggctt cctggcctca gcccctttc 54600

-continued caggggagta aatgattctg tcttgctggg gttccaggca ccactggggt acagaaaaaa 54660
ctcctgcagc tagttcaatg tctgtccaaa cagcaactca gttttgtgct tgaaacccag 54720
ggccctggtg gtataggcac atgaaggagt ctcctgatct gcagattgca aaacccatgg 54780
gaaaagcata gtatccaggc cggtatcac agtcccgggt atcacagatg acgggttgat 54840
gggtgcagca actgcatgca aactgcatgt ttgcagttcc ctcggctggg ggagggaggt 54900
ctcccggctc cttgcacttc ccaggtgagg cgatgcccca cctgcttctg tgtgccctcc 54960
gtgggctgca cccactgcct aatcagtccc aatgagatga acttggtacc tcagtcagaa 55020
atgcagaaat cacccagtgt tgatctcact gacagctaca gactggagct cttcctattc 55080
tgccatcttg ccagatgtaa agtgtagaat ttttgatttt gtttttttgc ttgtttatgc 55140
aattagtgtt aagtcatcat cagtttaaaa taatgagttg taagatattt tcaagcctca 55200
tggtaacctc agatctaaaa catatggcag acacacaaat aaaaagcaag aaattaaagc 55260
atgccactag agaaaatcac cttcactaaa aggaagacag aagggaagta acaaaggaag 55320
agaatatctt caccagaaaa caaataataa aatggcaaga gtgagtcctt acgtatcaat 55380
aataatatta aatgtaaatg ggctaacctt gccaatcaaa agacagagtg gttgaatgga 55440
cccccgcccc cacaaaaaaa gacccaatta tctgttgctt acaagaaaca catttcaacc 55500
tataaaaata cacatagact gaaaattaag ggcttgaaaa aagatattcc gtgccaatag 55560
aaaccagaaa agatcaggag tagctatact tgtattaggc aaagtagagt tcaagataat 55620
aactataaga agagacaaag aaggtcatta catcatgata aagggatcaa ttcagcaaga 55680
cgatataaca atttcaaaga aacatctaac ttaatctgca ctgtagacca aatataccta 55740
atagatattt acaggacatt tcatccagca attccaagag aagaatacac attctcctca 55800
gcacatagct cattctcaag gatagaccat atgttagatc acaaaacaag tcttgaaaca 55860
ttctaaaaaa ttgaaatact atcaagcatc ttctctgacc agtacagaat aaaactagaa 55920
gttaataatg agacattttg gaaactatac agacatacac atagtaatta aacaatatgc 55980
tcctgaatga ccagagggtc aaggaagaaa ttaagaagga aattgaaaat tttattgaaa 56040
taaattacaa tggaaacaca acataccaaa acctgtggga tttgtttgtg tcttttttac 56100
ttccttgagc agtggtttgt agttctcctt gaagatatga acagacactt ctcaaaaaaa 56160
agacatttat gcagccaaaa aacatatgaa aatgtgctca tcatcactgg tcattagaga 56220
aatgcaaatc aaaaccacaa tgagatacca tctcacacca gttagaatgg cgatcattaa 56280
aaaatcagga aacaacagat gctggagagg atgtggagaa ataggaacgc ttttacactg 56340
ttggtgggag tgtaaattag ttcaaccatt gtggaagaca gtgtggcaat tcctcaagga 56400
tctagaaccc aaataccatt tgacccagtg atcccattac tgggtatata cccaaaggat 56460
tataaatcat tgtattataa agacacatgc acacatatgt ttattgcacc actattcaca 56520
atagcaaaga cttggaacca acccaaatgc ccatcaatga taggctggat aaagaaaatg 56580
tggcacatat acactgtgaa gtactatgca gccataaaaa aagatgagtt tatgttcttt 56640
tcagggacac ggatgaagct ggaaaccatc attctcagca aactaacaca agaacagaaa 56700
accaaacacc acatgttctc actcataagc gggagttgaa caaggagaac acatggacac 56760
agggagggga acatcacaca ccggggtctg ttggggggtg gggggcaagg ggagggaggg 56820
aattaggaga aatacctaat gtagatgacg ggttgatggg tgcagcaaac caccatggca 56880
cgtgtatgcc tatgtaacaa aactgcatgt tctgcacatg taccccagaa cttataaaaa 56940
tcctgtggga tacagcaaaa gcagtattaa gagggaagtt tctagttaaa agcacctgca 57000
tcaataaaga gaaaaacttc aagtaaacaa cctaatgatc ttaaagaaca agaaaagcaa 57060
gagtaagtca acctaaaatt agtagaagaa ataataaagc ttagagcaga aatacatgaa 57120
attgaagtga agaaaacaag acaaaagatc aacaaaataa aaagttggtt ttttttttta 57180
aaagataaaa ttgacaaacc tttagccaga ctaagaaaag aagagggaag atccaagtaa 57240
ctaaagtcag agacaaaaaa ggagacatta caactgatac cacagaaatt caaaggataa 57300
ttagtggctg ctatgagcaa ctctatgcca ataaattgga aaatctggaa gaaatggata 57360
cattcctaga catgtgcaac ctaccaagat tgaaccagga agaaatgcaa acctgaacag 57420
accactaagc agtaatgaga ttgaacctgt aatttaaaaa tcttccaaca aagaaaaccc 57480
tgagacttga tggcctcact gctaaattct gccaaagatt tcaagaacta atactaatcc 57540
ttctgaaact attatgaaaa atagaggagg agggaatacc tccaaactca tctacaaggc 57600
ccgtattacc ctgttaccaa aaccagacaa agatacatca aaaaaaaaaa aaaaaaaaaa 57660
aaaaaaaagg aaccacgggc caatatccct gataaatatt gatgcaaaaa tcctcaacaa 57720
aatactagca aagcaaattc agcaacacct taaaaaagat cactcttcat gaccaagtgg 57780
gagttatccc aggaatgcaa ggatagttca acatatgcaa atcactttat gtgatacatc 57840
gtatcaacag aatgaaggac aaaaccacat gagcatttca attgatgctg aaaaagcact 57900
tgataaaatt ccacatccct tcaacataaa aactgtcaaa aacctaggta tagaaggaac 57960
atacctcaac ataataaaag ccatatatga cagacccaca gctagtaaca tactgaatgg 58020
ggaaaaactg aaggcctttc ctctaagacc tggaacatga caaagatgcc cactttcatc 58080
actgttattt aacacagtag tggaaatcct agctagagca atcagacaag agaagaaaat 58140
aaagggcatc caagttggaa agaaagaagt caaattatcc ttgtttgcag atgatgtggt 58200
cttatatttg gaaaaatcta aagaccccac aaaaaaacta ttagaactga taaattcagt 58260
aaagttgcag gatacaaagt caacatacaa aaatcagtag catttctata tgccaacagt 58320
gaacaatctg aaaaacaaat caagaaagta atcccattta aaatagctac aaataaaata 58380
cctaggaata aacttaacca aagaagtgag agatctctac aatgaaaatt ataatacact 58440
gatgcaagaa attgaagagg acccaaaaat ggtaagatat ttcatgttca tggactggaa 58500
gaatcaatat tgttaaaatg tctgtattgt ctaaagcaat ctacagattc agtgcacccc 58560
ctatcacaat accaatgaca ttcttcacag aaatagtaaa aacactcctc aaacttatat 58620
ggaatcacta aagtcccaga atagtcaaag ctatcctgag caaaagaaca aaactggagg 58680
gagcacatta cctgagttca aattatacta cagagtcata gtaaccaaaa cagtatgtac 58740
tgacataaaa acagacacgt agaccaatgg aacagaatag aaaacccagc aaacaaatcc 58800
atatgtctac gacaaactca tttttgacaa aggtgccaag aacatgcatt gggaaatgga 58860
cagtctcttc aataaacgat gctgggaaaa ctggatgtcc atatgcagaa gaatgaaact 58920
agacccctat ctctcaccat ataaaaaaaa caaatcaaag tgaattcaag aattaaatct 58980
aagacttcaa actatgaaac tactaaaaag acattggaga aactctccag gacattggag 59040
tgggcaaaga ctgcttgagt aatccctaca agcacaggca accgaagcaa aaatggacaa 59100
atgggatcac atcaagttaa aaagcttctg cacagcaaag gaaacaatga gacagcctgc 59160
agaatgggag aaaatatttg caaagtgccc atctgacaag ggactaataa ccagaatatg 59220
taaggagctc aaacaaccgc acaaggaaaa catctaataa tccaattaaa agatgggcaa 59280
aagacctgaa tagacatttc tcgaaagaag acaaatggat gaaactggaa accatcattc 59340

-continued

```
tcagcaaact atcgcaagga cagaaaacca aacaccgcat gttctcactc ataggtggga  59400
actgaacaat gagaacacat ggacacagga aggggaacat cacacactgg ggactgttgt  59460
ggggttgggg ggagggggga gggatagcat taggagatat acctaatgct aaatgacgag  59520
ttaatgggtg cagcacacca acatggcaca tgtatacata tgtaacaaac ctgcacattg  59580
tgcacatgta ccctaaaact taaagtataa taataataaa aaaacaaatg acaaataaat  59640
aaatgaaaat gtactcaacg tcactgatca tcagagaaat gcaaatgaaa actataatga  59700
gatatgaccc caccctggtc aatatagctt ttatccaaaa gataggcaat aatggatgct  59760
agtgaggatg tggagaaaag ggaatccttg tacactgttg gtgggaatgt aagttactac  59820
aaccaccgtg gaggacagtt tcgaggttcc tcaaaactaa aaatagagct acctctgatc  59880
cagcagtccc actctagtta tatatccaga agaaagaaaa tcagtccagc agagaaggat  59940
ccgcactcct gtgtttattg cagcactatt cacaatagcc aagatttggg agcaaactga  60000
gtgtccatca acagatgaat ggataaagaa aatgctgtgt atacacgcaa cggtatacta  60060
gttagccatg aaaaagaatg agaacatgtc atttgcaaca acatggatgg aactggaggt  60120
cactatatta agtgaaataa gccaggcaca gaaagacaaa ctttgcatgt tctcacttat  60180
ttgtgggaga taaagattaa aacaattgaa ctcgagatag agtaaaagga tggttaccag  60240
aggctgggaa gggtagtggg ggttgtgagg gaagtagaga tggttaatgg aaacaaaaaa  60300
aaaatagaaa aatgattaaa acctggtatt tgatagcaca acagggtgac tatagtcaat  60360
gatttaatta tacatttaaa aataactaaa agagagctgg gcacagtggc tcacagctgt  60420
aatttcagca ctttaggagg ccgagtcata tgactcactt aaggccagga gttcgaggcc  60480
tgcctggcca acatggtgaa accccttct ctacaaaaaa caggaaaatt agctggactt  60540
ggtggcatac acctgtaatc ccagctactt gggtggccga ggcatgagaa tcactcgaac  60600
tcaggaggcg gaggttgcag tgagctgaga tcgcgccact gcactccagc ctgggtaaca  60660
gagtgagact gtctctaaat aaataagacg aaaagagtat aatgaggttg tttgtaagac  60720
aaggggtaaa tgtttgaggt agtagatacc cccatttacc tctatgtgat tattatgtac  60780
tgtctgtcta tgttagaata tctcatggac cccataaacc tatacaccta ctatgtaccc  60840
acaaaaagca aaaagaaaaa gagcttatgg gtatcaattt ttctgttagt accgcttttg  60900
ttgtgtccca gcaagttttg gtacattgtc ttctcatctt tatttgcatt taagtatttt  60960
ctaatttccc ttctgatttt tttttttttt aatttaagtc ccaggacaca tgtgcaggac  61020
atgcaggttt gttacgtagg taaatgtgtg ccacggtggt ttgctgcacc tgtcaaccca  61080
tcacctaggt gttaagccct acatgcatta actatttata ctgatgctct ctctccctct  61140
gccccccttt ttctttgatt cattggttaa gagtatgttg tttcatttcc atacatttgt  61200
taatttttcc attttacttc tattattgat ttctaagctt atcccattat cgttggagaa  61260
gatcctttgt atgactggca tctttttgag tactttgaga cttaattcgt ggcctgatct  61320
ctcctgggaa catttccacg tgcacttggg atgcacatgc atgctgtggt catgggtcga  61380
gtgttctctg catgttggtt agatctaggt ggcttattgt gttaagtcct ctattctgta  61440
acttatcttc tgcctggttg ttctattcat tatagagaat gtggtactga agtctctcac  61500
catcattgta gaactatttc tcccttcggt tctgtaaatt tttcctttgt gtcttttgat  61560
cgttagctgt tagaggcata aatgtttaca atggttatct gtaacatctt cttgcagcct  61620
cgaaccttta agtgtgcagc gtcctctttt gtctcttgtg acctttctag gtttattata  61680
aaaccatttt tggctgatgt tagtgtagcc actctgcttt ttgtgtttgc catttgcatg  61740
```

```
gaacctcttt ctccactctt tccacccttt cactttcaat ctttttgtgt ctttggctct  61800
aacgcgagtc tctagtagac agcatgtagc tggatcatgt ttatctattc tgccactgcc  61860
gatatcacct tttgatatac agactttaca ttttcataaa atttaatttg tccacgtgct  61920
tagcccctgt gatccagcaa tcccactgct agttatatat ccaaaaagaa agaaaatcag  61980
tccagcaggg acagatgcgc actcctacgt ttactgcggc actgttcacc ggagcctgtg  62040
ccttcaatgt cgtattcaag aaatcatcct caaatccaaa gtctttctat tttctcctat  62100
gtgttcctat tgctttaggt cttacattta tacctttgac ccatattgag ttaatttttt  62160
atatccagct ttattctttt gcatgtagat actcagttat cccaccatca tttgtcgaaa  62220
agactatacg tgaacttttt gaatttgctt ttctcacgta atagtatttc ctagagacca  62280
ctacatatca gttcgtgggg tccttccata ttctttttta cagccacccc atactttatg  62340
gttggatgtg ccatgcttat tcaaaccctc tcctatttat gggcatttag gttgttctga  62400
tattgtgcaa tgataaataa tgttgcaaag tatagcctta tacatatgtc tattgtattc  62460
ttgaaacaat gttgcaaaga ataacttcgt aggtatggat gttcctattg ttggaggtgt  62520
tatcttcagg gtagattcct agaaatggga gtgttgggct gaaagagaag cccgtagttt  62580
tgttggatgt gaccaaattt ccctgcagaa cggttgcaca tttgcactcc cccagcaatg  62640
catgagcata ccggtttttt ttacagttgc gccagcagcg tgctgtcaca ccactttttg  62700
ccaggtccat agctttgttt taatctgtat ttctgtaatt acattgaatt tgaatgtttt  62760
ccctgtgtct aaaagtcatg tgtgtgtgta tttgtaaatc gtctgtcttc tcatttccaa  62820
cttcttccat tgggtttttg gttcttggtc tctcaatttt taagtcattt atattgtggg  62880
aacgtttgtc tggactaatg tgaattgttt tcccagctgg tcacttgtct ttgactttgc  62940
ttatggtgct ttttgctatg agaaatttcg catgtttata tcatcaaatt tatcatgctt  63000
ctttctactg actccggatt cagggccaca gttgagagct ttttcctcca ccgaggttaa  63060
ggggaatcca ctgtgttttc ttctggaggt ttggggtctt gtcttcagca tttagctcct  63120
tgtccgtttg gagtttgctc ttgtgcatga tctaaggtaa tcttttctca gagagtggcc  63180
tgagacctct tccttagaag ttcaccccac tggctggggc cttcacgagg cccctctggc  63240
ctctaagtgg agcatggagt gtggggtcat cgggcaggac acgagatgcg caggaggctg  63300
tgactgaggt ggctgtggga tgggacggcg tggtttgctc tagagggttt gaaggaaggg  63360
tgagaagtca ggaccactgc tgtagaaaac agggtttgca ggtagataag gtggcgggtg  63420
cagcgggagg aagagaaaag gatgctgctg ggacccctcg cacctgggag gatgcacttt  63480
ctgtttctga catgggtcag ggttggggcg aaggagtcca gctggggaca tgttattttg  63540
gaggtgtttg tgaggcagcc aggtgaggtg ggttgaaggc agtaagacct gcaggtggga  63600
gctctgggga gagagtgcgg gctgggctca caagttaggg gaggtgtcag tgtgtaaatg  63660
acatgagcgc aggggctaga cagggcctcc tgtagcctgg gtgggtggaa gggcagaggg  63720
caagggccaa gtgatggcag ctgtggaggc tgagggcaag gaaggcaagt ccgggaggtt  63780
gggtgtcctg cagcctccac aggggcaatg gaggaagaac aaaggactct gtgttgagcc  63840
ctcctgagag gttttggaac tggccttgac ttggtgatgt ggggttatga gttttattcc  63900
acacacgtat gtgggagtct gggtcctggt gggtcccagc cccgtacatg gaggctggga  63960
ccctgccctg aaacctctca gacacaaaca cccagctcgg ccccacagag ctggcctggg  64020
ccccagcagg ggtctgtgtt gccttggccc cacggcagtg gagctggggt ttcccaggga  64080
```

-continued

```
tgctgctgct gaaggtgagg tttgcaaaca ctaggcatgc atgtttgagg taccacaacc  64140
tccaccaacc catggtggtc accaagggtc tttgggctcc tgtggggacc atactggctt  64200
gtctgacttg ccgttacccg gcggagatat gtcttggaaa gactttaggc caggagccca  64260
tcattgtcct ggaacctggg cttggcaggg caagctttgg ggagcactgt ccagacagtg  64320
ccctggacac tgcacctcag gtcaggacac agctcccgag gcctggctgc tctgcatggg  64380
gaggagtgtg ggtcctgagt ggagtgtccc atctgtcatg cagagagggt gatgatataa  64440
ccagctgggt gttcgcacct gagaggtttc ggggcagggt cccagcctcc atgtacgggg  64500
ctgggaccca ccaggaccca gactcccaga ctagcaggtg ggcttctcag agcacagagg  64560
gtgtgggtga cccagatatc ctgttgttgc tcagagaccc ccagggaatc cttgaagatg  64620
gcagtgacca cctggcttcc tctatagaaa ctccccgaat gggagggatg ggaaagactg  64680
ttgaactaag ctttttagga agaaagccat caattcccct gctctcatac aggcttgagg  64740
agggctaagg aaagtcacag ttgaatgcat gctccctcca cacccatgtg cctgatgcac  64800
acagcctggc ccttgtgggc actggagggc accctacagt cacagaggca aacgaagaat  64860
gtagagctcc agctggatga gggccgtggg gaaggggcac agccctgggc aagggtgtgc  64920
agagtctgca tgggatttga ctgagcaatc tggaaggctt cctggaggag gagctattgc  64980
tcagggtgaa atagaggtct tgaaattagt acaacacatg ccccatactg gggaatttgg  65040
gggtccctgg gggaaggact ctgttaccaa aagcacacag cacaggttgg gagagcaact  65100
atctcaaggc ttttatttgc tgtttcatga aactgaaaat ttaagttttt aatatcacat  65160
attatttcat gaagagtggc ttcggacttt ggggtagggt ctggtaggat cccagggccc  65220
cttcccttgg catcatcatt gtttcccctc catgttcaag ttcagcatct ctgcacccct  65280
tgcctggcaa accccatctt cctgtccaaa gccagacttg gctccctttg ctccagtgag  65340
tggccgttgg ctgggaggct gggtctgtgc tgtgtggggg gtgtttggtg tcctaggagg  65400
agtctctgtc ctgagcagag acagaggaag gcagggcagc ctgctcagag gatgagccca  65460
gctattctgg gaagcaggca ggaagtggca gctccaggtc cgggtgtgag ggcagtagtg  65520
caggtcgtgg tcccagatgg ccacggaggt gtcagcgttt cactcccagc acgtcacgcc  65580
acgtcccttt cctctgcttt gttcctcctc agctgtgaac tgtctgggac tgggccagga  65640
gacagtcctg ggatagggaa agaaaagagg ggcttccggg ggtggggagc ggggctgggc  65700
ggctgctggc tgagccaagt ggactgggag gtgtggacag ggaaccctgg cggggccggc  65760
caatggtggc gtgatgcagc ctggcttggg aaatgcccat ggaggtgaca agtgacagcc  65820
gggaacagac ccactgccag ggctgcctct ctctttagat atgtcctggc atctgacttt  65880
ggtttcctgg tgtttaaagg ctaattggga tcggtcgtgg tgcctcaggc ctgtcaatcc  65940
agtacactgg gaggccaaag tgggaggatt gcttgagcct aggagttcga gaccagcctg  66000
ggcaacatag caagacccca tctctaaaaa aaaaaattaa aatattaata ctagctgggt  66060
gtgctggcac atacctgtgg tcccaactac tcgggaggct gaggtaggag catcacttga  66120
gcccaggagt tcaaggttgc agcaagctat gatcttgcca ctgcactcca gcctgagtga  66180
cagaacgaga ccctgtgtct aaaaaaaaaa aatttttaaa taaataaata aaggtttgtt  66240
ggacatgtta gctcacgcct gcaatctcag catttgggga ggctgaggca agtggattgc  66300
ttgaggccag gagtttgaga ccagcctgac ctgcctgggc aacatggtga aaccccgtct  66360
ctactaaaaa tacaaaaatt agctgggtgt ggtggctcac atctgtagtc ccagctaccc  66420
tggaggctga ggtgggagga tcacttgagc ccaggagtag aggttgcagt gagctcagat  66480
```

```
tgtgccactg cactccagtc tgggtgtcag aaccaggccc tttctcaaag gaacaaacaa  66540
ggctaacatg ttgggctttc tctgcttctg ggcaatgtcc gtgaaattga agccgcactg  66600
gtgttgttcc acccttcctt ccagctggtc tctgaggccc aggccagatg cttctctggt  66660
tagcagcaga ttctaggcca gagcctgcct ccaggtcctg ggaaggctgg cacgctcaga  66720
tgcactcctg ggcgtggcct tcctccgatc acagtgtgag cgaatctccc tgcccatcac  66780
tctgctcccc tggcccagac caggccatgc ctcagggctt ctgcacgtgc agttttctct  66840
gcctgcaggg tctgtcccta gctctctacc cgattcagat cccacaccag ctcctggggc  66900
agccctcttg ccctgcctct ccccgagacg tcaccctttc tcttttcccc attggtggtg  66960
gttttatgtg ttcatttacg gtttattttc tctctccctg tgtctgttat ctgtctctgc  67020
acccctggag cccagcgtgg tgccaggcac acactacgtg cctcctgggt tgggggcagc  67080
agggacaaaa gccaggcatg ggatgtggct cttgtgggat gcaccttggg tgtgactgtc  67140
acggaaaagg aggagacgtg gggtggggaa gggggcagcc cctactgttc ctggcagcag  67200
ggccagaatt gagagccaga ggttgccact ggagggcttc ctggggaggc agctggcacc  67260
gcctgattcc tgtttctgaa tgccctctca ctctccccca cccccatgga accagaacca  67320
cctcgtcagg cccagcagcc cttcagggtc agtctctgca tgggtggtaa tatggcttac  67380
ctgagtcctg gtcagtctgt ggcctgggag tccaccctcc atgactagtg gtttgtggca  67440
ggtgacgggt gagtggtctc catgctccca gccgctgtgt agaggtgcca acctgcccct  67500
cctgccagag ctgggctcct gttgggcggg actgaggata ccgagacaga aataaaactg  67560
ctaaatgcat ctgttgttga ataattcaat gccccatgcc aggcctgttg caaaattagc  67620
cacttcctcc ctccaggccc atgagtgact cctggatttg gtgaaagcca ggcctagtgg  67680
aattgtggcc cggaaggttc tctgggagct gggaacctcc atgcaggagc ccaggggagg  67740
gggtgcttgg ccacatgcgg gcccctcaat ctgccctgtg gagcccggcc tggcctgcag  67800
ccccctgtgc agggaaaaac ccgcggtttt ccctggtgga gggcacaggt cagagcgggc  67860
atggacaggg catgaggaag cagtgcagag gaagcgtgag catttgtctc gggccagctg  67920
gagaaaggaa atggggctgc ttcctggagg gcagagacat caggggctgc gctgtcgggc  67980
tcggcgtgca agatttgtgt ctcatcccag ggttaggtgc ctcccaaatg ccagggcttc  68040
ccatgggcca tacacactca gtcgaacaag atttgcacaa aacctgggcc ataagctcgc  68100
tgagcacttg gcctgcccag ccggtgacaa tgagaaccgc acatgctcag ccttccctgg  68160
actcagggcc ctacgggtgc tggagccggg gcgggagagg gccgcaggct gcccctgcct  68220
ctgcatcctc cccgtcgatg cctggggcca ctgggattgg cagaaaaggg atgcccccga  68280
gatgggcagc caggagaact gtctgtctcc tatcccaata tgcctacctc cctctctgaa  68340
tccccatttc cccctcatcc ttgcccccac acacccagat ttgcaatggg acacacggcc  68400
acctgggatg acaacccctc ccagtcttcc ctcaagacaa gtgtggccat gaccgcatgg  68460
ggccagcagg gtgtgagttg aagtgtcccg cagtggcttc cggggatgtg cagccctgcc  68520
ctgaggccct ctggccgcct cttgctctct gagcagggat gtccgtgcct tgggcctgag  68580
gctgagctgg gctaggtccc tgggtgtctg gggccacact ctctggtcca gcctgctgtt  68640
acaggggatg cctcagggcc accactggtc atggaggctg ggggcgcctg cctgtctgcc  68700
cgcctggagt tcaggtaaac aaccccactg aggaggcacc cctagccgtg ggagttggcg  68760
tgtcctgctc cccagggcgg tctgtcccct tggcgagatc cttgctgtgt cagcagaggg  68820
```

-continued

```
ttttcctggc ccagggtctt ggggagcaga tgatggggct ttaggagctc tggctctggg  68880
aaggcagtgg accctggagc agggatcttg ggaggatgga gagttggcgg ctcaggaagg  68940
aggctgctca agccccggcc tgctcactgg gaagagcggt ccttggagga gagagctccc  69000
gaggagaaag ccatgatgct gtgctgcgct ctgggccacc aggtcttgtc tggggggaat  69060
cctgaccctg tgtgatgtga gtgcagggac tcccccaccc tccgaccagg acctttgtac  69120
tctcctggcc gtgtcattgc acaactccag ggccgtcac tcacctgagc cctctttgct  69180
cttcttggct gttccctgat atggccacgc agagactatc tctaagtgtc agttctggac  69240
tcagctggaa aggtttcatg acctcaaggg acccatggga cttgagggtg gggcagctgt  69300
ttgccctgtg gatcaaaggg gagtgtctgg gatgggatcc acctgccctg ccctcaaagt  69360
gctgggcagt ccctcagagc catagagcct agggggtctt gggccctctt ccccagggca  69420
tggcccaggc acctgctggc ctgaggtccc tgctgggccc aaggcatccc tgccgtgttc  69480
agagttccac aggcaccagt ccaccatgct ggggcctact gggagagaca gccacccgcc  69540
tgctgtcggg agcctccatc accagagcct gggggtgtcc cagccaccct ggccgctgtt  69600
tctctgcctc cgcaccggcc tctctcctga gttccatcca tccctgcagg ttgggttctc  69660
ctctctcctc tgggatctgc acaggttgcc attctctctg cctagactgg gcctccacct  69720
ctgagaagcc ctcccttatt gccccttcca gtgggctggg agagggagga aggccaggtg  69780
cagaaagaga attcacctgc ccggctaaag ccccacctgc ctatttcaag gcctctgatg  69840
ccccccggcc tgcaaggtgt gtgcatgggg cctgtcccat gctggctcac ccagctgctc  69900
agagaggcaa gtggctcccg ggccccacag tgacactggg ggactctttg tctccatttg  69960
gggggtgtgc aggtcactcc tggtgccctg gtcagcttcc ccaacctgag ctgccctcag  70020
ctcctggctt ggccctccac ggagtgggag atgcccccct cccctgccat tatcgtacct  70080
tacctcgctg gcggccatgg aggcagtgag aagagccgag ggagctggcc ggggcgcatt  70140
tccgtgcagg acactggctg cctcccagct cactcttagc ctggtcatag agcccggcag  70200
catcttgcca ggtgcctgtg gtcccagatc ctggggctgc ccatctctg gaatattgag  70260
gtgtggctgg ggctgatctg aggatgaatg tggctcaggt tgccgggtgc ccttgacgca  70320
ttcccatgtc ccagtgggga aaccaaggct caaggaggcc acacagcagc tccatttcca  70380
gggacaccca gtgttctctg tagtgggtag gaggtttccc tatacaggag accaagctac  70440
agcaagaaag acttggccgg gcgaggtggc tcatgggcgc ggtggctcac gcctgtaatc  70500
ccagcacttt gggaggccaa ggggatcacg aggtcaggag atcaaggcca tcctggctaa  70560
cactgtgaaa ccccatctct actaaaaata caaaaaatta gcccggcgtg gtggcgggcg  70620
cctgtagtcc cagctactcg ggaggctgag gcaggagaat ggcatgaacc cgggaggcag  70680
agcttgcagt gagccgagat tgcgccactg cactccagcc tgggcgacag agccagactc  70740
cgtctcgaaa agagacttgg gctagatgtg aggagggact ttcccaagta gggatgaacc  70800
ctgaggaccc acaccctgag ccgccagtgg gtcgtgttga cctggcagct ccagggcacc  70860
tgaggccttc gctgtccttc cgcacctcgc ccccttcccg agtggaggtg ctctgggagc  70920
tctgcctgct tcctcaagtc tttcttgttt ttttatgtta ttttatttta gatttgagga  70980
gtacacatac ttgtctgtta cgtgcgtaat ggtggggttt gggcttctcg tgcgcccatc  71040
agccggatat tggacgttat actcaatagg taatttttca accctccccc tctcaccctc  71100
tccacctccc ctttggagtc ccagagtgac ctttctccgt ctttctgtcc aagcatccca  71160
tctgtctagc ttccactcat gagtgagaac gtgccgtgtt tggttttctg tttccggtag  71220
```

ttcacttagg atcatggtct ccagatccat ccgtgttgct gcaaaggaca tgatttcatt 71280
cacttcttgg aggctttaac gcctgccctg tgtgagggag ggcggagccc ctggcccagg 71340
ggcggggagg cctgtccacc cctcccaccc gtccccgagg cccctgctgc ccagcaagac 71400
caccaccctc tgctccagga cagcgcagcc gccatcagtg ggggtgaggg gacaaggctg 71460
ctgggaccag gcctcgccca ggcagagcct cgccatttct ggggtggggg gtgcacaggt 71520
gcatctggtc tgcccagccc ctcctcaccc taggcaggcc tctcacagag acaagacgag 71580
tgtcctaggg cagataggc cacatccatg gggtcacttc agtttgtcct cccggcgcct 71640
tctaaatata ctctctgtgg gtgtcttatc acagcccagg gagccaggct tggtgtggcc 71700
ggccctggga gcacagagcc ccgttcccag cagccctcgg ccctgggggg cttgtgctct 71760
gccgggccac ctgcaccctc cgggccccag gagaagctca tgcctttcct gcttgcaccc 71820
cagagcctgg ccacccctgt cctctgctga ggccctgacc acctctatgt gtgccatggc 71880
tgcagtgaca gcccagaccc caggggccgg gcatcccaca gctctcctca ctgagcccct 71940
gggcctatcc gcccacgccc aggccagggc tcctgctgga atctccctgt ggaaggccag 72000
gctgcctgga tgcccaccac tccaggctta cttctgggtt gtagttttcg gggtgcttcg 72060
aggtgctgtg gggacctgtg atgctgtcag ggagacccgg agtccagttc tcgccaaccg 72120
ctcgatgctg tgtgacttga ggcaggtccc ttaacctctc tgagcttcct cctctcctgt 72180
gaacaaagga tgggtccact tctcaggctt ctcatgaagt ttagaggcga caggaggagg 72240
tgggctttaa atggctcagt cccagcgtcc cctcatgcct gggaccgctg acccaccggg 72300
attcttgggg gccaccatag agcctgtttt taaaggggat gtggcggcca gctctggggg 72360
cacacgttcc tgtttgaatt ctcaatctcc gggctcaaaa ttggccccca gaaagccttt 72420
gagatggaca gggagctgga ccttcccaat tcggttgccc ttgcttgatg tttacatgcc 72480
actgttgggt gctcctgatt gtgtagcggg tcccctgaaa ccaacacaca ggtgcagaca 72540
cccacatgcc atcctgccag agccctgggt tctcagcagg actctttgcc gggatcctca 72600
tgctacggcc accacctgat tttgtcgata aagttttatt aggacacagc catgcccggc 72660
cgaatattgc cacagaggcc acctgcccca ccacgcctag gacatttcct ctctggccca 72720
gaggtgtgcc agggctgcac tggctcttc tggtggggag ggacattgtt ctggcccctc 72780
ctgatctctc ccccaccttg ccacgacccc ccagagtttg cctggtgtca ccgggaagct 72840
tcctggctgc ccgagggtcc cccagcacct gtccctctag ggcctctgaa gggctttgac 72900
gtgacactcg ggatggcatg gcagggccct caagcacggc tgtgttcacc ccccaggctg 72960
ctcctggaaa ggagggatca gggcccaggc tccacgctcc gcactgaggt gtggtcgagg 73020
gccctgggcg tccgggtgag atgggaatga gcccttggta ggtgccaggc ggggccagcc 73080
ctcatcccca ctgcaaggcc tgagcgtcca ggagccccgt gcgcagctgg acccatcagt 73140
ccccaccctg cagggccgtt gaagagggaa tgcacacctg tcacctcttg gtgcgggggc 73200
atccaggttc ctggcgatgg ggatggggtg agatgcacct gatggacctc caggtgggaa 73260
gctcctggga caccctggag ggctctggtg ggagacatgg cattctgtct gcaccgaagg 73320
gggctcaggg ctgagaagcc ctgggacggg ttggatttgg ggcgcgttcc ccagggcccc 73380
acgcgtgttg agtccccgct gcgtcactgt ctggcctgtg gcgcctcacc tctctgtctg 73440
gcaggactca ggcagaatgg aagtaaaggc aggaccttgt cccaggacat ccaggcatgt 73500
ggcgtggcaa ccaggtggga tggcagggtt tccccctggc aggatcccca cctcctgcac 73560

-continued ctgtcctgac ttggtcttct ggggcagccc ctaagacgct tcttcaggga agagggaccg 73620
gtttggccag tgggaccatg gccctgggag catatgcctg cacgtcctgc ccgctcacac 73680
ctgcctgctg ggggggccat gcctgcgccc gcagctcacg tcagagccca ccccaggagg 73740
ctcccagcga tctgtcaacc tgtgctgttg gcatgcagcc tgggggtgag gggtggcgga 73800
acgctgcctc agtaccacgt cctgctcaaa ggccacttgc gagctaggct gagcctgtgg 73860
tgtgcggtgg gataggaagg aaaagaacag agtctaagga gcctaactca cttccagatt 73920
cacccggagg cctgcatgga ggaggcggca ctgagacttc attcaccgag cttgagggtt 73980
taccctaaca ttcattcaca ccatcagtca ttcagcaaac acttcacaaa cgtgcatccc 74040
acgcctggca ctgggccttc ggagggaggg aatgcagctg gtgggcccct gcctggggag 74100
cccctgctct ggtcggggag gcagtggtgg cagtggctgc ctggcggtcc atgaactggt 74160
gcaagccaga gccggaggcc tcctgagagc ctggcaggga agcccaggcc agggcctccg 74220
cagaaggagg gtttggggtc caggcttcat gtggggggtc ttgtaacatg ggagggtaga 74280
cgctgccttg ggacaggaga gacagaggcg gggggaccag gggagtgggc tgcagttggg 74340
gtgcaggcct ggtggccccg gcagggggac cagcctctgg ggaggtgctg caggcacagg 74400
agttctgtgt ggacccagcc gaaagctggc aggaagggac ctgtttcttg gggttcccag 74460
tccagatctg tgttggaaaa agtgtcagct gaaaccccaa gaggctgggg acagccttgg 74520
tcctgctgtg ggacacaggt ttaatctcca gatggctcct ggataggcgg gctggcggct 74580
ctgtctaacg gggacagcac acttggggct tcgggagaca atgagggcag aaatcttacc 74640
caccggccac accaagtcac ccattgttgt gtcccttggg ctgggatccc atggctttca 74700
agaacttttt aaagaaatga gactcagctg ccgcggaaca agccacaggt aaagagtata 74760
agacagcgtg aggcatgggg tggccacggg agccctgggc caaggaggcc cagtctggtg 74820
gggaggcgtc cattcacccg gagctggacg gggaggacca ggctgtgggt ctgtgaagcg 74880
ggtgtgggat cacatccacg ctccttctgt ggtttgtgcc ctgttgtggc tgccagggga 74940
ggggcttcca aggccctgcc aaccagctgg gcagtgtgga caatggcaga cagggtgctg 75000
tgtgggggcc tgaggggcaa tggttggggg gcagctgttg ccgttctggt gagaagtggc 75060
ggtccctgaa gggctggggt gctagggagc ctcatggacc tactcccgac gtggcagctg 75120
cctgctgcag atgggccagc catgtcccgc ctgtgccggg aatcaccacc cccagctccc 75180
ttctctccaa catgacaggg ttcgggtgat gccctgtggg ctgaatggtg agagaggcgt 75240
ccctgtgctg acaccagtgg gcgtggacgt gaccctcttt ttaaaagaat tttttcagat 75300
gcaattccat taaggatctg gaggtgagag gatgaaaagg aaactctgag ctttgagtac 75360
atttttaatt atgttttaaa aattaagaca tgaggccggg catggtggct tacgcctgta 75420
atcccagcac tttgggagac tgagttggga ggatcgcttg agcccaggaa atcgaggctg 75480
cagtgagcca ggatcatacc actgtcctcc agcctgggtg acagaacaag actctgtctc 75540
aaaaacaaaa caaaacaaaa caaaaaacca aaaaacaaca acaactaata tatgtttttg 75600
accaatacct aattctgttg tttaagaatt caaaatctac caatagtgat cataagtaat 75660
gtattaaata cttacatagt acagcaggtg ttggcccccc cccacaacat tggtttccat 75720
ccctggaagc tgcaaatgtg acctgacata gaaaacaccc ctttgcagct gaggctgagg 75780
gtcccgagag gcgtgattgc attatccagg gggcccaagt ccagtgacac gtgtcctcct 75840
aaaagacagg acagattcaa caaaggagga tccggccaca tgctgcacag cacgggagtg 75900
atgccgccac ccacccagga cgcgggagcc cgcagaggct ggaaggctga aaagggccct 75960
gtcgccccca ccccccagga tgacgtatgg cctgatgtgg cattcctgcc tcaggaccat 76020
ggcaccaagt ggtggcgctg gggcccctgg agtcggccag tctgggcacg tcccatgctg 76080
tgtctgagcc tcagtgtccc catcgattgg tagtgcctcc tgaaccccaa tccagggggc 76140
ttctgggggg cagcctggga ccagacgtgc ctcaccaggg cttctgtctc ctcaccagga 76200
cttccatgat gtgacacctt ccacatgggg ttcagagcgg ggaacctgtg cctagtgtcc 76260
agcccagcgt ggggccctcg gtgtgggcca gggctcaccc ctttgggagg ggtcgggaga 76320
tgcctggccc aggctccatc catgcagagc caggaagcag gtgaacctgt ggggaccttg 76380
gcgacctcca aaccctgctg aggctgcctg ctgacagcca ctggtgaggg gggtgacagc 76440
cactggtgag gggggtgacc agctggtagc tttttctgag gtgcagattc agccctgggg 76500
aacagccctg gcaggctgtg agacctctgc ccctgggcgt ccacatccca gggctctgag 76560
ctcagcagcc ctggagccgg cagccacatc agggatggag ggagacctgc tggtgaccag 76620
tgagtgagca ggggaagcct gtcctctcca gcgcccagtg tttccttcct ggggcacatg 76680
ggatttggag gcatttggag tctcccagga tgactttttt ttttaagccc ctagaagtgg 76740
tttggggttt aagcgtcaat atttaatctc ttgaagttac acattcaagg ccctatcctg 76800
ccttcggctt taggttcgct tcacaaaccc attgtctgct tatcagcctg gcgaggtccc 76860
gtccccagta ggggtctttg aacattgctc gatctcattc accagccacg gggaacattt 76920
tgaaccctct gatgcttgct ctatgaatgt tgtttgcttt aaaaaaagtt tttttttat 76980
tgtgataaaa tacacataac acacaattta ccgtcttaac tctgtgtcag gtcacggccc 77040
agtggcaata ggtacattta catggttgtg caaccgtcac caccatccac cccaaaactt 77100
ctctcccaaa ctgaaattct gcacccatga aatcccactc cctctccccg gccccgccat 77160
cctgctctcc gcaaccgtgg atccgtcctc cccatgtcca cagatcccct ctccctcggc 77220
cccgctgtcc gcttccctgc gacggtggat ttcgctgctc tgggcctttg cgcttctgtg 77280
actggcactg tgtgttatcc ggtgtcctca aggtgcctct ctgctcatgt ccttccatgc 77340
atgatgcttt cagactgaca aaactcttca agtattaacg taatttttaa tgtttacaga 77400
ttcaagaaat taagcatacg gtcacgagag tgcaaagttc tgtgaaacgc tccagtggtt 77460
acacgccccg gggtttcagc ttcgaccctg ggtgagttcc atggtgcagt ggcttccagc 77520
tggagttcta agggcacccc ttgagctgcc cacgtgtctt tgcacgtgaa gtaggtggct 77580
ctctttaagg ttcctcaact ttattgggaa acatctcagg gttacaaaac gccccccatg 77640
ggctaaagag gctgtcactc actgtgtgtg gggcctgtcc ccgagtgggc atggaaggcc 77700
agagtcccgg cacagccccc acccggactg gatttgcttg gcgggtcacc tggatcaacc 77760
aggcccattt aggagcacca ctcaggggcc ctagtgtgtg cggcagggca ggtcatggag 77820
tctccagcct tcagctcgcg ttagccccag gccatctgag ccgtggagcc cacccaggcc 77880
cgctgcctgc accccggggg agccctccca cagcgtctcg ggctatgacc ctggcagggt 77940
tcctgcattc tcctgtgttc ccgggcaccc ggggctgaga tgttgaaatg atgtcggata 78000
attcaccggg tgccttcggg gctggtactc gccgtcactg ctcctgaggc ctatttgctg 78060
tcaaggggaa caagtaggag gttgttttct ggggtgcggt gggctccccg ctcatgcagc 78120
tccccgcccc ccgcatgacc acgccctctt gggagctcgg gtgggacagc attcagggga 78180
ccacatgagc tggggggggg tcggtgtctt ctctccccca ccccttcgct agcctgtcct 78240
gcttcccact ccgagtccaa aacacgcata ggattcgtcc tctcccaggg ccttagtttc 78300

-continued

```
ccggctctgc agagtggggg gctgtgactg cctggccttg gagctgaggc agagggggtg  78360
gtaggtggcc ctgcagaggc aggaggggac acaggcaccc caggccctga gtgcctcaag  78420
ggcagggacc ccagctcggc acctgtgagg ttcccagctc cgcccgagac aagaatagat  78480
aaagcggtaa ataagataaa actcttttta tctggagtag ataaaagtaa gctttgtcat  78540
ataattcctt ctgaggctag cacggtatat caaaatatcg gaagaatcat ttagccttca  78600
gaatatggca aggctgacag ccagcctggc ccatgggcac ctgtccccac catctgcctg  78660
gcctgcgggg gaacgttcct cagcccctgc tggctcccaa cccccgggcc tggagccctg  78720
tcttctgcct cagccgcgat tccactgcac gggactttcc caggcacctc tgcccaggta  78780
gttggggtgg acgcccactt gggtgcacac tctgtggggg ctggtccagg accacccatg  78840
tgcagtcttc cctggccaca tcctgtattc tcccgcaacg cccagtcaag aatcttcctg  78900
ctgcagtaac tccacatatc tgagccagct gtgtctcctg agcacaggac atgggcagga  78960
gaggcccctg cagctggaat ccgcgccatg aagcccaggc gcgtggtatt tgcagccagt  79020
caccaagttt tcaagccctc acctgcggcc tgtgagtgcc caccctgcac atggtgctaa  79080
ccagcatcca tcactgcttt ctttttaat ttaatttaat ttttttttt ttgtggtgga  79140
gtcttgctct gtcacccagg ctggagtgca gtggcgcgat ctcggctcac tgcaacctcc  79200
acctccctgg ttcaagcaat ccccctgcct caatctcctg agtggctggg attacaggag  79260
cacaccacca cccacgccca gttaattttt tcatattttt agtagagacg gggtttcacc  79320
atgttggcca gactggtctc gaactcctgt cctcaggcaa tcctcccgcc tcggcctccc  79380
aaagtgctgg gattgcaggt gtgagccgcc gcgcccggcc ccaccactgc tttctatgct  79440
gtggccgagg tcaccaactg ccactgtgat ggacggctgt cacccaaaca gcacgagaat  79500
cgaaaagccg tgatggcaga tgcagaaggc agcgtcgcct gtggtctttt agaagggcag  79560
ctgtgaagtg gggttatctc agcttccaca ttgcatcacg gtgcccctgt gaagggcaga  79620
ggagctgcag gtaattctgt tcgctcgcct ctgccttgga ggaagtttac agtttttttt  79680
tttttttttt ttgaaagttt aaagctttca acctgggcct ggaggctgca gggtcagcag  79740
acctgggtcc tgcccatggc cccctccct cctcaggcct ccatttgctc atctgagagt  79800
ggggggagtg cagcgccttc cgtgcaggtc actgagaggc tggggcagtg gcgtggattc  79860
gggtgcatga ctcgcagaca tggctgtcgc ttggctgaac ggtggcccct gaggtgtctg  79920
tgtccttgtc ctgtgaacaa gttaggttgt gtggccaaag gggctttgca gggtgactga  79980
gggatggctc gtgagagggg aggttgtcct gggttacccg ggtgagccct cactgtgatt  80040
gtgaggattc ttctaagaga agcaggagga tctgagttgg aggaagagac gggaggatgg  80100
aagccaggct cggcgacggg aaagctgctg tgccaccctc accgcagccc tatccctgct  80160
cacgtgcacc aagaccagag cctggcaagt cgtctcatac cgagggtcaa aggggcccag  80220
ggcccagcct ccagggaccc cagccatgcc gggtcaggga accaggctgc agtcctgtgt  80280
ctcctcctca gtttacccca attgtgacct cagaagccct tggagcctca gtttccctac  80340
ttgtagcatg tgtttgatga tagtgtggca gtgatgtcac agtctggcag ggtctcgtgg  80400
gggtctgtgt tactgtctgc aaagcactgg ctgggccagt ggtcagtgag caggggcgtg  80460
ggtagcgggc agtggcctgc agtccccagg agcacttcct gttgctgaac agacagcaac  80520
ttagtggatc cttcccaggg cccctggtgg gtggtgggtt ttgccacatc tttgcagtag  80580
acagcactgg cagcttccgg cttatccaag gcctcagggt gaagtcgacg ctcgctgctg  80640
attccctgct ggacgtcagg tgacacttcc ctccacagcc tgggaagaag cacctgtggg  80700
```

-continued

```
ccacttcttt gtgttgataa ggaaactgag gcaggggagc tgcctgggtc accagtgggc  80760
actgcatctc catgtgcaga tggtgccctg gccctctctg cacgccgtgg gcctggggag  80820
caggcaggtg gcatcttctg ccccgggcag cccggctctg cttcctcgtg gctgagccag  80880
gctgtgtcta atctcacttc cctgctcact gcaaatcaaa acaaacagac gtccaggagg  80940
attaagtgtg gcagtcatgg cggagggagc cctggtaggg tggagagagc caacagttgc  81000
accagcaagg ggcagagacc cagcccagcc ctgggggctg cagggtgtgg ggacagggcc  81060
tgcagcttgg cacaaagact cttctaagaa cctggaggga accctgctcc ggcagtgggc  81120
agcatgctgt gtgcaaggtg agccagtctg agcccattcc cagtgcccgg aatggtgccc  81180
agtgcagatg ggcactcacc cttccaacca acctttgctt gtgtccccgt gagatccaca  81240
gattcaccct acggagggct ccccacaggg ttggcccgga ggctccagct gtgtctgttg  81300
aacaaattac tctgcatcca ccgcgtgcta gcgctgtgcg gattatagtc ccagagacag  81360
atgagagcag gggtggtcag tgtaggagca cccagaggga gcctggcagg gcctggacat  81420
cctgtccaag ctggccagga ggagtcctca gagccaaagc agtgtggagg gtgggggtgc  81480
agagagcgtc cctggctgga agcaccgcgt ttgcaaatgc caggcagctt atgcagccag  81540
cgctttgggc aggcgggagt caggggggact gaggcccaag gaggggtagg gctgcatgcc  81600
agccttccag gtgctcctgg gaaccacgtg gctgatcaga cttgtgcttt gggtcgaatg  81660
tcccagtggg ggagtaacct cagggagcag aggaagggtc atggtggtgg ggatgaagca  81720
gcagcattgg ggcttagaga ttaaatgaag gaagtcccac ggggctgatc acctactgtg  81780
caccaggctg cgtcccgggc atggactgca gcccacagcc ccactcttgg ggtgctcatg  81840
gtctaggggg tggacaacag actctggtcc cagcgatgat gcttgagtat aaaggacaca  81900
gttggggtgt tgtgggggcc agggtcagac atcagagctg gcctctgcct atgagacagg  81960
gcccgctggc aggaccctca agctgggctt ttaggctggg cagcagcagg tgcacgggcc  82020
ctgaggtggg ccgggctggg cacagtcagg actggcaaca agggccggga ggagctgggg  82080
tgatctgggg ccatcgtggt gtaaatactg gggcacgaca tggagggttc actgactggc  82140
tgggtgtgtg ggctgggggc gccgagggtg gaggtgggca ctgtggtcag ggggagatga  82200
ggatggatgg gcagggtgca gacaggggct ggctgggttc ggctctgcag gtagagctga  82260
ccagtgtggc agggacaggg tgtcggtgag gcaggtggct gaggaaatgg tagctgcagg  82320
ttttggcccc agtcccagca gcgggactat ggctgtgggg agggaggaac ccagggaggg  82380
ggcctgagca ggtctttggc tgagtgagcc ctcaagggcc tttgggtagg gctaccagag  82440
gccaggaaag gattgtcctg tccacaggag cttggggaag ggggtggggg gccagagccc  82500
caccttcccc agaaacctcc gtgcagcagg aggatgagcc gaggcaggct gtgctgggag  82560
gtagcctgtt tgttgtgggc tctgggggcc tggggagggt gggctgggct gtccacatct  82620
ggacaggtgg aagaggatgg gttctgggtg gggctgactt caggaggctg gatgagaggc  82680
aatgcagggg gccttctggc tgtcctgggg tgggttagaa gccactcagg atggcaggat  82740
ctcagggagc ggagggagcc tggggcaccc tatgccaggc agaggatcta tgccggggcc  82800
cccagggtct gtgtgtggct ttctctgttt gtgtctcccc tggccctggg ggccatgtgg  82860
ccatctcctg gctctccggt cgctgaggat ccacgggggt ccctggagtc tccggagccc  82920
gtgggaatcc ccctagaggc gggaggaagg ccgggcgggc cctggagggt acgtttgcag  82980
tggcagcagc tccctatctt tatggttccg gcgatcagag aaggcggccc gtcttttctc  83040
```

-continued

```
tgcgggccca caggcccaga acgttggccc cagggtgggg ctctgtgcgc cttccctttc  83100
atgagttctg tggctcggcc tcggggcctt ggaaaggagg aagtgaaact ggaggagagc  83160
ggcccacagc ctgccgcctg gaggctcctc tgggaagcag acgcttggtg caggtgtcag  83220
gacccccacc tggcgggctg gcttctgtgc tgtgaccacc aacacccctg ccctgggccc  83280
tgaactcctg gacagggggc gttgactgct ctctggaagt gatttgtaaa atcagctttg  83340
tagagacgta attacacact gcagttcatt tgtggctcta gggccctaag tggctctaga  83400
atgttcagag ttgtgtagcc accaccacca tccacatcca gaacgtttaa ttaccccaaa  83460
agaaaacccc acgcccacag cagtcccgcc ctggggcagc caccagcctg ctttctgttt  83520
ctgtggctct ggctgtccag ggcgtaacca cactgcaggt ggtcagcagg tggtcacctg  83580
tctgtgtctg gccttggcgc catgtttctc ggacccatcc acgtggcagc atgtgttggt  83640
gcttcgtccc ttcccgtggc gggacggcat ccctcgtgcg gacctacctc tagtgtgtgc  83700
ttaccagcta atggatgact gggttttcga agcactgtct gttcctacct gggggcgggg  83760
ctgaggccag gggcccctcc actccccagg tgcatctgtg ggatgggcag aggccgtgat  83820
gctgactgcc gtgtccctgt cttgcagctt cctcatcgtc ctggtctgcc tcatcttcag  83880
cgtgctgtcc accatcgagc agtatgccgc cctggccacg ggactctct tctggatggt  83940
acgtagcatc tgagggcatg gctggatgtc atggctgcct tggaagctgg catctccctg  84000
gcgctgggcc ccataaggtg gggggcagag ccactcccag ccccttgccc acacattggt  84060
cctgccctga tacaggggc acctccccag cccccacact tgccaagtga cttgggatgt  84120
atgtgccaca ggcgaggggg accaaggact gaggggaacc tggagctggt ggtctgaaag  84180
ggcttcctgg aggaggggct tccaggctgg gctggaagga aggaaggagg aggtagggta  84240
gagctggtgt ggccagcaaa ggcctgcccg agccttcgtg tccctggggt ctgggtgact  84300
ctgttcctgg gttatggctg gcacacaggc cctgctggtg tcccagcagc agcccccacc  84360
ccaggcacct ggatggtccc ttccattggc ctgagcggtg tctgtgccat ttctgccagg  84420
caggtgctga gagcagggca gggcaggctc atagcctggt gggaaacccc aaagttgatc  84480
tggccgtgag gctgcctgga aggtggggtg caggggggcca gctgtgtctg gagcccacgg  84540
ggtccccacg gaagccacct gaatgtgggc cgtgagcagc aggactctgg caggactggg  84600
tctagcacct ctccgtggcc aggcttttgt gttttcctgt cttgtcgtgg aatagttcta  84660
gtatctacaa aggaagagag tgtcacgact cagctcccgg catgcacagg cagatctggg  84720
ctggtttcat gctgctttct ggcactgtgt cttcctggcc aggggagccc gtccctccgg  84780
ggtccagagt cctctcgcga tggcctcggc agtggtatcc gtctcatttc tagggagtcc  84840
gttttacctt tcctttgttg cttctggacc ttgagccata gctggaagaa ctcacctgtg  84900
gtttcctcca gccctgacca ggttaactgt gtgtgctcca tggtggctgg gagtttcctg  84960
ggtaagtggt gtgaggcaca ggcctgctgt cactcttccc tcgtcttccc agttctccca  85020
gcactatgtt ttccacagtc catctgtcct gcctgactgg aggggccgtc ttctctgtaa  85080
accagacgtc cagaggcagt aggaagggtc tgctttgggg tttttctatt ctgtcccact  85140
ggtctcctgg acttttcctt taccagggcc ctactgactt ggtggtcccg gtactaaagt  85200
caatttcatg atgtcacttt gtgcctcggc agggctttct ttttcggggg tttcctggtg  85260
gcgcttgcag ccttgctttt cccagtgaac gttgccatca ccttatccag ccccgggaag  85320
aaactcgaag gccgcgggtg aataaactgg gggagactga catctcggtg gtctccagga  85380
gcatggtgtg tgtgtttatg ggcagcattt tatggtttcg ttatgtagat tgcaggcagt  85440
```

-continued

```
ttaagtctat tcctcatcat aataatattg agagaataag ttgttattgt tgccatcaca  85500
tagggagttt ctagtctatc atgttttcca ggcactttcc tggcgtctgc gaaagctgtt  85560
aatttctgct acagcctgtg gtcctgctac ttctcgtgac tgtggtcgta gaagtttttc  85620
cctctgtcct ttgcatcttt tgcgtttcca gataagggat gcctgccagg agggcagatt  85680
gctgcttggg tctgtccaga gctgggggtg gtacctgcgg ccagcggggc cctcctggct  85740
tctgtgggcg ggccggctgc caggcggggg gtgcgcacct cccgtgctca ggaagggtcc  85800
ttcaggtccg atgcctggcg tggttttacg gtgaccatgt ggattctggt caggggtctt  85860
tcctgcttct gtgaggtgct cctgtcagtg aggggccccc cttgccttcc tggaataaac  85920
ccccttggtc ctggcgtgtg agtttcatgt cctatcacat tgtactctca tgctttgttc  85980
agacttttgc actgccctgt gaagtggggt gtgtgtgtca tcttgtggtg ccatcttggt  86040
tggggtgagg ccgtccttcc cccacagggc gatgtccaat acccttggca gcatgggcct  86100
catgttttat ggggtcccca aggtacctgc ccaggatccc caagtcctcc tcacccacca  86160
cagacctggc tctcagatga gcacccagcc aagtctctgg ccatgtctag caggaggatg  86220
ttctgccccg gccaactgac agggttggct caactgcagg agtgggcacg gcatgtcctt  86280
tgctggttct gccatggggc gggtctgtgg ggggtccctg acctggtagt tgtccctgga  86340
gggcctgggg ccaaggatgc cagtggttcc caggctgtga gagccgcgct gccaaacatt  86400
cccctggaga gtctccgtgt gaggcccttt gtacctctgc aggtgtgtgt acatgtgtgt  86460
atgtgagtgc ccacatgcac gggaatgtgt acacgcatgt gcgtgtttat gggtgagctg  86520
tgtgcttaag tgtgcatctg tatctgagta ttatgtaagt gtgcatacac atgagcacgt  86580
ggggactttc acgcatgttt ggctctgttt caatgtgtgt acatgtgtgc acatgtgtat  86640
ctgagcgtgt acatgtgtga atgtggccac atataggcac attgtagtgt gcgcctgtga  86700
gcatgtattg tatgtttatg catggctgtg ttgtgtgtat ttatgtatag ctatgtgtcg  86760
ctgcgtgtgt gtacctatgt gtatgtacgt gtgttcatgc ctgtgctgtg tgtgagacgt  86820
gagatcctgc ctgtcccgtc cctcacgtac taacctggat ctaggtggtt agcccctcgc  86880
ccccaggtgg cctgggactt gcctggtttt aaatggagcc ccggtgctaa cgtgagccca  86940
cccaggtgct cctgcccagc cagggctgtc tgtcagcacc acagcgtcca agttcaggtc  87000
ctcacttcct aggtggttat ctcccaggca gctgggaggg cgaagcctgg agaagcctgc  87060
acccaggccg gccctgcagg gaccttcaga cgtgccctgg gctccacatg cccgtctgca  87120
gctcgagaat tagacgtgtt ctgggctcca catgcccgtc tgcagctcga gaattagacg  87180
tgccctgggc tccacatgcc cgtctgcagc tcgagaatta gacgtgccct gggcttcatg  87240
tgcccgtctg cagccctaga atcaccagca gcaccccaag gcccccatgc ggcatctaaa  87300
ccaggcaggg gacaggggca tggagcagac caggtagggt tgctccctag gatgcagccc  87360
tgcccaggca ggagggcaga ccctacacag tgctgagctg tgcccccagg gaagcctcca  87420
agatggtcct catcccagca gccctgccca ctgtctgcgc atccctgggg tctgtgcgcc  87480
acctggtggc tatttgctga actgtggcca caaacccctg gtcagcagga accggccctt  87540
tcactgccct gcagctccct ctcctccggg gtggcatggc agagaagcag cccgtggccc  87600
caagcataga gccccctttc tgctgtagtc cccctgcag tcccctctgc cttttccact  87660
gcttggaagg cagagagacc ctggccgcct cccttgtccc tttatctgtc atgccagctg  87720
cctccctgcc acaccttgcg tctcaccagg caaccctgca aacagcagct ggggaggact  87780
```

-continued ttctaagaca aaaacctgat cattccagaa gctccctgtg acgtttaggc tacattcccc 87840
aaggtggtgc cacgttcagg cccatcacct gtaacactac ccaccccacc tcacccagcc 87900
tgggctcact cactccaggc caagccttgg acattcctgg ctgccccagg gcctttgcaa 87960
gccctcttct ctggacctgg ctgtcctcgg gagtgtcagc actcagcctc ttgtcaggtt 88020
tcaggcctct gcttggcact atcctgcaca ccatccccgc cgacctgccc tgttctgggt 88080
tcatggggct ctgggaggct cacaagcatc tgtctgcctc aggccattcc acactccctg 88140
agggtgggac cccgtggctg cgctaacccc acaagctctg catggcgctt cctggccgtg 88200
catgtccctc cctgcatcaa atgcataggc cagagttgcc caacgaggac gacccagctt 88260
ggtatgtgct cccggcttca gctgcccctg agtgatggag acaccctccc actcgccttg 88320
ccacacttcc cagcagtctc tcgaagcact ggccgcgtgg aaacaaatcc ttcaagggga 88380
tttgagggtc caactgtcac tcagtcatgg ccatggtggg ggcacgttgg ggacacagca 88440
gagagtgagg cagccgtggg cctggccttg acaggcggat gtacagacac atcagggccg 88500
agactgaggc gtgggctctg ggtggggaga cagtgaccac ttgcttggag gagggggcgc 88560
tcaggtggga ggggcacagt gagaaggagg taagctggtg ctggcggggc aggcagggac 88620
ccctcccagg gctcacagct tccagcggac agcaggcaca gggctgtggg gatcagagca 88680
caggcagaag tcacctgaca gcaggttccc gaggcttcag gcctggagga gtgaggacgg 88740
ctgttgggtt cttgattcca gcagagggag gctgtgcagg gttgcaggaa ggacggttgg 88800
gggcgcttcg gggaggtacg agaagcaaag gtgtttgcgg cccttggggc caggcggcgg 88860
gaaggcctgt agacgccaga gggcgctcgt gctacatgca actcaggagc tgctggcacc 88920
cgccaaggag tgctgagcgc ggggagccca aaccacagcc ttggggaacc caggaggggc 88980
cgggcgggtg caggacccgc atgagggatt ccgagagcac gatgtttaaa tgttggggga 89040
aaaaatggat caaagcgatg tgttcccagg gagcccctgt tttctcgttt cttttcgtac 89100
gcccagcttt gcagtgccag aaagctgtta tctcagcact gctaaggaaa ccccagcgcg 89160
gcctcggagg gattaggcat tctgctgaac cagggatatg cggtgggcct gaaaaagcca 89220
tttcgggagg aatctggtct cggctggggt ccggccggca ccgtgaacac cacgtgaaca 89280
ccacgtcgga aatctgctgg gcagggagat ttcctcaagg cctcccaggg aggagagcca 89340
cttcctgggc tgcaaagagg gccccaacct ggcttctgaa ttcagagggg gctgtgtgtg 89400
cacgtgtgta cgtacgtgca tgtgcacgtc tgtgtaccca tgtctgtgga agtggcacac 89460
gtgtgcatgt gtgcactcag tgtacgtgtg cgtgcctgtg ggtagctccg tgcgcacatg 89520
cgtacacata tgcctggtgt gtgtgtgcac acgtgtgtct gacgtgtgtg tgctttgcgt 89580
gttcttgcct gggaaggagt tcccggtttg ggtggctctc ctgtttcttg ccgaggccag 89640
ctgctgctag aaactggccc cctgctctct gcagtaagag accctgccct ggcccaggtg 89700
agggcctggc ttttgtctcc aggatcacag cttttgtcaa actccacaca aagagagagg 89760
cactcaaaag cacaacacaa acacggctag tccgcgcctt tggtggtgaa cataccaggg 89820
aattgtcctg caatgcctgt ggttaaaaaa ccccgtgagc tgcggccccg gaggcctagg 89880
ggatgaggtc atcgctgcgg cttcctcccc tctgctgagg ctccctccgc cccgcccggt 89940
ggcccacccc tcccgccagc tgcagcctcc actgcctggg tttctgctgc gccttcagca 90000
cacagcgagg cctcagtttc cctcccagct cagagcaagg cctcagtttc cctcccagca 90060
gcaaagtgag accctgtagg gagtctctgg gcctccgtga cggccctggg cggccctctc 90120
tgtggaacaa ggtcgggtcc tgtcctcagc gccctggcct ccacttgctc agggcgcccg 90180
caggcccgca ggtcctcacc tggtgttttt cacctgggac ccgcagctgc tctgatgagg 90240
agcctgctct gcgcacggcc tggggcggtt tcccgcagca ccatttctgc cgctgccggg 90300
aaaagacgca gagcaaaggc acctttgccc aggttgggga accagtgggt gactcaggat 90360
tttcctccac ccaccccgag gtctgactcc ctctgcagct gccgcccgct gagggttgtc 90420
ttcctccctg cctgcctcgc cctgcctggt gagctcctat gggtctgacg aagccccgtc 90480
ctgcacactt gcttcggggg caactcccca ctagactggt tgcccaggga cgggggtacc 90540
cactccctcc tcagggctgc agggtgctct gggaagagtt gtgtccctct gtgggcctgt 90600
gggctcactt gcctttttgt ccctgtcact tgggagctac ccagctaaga ccggtcccca 90660
ccacccaggc cactctgagg cttcagaacg cggtcgtctt ctccctggca gggttgtttc 90720
cgcctgcatt tgttcagcca gcaaatcttt attaagcacc tactgtgtgc caggatctat 90780
gtgcaagcag cccatgggct catgaaaggc agagctggac tgagattccg cacccctggg 90840
atcctcactg cagggccctg tgtatgtgcg ggctggagcc ctggttcctg tctgcactga 90900
gcccctggag ctaggcccag aggacttgac agatgtgggc cctctgtctg cacagccccc 90960
agggcacggg gtggcctgca gctctgccca gccagacttc aggtcactgc cccatgagcc 91020
tgtaggagaa acttctcact catctgtcct gagacctgcc tggagcccac cccagggaga 91080
cagaggctct cggagcctgt tcagggtgaa aggacgctag acactggcct gcaggctttg 91140
ggcgggtaag ggtagcgaag gtgaaagtgg accaggggca ggtggagcag ggtaggccca 91200
agtgtctgtc tggggcagct ggggacaccc aggtgggctg aacttcagct gccacccagc 91260
ttcagctgcc aaggctcctc ccgggtcagg gtcgacccct gatgtcccgg caagagttcc 91320
aagaacaaag gctcagaatc caccaagcgg aacttgaagc cactgccctg tggggacagg 91380
agaagtgact tggccggctc tccggagccc agtgttgatc actgaggacc accggataca 91440
agtccctcct gccttcccct ttagtgacac tgaagctgtt gaaatcccca tccaccagga 91500
gctcctggtc ctggggagcc ctgtgcaacc cactcactgc ctttcagagc cctgtggcgt 91560
ctctctcatg cgctggccgt agagcttcct gaaagcatct ctatcaccca ctctgcacct 91620
gagagagggc ggtcaggtga ctggtacccc ctgaagacct gggaccaggc cccctgcctc 91680
tgggaatcca tcaaaatgct cccttctgag gccgctttgc tgggcgtagg atcagccttg 91740
ctttgagggc tgtttaggag aggaaccccg gcgctgctgc tccccggagg cagccagtgc 91800
ttgtgatggg caccctgcct ccagtgttct gcttcagggt gtgggatgca cagctggggg 91860
caggggcgct gctgaagcca cagtctcaga gcctgaggcc cacggggcat ggcatgaaga 91920
cccggtggtt ctgttccccc gggacagcct tggtccagcc tcactggcca catgctctgc 91980
cgagcacacc cgctgctgtc cccagccacc cagccccatg cacaggccac gcggcgacag 92040
gggctgctga aggaaggctg gtccgctccc tgcctgtgac aggagctcag gctcagggca 92100
gcaggggcgc tcagctgggc cgcggctcca cggtgttaag ggattctaga aatttcctgc 92160
tgtgccaggc tgcagcagag actccggccc caccaggctt cctgtacttg gtgataaaca 92220
caccatccgc actgcctgcg gctcttacag gaatctctcg tgcaccattg ctcaaccccc 92280
gagagttatg gaaggaaggg aggctggggt gggtgccccg agtgccttgt tggagtggag 92340
gctggcgctg ccctgcccca cagggtggct ggcagggctc agcagttgcc tggcctgtgg 92400
gggcagagga cctggggaga catgctgagc cctcccagcg agacactgag ggtcgggagg 92460
gtaacatgtg attttgaggc cacccgctac agcttcttgg gacctccttc tctcaggcgg 92520

-continued

```
gtctggaacc caacagagct ggtttgggcc acagcagtgg cttcccaggc tgggcttcaa  92580
aaccggacac agggcgtggc tctccctccc agcctgccag agggaccgct gggcctatct  92640
ccagccacgt gggtcgcgag agtcgacctg ggctgcgtga tgggggaccc caggctgggc  92700
ggcttaaacc gtggaggtcg ccctctcaca gctctggacg atggagggcc gagacccagg  92760
tgtgggcagg gctggttctt ctgaggcccc tcccggcttc tgagggtggc tagcaactgt  92820
cttctagatg tagtacccca atcccccca gtccctccct ttacctcaca gggcatcctc  92880
cctgcgtgtg agtctggagc caaatttctc ctctatgtaa ggacaccagt cttactggat  92940
tggaggctac cctactccac tgtgaccccc ctcctaactg atcatatctg cagggacccc  93000
atttccaaac aaggtcttac tctgagtact ggggattagg gcttcatcat atgaatttga  93060
gggcaaccca ggggtctcca aaccatggcc cacagggtgg ctccctgtgt gtgtaaataa  93120
agctttatta gcacacagca ccacatactt gagggcctaa tgcctctggc tgctttgtgc  93180
catggcagat ttgagtcctg ccatggagac catgcagccc acagggccta agatttctac  93240
tacctgacct tccaggaaag gtttgccacg ctatttattt agcaggataa ttttggaaag  93300
agcagttgct aggggcattt aaacttgcag tcgaattagt aacaatttta tttttgggga  93360
aaatagaagt gggagagcgt gtgccccggg ccagcccacc gtgccccacg tttctacagt  93420
gcccaggttg gcgcagggcc ttttggttcc acagtctgtg tctttcttcc tgggtgtctg  93480
aattttgatt taatctcagg cttgtcagaa cgagcagctc ccaggcaccc tctgccaggt  93540
cagcagtggc tttcatcttc tgccatttgc tctgcacgtt tctctctata tgcaaaaacc  93600
tatatgggtt ttgtggggtt ttttgttgtt ggttttttat ttttattttt ttgagagaga  93660
gagggtcttg ctgtgttgcc caggttggag agtagtggca tactcacggc tcactgcagc  93720
ctcggcctcc tggcctcaag tgttcccact tcagcctcct gagcagctgg gactgtgggt  93780
gcgtgccacc atgccccgct aatttttgta ttttttgtag agatagggtt ttgccatgtt  93840
acctaggctg gtcttaaact cctgagttca aacaatcctc ccacctcggc caacccaaag  93900
tgctgagatt ataggcatga accactgcac tcagcctgct ttgtttttat cctgagtcat  93960
ttgagagtaa gttggaggca gtatgaccgt ttctccgtat aaagcccgtg tatatcctct  94020
ggaatgagga ccttcaactt agccagggtg tccgactctc aggacaccgc tgtccatttc  94080
acagcctgca tttaaggctc gtcactggtc ccagtgagtg tggctggttt tttctcattg  94140
cacatggctg tcacgcggtt tcagcttctt tgacctggag cagccctgcc cggccttccc  94200
ttcttggtct ctctcttggg cagggaaggg cggtggacat ggaggcttgg ggacagtccc  94260
ctggccccac ggatgttgtg tggacgagtt ggagggctca caggcccctc cgtggggccc  94320
agggcagagg cagcaggcag gctgtctcca ccacgatgga catcatttat gccccagcca  94380
ggtcccctgt cccaggaccg cggttgacag ggtttggatt ggctgcgttc ctgtctgaag  94440
gcagctgctt gggaggagga cagctgacat tctttcatgc gaaatctgct tgcgggagag  94500
tcgtgaaagt gggaatcctg ggctggaacc ggaacgttcc ccgagtacat aggaatcctg  94560
ggctggaacc ggaaacttcc ctgagtatac ggggccttgt gtgtggaggg gccctacggt  94620
gaatcgtttt ctgtaacaaa ggcttcctct gtgcagccca cacacgggcc tcacgttatc  94680
ttctgcaggc cagaattgtc atatatatca agtttgttca gaacaagatg gggtggggtg  94740
gggggcagtg aggggcctgg ggcaggaggt agaggaaact gcaagatttt ttaaaccttc  94800
tccaaaaaca cgtaacccga ttctgtccaa gcgatttgtg agaatggggt tgacacccct  94860
gggctggaac ctgggaacca ccagtcagcg tctttcctcc agggaggctg tgcagaggga  94920
```

aggcagtgag ccccacctgg gtttgaggaa cctggggctt caagggaggc ggtctcagcc 94980
catggtgctc cggccagggg tggggcagcc gaggcatgag tggacgatgt cccgtcggca 95040
gcccgtggtc cctctggggg gcaaggtgcc tgttccccat tgctcctcca ccagaacacc 95100
tcctccagat ctccgccagg tgcgcccccct gaaggaaaag gggatggggg cctggctcgt 95160
gcctggtggc aagtcctctt gggccccaga aagaccccat aatggccagg tagaagctcc 95220
tacctgctgc tgcctgaaga gtctggggcc ctgtcggctg gttccatcgt cttccctgtt 95280
ttcaagctac aggagcgcaa tctttccaga gcattgagtg gctagaggaa cgggcttacg 95340
ctaggcaggc gctggcatct tagacaatac ctgacatctt tgcgggagct ctggtgagag 95400
gccccacaag cgtgtgaccc tgtgcggact ccaccgcggc agcctgggag ccaagccgat 95460
ggctgtgctg gccgaaggga acaccgccat ggtgctctgc tctctgcagc cctgggtctg 95520
gttggaagtt gcatccctgg tgaagggcgg ccgcggcttt ccagctctcc caggccagtt 95580
cccgtgtttt ctctcccgcc ttccccatag tccaggacaa aagtcagacc ttggtggggg 95640
gtgcgcctgc tgcaggggcc cccaggcttc tccattcggg tttagtggga ttagagtgtg 95700
cggccatggg gacaggtgtt tcctttatgt tctgcctgag ggctggaaag agcctcatca 95760
gtgagtgcca cgttcggtgg gggtctctgg tgcaggggag ccggcgggcc gggttgggtt 95820
atgtccttgt tttcacatct gaccctggcc agctggagag cctcgcttga agcgcagggc 95880
agcagctgac acaacacaac gggaacgggc tgagcaggcc gggcgcaggc aggcttgggg 95940
gagctggcac tggcactgca cgtggggctc ctagggggct gctagggaag tcattggggg 96000
ataataggat ccaccctgtg ggcccactg gccatggagt actgcacagt ggggtccacc 96060
cgctgtgtcc ctgaacaagg aggtagcctg aggtctcctc tgacgctggg cagcagcctg 96120
gggaggaggc tgggcaggtg ccaggggaac cccctagagg gcattacatt cagatgagtt 96180
ctaattatgt tcttggcttc ccaggtcaca cagagtgaaa accagaggcc ctggccgtgc 96240
accattgaag tgtgtcatca tgtgactttg caggttgggg ggacagggct cggtgcggcc 96300
tcacggggtc aggagccacg gctcgagcac ctcggatccc agccccctgt tcagggccag 96360
gcctagacag ctcttcccac gagattttct ttctcccggg tataaaactg gccaacggga 96420
tgcctggtgg gatgactggg gtacctgggg ccaggggcgg ccagcagcct cctcagtagc 96480
ttgtgggaga tgctctcaac cccaaggtca gctccagctg gcctcaggag gagtggatgt 96540
tcccttcagg tgtctttagg accctggcaa ctggggacaa tagtctcctc cccaaatatg 96600
cagtcttgac tcctggccac ttgggaaggt gcgttctggt cctctgggcc tcacagcttt 96660
gtgccctcta gggtggcaat gggaggcaga gagcacagcc tggggacttg ctgtgagggg 96720
actgcattta gatttttagg tgaagccaat ccctgttggg ctgagaaaag tcctgggcgg 96780
ctgtgagctg gtggtgagtt ttccagactt ggtcatggtc aaggtagttg aagtcggggg 96840
ttgaaaaaca cactcgtgtc cagcccagat gccttatgga gaagaggatg cacaggcaca 96900
cacgcacaga catatgtgca cggatgggcg tgtggacgta tgcacacata ggtacccatg 96960
tggacacact cacgtgtgtg tgcacgttca ggctcagaca cgtgcctgca tgcacacgtg 97020
cacacgtgca cacccagccc tggacctcag gcaggcaggg agagagaccc ccttggggcc 97080
gcgttccatt tgcacattta atccagaaac tgtcagcatg ggaagcctgg atgagaacaa 97140
aatgtcaagt gtgtgccgag aggcgcaggc cagccccttt tcctggcggg gcgatgatct 97200
ggtcagtttc cgagcaccat gtgctgagaa tgatgcgtgc attcagagca gcatttggtg 97260

-continued gggaacctgg gggaagggcg ggcgtcttta tttcatttta gctttcttta gcggggcctg 97320
tgtctcttct cactgaccgt tttctgaaac tggctgggga gggtcaggga tggctgctgt 97380
cctcggggga gggactgagc tgggcccttt tcgttggtta gttctcagtg tggcctaccc 97440
agccaggtcc ctggacctgg cggtggctat gaaagcctgg gattgaggac aaagccatgg 97500
ggacgccgtt ttcgggatgc ttgtgagcag ggctttgtcc ccaccgttag gatactctga 97560
acgttcccag aaagcccccct tctgctcaag ttctcttgct tcatctcagg ctcaggtgtt 97620
ttgagttttt tttttttttt taaatgagga catctgttag accacttagg agttctagaa 97680
cctttggaaa accccctctc atcccgggag tttgtaagaa tttgtagttt ctccccagag 97740
ttcatggagc cccctgtcaga ggcgctgagg cccaggtcct gtggctggtc ctcgcataga 97800
catcagctaa gggggtttgg gggccagtcg gcagcctctg gaggcctctg cacccctcct 97860
gtgaaaggcc ggcgcagagc tgcaccgtgg ggtcccctgg cttggggtgg gcctcagagg 97920
ctgtcgccgt gcctgctgtg gctctccatg gccctggagc ctgggattgc agaaagactc 97980
ccagaccttg ctggggaaac tccaggatat gggggtatcc agactcctga gacttccccg 98040
tgggtccaca cacgtcacca atcctctctg cacctcagct tcctcatgtg tgaaattcag 98100
gtcatatcag gacctcagtt cctggggctg tgccgagggt gtggggacat tgggcatgaa 98160
ggttctcagt ccagagccaa tggccaagag ggcaaaaggg tgttggtgga cgatgcctcc 98220
tcccctggcg ggggcgggga aggaagtgct gggggaagcc ggtgtaaggg gccccgtgcc 98280
caccaaaggc gcgctaattg cgaaggaggg gcctcagcca ggaaccgcca tagcctcagt 98340
tttatttatt ctgctcactc aaacaaaaaa tcagctttgt tgaggtataa ttggcataga 98400
gtggaaggcc ttgtttaaaa tgtaggattt gacaaatctg gacatgggtg tacgccacag 98460
gaccatcacc acaattgaga cagcaggcac atccgtcacc cccagaaggt tctcgctccc 98520
gtcgctggcc cctcctccgc tgctcctggc tccggagggg acccctggtc tgtcttgtca 98580
gtgtagacgg ttggcgtttt ctggggcttg ttgtcagtgc aatcatacag tgtgtggttt 98640
ttattgtctg gttccatatt tgagagtcat ccaggctgtg gcatgtaata attcattcct 98700
ttttcattgc tgagccgtat cccattgtac ggacgcattg cagtctgttt atccacttgt 98760
gtgctggcgg actctgtata aaagtgtttg tagggactta tatttccttt ctgcatgggt 98820
aaatacctag gtatagaatg gctggataat gtggtgagtg tatattttta actatttaag 98880
aaactggcta actcatcaac ccttgacgtg gtccgtcatt ttcatgttag ccagtctaag 98940
aggtgtgcgt ggcatcctgc tgtggtttta actttcattt cctaaggacc agtgatgttg 99000
aatatctttt cacgtgtttc attggcatcc aggaaacatc tttggtgaca tatcttttta 99060
aatgtttcac ccattgtaaa attgggctgt ttgtcatctg agttgtaaaa gttctttgta 99120
tattctggtt acatagatat ttgttttaca catgtattct ctagtcggtg gctttccttt 99180
tcatttattt agtagtatct tttttttttg tttgagactg ggtcatgcac tgtgctcagg 99240
ctggagtgca gtggcgtaaa cgtagctcac tgcaacctcg aattcctggg ctccgaggat 99300
cctcccacct cagcctccca agtagctggg actataggca tgtgccacca caggtgctaa 99360
ctttttaaag ttcttgtaca gacagggtct cactttgttg cccaggctgg tgtcaaactc 99420
ctggcctcaa gcaatcccct tgcctcggcc tcccaaagcg ctggaattac aggtgtgagc 99480
cactgctcca ggcccaatag tatcttttaa agaccaaaca ttttcaattt tatgaagtca 99540
aatatagctt tttcctttta aatatgtttc atgcttttca cattctattt aggaaatgct 99600
taccaaacac actcttacta agattttctg ctagtagttt tataattttt gtgcttacct 99660

```
ttaggcctag gatgcatttt gagttaattt ttctctatca tgtaagacat aggcggagat  99720
tcatgtgttt tttcttatgg atgactgact ggtccagtgt catttgttga aaagagtatc  99780
ctttacccag tgaatcatct tgactccttt taagaggttc agtttatcat aaaattgtct  99840
ctttctggac actctactgt gatccgttga tctgtccttt tgccagtcac acactgggat  99900
tgttacagcc ctataatacg gttaaaataa gttagggtaa tttagccaac tttgttttgc  99960
tatttcaagt tgtgttggtt gttcggggtc ctttgcattt acatataaat tttggaagct 100020
gcttaccaat ttttgcaaag cctggtagaa ttttgtttgg gattgcattc aacctaaaga 100080
tcaacatggg gagaattgat gtcttaacca atattgaatc ctctgatcaa tgagattatc 100140
tatctcatat atatatatgt gtgtgtgtgt atatatatgt gtatatatgt atatatatgt 100200
gtatatatac gtatatatgt gtatatatct atgtatatat atgtgtatgt atatgtatat 100260
atatgtgtat atatatgtgt atatatatgt gtgtatatat atgtgtgtat atatatatat 100320
ggttacatac ctaatatgta tatggttata tatctcttat aagggttata tatctcatat 100380
acatatgagg ttatatacca cttatttaga tttttaactt ctgtcagaga tgtttcatag 100440
tttttagtgt ataggttgta catcttttga gatacctaag tgtttcatat tttttatgct 100500
atggtcaatg gtatttcttc taatctagaa ctgaaattca ttttgacaaa tttatcttga 100560
atcttgcaac ctttctaaac tcatttgttc cagtggcttt tgaaaaaatg aattccattg 100620
atttccttat atgaatgatg ttttctgaac atagagacag ttttacctct tttttttcaaa 100680
tgtggacgcc tatttgtttc tttttctggc ctgattgcac tgggcggctc atccactgca 100740
gtgtccaata caagtgaaca ctgctgtgtc cccagcctta gaagacacac atcattgttc 100800
accgtcaagg gtgatgttgg ctctgggttt ccatagatgt ctttaccagg ttaaggaaac 100860
gtcccctcta atactattgc tgagagcttt taatatgaat gggtgttaaa ttttgtcaaa 100920
tgctctttga tacatctttt gatatgatca tgtgctttct ctacttcagt ctcttaatat 100980
gataattaca ctgattcatt ttcacaggtt ctgtattcct ggataaacca cacttggtca 101040
tgctctagta ttctttttgt atatcattgg acttgacttg ttaaaatttt gctaacaacc 101100
tttgcatcta ggttcatgag ggatattgtc tatatatttt cttgtaacgt ctttggcttt 101160
ggtattagag taatgctggc atgaggagtg agttgggaag tgttctctct ccctttttaga 101220
ggtggagttt gtgtagaatt ggtcttattt cttccctctg tgtttggtgg actccatcag 101280
gaaagttgtt taggtaggcc tggactttgc ttgatgagaa gattgttaac tagattttaa 101340
attgacttaa tagttttatt caggtgattg ataatagtta tattcagttg attgataata 101400
attatattca ggtaattgat aatagttata ttcaggtgat tgataattat attcaggtga 101460
ttgataatag ttatagtcag gtgattgata attacattga ggtgattgat aggtgataat 101520
tatattcagg tgattggtaa ttatattcag gtgattgata attctattta ggtgattgat 101580
aattctattc aggtgattga taatagtggt attcaggtga ttgcttcttg agtgggcttt 101640
ggtattttgt gtatttgaaa gaatatgttc atttcatctg ggtgttaatt gtattggcat 101700
aaagtttttc agaatatcct gttactatcc tttaaacagc tatagaattt gtagcaatgt 101760
ctcttctctc attcctgata ctagtaattt gtgcctcttt ctttgttagt gtaatcagtc 101820
agctaaagtt ttagcaaatt tatggatctc aaagaatcag cttttggttt cattattttt 101880
tttctttttg gttatttgat taattttaat tattttattc tgcctactta gttttaattt 101940
gttctttttt ttctcgtttc ttaaggtgga agctgaggtc attgaataga aatttttttt 102000
```

-continued tcctttctaa tacaggcact tggtggtata aacatccaca aattttgtgt ttttttatcc 102060
catttaaaat attttctaat ttcctttttta acttcttctc tggtgtatgc attatttaaa 102120
agtgtattca aaacatttag ggattttcaa gatacctttc tgttactgat gtctaattta 102180
tttatggcta tagaaacact taatataatt tggtctctta aaatatatta agacttgatt 102240
tagggcccag aatatgattt atcttggtaa atactccatt gtgtgcttgg aaagagtgtg 102300
tactgctgtt gttgggagga ctgttctata aatgtcaatg agactaatgt ggttgatgat 102360
ggcattgtcc aagtctacat cagtaatgat acatccttac tgattttgta tctacttgtt 102420
ctattaattc attcttggga gaaggatgtt agaatctcca actgtatttg tggatttctc 102480
tcgttattct tcagttcttt attctttatt agttttttgt ttaatgtatt ttattttttg 102540
cttttgtcat ttaaaaaatt atttacattc tttattttttc atttttgtgg atacacaata 102600
gttgtacata tttatggagt acatatgata tttcaataca agtataccat gtgttcaatg 102660
tgttttgaag cttcgttctt gggtgcatta gcatttagga ttgttatgtc ctcttgagaa 102720
gtcaacacat ttgtcattat gaaactgcct ctttatccct ggccactttc tttgctctga 102780
aatctgcttt gtctgagatt aatatggcta ttctggcttt ttctttttat cattgttagc 102840
atggtatata ttttactcat ttactttcaa accatttgtg tctttagact caaaacttgt 102900
ttttcatatg aagcatatag ttgagtctta ttttgtgagt caaactattt ttctcctgaa 102960
aagtacagct aatttgcatt tattcatagg actgacattc ttggtctcaa ctctgtcatt 103020
gtcttttata attacgtgta ttttgtcacg gttgctgttg tagttttctt tacaatatgt 103080
gtattatttt cttttaaaaa catttgggta attaggaggt tgtattattt atttatttat 103140
ttttgcgaaa cagtttccct ctgttgccca ggctagagtg cagtggcatg atctcagctc 103200
actgaaaccc ccatctccca gggtttaagt gattttcgtg cctcagcctc ccaagtagct 103260
gggattatag gtgggcgcca ccacacctgg ctaatttttt ttgtattatt agtagagacg 103320
gcgtttcacc attttggcca ggctggtctt gaactcctga cctcaagtca tctgcccgcc 103380
tcagcctccc aaagtgctgg gatcacaggc atgagccacc gtgcccagcc tgtatttttg 103440
tcctaatagt tacctttata catatgcctt tcaaagtttc cttggtccct ggtttctcat 103500
ttaacccttt acagtctggc ttaccgtttt tattaatctg ccttaacttc tacttagtgc 103560
ctataccaca aacaataagc tgactccatt tccatctttt ataagttcag acccccacaa 103620
ccttgggtgg actactgact acttcgcggg taagaaatgg tgagtggcat ggaaggggag 103680
gggcggcagt tctcagtgga gcggccgggc tgcgagtctc tgtatggagg tgaaggtcca 103740
gatgttgggg tttcagggtc aagcattcct ggcagagagc atggcacgtg ccaagacccg 103800
gatggggcgt gtgcctggcg cgggtggagg gagctgtgag gagcctgtag cattcagaga 103860
caggggagca gggagcggtg ggggatgagg tcagggaggt ggcaggacct ggcgtgtgag 103920
ggcttggggc gactctgggg agttagggtt tcgctctgca tgacaggagc ctggggcctg 103980
gcatggtgtg actcagactt aacgccgccc ctctgactgg tagaggccag gcccaggata 104040
aggtggcggc aggcaggtct ctaagcagtg gcagctcaga cccgaggtcc cagggtcatg 104100
cgtgtttgtc ctgattgcac gagtcgtgtg agcacagaaa cgtaggtgga aagatggtgg 104160
cttcgtccag ggaggtagac tgggaacgtc ttttgctgct tcccttggat tttgtttctc 104220
aaagtctgaa tcaagcgtgg cagaagaaaa tacagcagaa catgggatgg gaatatccat 104280
gcgtataatc ggtcaggtta gttgctgtat tctgacttat ttgaaagatt tcatagcgaa 104340
caaagaaaaa ttccggtata actataattt ttccatagca gtttatattc cctttctcag 104400
ccttgtaggt gtaggtggag tgtcctaagc tctgggggtg gggggacacg tttacgtgtc 104460
tgcaaaccgc tacattctgc taagacatct caggagcccg ccaagccctt agtgaaaagt 104520
ttcttaaggc ggtttcatag gtgcgtgtgg ggctgttgga tacagtgacc cacttcaagg 104580
tgacatcttc ttcttgcatc tcagatagca ccaggtttgt gtgtttatgc gtgtgcacac 104640
acggtgttgg gctctggcgg tggcctgggg gtgcttaggc tgtgcacaaa tgcccacgca 104700
cgtacacaca cagacacaca gcctgacttg gcccaggtgg gtgggtgtct gaggagaagt 104760
tcgccattgt cgactttggg gtaaagtgag gacctgtctg gcgggaataa aggggcccta 104820
ctgtcccccg aataccactg ccccagccct cctgagcccc tgtgactgaa aaatcctcac 104880
tttggaggat gtttggtgac aggtgctggg gcccggacac gacctggttt cttcatccca 104940
ggggctgtct ccagggtggg ttctagagta catccagctt ccacccaagg gagagtggct 105000
gggtggagag gggcaggct gagatctgag aagccaggct agggggttgt ggagcaaatg 105060
atgatgtctc aaccatgtgg ctttaggtcc ccagcacgtg ctagtggcca tcagcaggct 105120
acagcatcca gccagtgcca ccaggagccc actggtgcca ggatgctggg gtggggctat 105180
ggggaaggaa gacatgtggg ccagggtgcg gggtgcggga caaacctggg tccaggcacc 105240
tggggcgacc ctccttggcc gtccttgcca tcctcgccat cctctctcca cacatctgac 105300
ctttgcctgc tttgggggca gtttgaggcc tcagattttc tacctcaaag cgatggaacc 105360
cagaagacat ggggccctcg aggagggtcc cccgggggct gcaaaagcag agggagtgga 105420
gtgtcaccgg gtgtcccggc gtgggcaggt cctgttgtgg agcctcgtga cctgctcata 105480
gcacagctgg gacacttcca gtgactgctc ttcgaggccc ggggtagggg ggtggggggg 105540
cctcctcctc ccaagcacct ggggtgggaa caagaggcgt tttgtgttct gcgtgggtgg 105600
ccctgggctc cccaggcctg gtgtgggggt gcctgggggg cagtggacgt gagcagcagc 105660
acgtggcccc cagtcatgag taccccaggc ccctatgcgc ctccttcccc atgactggcc 105720
ctgggtggcg gagagacccc tgggcaggac acccctccct ggcttttcct tctgcaccac 105780
tcaatctggg ggttccggct ccttgcccac cgcccccgcc acccagcgcg agccgcgtag 105840
aggagcagga agggagccag ctccacctcc agtagaccca gagacgggga ggccagggtg 105900
caggggactg tttgggcctc gagagggacg gaccccagaa ctggacccca atgtgcaggt 105960
ctgggtgtgg atgtatctgt atgtctttgc ggagctcaga tgagagatgc tcagagttgt 106020
ctgtagagaa ccagagccgc cgagcccggc ctggatggac atcccgcagg cagtgcacgt 106080
ccctcccccg cctctctttg ccgttgccgg gactgggccg tgtgcctgga gtttgaactt 106140
tcctgatcac ggggtgagag ggtctttgca gttgcagagc cgtggcgtgg cgcctggatt 106200
tccgacacac tgcagcatct gcatccttgc cgtcacccct cacacccccct gctaaggtcc 106260
ctctgggggt tgaatgaaaa ggcataggta gaaggtggga gaagcccacg ttctgggagc 106320
gtcgcagtgg cccagacacc catgttcctc cctaggcagc tccatgcgcg ggccccggag 106380
ctggaaagca gccaagggca ctgcccgccc tgggagctga tgcctgacat gcatcctcgc 106440
ctaggccaga gtgccaggca gggtagggga acaaatgcca acacgtgagc tgagtgaccg 106500
gaagaggggg cgcctccctg agcaggtgaa tgaagggtgc tggggtggcg agttgagggc 106560
caacagagat ggtgtcccgg ctgatgtagg gtcaggggct tctggaagga gcctcacagg 106620
aagggcaggg cagcaccagg ctcagcccag gaccagagcg caaatagggc tggagtcccg 106680
agtacaaggc atggacagga gccaggcttc acctagcacc tggctccccg ggggcccaga 106740
tggcaggcga ggggtgcctg gggaggctgc caagtgaggg gggggcacag actgagacag 106800
ggtccccgtg ttccatccat ggggtacagc tgctcccagg ccagactctg gcggtagcag 106860
gaggcagggg aggctgtgct gagctcagtg ggtttggtgg ggtcatagct gcctctccct 106920
ctaaatagat taactaaaaa gtattgttga ctgactcatg catttcttag gttttcttat 106980
tttctaattt cttcttttaa atttaggttt gtcgaggttt aagttacata caggaaaact 107040
ctccccctct gtagatgtcc agttcgatga gtcctggcaa acatttatgg tcctgtaacc 107100
acccccaaag tcaagatcca aggtgttccc atcacccgaa agctccctgg tacccactgg 107160
cggctagccc ctccccgcac ctgggaaccg tggacgtgtt tcctgtcccc atggttttgc 107220
cttttccaga acgtcatgtg aatggaatct cgcggcgtgt agcctctgcg cctggcttct 107280
gtcacttagc ataattcatt tgaggcccat ccgtgtcatg gtctctgcat tcagcagttt 107340
gtctcctttt atttggaaag gataaaatgt accacagttt gtttatccat tcacaggctg 107400
atggacattt gagctgtctc cagttttcag ctgttatgat taaagctgcc atgaatattg 107460
cgtgcagttt tttgagtaat catatgtctt catttctctg gggtaaatcc ctgggagtgg 107520
gattgcggga tcatgtgtta gatgcatatt ttcctttcga agaaactgcc aaagcatttt 107580
gcaaaatggt aggcccgttt tccactctta ccatcaatgt acgagcattc tggctcctat 107640
ggattctcac cagcacttag tattgtctgc tttttaagct ttgcccatcc taaaggctgg 107700
agccatattc cgtcatggtc ttcatttgca tttccctagt gacgaatggt gttgggcata 107760
tttgccattc atatatctcc tttgatagag gatctgtcca gtttgttgct ggttttaaca 107820
attaggttgt cttcttagaa taatcatgtg agttgtaaga gttgtgtcta tgttctggat 107880
atgagtcctt caccagatct gttttacaaa tatttttctcc cagtcatggc tttgtctttg 107940
cattttctta acaggatctt tcaaaagagc agcagttttt aattttgatg aagttcaatt 108000
catcagggtt cttctttttt tttttcttta gggttcatgt tctttgtgtt ctgtctaaga 108060
aatattcgcc taatccaaga ttacaaagtt ttttctcctg ttttctgtag aaattttata 108120
gtttcacatt tcttgtttag atctgtgatt catttcgagt ttaattttat atatggtgac 108180
aggtatggat ggaggttaaa tctttctgca tgtggttatc cagttgtccc agagactttt 108240
ttcccattga attactttgg cacctttgat gaaaatcagt tggccgtgtg tgtgggttcg 108300
atttctggac tttgtcatct gttctgccag gaaagcactg tcttgattac tgtgactttt 108360
atgctaagcc ttgaaatcag gtcctgttaa tcctccaatt ttgttcattt tcaagagtga 108420
gctgttctgc cagctccttc acattctcat gaatatctta gaatcagctc gtcaattcta 108480
ccaaaaaaaa aattggctag aattttgatt ggcattgcat tggatatgta gataaatttg 108540
gatctcatac acgtcttagt aataccgagt tttctgatcc acgaacacgg tctctctccc 108600
cagtgcctca tgcacgtctt agtaataccg agttttccga tccacgaaca cggtctcgct 108660
ccccagtgcc tcatgcacgt cttagtaata ccgagttttc cgatccacga acactgtctc 108720
gctccccagt gcctcatgca cgtcttagta ataccgagtt ttctgatcca cgaacacggt 108780
cttgctcccc ggtgtcttag atatttttca acaccactca tcaggattgt gtaattttta 108840
gtggtgtgaa acttgctaga tttgttccta agtattttat gtttttgaag ctactgaaat 108900
gatattgttt tctcagtttc acttttggat tatttgttgc taggatatag aaatacaatt 108960
gatttgttcg tatattaacc ttgcgtcctg tgactttgct catgttactt attagtttga 109020
gaaggtttct tgttcatctg ttttgggggt tttttttgtt tttttttttt ttgtttttttt 109080 gtagattctt taggattttc tatggagatg attgtgttgt ccacaattaa gtcagtctta 109140

-continued tttttgcctt ttcagtccat atactattta tttcttgttt ttacttgaat gcacctgaca 109200
gtgtctgcca gtggggagag ggctgctatc cttatcttac tcctaaggtg aagtgaggta 109260
atctttcacc attaggtgtg gtgggagctg tagggtttta gtagaagcca cttatcaggc 109320
caagaagttc ctcctcttcc tggtttgctg ggaatagaga gtgcgtcaag aatagctgtt 109380
ggattttttg acaagtgctc cttctgcctc tattgagata atcatatcat ttgcaacaat 109440
ctcaatcaaa ttctttctta atttgctagt gtggggaatc gcactgattg actttcaaat 109500
agcaaagcaa acttgcttcc cttacacaaa gcccacttgg tcatgatgaa tttttatttt 109560
attttatttt atttatttat ttatttattt tatatgtatt tgtacttttt taaatttttt 109620
attttttga gatggagtct tggtcttttt gcccaagctg gagcgcaatg gcgtgatctc 109680
ggctcactgc agcctctgcc tcccaggctc aagtgattct cctgcctcag cctcccgagt 109740
agctgggatt acaggcgccc gccaccacac ccagctaatt tttgtatttt taggtagaga 109800
tagggtttca ccatgttggc cagggtggtc ttgaactcct gacctcaggt gatctgcccg 109860
ccttgacctt ccaaagtgct gggattacaa gcgtgagcca ccatgcccag ctgtcatgat 109920
gcgttttaaa acaccttttt ggatgtgact gacttcggtt gtgtgtagaa cttccacgcc 109980
cacgctcacg agggcgtcac ctgccatgtg ttggctgttg tgtctggttt tggcatcaga 110040
tgccgctggc atcagagaat gagttgggaa atatttcctg ctcttcaatt tttaggaaga 110100
gtttgtgtag aattgcaatt atttctccct taaacatttg atagctagaa catgtggagg 110160
tatctgggcc tggagttttc tttgtggaga agtttgccat tggaaagtca gcagatacag 110220
ggctatgcag gttgtctatt tcttcttgat gaggttttga ttgttcatgt ctttgaaagt 110280
atttgtcccc aaggagcaga agccccagcc caaatttgga aacaagacca tgttgtgctg 110340
acatgtcatt cctgagcagc ttaggggctg tggggtttgc agacctctga atgcagccat 110400
ctgcaggggg accctcctca gtgccctgag agggggcctg ggctgggtgg tctctgctgc 110460
tggccatccc actgggcact gcctccccag ggattctgca acaggacacc gtaaggggca 110520
cgggggacaa agatcagact ttctctgttt ccttccagct ttgctcccca gggaggcagt 110580
cccttctcag aggaatgaaa tttaagaaga caggccctac aatttcacga caagtctgct 110640
tttgactctc ccgtttactg tgtaaacttc agccctaaaa caacatacat ccttctgaag 110700
ttgttcacat attagctctt aaaacagcaa aatccgtgca caatttcctc tcaatccctt 110760
aaaacattcc tgaaaggggg ggaaaacaac tgtttaaatt caccgcctgt tattaaaatc 110820
tctagatttg cagaatcaga gtgaggtact cagcagtcag aaaacagact agacaggccc 110880
gtgtgcacac acgcgctgac acacgtgcac acacacacgt ccacagggca gcctttaata 110940
accgcaggcc ttcctgtccc aacactgcgc gggcccctga agggccggtg tgggttgcag 111000
ctcctcaatc tctgctaaag taaacagggt tcaaccctgc ggccttctca gcactctccc 111060
caagtcaaaa gaagggtgct cagcccctgg tctctttggt ttgccaaact tctagtgctg 111120
gtgaaattct taaatatgac atttttagaa gcttcggctc ctggcagata aaaataatgt 111180
cccccgctcc accccctttt ccccctatcc cagttctagc taagacagtg atcagagggg 111240
tgcaccgtct ttggggttaa cagccatcag cagtggggtt cccaggctga aactaaatcc 111300
tcgtttaact ggcctggaga cggaaacagc cctgcctggg gaagatgggg gatttgcttt 111360
aaatacgtgt aaagctgcct gccaggcggc taatggtgtc tgcagccagg cgtgggcgtc 111420
tccgggccat gggctccccc accacaaatt gcagggcagc cggcttgggc cactcctgtg 111480

-continued tgtgcggggc cctgggtatg attcctggga ggcagctccc aaactgtggg gctcagcaga 111540
ggattcaggg cctgatttgc aggcagcccc acctgccttt ttgactgttc agagccctga 111600
gtgcctccca tatgcccaca ttttcctgcc cctgggcctt ttcttctggt catcggcctg 111660
gagtgcctcc actggcacat tgagttctgc cttcagagcc tgggttttct ggtggaatgg 111720
ggcaggggta ggctgataga cctcttggag agacagggcc cactttcttg taggcccaca 111780
gggaccccgc ctggggagag agaagcttca ggccctgagg cctatggcct ggacctctct 111840
agagacccta gaacagacct ctggcctggc cttgctgatg acctggagcc cctgggtgcc 111900
agctgcagcc ccctgcctgt ccaggagtct gagctccagg tatcagcgag gtgggttcgt 111960
tctgaggctg tgagggagtg ttccaggcct cccccagcta ctgtggaagg gttcccggtc 112020
gacgcatcgc accagaccct gcctccgcct ccatacagtg ccccccggcc tgcaagtcca 112080
tgtccaggtt tcccgtttga taagaacacc agttgtatgg gaataggggc ccaccctaac 112140
cacctcatct tacctaatag catctgcagc aaccctattt ccaaacaagg tcacactctg 112200
aggtgtgctg gagggtctag gacctcaaca tatgaatttg cggggcgggg gacacagttt 112260
agccggtagg aatacctacc tgtcagagga ttctttaatc caagggtccg taaaccatag 112320
cctacaaacc tggctgctga tctgtataaa taagatttga ttagcacacg gccacgtgtg 112380
cttgtgaaca tctcatctct ggctgttttt gtgctataac agcacaaaat tgtctgctgg 112440
agttgttgca acagaaatcg cgtggcctgc aaagcctaaa atatttacta tctggcttta 112500
gagaaaaagc ttgtcaagcc ctgttctaaa ctatgaagac aatgttggag gttgctttct 112560
atacccacag agccgttgat ggggtgaagg gagaggggtg aaatgcagtc acacgcaaat 112620
tcttatcttc ctgaggagaa agccttaggg agcccactac agtggacact gtctttagag 112680
agtagcagac ctggctgtga gtttgaggaa ccagtgaaat gagagttcag tgacatcctc 112740
aacttcatga ggatcagaac atggataaca tgtggctcaa ctaaacaacc aaaagcaaaa 112800
gggagaagtc aacagagtca aatagcaaat ataaggacag aaagagtcaa atcaaatgcc 112860
tccaacttca caccaaatgt aaatcgcctg aattcctctt tgaaagacag agaaggccgt 112920
gccgtagctc tgggctttta tcttttaaca aatacattgc tcagcagcat taagtaaggc 112980
aaagcaataa tgggtggttg aaaaataaag gaatggccaa agagaggcca agaaactgca 113040
agctaaaaga agaaaaggag agaaaaaaca gggagatcag gatgaatatc aacactgaag 113100
cccaaacaag acaagtgtga atgagatcag gcactattag aagacctgac tgtaatcttt 113160
aaggcatcat acaacataaa atacataaag caaaaactat tgaaaatctg caaggacagg 113220
aaggttaaat atgataacgg gaggagattt taatgtacct cttttggaat aggacagttc 113280
tagtgggcac aaaataagtg aggacatgga caggtaaatg ttgtaatcat gagcaatttc 113340
agattctaac agtaatttga aataactcct gttcttgtta tctatagcca tgtaacaaac 113400
catccacaaa tctagcacct tcaaaatacg catcacgcct gagctcgcta gcctacagtc 113460
tggcagggct cagtgggacg gctcatctcc cctctgcata gtatcagctg gggctggagc 113520
ctccacagca ttgcatctac atggctggta aggctcctgt tcatgagggc ttctccaagg 113580
ctgcatggat tcctcacatc tcagaaatga acagtccagg agacaggcag tgccagggac 113640
tgagagccac ctggctgtat tctcctgatg caggtgtcac agagcccagg ttcagttggg 113700
gaggactggc aaagaacttc ataggactgt gctttaaaac cagcactatc acttcgaacc 113760
ctagtaatgg agttgttttg ttcccttatg tctgcggaac acttacaaaa ccaatcattc 113820
atgtggctac aaacaaatct aacctacctc aaaaaattga gatttaactg gccatgttct 113880
ctgatcaaaa cccaatatca tgagaaataa atgattaaaa gattggggaa gaaaaatccc 113940
ttacctattt gggaattaaa caacactctc ctaaatagcc agaaagaaga gattgatgtg 114000
ggaagtgcgg gccctgtagg gcgttatgag acgtaggccc cgctgcctgc cccagcccgt 114060
acatcactcc agctgccccc cagcaccaac tgtagatgct tttattttgt aaattccatg 114120
ccagtgccca catcgcttgc tggtggcttc actgtgtttg caaatgttgt cccccacgtg 114180
gattgaaatt catctattgc ctgaaagtaa tgaagtatgt gccttgcaca ctgtgtaagc 114240
atacgtgttt attcagtgcg tcctgggttc tcaccccttg ccaggtgatg ggttgattca 114300
gtgtgctggg ggtctccagg cgggggggtc cacatagttt ttgcttcatc agaatctgct 114360
gataagccca gttcggagca gagactagat gggccagcct gtgggcactc tgcctagcgc 114420
catctgcctc tcccacccca ggcaggtgtc aggtggctgc tgcgccctgt gtccgcctcc 114480
tgaccttgag aacacccagg tgggggagga agtgggccgc gcttcgggaa cccccacccc 114540
gccggcttgc gcagcgagct gggtcccagg gctggaggca cctcattaaa ccgcctgaaa 114600
cgtgtgtaac tctagtcggc ccccgtaagg caccggcagt acatgtgaaa ttaaaattac 114660
tgagaggccc cactctcctc ccctccatgg gtgggcagcc ttcatgggga ggccaaggcc 114720
cggaagccgg cagtcctggg aaagatttgg ccccaatgat aatgggccca agaatgtgct 114780
aggcccaggg tgtggtccaa gttcctttct tagctaaccc ctccaccctg agaagcctcc 114840
cccactacac ccacacatgg ggccagctgc cttgagcacc tcctgctcag acccaggtga 114900
ggtacctgag tgacaaatgt caagagtttg cagttactcc cagagctacg gacaaggggc 114960
aaggtggggc tggaggcacc ggctcagcaa gaggggtcac ttgagccttg gcctgcaggg 115020
aggttttgct caaggagtgt cccttgagca aaatattgca ctttcgttgc tctctgaaag 115080
cctaccaggc agtcttccca gaggtgcttc ccgggaagcc cgtggagagg atgcattcga 115140
cacccaaggc cttatggaat cagtcctggg gcctggaggg tcgtagagaa atgtgtgaac 115200
atggctcccc ttaggccagg ggtagacgca ggcacaggga ggatcaggaa agccctggat 115260
cttgttgaca ccccgggatg tgcccttgtg gctacttaga cgtagagccc ggggcagggg 115320
gagggccagc ccctgtggtt ttagcctcct gagagtctcc ccagacagcc cacaggggac 115380
actgggcctc atgccgcctg tcaggatggt gtccgggatg tggggaccag acgacagctg 115440
tcacccactt gcagggcccg gctgcccggt ggatgggaac ggccatcccc atgacgaccc 115500
agcaagtccc ttgcctctct cgctcaccag gaagaagaca cgtccgggca gctggcaggt 115560
ggggctagtt ctggagggaa agcggcctcg tgcctcccag agtcaccccg aaatcattaa 115620
cggggagaca agcacacaga gcagctggcc gattgcagct ctgaaggtca gagatggccg 115680
ccagctgtgg gaaggcctgt ggctagggct ctgctgcctg cttcctgggc aggggctcct 115740
tcctccctct ctgtctctgg ggtcccatgg gaagtcaggg tggggcctgg tgtgtggctt 115800
ccgctggttt cctgggtgtg tcttcctgca gggccaggac ccccagagtg ttccagtgac 115860
ttcagagagg ggcagccaga ccaggaggag ctccagaggt gccctgtggg gagaggcagc 115920
gtcccaaaca cgggggaggg ggtaccgcca gcctggggac agatagcagc atctcagcca 115980
tggggggccg tgacatccgg tcaggagggg gttagcatct cagacatggg ggggagatgt 116040
ccagcccagg ggaatgaggg gggtgatgtc catcctgggg aggggtgaca tccatcctgg 116100
ggggacggag gcgtgacgtc catccttggg ggatgggggg gtgacgtcca tcctggggga 116160
gtgggggcgg tgacgtccat cctgggggag tgggggcggt gacgtccatc ctgagggaac 116220

-continued agggggtga cgtccatcct gggggaatgg ggggggtgac atccatcttg ggggtactgg 116280
ggggtggcgt ccatcctggg actggggggt gacgtccatc ctggggggac ggtgggggat 116340
gtccatcctg gggggacggg gggtgacgtc catcctgggg gcgggtgatg ttcatccttg 116400
ggggacgggg gaaggtgatg ttccttctgg gggggcgggg gggggtgacg tccatcctgg 116460
gggagacagt aacatcccaa acatggggga tgatgtccag agtgggggtc ttcaggtctt 116520
tacgggcccc tcagcctccc cttccacacc ccaagtacag cacccacaag gcaggtgcct 116580
gggagggaga cacacctgtc ccctgcctga agtttctcag caggattttg ggcacaaggt 116640
gggtagtgag ctggtctcag cactgagctt gcaggtggag aaggcgggcc cctgacttta 116700
gggcgctctg ggtgggatga ggacagacgt ggaggaaagg agggatccca gcagaggcag 116760
cagtggatgg gggagggctt caccgcaggg agagtgaggc tgcgcggtgc cctgcaggac 116820
agataggaac tcccaggcct gtaatcccag cactttggga ggccgaggcg ggcggatcac 116880
gaggtcagga gatcgagacc atcctggcta acacggtgaa accccgtctc tactaaaaat 116940
acaaaaaatt agccgggcga ggtggcgggc gcctgtagtc ccagctactc gggaggctga 117000
ggcagtagaa tggtgtgaac cccagggggt ggagcctgca gtgagccgag attgcgccac 117060
tgcactccag cctgggcgac agcgagactc cgtctcaaaa aaaaaaaaaa agaaaaaaag 117120
aaaaaaaagg aactcccagg gtggagctgt ggacagatag gaacttccac agccaggaag 117180
gccaggtgac gtggagggcc ccaggcagct gggccagcac gggacggggc gtcaggtcag 117240
cggggctctt ctgtgctgtg tgcagcatga gagtctgtac cccacctgta ctcaggaccc 117300
tgccccccga ggacaaggtc gcttccctct tgagcacatg ggacaccacc ttcctgctac 117360
actattccca tgccctttcc acaggcccag gccactgttg tcatttcgcc ctccccacag 117420
tcctaggagg tgggcactgc tggtgcccca ttttacaggt gtggatgctg agcacagaga 117480
ggctgagctg ctcgtctggg tcccccgcct gggatgccac cagtgtcctc acaccagcct 117540
gctcctgccc tgtgcccatc ctcctcctgc ttagcgatcc tttctcttgc taatgtgtgg 117600
gacaaggggc tctcaggggg cctggccaag gtagcgggtc cccccaccat actcccagtg 117660
ccacccctgg ctgcctggag ctagctgtgc aggggcccag aagccctccc ctccgaggag 117720
gtgggcctgt tccaggctac cttgggcggg cagggccttg ggtggccagg gcctcaggag 117780
ggacacagag ggccccactc aaggtcacgg gctgcacgtt ccatggggcc tggggaagca 117840
gccgagcaga aggatgcagc ccgactaagg ctgcctcagg gtggcacccc agcggtgccc 117900
acactaaggg gacacttggc aggggagggg ctgtggcagg gcagggtcat gtccccagca 117960
gtaaggccag gacagggcag ccggaccccg actgtgccac cctcagccca gtggatggtg 118020
catctcacct gggcctggcc ggctgcactg tggcgcctgc cccaggccag gctaccttgg 118080
gcggggtggg gactggtact ccccgggggg tgggggtgag ggcggaggtg agtgtggatg 118140
aggccaccag ctgtgcccag cacgtcactg agggcccaca agctctcagc acaggctggc 118200
ggctgagagc agctggccac aggcaggccc tgggagcaaa gggcgctttg agctgcctga 118260
gtgcctgcat tgccctccgg ccagctgacc ctccccggag ccgaggctgg ctctctctgt 118320
ggcttatcag ggccgggccg gtgtggagtt ggaacagctg gccccaaagc ccgccagccg 118380
ggctctatgc tgtggggacc actgccccca cagggaagcg cctggctcag cacaggccca 118440
gccctctggc ttcctcgcta tgggaggggg tgagacccta atcccgggtc cccacagcac 118500
cctcagccta acccctgtgt ccacccctct tcagagtctc caggccccat cttggcctga 118560
tgaggcctca ttgtctccta aaaagtgtgg gtacagatct caggcttttc aagggtgggt 118620
ggattcctgg ctccagtgga aggtccccag gcctaagtct atgggggcgc cagggaggcc 118680
ggctgtgttt ctgcatcctt gaccctggcc ccttccacaa agctcagctc tgatccttcg 118740
tatttaatct tcatcttccg ccgtctttaa aattaatttt cctttaaaga tactgtagag 118800
cagtaacatc agagacacca aaatagacaa aagagataat agaagagtaa tatcagagac 118860
actaaagtcc tcgcgataag ggtctgcgag gcttccttta tgttttgcaa aaaaatctat 118920
atatttcatc cagagagaca ggatgtgagc gcagctggtc agaaccagtt atttcaggct 118980
gccctgtgat ctttcccacg tgattgattg acacagggac cttctctagg gtcctaaatt 119040
atgtggttcc agcagcatgg aacttcaaaa cacattgaac cccagaaaat cttcgctatg 119100
ttggagattc gccggctgat aaaagcaaaa caatagataa gatggccagg tcgaccttca 119160
gccttctcgg agaacaccgg ttccacggcc ggttgcaaca cgtttgagcc aaagtgcgac 119220
ctttccccgc tctgttcact cggagactaa aaatcccaga taagcacctg ctttgctaga 119280
cccttgctgg ccctccggct tcgggcaggt ctcctcttta tgccactgta accccacaac 119340
accggatacc agcatggggc cggcctgcgg ggccatgtgt ctcctcctgt gtgaccttga 119400
gctaccttga gcttccattt tccttccgca ccatgcactg atttccccctg ggttgaggtt 119460
gagggtccca gggtctgtct gcctaatgac aagatttcag taccaatagc gaagccgtca 119520
gtggcagtga ctgtgcctta gggtgtcccg ttggcatcca gggcccccca tgaaggatgg 119580
caccgagcac cattcaacat aagtcttgtc agcgttccga tgaaacaaga ttaggggaat 119640
tttacagctt gcctgtgttt ttccacccag ggccctttgc actgcctgct atttgttttc 119700
tgtcttcatc ctgagagggc tcaaggtctg catgccattt tgcaattgac aaatggcttg 119760
tgcttagcta tttcgttgaa tgctgaacta acaatagtca gtgaagatta agaactaaag 119820
gctcaaggac agctacagat gaccacagct ggagtgcggc agatactcgg ggccgctggg 119880
tggccctgaa ggcccacaga atccttttgg agacctgacc cgcgggagcc caggtgagca 119940
accgccacgg gccagggccc ctcgaggcac tcatttcagt atcagagaac acacataacg 120000
taaaattcac catttcagcc atttcagcca tttcagccat ttcacagcgt gcaatttggt 120060
ggcatttagt atgttcacaa ggcggttcag ccaacacctg tctccggttc cagagctttt 120120
tcatcacctc aaaaggaaaa ccatccccat tgcccttctc ctagttcctg acaaacatgt 120180
tctttttaaa cattatggtg aaatataagg ccaggcgcgg tgactcatgc ctgcaatccc 120240
agcactttgg aaggctgagg cgggcggatc acctgaggtc aggagtttga gaccagcctg 120300
gccaacatgg tgaaaccttg tctctactaa taatacaaaa agattagccg ggtgtggtgg 120360
tgggtgcctc taatccagct actcaggggg ctgaggcagg agaatcactt gaacctggga 120420
ggcagaggtt gcagtgagct gagatggtgc cactgcactc ctgcctgggc aacagagcaa 120480
gactctatct caaaataaaa taaaatggaa atatgtttta ccatcttaac cctttttaag 120540
atcacagttc cttgcgacca tcgccaccat ccagctccag agcttttttc atcttgcaaa 120600
actgatgaaa gtctgtcccc attaaacact cactccctac tccccccttcc ccagcccctg 120660
gcgcccatca tctactttct acctctgtga atctgatgac tgtagcgacc tcacgtgagt 120720
ggaagcagat agtatttgtc cttgtgtaac tggatcattt cactgagagt aatgtcttca 120780
aggttcctcc atgttgcagc ctgtgtgaga atccccttcc tttttaaggc caaatcctat 120840
tccgtggtag ggagggacca catcttccgt ctccgtcggt gcactgaggg acactgggct 120900
ggttcccctt tttggctgtt gtgaatgttg ctgctgtgga catgggtgtg tatggatctc 120960

```
ctttaaagag accggggaca gactccaaag tggaattgct gggtcataca gtaattctgt 121020
ttttttctg gcatgttatt taaacagact atttgttaga gcagttttag gttcacagca 121080
aaatcgagcg gctggtcatt tcacgcttta aaggagctgt ggcattctac atcccccagc 121140
agcacacaag gtcccaactt ctccggatcc ttgggagcac ttgtcactct gtttggggtg 121200
gcagccaccc taatggatga gaggtggcat ctcgttgtgg tcttgatttg catttccctg 121260
atgattagtg acactgggca cctctccgtg tgcctcttgg ccatctgtgt atcttcttca 121320
cagaaatgac tgtccaagcc ctttgcctat tttttaaaaa ttgagttgtt aggaactttg 121380
gtttttttaaa taattttaaa gcacacaaat aagacacctg agagccaact tataacacgc 121440
cccaggatgg acatggattc acactcatgg tagaacagag ctgagggtgc agtgtgggat 121500
gggctgactt gtggccaggg gaaagacccg tggcctatct tgttttgggg ggcagggacc 121560
cagaaactca ttgctttcag gccttgctag aaaagcatac agtcgaacga gtgggtccga 121620
tgtggagtgc agtggcatca gccaaggctc cgaggcgttt cttcccactt cacatgtctt 121680
ttctgttgtt tctgcgaagg tgtctcaggg aggggcagaa cccatggggt ttggcttcct 121740
gaccctgaac gtctttgtcc caggcccttc actgggtctg gaggaaggag ggtgctgtgg 121800
tcctggtggc tcttgtgcct gcacccgcct tggggccatc tgacacccac accctccctc 121860
caggccagac ccagctctcc agcttcccgg ctgcccacta gatgaccacc aaggcagggc 121920
ggctggtggt gctgacggct ctgtgaggcc caggcctgtc ttccccacct caccccacag 121980
ggctgagaca cctccctgtc ccctggcagg gctggaggct ctggagtctc tcttggttac 122040
cctctctctc ccagggccac ttttgcagcc tggtgtcctt atctcatgtc tgggtcccct 122100
ttgccaaggg tcctccagcc tttggcctgc acccactcat ctggcagtaa cagggccact 122160
tccagaacca ccaccatgcc caggtcatgt ctgtgcatga gagtggtcag ccctccatgg 122220
caggcctggc ctcacctgcc agtgtcctct cccacacccg aggacacctg taccttgtcc 122280
cggggcgggg ctctctctgc catggacgcc agtcttccct cccctaagct gcgggtgacc 122340
tgacctagtt gagcctggct ttcctcctct gtaaaatgtg aacagaggcc accaccccca 122400
ttatgtgggt ctgtgtttgc tctgtgcacg tctcggtgcc cagatctgag gccctttttgt 122460
ccatgaagcc atctgcagcc aggaggcggc cttgctttag tctgaaggag agtgaccagg 122520
gtaggagggg cctccttgtc cctttggtct gtttgtggtc tcagtggaga ccaaggacgg 122580
ctcttcttct cgtatctacg gggcagagct cagggccgca ctccatcagc atcccgggcc 122640
attgcatcct tgaccccggg gggcttgcag gcaccacata gatcttgtga gaggcgcttt 122700
gtggggctgg atgatcctgg gtgcccctca gagaaggccc tggggctggc cttgttatca 122760
gtgggggagt caggaagtac cccggttctg tacctgtagt ggatggggct ctcagaggga 122820
ttgggggtga tgggggtgct gagctggcct gagaagggtg gggtaaccta gggggtggag 122880
tgggggaggg agagagcact cctgacacag ggtcctgagg aggcaggggt gccccaggga 122940
atggggggca cctggggccc acgggaggct ctgggggaga ctgggcggtg agcccctggg 123000
aaggaggcct cagggacagc cctagactgt caccctcagt gtggacagca ggagctatgg 123060
cagctgcttg agcaaggtgg gcaagggaga agtaccaaat gtgtgcaggt tctggggagg 123120
agcttgaggc ccctttagtt cacctttgga acttaggacc aagtctgcaa atacagatga 123180
acccagggtt aggagggtgg ctggggcatc acccacctgg ggtctggact gctggaacca 123240
gggggaggca ggcctgccat tctgtgagcc tgctttagac tggggatgtg gtcccgtgaa 123300
tcaggggtgg gccatggcat ggcgtggggg accagccctc ctccctgtcc ccagctgagt 123360
```

```
gtgagctccc tggggtcttg ctgtggcctt ggccctgggt gttgtcccac acagcccagg 123420
agagcgtttg aggctgatgg tggtggagat agttttatct ctgagcaaac attccatctt 123480
gctgtttcca gcctagagat ggtgagggga cttttccttg gctctttcct ggcctgctag 123540
cagcaccagc ctaattaacc tgacaagcgg ggcctcccca gccatgcagc cttgcactgc 123600
cttcccacat ccagctggat ttggggatca gtgttgtttt taatcattcc taccaccttg 123660
tcccacaggc aggagtcctg ccatcttcga aggccagccc ctaaacaggt tccctgagtg 123720
ttaggtcaaa ataactttaa aaagacacgc agctatccac agcaatcctt aatagttact 123780
tatctatttc agggtataac ataagacaca cctatcattt cagacctgcc taggacatgc 123840
ctggagaagg tatttaagta attttaaaag tgcatcaaaa caaggtcagg cgcggtggct 123900
cacrcytata atcccarcac tttgggaggc cgaagcaggc agatcaccta aggtcaggag 123960
ttccagacca gcctggscaa catggcaaaa ccccatctct actaaaaaaa tacaaaaaaa 124020
ttagccaggc gtggtggcat gcgcctgtag tcccagctac tcaggaggct gaggcaggag 124080
aattgcttga acctgggagg cagaggttgc agtgagccga gatcacgcca ctgcactcca 124140
gcctgggtga cagagcgaga ctctgtctca taaataaata aataaataaa taaataaata 124200
aagtgcatca aaacaagaaa aaccctgcta agggccagtc tgctgggtgg tggatgggtc 124260
agcagagctg ggctgggagc cgctatgcct ccccatcaag gccaccaata gtcgggtgag 124320
ccggcctctg tgccgtcatg ggcaccctgt ctcagctccg gggacttgga gctctgtgtt 124380
tccgtggcct ttttcacgat gaccaaacaa aggcgggtgt tatggtgtcc aggcccggtc 124440
tccctaacgg gcagtttctc agaagcaaag accgacgaga cagagctcct gctaccagag 124500
agccctaggc cggctcattg gaatagtcat ttatttgttc cttcattcgt tcattcagca 124560
tgtccatgtt gagcactgac tggagcaggt cctgttctgg ggcctgggaa atgggggtgg 124620
ataagaccaa ggtagcctct tctctaagga gctcagccgg acctcagcct agagccctgg 124680
tccccaggag ctgaggacag aggtgggacc cacacccccc ccatgaggcc acagagcctg 124740
caggtgtcca caccttttgt ttttgttttt tgatttttgt ttttygtttt ttgtttttttg 124800
agatggagtc tcactctgtc acccaggctg gagtacaatg gtgtgatctc ggctcactgc 124860
aagctctgcc tctcgagttc aagcgattct cctgcctcag cctcctgagt agctgggatt 124920
acagggcgtg cgccaccatg ccaggctaat ttttgtattt ttagtggaga cagggtttca 124980
ccatrttgat caggctggtc ttgaactcct gaactcgtga tctgcctgcc tcggcctccc 125040
agagtgctgg gattacaggc gtgagccccc gcacctggcc cacacccttt ctttacctta 125100
cacccctgcc atctccagta tgcacctgtc cgcacacacc cacacacccc tgaaggattt 125160
gacrtcatga gccaaaaaca tttttgcaaa aggaaagcaa ctaagctccc agcgtgtctc 125220
cccttatcca ttgggcttgt cccaaacaca tgccggatgg tgtaagtatc attccatcct 125280
aattaataac atttgggagc cagcgatggc agtgtccagc tgactgctca tagtggactc 125340
cctggtgggg gcgtggcatg ggagcaaggc cagccactgt cacccagtgg gagcagaagt 125400
cccctccagg gcccggcttc tgagggagga carrmargag tccgcmrgaa gtgggcctga 125460
gacgccgtat gcctgtggct ttgtggcttt gtgtggctag cgcctctcac acgtgggggc 125520
tggtttcatc ttccagcccc acacaccttc cccaagggcc tcccgtacac cccggctgcc 125580
tgggcgctgg gctccagcct gcaggtggcc gctgcacttt aagtgtcaca atgggctgca 125640
cttcacatga aagctgcatt ttggcaataa gtccccacca agcccactga gcctggccct 125700
```

gctgcatcca cactatacag ctgaggaaac tgaggcccag ctttccactt ctgtgcctag 125760
ggggtgggat ccagctccga rggtcttctt cccactcctc caggaacctc cgccctctgg 125820
tgtcggtgga gttgaggagg tgttggggtg tggaggggcc aggtgactcc ctgtaagggc 125880
aaagtgatcc agaggctgcc cctaccgcag gtacaccagg ctcaaaggcc agctgtgagg 125940
ctttccgggg ctggatctgg tgggaaagtg cttatcacgg agggcacccg gggttcctgg 126000
cgtgggaccc cctctgaccc aggctagggt tcctggcgtg ggacgccctc tggcccaagc 126060
tggggttcct ggtgtggggc cccctctgac ccaagctggg gttcctggcg tcggacgccc 126120
tctggcccaa gctggagttc ctggtgtggg gccccctctg acccaagctg gggttcctgg 126180
cgtcggacgc cctctggccc aagctggggt tcctggtgtg gggccccctc tggccaaggc 126240
tggggttcct ggtgtggggc ctcctctggc ctgggtgggc ctggcctgag agctgcagcc 126300
tcacctgggc tccactgcct atggacatga gctgaagctg ctcagccttc crgggcctct 126360
gtgcgcaggc atcaccatcc gcagcaggcc aggacccggg cctgctgttc tcagggtgtc 126420
cttcagcgga ggctccagca tggctgggtt caaacaggtt gcagggtctg aagccactca 126480
aggccgagcc tgcctgcagt gagcgtccca ctctgtccct gcaggagatc gtgctggtgg 126540
tgttcttcsg gacggagtac gtggtccgcc tctggtccgc cggctgccgc agcaagtacg 126600
tgggcctctg gggcggctg cgctttgccc ggaagcccat ttccatcatc ggtgagtcat 126660
gcctgccctg tggaggtcac gcccaggttt ccagaccagg aaggaccccc acctcatgac 126720
ccctaccaga tggagtcccc taaggactgg ggaaccccaa ggccagcagg gggtgactgc 126780
ccaggaccca gcacaggagc attggcagcc ctcagcagcc tctgcactca gacgctgatc 126840
atggtgttgg gggtaggggg ttggtccctc acagattccc atgagcctca cagcccagca 126900
tagcttcatg gtgggccagt caccctcggc agcctgagaa ccatggtcca ggcctgaggc 126960
cctgcccttt ctggccactt gcagggctca gcacagggcc cagcctaggc cgggggctcc 127020
acatggccag gacagaggtt gggtctctcc gtttagatgc tgcctgcctc cctatccgag 127080
gtgtctccat ktccccggtc atcagggcgt gacccgtctg accagcaagc cccttcccca 127140
gacgagagca gggtgtatgc tcttccctgg ggccctggct gtggcgatca cgaaaagctc 127200
cccctctcct gcactccaca gacctcatcg tggtcgtggc ctccatggtg gtcctctgcg 127260
tgggctccaa ggggcaggtg tttgccacgt cggccatcag gtgcgtctgt gccacaagct 127320
ccccccgcca tgccgcccca ccccgagcac ccctcctgag ccgcgggtgg tctcacgccc 127380
catccacctt gctcagatgc aaggtgcctt ggtgcccact gcccccgggg gcactgagcc 127440
atgtgctggg atgggtggag cagggtgggt gcaggcaagt gtggagggca cggctcaacc 127500
caagatgcct caggcagccc taggctctgg cccagcacta gcgcctctga acttccagga 127560
cttgggtggt aacctgacca tctgggcaca cagcctgccc atctgcaaac tggggtgacc 127620
caaggagccc cccagaaggc agtctgggga ctgagggaat ctggaggtac ctggccgacc 127680
cccagctcag ccctgtgtgg gcagattcag agcaggctct ggggggctgc gcctgagagg 127740
gagattccca ggcccctgtc gggatggaca tatacccagc ctccccaccc agagtggacg 127800
cctgggaggg gcaggggcag ggacacccat gccatcggcc agccctaggc ccggcgtgaa 127860
cagctgagcc cagcctggct ccctcagccc cacaccatct ccttcgcagg ggcatccgct 127920
tcctgcagat cctgaggatg ctacacgtcg accgccaggg aggcacctgg aggctcctgg 127980
gctccgtggt cttcatccac cgccaggtgg gtggcccggg ttaggggtgc ggggcccagg 128040
ttggggacag gacggaggga gcagagcagc ccacactagg acagcttgag atgcgctgag 128100
gccccggggg ccggtgggtg cctgggcgca ggggtacctg aacggggccc aggatctcag 128160
agcaagccca agcttgagcc cagcctggat gctccacccc agcctggtgc cagtgaccct 128220
ggcctgccag gctgatggtg tgctcacctt cctctgagct gggggcaaat gaagacagaa 128280
agtcagaaat gaaaaaccca ggcaaatcaa ggacccggtc aaggcagggc caccagactc 128340
cctcccgagg gctgcactca gatgggttca ggctgcactg gcccctggct ctgtggggtg 128400
aggggaccct tcctctccct gaggatctcc tgggtcctgg tccattcttg gttctgtcac 128460
gtggcaggaa agagagctgg gcaatcagtg gagcccgcgc cggcccagac agtgggccta 128520
gggcgacccc agggctgagc ctcattctgg gggtaacccc cacccgccac ttaccggagt 128580
tgtgaggagt gggctatatt gaagccggcc ctgtgcatgt gaaccgcgct ggagcggcgt 128640
aggacgccca gtgatcgctg ggactcgctg ccttaggcgt ctgcacagga ggctcccagc 128700
ctgcggttcc tggagcccga cactgtgtgt tttctggcct aggagctgat aaccaccctg 128760
tacatcggct tcctgggcct catcttctcc tcgtactttg tgtacctggc tgagaaggac 128820
gcggtgaacg agtcaggccg cgtggagttc ggcagctacg cagatgcgct gtggtggggg 128880
gtggtaagtc ggaaacttcc aggcatgggg acaggggcag ctcaggctga ggagtgggca 128940
ggacatctgg gcactggtgt cttgagactt cgggccttgg caggggcttc tcacctgcac 129000
gctcacaggc ctctgtccac aaacctgtgc ttggagccgc tggcacaggt ccccacgctc 129060
agtgttgagt cctttggcat caccatcttg aagttctgaa tggtctcatc cttgaacttg 129120
agatttgaga gggaaatcgg aggggtcact ggagcgtgtg ttgggggctt agcggtttcg 129180
gctcccccat ggctctgcct cccgccatcg tcctaggttg cccattccct gcctccaccg 129240
tggccctcac cctggcaggg cccaaggaga gcggcgtcag atgcatacct cgcgtgtctc 129300
tgagggtcca cacaggccct gtaagtgccc ctgtccccaa ggagccagac atgagacagc 129360
aaacaggaaa gaccatgatg gctcaagaga ccccagcaga gatcagagag cccccgtgtt 129420
tccagtggat gctgggcctg caagttctgg agccgggcct gggcagtggc gacataggtg 129480
cagctgggcc tagggaagca gggacccggc ctgtgggccc agaggctgcc cctggctgtg 129540
aaggtgggtt ccggccacct agagcagccc gggagccttg gggaagccgg tgtgcagcag 129600
gcagatcccg cactggaaca ccgagccacc caaagctcag agaggctgtg cgggaggggt 129660
ggggcagggt gtcttgggcc gtgtctgtgg gggcttcctt gagggactca ggcttgcacg 129720
tgggagaggg agatgttccg atgaggatgc agctgcagga atcagggtgc gccctccgag 129780
ctgcaggctc cccaagtccc aagtcactgg cctgtgggcc cagcagcagt ttctcatggc 129840
tcagaggacg ctggctgagg catttttagg gggcaggcct agcttgccag tgtccctctg 129900
ggagctggtg gctgccttca aatcctccag tgaaagtcgg cgtttatata tgcatggagc 129960
tcaagggctg cttctagggg gaacacgtgg gtaccccgag gggagtagct ggctggaggc 130020
cagagtgcag ggagggaatg actccatccc atctcccccc acagctgcag ggccaggtgg 130080
gccgtccaca ggccactaag gcccagggtg gcaccatcac accttgggga gtggccctgg 130140
gtggggaccg agaagcccaa gtgccgaggt gacagggtga cccctactct gccgccacaa 130200
gcctgccccc gcgtctgccc ttgtctaccg acctccgggc tcactcagtc cgataacagg 130260
ttagatggaa tcgtggtagc aacaggggct gggggctggg gaggaggccg tcgaagccca 130320
cacagggtgg gagccaaggc ctgggggccg cacgggggct ggaggtgggg gcgggcaggg 130380
cagccgtggg aaacacgtgg tggtgccagg acccagtccg tctgccccga gtcctccttc 130440
cagaaaggac cggacttgct ggctctcggg accccccacc accatcagag catatctggg 130500
tggggtgaga agcctcccgg tggctcccca ggcaggcacg tgtccctgcg attgctgtgc 130560
ctcctccctc cccctcaacc gccgcttccc ccatgaggcc agacactcag cagtggctcc 130620
tgacgtaggc caagtcagca ggttttctgg aagcttccaa agtgctgcaa tgctcaggga 130680
tggcaggggc atgctgacac agctcctggg ttggggcagg ccccactttc ggcctcttcc 130740
cgccttcctg gggcctgtg tccccgaagg ccccagtgtg gcaggcctga gcaggtttgg 130800
gcagcagggc ccagcccccc tgcgggagcc tgcctgcagt gagtgtggat gggtagggcg 130860
tgctcggggg atggacggcc cagagccagg agagttcccg ggaggctggt ggcaaggtgg 130920
gcagtgagga gctggcggtg cagcaaaagc cagtgggtac tggccccggc acggctgata 130980
agcagtgccc agccttcgct gctgccctgc ctgccttccc agccgcccac tggagctgtg 131040
ggcagcggac gctactcccc agccccccag cccgcagcag agcggcactc ccactcccac 131100
acctgtgcaa acatccgccc gctggccggg aacacggccc ctttgtgccc ggcttggcat 131160
cagtgccccg gcccacaccg tcagctgcag cccgagcctc ggccatcgcg cgccctggcc 131220
tggccattgt tcccgccagg ccccgcgccc ctggtcgccc tgggcccccc accgcccagg 131280
gctgtggggc aaacagctcc cattcagctg ccctgcagct gtctgggggg agcggcccct 131340
gaggcctgag ttatgggctg tgttcctggc atttctcgga caaacagaac ttgagaaacg 131400
caagaagggg cagcagccca gatgggggct tttaagccag ttttgccaat ttgcaactgc 131460
gccctgagca gttgttttct ttcagctcct ttgtcctgct tccttcaccc caccggggag 131520
tgaagtacgc cctcgccggc caggcagcca gggctgctcc atgtctgtcc gtccgtcggg 131580
gctgccacag gcccttactg ggtgggaggt ggcttcctgg aggccaggcc attctgatca 131640
tcatgctgca tctgccccag accttgcctg gactctgtgg actcctcacc cctcagacac 131700
accctgagag ggtgctggag ctgccacaac aaagtccgcg aactgctggg cccagagcaa 131760
cagaaactca tgggctctag aggccagagc ccgaagcgag gtgtgcacag ggcctgcccc 131820
tccgaaagct cagggagaaa tttcctctcc tctccccgtg gctggagact ccaggcgtgc 131880
ccggtgtgcg gccgcctctt tcctctgtgt caggccctgt ctctcatgag gacacttgct 131940
gttggcttta gggtccaccc aggtgatcca ggaggagctc atcttgattg aatcttcaaa 132000
gagcctattt ccaaatatcg cattctgtgg gtccaggtga atatgaatta ggggggatgc 132060
agtccagcct aggacagtgg gtggcccagg tggacttcct gggaaggtcc ctccccttgc 132120
cggccaccag tttccacagc tgtccagcga aggcgccggc tcagtggttg agtgtcccct 132180
cctgtcccct tcgccggggt ggggatacgc aacttggatg tgagaactct cgaatcccct 132240
gagtgtggcg cctgccctgg ctgccaaggc gtttggggag aatttaagac ttttctttgc 132300
ccttggaaca aaatgcgttt gtttgtgtta aagtttgagt ggagggagaa gcagtttttg 132360
caaacacggg cttctctgtt cagcgcccgg gggtctctac aaacaggagg ctgccgggct 132420
gtgtttgccc ctctgcacct aaatttagaa ttgaaagtaa agaagctgga accccattcc 132480
tacatttcag ccgccttttg aagtcgagtc tgactgcctg ctgttcactc tctcctcacc 132540
tggagcctcc agaaattccc gcctccctgg caacgctgca ccctggcggg gcaaggccag 132600
aaggggctgg gggctggtgc aggggtgtgc gtgagggcag ggcctcccag acagtcacag 132660
gccagccctg ttggcactgc ccagcgggag gggtggtgtc aggaagagct ggggaagcca 132720
aggcgccgtg ggccgagggg cggcaggacc tggccaccca ccgagcccct gggtcagcgt 132780
tcttcctcct cctggagttc cgtgcaaagg ggaacgagtt cagctgccct actgagtggg 132840
cctggggaca gaggcagagt acgcacctgc tgtgtgcctc agtttctcca tctgcacatg 132900
ggagacagca gtccgtctcc cagggccaat gcagggcccg ctgcaagggc tgctgaggac 132960
tgtaatccca gaggctgcaa ccgatccctc tgctgcggag actttccctg gaccgaaagg 133020
gcctcctggt gaggctgggt ctccgtttgt ggactcactg ttgaggcgtg tggtttgcgg 133080
tcctgctgtg tgccaggcac cggcaggggt tcgggcagcc ctgtcttgct ctctctgtca 133140
cagtcaggag cgagaagcat ggtgtgagct ggggctggcc tgtggtggtt cgcaggtggc 133200
catgggaagc accgccggag tgtccctgca ggactgtttc ggcccaggag cagggaggcc 133260
tccttgagga agtgacagct gagctgagac ctcaagacac agtcacctgg gccaccttcc 133320
ggcagggcgc tgagcctggc tgtacctcgg ggaagacgcg gcctggggcc tgggtgccat 133380
gggggtgttg acggtttcac caccagcccg tgtgtggggc tccgggcttc gtgagtgagg 133440
agaggactcc atgtgacggg gaggcctggc cctcgtgaat tggtgttcgt ttatttactt 133500
tctcctgctg aaaggaagca ggtttatttt ggggtgtgtg tctgcttttg cttttaccct 133560
gagagtttgc cagcctgctg gcttgttccc ccaccccac ctggtggcgt cagcccctt 133620
atggctgttc ctgagagaca ggccggagtc tccagggcgg ccccacgggg gctgggcgtc 133680
cccttggaat gtgagtgcct ggcctgttag agccccagga ccgctggccc cacccttctc 133740
tgtcccagag acagtcctgc cccccaccca ggggcctccc tctgtccacg gctccccctt 133800
tcccaggcca cccccctagg cccctttcct ccaccttcat tggccctgcc ctctgtagtg 133860
tcacccaggt cagtggggcc ctgtcctgcc ctgtcctgag gagtgcatgt ctctgagccc 133920
tgcatggggg gagcccacca gctagcagag gcccagaagg ctctagacag gctctagact 133980
gggtctctaa gtctgcaagg ggcaccaaag cactttacaa attccaggag tgagtgacag 134040
gctggccacg tgccaagccc tcacccagca ggcagcccgt gagaagtgtg ttgtgatcat 134100
gcaccttccc gagaggggga aactgaggta cagaacatgc tggggctttg cctgaggcca 134160
gacggacagg gtgagaactg ccccccacac tcagagccac ggtgccagcc cagccttgcc 134220
agcagggcag ccacaggact tccaggcaag gtgacggtgc caggtggggc ccgaggccct 134280
cactcatagg gcattgtccc acatcccctg gaaccactga gacaggcatc gtgccacgag 134340
aggggacacc tgcctggacc tctgtgtgct cagcctactg gggcactga ggccgagggc 134400
ccagctctgc gagatcctgc atgggcttcc ttccaagccc tggagagggg agcaggcctg 134460
ggagggcgcc cttggcccag agcctccatg aagagccagg ggcctcctca tggctggggc 134520
cccagcacag tgacctggga atggctgtgg ccgcatggga tgtcccggag cccctgccgc 134580
cctccttgga gctgtggggc tgagcttggg tgctgcgctc tcctgactcc atccttaggt 134640
gcctcctcac gggcaggctg ggctctcgag gctgggcaag gtcggggcct gcaatggctg 134700
aagcagcctc ttagcccatc tctgccttcg gggtggccac agcggggaac gtgggtcctg 134760
caggccttgg tccagctgtc tgcctggcca ctttctaatg gggagccctc agcacagtga 134820
ctgcccagcc tcagtttcct ccttcgtaga tgatcttgac ctgagagtgc cagctggggt 134880
gtgacacctc tgggctaccc cctcctcccg ctcttgacca ccccttcctc tggacagacg 134940
accaccacat ctccagccag gaccacccct tccttctggg caaatgacta ccacgtttcc 135000
agccggggcc agtgagctct gggagccagg gcttggcatg cggctggagc tcaggtttct 135060
gggctggcct ctgtcctccc ctcgaggcca gccttgagga ggctacttct gaaaggaggg 135120
aatagaatcc cagtgtttct cagggaggaa catgggggga ctagaaggct ccccatgcct 135180
cccgcccctt cacatgggag tgaaggcaca ggccagcagg agggcggggg aaacacactg 135240
accagtgggg tgtgcgttcc ccgctcgccc ccacagttcc tgccatgggc gtgactttgt 135300
gtgcctcata tggctggtgc cctggcaagg agccacggcc caggagacag acatgtggat 135360
ctgcattcca ggtggtgggc catcagggac taatccccag catggtgacc ataaaacagc 135420
ccattcctga gctgcctgtg tctgaatgca ggaaaaacaa acaggtctgc agggaggggc 135480
cgtttccttg ttaacttgag gatgagggtc tggggccggg tctgggcaga caggcagacc 135540
aggcgaaggt ggggtcctgg agctgcgtcc tgctgtatgt gtgctctcca cggtgggcag 135600
acacccaggg gcacttctgg ggctggcctt tctctccctc tcggggcacc cctgccttct 135660
actgaccacc cagccagcca gcaggagccc acgtgcaccc agctcagccc caggaggtga 135720
cacccccacc ctcagcagct ctcgtctgtt tgggggcagg tttggaaggt ggtctcgggt 135780
gtccttacgc gagcaggtgg ctacctcacc tgctcacctg accccaactc cactctgact 135840
tccaggccag ccccactcca ttccaccttc atcatgcagt ttctgtatta gatttttaaa 135900
taatcaaaat atggtatttt catttaaaaa gtaatgcttt taaaatatat taaaataatt 135960
taatgttgtt attagaacaa tgtttaatat gccagcccgt gccatttgtc ttgatgcctg 136020
ggtttgctgg cgccccttac gcttggcacg caaggcagga gctccccact ggcctccccc 136080
aactgcttgc cgcccagccc ccctcaggcc aattcctgcc tctcagccta tcttgggttt 136140
gtcctcggct gcctcgggag gcagccgtgc ccaggcctct tggtctcagg gccccttggt 136200
gcccctgacg gagaagcctg gctcgtgggc attgtgccat cactatttaa tacagtggag 136260
gcatgtaaaa acaattccat attaatttat taaaataata gacccattac attttcataa 136320
tgtcatgaaa aatttctata ttttccaaaa caaatattat cgaaagaaaa atatgcattt 136380
ttgcaaatct ccagaaagcc tggctcccca gaggacgggg atccccacgc ctgtcccgga 136440
actgtctgtg aagagcaacg tcccactgct tacgcttggg tgggagcagg agtgcctgtt 136500
agtgcccccc agccacagag agtgctgccg tccctgagcc cagccccagc agatcatcag 136560
cacacatttg cctggggaac acagacagcc ctgtcctgga cgcagccctt caaccctgct 136620
tctcatacct gacccccacc ttgggcgctg gtctgccaca ccccaccacc cctgctttct 136680
tcagcctgac cttgtcctcc cggacccagt gctaggagga tgtccaggcg gggtgggact 136740
tgggcctgcg ctgggctgct cctcaagtct cgggctgcac gtgccagcca ggcagacggt 136800
gctgagaggg gcccttctgc agagcggagg cagagcccgg agtggagggg tgagcactgc 136860
ctcagggcat tggcaggggc tgcgccagcc caggcacagg tctgagggat gaataggagg 136920
ttgctggatg aacaagtagg aatcagcatg ttcatactga aggggtgagt gtccccccaa 136980
aaaatctgga ttagacagac tctggagccc tcttgctcca ggttgcaggg gccctccgag 137040
ctcaaggcca ggataggcca gggtccctgc cctgcccagg cccttctagg cccgtttctg 137100
ggccacctgt gtgtgctttc ttggacttgc tgtagacttg gtaaacagtg gatgtgctgg 137160
gaccctgggc tgagcccctt tgggctgaga gctcaccagg tggaagtcac tccccagggc 137220
aggactggca cagggtctcc gatgccccgc ccactttgca gccctgtgtc tgcctctgca 137280
actccccacc ccagtgcacc tgggccctct ggggaaggta gcggcagccc agcctgtgca 137340
tgtgggtgca kgccctctgg ggaggacacc ctgcagacga ggggctccgg ttcccccakg 137400
gcccccctct ctgccagcca ctgtcagcct cacccatggc ctggcttcac cctgcaggga 137460
cctggctgcg ctccgtgtgc ctgcgctgtg cgttcaaggt gtctgcacct gaatgtgccc 137520
tgagagtgtc aggctcggac atggggacca gctccctttt cacatgacct tgtcatctgt 137580
gtgacgcacg tgcgtgtgcc gggtcgtgtg tttccgtgtg tgtgtgcaca agcacagaca 137640
cgtgcacgtg tggagcatcc catctctgca tggggcacgc ttgtgagtgt gcacccacat 137700
acacagagcc gggtggtcca ctgaaagggc ctggcagtaa acagcttcct gtgcacattg 137760
tgtgtgtggc aggggcatgg gggcatgtgt gtgtctctta aggacagtgg cgctgcaggg 137820
agagctccgt gtgcagctgt gggaggtagc ctgcaagcag cctctgcaga agcatcctgg 137880
ccataagcga acgtgcggtc agggcactag tggggcaggg gcctgggtgg cggccagggc 137940
tcagcagagg cctgtcccgc cctgtggcct ggcggcggtg gctggcgttc atcactgttc 138000
gttaacgtgc tcatcggtac agcctggttt cccgcaatgt ggccgcttct gctacctgag 138060
cctccgagcc tcctgctgtg gcagttctgg gcagtcgcgt gagccgtagt gcacctgcct 138120
ctctgtccgc gtgkgcgcmt gtgcacccct gcccgggggt ggccatgggg cttctcccca 138180
ccctccctcc tcctcagtgg ctggtggaaa ccacagggtg gcccagggac cctggtcctc 138240
gtgggggctc aggtgggccg gggtttgttc ttgccttcca tcagagtgtg ttaaacaggc 138300
ctcaggcctt cctgccatca gcactgggcc catagggctg ggaatccagt gggggtctcc 138360
atgtggttcc cagctggggc attcctgggc ctgcaagcgg tggccgtcac ttgaccttga 138420
ccagaagccc caagccggta aatgctgtgc tgtcctgagt gtggtgccca gagcagggct 138480
gcaaagacct cccgcagcca cagccatggt ctgggccacc atgcctgctg tccagatgag 138540
cccaggcagg agcctgtgtg tccacagggt gagctgtgcc tgagggccac tctgggtctc 138600
cttgttgggc tcagcgccag ctcctgaaga acccagcagg cagcctgcac ggaccaggcc 138660
cagccagggt aggctcctac gtcctgcaga atgacatttc caggctcaga ctggaatccc 138720
caggaagcaa acctcagatg ccagcgcggg ggaaagggtg gggggagcct tctattgtcc 138780
caccacacgt cctggacgga tggctctccc accaagaaga aggcttgagc tgcatcttgt 138840
actctcagaa aagaggaaaa taaaacatct ggtgccctgg agtggcgtca ggaagcagcg 138900
cgtcatccca gcccctgctc tttgttgacg accagcctca gtgggagctc ccggtctcct 138960
gggggccggc gcacagcaac gtcggtggcc caggggccca gcctcctggg gacaggcagg 139020
cagatgaggc agccggtgtg gggcgagctc ccaggcccac gttcccagcc agcaggcctg 139080
gcccttcgtg ggtgctgggc tccttacatg tgctggtggg acataccttg tgtgtgacgc 139140
cgagagcctg ggagacatgt gccatcccgc ggctctgttc ctggtgcttt cgccgagtca 139200
cacggggtcg tcctggtggt cagggtctct tgccggcctc tccgctcatc agagtggtgg 139260
gtttgggtta ggcagttggc cctcccgagg ctccagtccc atccgtggct gaccactgtc 139320
cctctccctg caggtcacag tcaccaccat cggctatggg gacaaggtgc cccagacgtg 139380
ggtcgggaag accatcgcct cctgcttctc tgtctttgcc atctccttct ttgcgctccc 139440
agcggtaggt gccccgtggg tgcgttttcc ctggctcctt ggacagctgg ggtcctgggg 139500
tggctgcacg cccctccctg tgagcagacc cacttacgtt cagaaccaag agggtgcttc 139560
ccttctagaa rgtgctatac tccagagccc cacctgccct ccctggggcc ctggatgcag 139620
acttcccgtt tgcagtcccc actggggtcc ttgcaggcag tgtgggaggc agcctggagt 139680
ggctgtgcat gggcgcagtg tggggcaggc ctgctcactc agccctgggt gggtgggcaa 139740
tgctgctacc acgccccatg gaggcagaat cttgtgcctg gagagggcac ttccacgctg 139800
tggctggggg ggttttgttc catgtccttt ccagtaaacc acagattgta aggtgatgtg 139860
tctagttcac aatgcctgta tgtgggtgtg tgtgtgtgtg ttatgtgcgt atgtgcataa 139920

-continued tatgtgtttg tgttgtgtgt gtataatttt atgttacctg tatactatgg gtatgtgtat 139980
atgtatcaca tgggtgtgta tgtactgtat gtgtgcgtgc atactgtgta tacatattgt 140040
atgtgcatat gttgtattta gtatgtgtgc tgtgttgtgt gcacatgtat gcattataca 140100
tgtatatcag tatgtttgca tatgtgtatt tatgtatctg tgtcacaggt atgtatccta 140160
tacatctatg tgctgtatat gtgtgtgcac atgacatgta gacatgtgtt agtatgtgct 140220
tgtgttagtg tttgtgtgtt agtgtgggtt agtgtatgtt ttagtgtatg ttagtgtgtt 140280
tgtgtgttag tgtgtgggtt tgtgtttgtg tttctgtgtt agtgtgtgtg ttagtgtgcg 140340
ttagtttgtg tttgtgtgtg tatgttagtg tatgttagtg ttagtgtgtg ttagtatgtg 140400
ggttagtgtg tgtgtttgtg tgttagtgtg tgtgttagta tgtgtttgtg ttagtgtgta 140460
tttgtgtgtg ttagtgtttg tgtgtgtttg tgggttagtg tgtgttagtg tgggttactg 140520
tgtgttagtg tttgtgtgtt agtgtgtttt tgtgtgtgtt agtgtgtggg ttagtgtttg 140580
tgtgtgtgtc agtgtgtgtg tgttagtgtg catatctatt gtgtgtgtgt gtgcatcaca 140640
catgcacgtg caccacgtga tctcctctgt agacacggag ttccctagct tcagggtggg 140700
tcctttgcat cccatcaacc gtccttgggc gargcagcag cagggtcctc ctcagctgar 140760
gactgccttc tcacttgcga ccccaatccc agtgcccagt atgacccctt cctgggcaca 140820
tacagatgga ccagcccacc tggcccccag aatggtccct gggaatgggt tagagcggct 140880
gcagccctgc cccatgggac tgggcccctt gctggataag acctggggta taagttctgc 140940
cccccatgct ggcccaggac aggcaggctg ggcccgaggt gggacttggg ggggcttcca 141000
gcactgacca tacctggcct tcccacaacg gtgaccggta accacgtcct gaggctgcac 141060
ccagctggca gtggcctgtg tggacgggag cctcctgtcc attccttccc aggggattct 141120
tggctcgggg tttgccctga aggtgcagca gaagcagagg cagaagcact tcaaccggca 141180
gatcccggcg gcagcctcac tcattcaggt gcggtgcctg caaggccctg gtcactgtca 141240
ttttggtcac tgttattgtt gcatccagcc ctcacggcca cctgtcagaa ccatcattgg 141300
cccctgcatc agcttggctg gcctgtgggg catactctgc ttgtggaaag ccttggctgc 141360
tgtggtgatg gggtgagcac ggggcattgg agcctgtctt cctccaaagc tgctcccatc 141420
aagggccatg ccctgtgggc tggagaggag gcacggccgt ggccatgcca ggagtggacg 141480
tggttggctc tgaggctccc ttgtgctccc attctccctc ccactgcaca acaacctgag 141540
ggctgagtct gggagtgggg tggccaggtg attgtcccca agggaggtag gacccagctg 141600
tgcagttggt gccttctgga gggcctggca tccctcaggg ctcgggaggc cctggtgcct 141660
ggaggtgagg actggcgatg gatggcatgg gcctccctct gggctcacaa ggccagtggg 141720
ctgggaaagg cagagccctg gagcaacagg ggcaggaagg ttctggaggc aggtggggag 141780
gcaggcagta ccaagctctg ggatgctggg ctctggctct gtcactccag gctctccagg 141840
acccaccaga gaatgggact gctctgttaa cgtaagcaag gacttggcac aggagtcact 141900
tgagaattgc gtccctgtgg gtctctcttg ttggccactg cagggccagg gctgccctga 141960
ggaacagccg ctgaggtgcc cagagggtgg gcgttgccgg gttgaatgac aagtgcccac 142020
tggggatagg gcctccgccc agtgcagtgg ctgggagcac agtgtcagtt cctctgggca 142080
cactgggcct gatgtccccc aggaaggccc aggacctggg cagccccgc tggctggcgt 142140 ccccctgca gtcctcgtga gctcgctgcc ccaggcaagg cccaggctgt caggggccag 142200
tcgcagtcct cctgcactcc tggctcagcc atcggggggg ctgtgtgctc ccacccttag 142260
cctggtttta tggcttcaca gtttctcctt cctgggagac cataaatcag gcccgtaaac 142320
ccgccttggt cccagcatga gcatgctggc cgcccacgcc tggcagggga ccacattgga 142380
ttcctggtcc cactccctgg gaaccacagg tcctttgaaa ggggttccct cggaagctgc 142440
acacactgtg ggaggactgg agtaggggcc ccaggtggca ggtgtgcaca ggagcagggc 142500
aggggtcatg gggtttgcca gggttggggg accacgtgga gtgctcagcc tgtgtgtgta 142560
acactcgggc cttggaaggc tgggcttgtg ccctcgcctg cctgtccctg ggtgctggat 142620
gggagtgagg gctgcaggtg cccctcgcca gctgctgtgt ctacctgggg ctgtcaccca 142680
ggagcccatc agtgtggggg aacattctcc actcggccct ctctcaggct catgtggcca 142740
gtgatgacaa ggccaccagg acatgtcctc atacaaggcc ctgggagccc ctcctgccca 142800
tctggacgct gcacaactgc tccccgccg ggtcccctgc cgatagtgtc ccctcctccc 142860
acccttccct tgtggtgctg ccatggggtc tctctgaaat gctggcttca gagctgcacc 142920
catgtgccat cagaggctcc cccaactgca aggtggtata ggcctctggg agagacctca 142980
cctcctgcca gccctaggga tcctgcctct ccctgccccc tgctcagcac ctgcaggtcc 143040
tgggcgaccc ctctttctca gcccttcctc actgtgtggc cactggttgc ccatttccgc 143100
attggtctcc tatgcacgct gtgtaccctg gcacctgggg atgatgtgcg acctgcccac 143160
ctttgcaagt ctctcctttg gctcaaggct ggctcagggc tggtaaagac ctctgtggtg 143220
tcccagctgt gggtaacaat tagcccatga ggcagtgagc tgcctggtgc agcaagggac 143280
caagccaggc tgcctgggca gagggtctgg gagctgggac catgtcaagc ctgtgactct 143340
gaggtcccag accctgccac ccagagggga ggggccaggc ctggggaaca gggaggggga 143400
gctgtagctt ccataagggc ccccgccggg tggctcagca ggtgacagcc tgtccccctg 143460
cccgacctca gaccgcatgg aggtgctatg ctgccgagaa ccccgactcc tccacctgga 143520
agatctacat ccggaaggcc ccccggagcc acactctgct gtcacccagc cccaaaccca 143580
agaagtctgt ggtggtgagt agcccacctg ccaccagggc agggccttct tgctagcagg 143640
tggggaggcc gtgggggccg cagcacgagg ctgggatctc accatgcatt tggcttggta 143700
cagcctgtgt cagggagtca gcatcgttcg ggacactggg ccatacaccc gatgctaggt 143760
tcctgccatc ccaatgtccc ccgacttggg ggtatgtagg accggtcatt ccagggccag 143820
ggcatgagag ctccagagat agagctctgg gagcaggacg ggctggaaag aaggctcttc 143880
agagggcctc agggttgggc tttccacacc gggcgcagtg ggtggtgagc agtgggcagg 143940
gggccgcgcg cagtgggtgg tgggaggggga gcagcagggg agggaggtga ggcaggggtg 144000
cagcgaaggg ggtctggagg tcacagggca gtggagtttg gcaggcgctg ggcagaagtc 144060
ttgtgacatg gctggggtca taaggggttg gggctgacgc tggcatggtt ccccttcctg 144120
gcccgtgccc accccctgtg gagagacctg gccttcccag tttccagctg ccggtggagc 144180
ctccgtgcct actgttccct gtgctggaat gttcccccag atttccacac agcctgctcc 144240
ctcacttcag gcgccctctt catgccctgc tggcccccag cctgttcccc cgatatgcat 144300
tctcccctac tggtcacagc ccctgttacc acctccactg gcaccatctt gtacgtttat 144360
ctgcttcctg ctgtcctgtt agcgaggccg tgagctcaca gggcagcacc tgggccaagc 144420
cccccacgtg acccccagca gccctgccct gtctctgtgt gaagacactg gagctggccc 144480
caggcctcag gtccctgtcc gggtgtatgt ggcgggggct gggctcgggg cggctgcaca 144540
ggcactctgg ggccggcgta gggcctggca gacgatgtcc aggaaccgct aatctgttgt 144600
cttgtttttt ttaggtaaag aaaaaaaagt tcaagctgga caaagacaat ggggtgactc 144660

-continued

```
ctggagagaa gatgctcaca gtcccccata tcacgtgcga ccccccagaa gagcggcggc 144720
tggaccactt ctctgtcgac ggctatgaca gttctggtga gaacccctca ggcagttggg 144780
ggccgcgggg ccgggaaggt cactgccttt tttgggagcc cgagcaagcc agtgagtttc 144840
tcccttgggc tgtggtctct gacaacgagg tatgaacaga cagagggtgg agcttctaga 144900
aacttctgta aaccttccag gtgccttccc ctcagagtct tcccaaggag gagctggcca 144960
cgccttctgt tgcgagagga agcctgggca ggtgatgggg tgggtcggct ccatccggct 145020
gtactgaggg aagggtgtgt tcctgattcc agctgcctgg cttcctccca gccgagccca 145080
cgggctctgg ttggaaagtg gctagggtga cctctgggcc tactggcagg gacgccagag 145140
ggaaggggtt tggggatggg gccctggagg agcagcacca ggcccgggta aaacgtgggg 145200
ggcctgacgg gacaggccct tctcatgcag cccaggggcc ccgagtctgt gcgtgatggt 145260
gtggctcgga tctgcgtccc tcctctcacc cctgcagcgg gggctgggat gaagctacct 145320
tctgcgggac ctgacgattg gatggcagac ctgtctaggg tttagatgtc ctccatccct 145380
ggtgaggggt tttacccacg ctaactcgta agcgtggctc tttgacagat gtggagagcg 145440
aggccctaga ggctgggctc gtgtgctcca gccacacggc gggaatacag cagtgcccgg 145500
ttgtggctcc cacgagtgag gccctggagg ctgggcccat gtgcttcagc cacacggcag 145560
gaacacagca gtgtctggtt gtggcccccc catgcctccc gccaacttct gctgttccca 145620
gaagtgcagc tggctgagca cagacacagc aggtgacctg tggtgatgcc agggcatcag 145680
cgcttggcct ccccacactg ctccagggca gacctggcct cctggctgca tcaggaggca 145740
cacgtgatgc atccgtcatc tcgggaccag ttttgagaca aacatcctat agggcaggac 145800
cgtgaactgg gtagctctac agagtgtgag gggctggaga cctcctgccc actggccacg 145860
gatgccacgg atgcccttga gagttaggag aggtggaagg gaccccactt ctccctggga 145920
gctccaactt ctcttgcatg tgacttcagt gcccacttct ggggactgtg atcccaaact 145980
gccaaattct ctagcagctc tcttaaaacc aaatgtgaag gattctggct ttttctgtcc 146040
tctgagccca gcgtggggta tttgagatag ctgtgctgcc accaggacag gggcgtgcac 146100
cttgtcttcc caggagaaaa cacagcaaag cctgtttgct ccctagtacc tcgtgcaaag 146160
gtgccatctg tggccctgct cgctgcttcc tctgaggcag acatagtagt gactgtgttc 146220
tgatacaaag atggcacttg cccgatgctg cactgcagca ccaatgcaga ggccctggca 146280
aatgttcgca gaagccccccg tcccagggcg tggtccccct tggaggaaaa gggcacctgt 146340
tttgaaaaca cttggttatc atggtgccag aaagcactag tttaggcccc acatgaaaca 146400
gtggccttgc cctcccagca tgggagagcc ctcatcttcc aggtggtggg gggagcacag 146460
catttgaagc ccactcccct ttgaccactt gctgttgtcc agacagacat cacgcacgtg 146520
ggccttgcat tggttcctgc ttactttgtc tctgctgacc cggtttctgc tccttgaagt 146580
ctcagccccc ttcttccatg attccaaggc atgtccctct aaggaggctt gaccccaccc 146640
tggagggcct gctccccact ctctgccttc catgccccat gggagggctc catgtggccc 146700
agtcccttgg aggctggacc ccactgttcc ggactctggg ctgttggaag ccaggccctg 146760
cctcagttgt gccaagtggc cagggttcta tgcctggcag aggaggtgtg ggaggccaag 146820
cgctgatgcc ctggcatcac cacaggtcac ctgctgtgta tgtgctcagc catccaagta 146880
atatgatcca ttcccttctc agcagccgtc cctttaccct ttggtcattt ctgcatccat 146940
ctctccctct cggacctctt cccagtgcct gggactaacc cgaatgtctc agcttaccag 147000
cagttgtaag gatgctgtca catcttatgc atggcagaga ggggacaaac ccacagtgtt 147060
```

cgcaaccctt tgtgctcgca ggcaccagcc cagcccgcca agctccagtt cattcaggat 147120
ggctcacctg catccccacc tccttggcag gaggctgggt ggtgttccct gccccttggg 147180
gctttcctgg gcatcccatg tggaagtcag caggcaagac caagtccagg ctcccgctcc 147240
actgggcacc aggctcccca ggacttagat gccatcagga ttgggctggg acccgaccac 147300
atctcagtga gcccccggga cgtgctcccg cctgcccgct ggagccggca caaagggcga 147360
ttgtgccaac caatgcccag tgcccccaca gctccggatt cagggctgag accattgtct 147420
ccatgcaaat gggggctttc tgcgcatgct aacgggcagg tgggcgtggc cgggggctgg 147480
ggacccagcc tgtgtgcggc ctggagaagc atcgcttgct gcttgctgaa tgcggggcag 147540
cccgaatcga tgccgtccat tcagcctggt tagtgttatg aagtcattag tgctgtctgc 147600
ggaatgttaa tgaggggcaa gtgcggagaa agtcaggcgc cttttgtgga atgctcctcc 147660
acggagaaga tttctctttc ctgctggagt ttgttctttc ctaacttgat aagtcagccc 147720
aggctggaac caccagcttt ctggagcctg agctgttggc ctggccccca gggacagagc 147780
gacccctgat aatccggagt cccctttgcc caggaggctc ttggagagcc ctggcttggg 147840
gagaaggaga tgctgatccc agggcagatg ccactcctgg ggaagcccca cagccccact 147900
cccgcaaggc gggtacgaac agccacactg agtcccccgc aaagtcaaac ccaggcctcg 147960
accttgtctg gctgtgcttt ctgttgtgtg aacctgcagg ttaggcagaa gtccccttga 148020
ccctgcctca gggctgctac ctgtctgcgc catccacctg cacacaagcc ccttcagctc 148080
gtgctctagc tggtgctgtg cggtgttggc cccatttata gatggagaaa cggaaggcca 148140
gggccatgtg gggaactcct gaggacacct gtgtgtcctg acacctcact gagcctgtcg 148200
agaggcacag gcaggtatgg cagtggcaga cctcagggga gggaggctgg gaaggtagaa 148260
ggtcccccat ggtagcatca gaacacagac taacctgcag caaaaatggg ctgtgtggtc 148320
cctgtagagc agcctcactg aggggaggca ccagccctca tcccacgcag cagggcccgc 148380
tgctgctccc tcaaccttct gacctgggtg gggagggagg ggaatgtcag cagccaccca 148440
gcccgagagc cagagcacag caggggctgg ccagcctagc cctagagtct ttgcagtgaa 148500
gcgtcacaga ctcctcatga aggatgcatg gggacccaac cgcatgccac ttggcttggc 148560
agtgtcaaag ggactgggga cctgcgagga tgcggtggcc attgtctgtg cccagcctgg 148620
ggagcctgac actcacagcc cggctgctgc tgccttgggc gtcctgaaga tcctctgtat 148680
gcttgtgggg tgggggcaga cacacaggca gcctcctgcc cagagggtcc aagcgggcat 148740
ggccatccac atctgcaggt cagaagaggc ctgggctgga gccgcatact ggccatgctg 148800
cctcgctgtc cctgcctcag agccactgta ttcactctgc ctggaactgt ctttcctgga 148860
tcccaggagt cctgaaggag ccgcctccat cctgagctgc ctaccctgcc cctcctccac 148920
tccagttgtc tccacagcca ggtcaccatt gaccaggttg tccagtcccc tcctcatagg 148980
ggagtggccc tttgtctttc accactgacc cttcccaagc tggtaccatg cctaacccat 149040
ggtgggtaca cgataaaaat gcagggctgt gccaccaggg ttttgtcttg acaaagggac 149100
tggaggcagg ttgtcagagt agggctggcc ggaggtggcc tcctgaatgc ccctaggagg 149160
ccagaggaga cttccccaaa ttcactggtc ctggaggccg cctcagaggc cttttgctgc 149220
tcagagaaca ctgggctgga aggtcgtggt ctgtgacgta ggatcgggga ggccacctca 149280
gaggcctttt gctgctcaga gaacactggg ctgtaaggtc gtggtctgtg acgtaggatc 149340
gggcagcacg cacctttcca cctggcctgg aggtgattct gaagggcttc tggggaggcg 149400
tcttcaaagc tgtgcctgtg tgtgtcacca cgtgtttgcc aggtgacctg ggactattgt 149460
gtggtttccc gtttgtgaag tggggcagcg tgctggagga gcatgcatca catacccaga 149520
ggtccccagt gtggtctggg gactcatcgt tcacactcgt gtgtgtgctt tctggaggca 149580
tgcgtcatgg aacagcctca cctctcactt ctgcacttgt gagcctggtt ctcacagggt 149640
caggctgtag cctcctcctg ctcccggctc cgcgtcctca gcccaacaca ccaagcctgg 149700
cctttcatgc actcctccat tcaaagccgt gtgttctgat tgtgcacttt tggtggctgc 149760
cacaggatta aatcctgaat gctttgccag ttgagatcaa aagtcacccc aactcctctg 149820
aaacctcact gggacctcaa ggtgctccag atcctactgc ctcctgccgt ttcctgggcc 149880
tttgttgccc agtattttgg ttttgtcttt taaacaatcc tctttttgtt gatgctgcat 149940
acattgagat atttactcac agacttgcag ttttctgtct caccatttgg atttaatttc 150000
ctttttcctg aagtctgtgt ttctttcagt gaaggtaaac tctcagtttc agtttgtctg 150060
aaatattttt actttgcctt tattcttgga tgatggtttc gttgggagaa agtaacaggt 150120
taatatgtac attttgtctg aagactctgg agctgtaaca ctgcagtctc ctggcttctg 150180
tgggtcatca ggctaattga ttttcctttg taagtgaccc tccctacctc tagtgacttc 150240
agaaaccttc cttttgactt tagtgttcag aggtttcaat gtactgtacc aaggtggtgc 150300
attattttta tttatcatgc ctacactttg ttgtgattcc tgaatctgag ggtttatgtc 150360
tttcatcaac cgtggaaagt cagtaccatt atgttgtaga atattgcctc ccctaatgct 150420
tctgatcttt tccagaaact tctatttgac catctcattg tcttcctcag ctgtctcata 150480
gattttctat ctctgtctcc ctctgcttca ttcacagaat tttctatgca gtttctaact 150540
cttgagatgt ttctgttcca ctgctttatc tacccactga gactttcagt tatatatttt 150600
ttccttccct ataaatcctt gtatgggggt ttaatttgct tgattttagc atcttgtacc 150660
tttctcatat tttaaactac aacttttaat ctttaggtca tttgaacatg catattttgt 150720
accctctatc ctgtcatttc atcatctgca gttcttggag agtctaattc tgttcactgt 150780
agttttttct gactcttgct catgatggct catttcattg tgggtttgca atttagatca 150840
tgagtttgtg tggtggatgt ttttgtttgt ggggttccta tgtatcctgt ataaggtaca 150900
tgcctctgga gaagctgcac ttttgcttgt acagggtgac ccagtgaacc aatccaggac 150960
cttcatgatc catgttttag atatgggatc ttctagacaa cctatgcagt gtaaacagaa 151020
accccaatct cctgtgagag caagtctaag taacatatat tgagaagaga gttttatttt 151080
ataaaataaa actgtcttta tttgcagaag acatggttat ctatgtagaa aatctgatga 151140
acatgcaaga tgaccactat gactaatata tgagtttagt aaggtggcag atacaagatt 151200
aatatgcaaa aatcaattcc attcatatat tcttgcagca aataaccaga aattgagatt 151260
tttaaaatac aggcgtgtct cattcttatt gactgcactt tgctgataat gcatttttta 151320
caaattgaag gtttgtggca accttgctca agttgaagcc agtactcacg taccatttca 151380
acaatcctag ggcccttaag aattatgcta aatctactct gcttatgctc tataatgaag 151440
caacaaagcc cgatgacagt acatctgttg acaacatggt ttactgaata tgttgagccc 151500
attttcgaga cctattgctc agacaaaaag atccctctca aaatgttact gctcattgac 151560
agtgcacctg gtcatccaag acctctgatg gagatgtaca agattagtgt tgttcttatg 151620
gctgctaaca caacatccat tctgcagccc ataatcaagg agtaatgcca actttgaagt 151680
cttattattt aagaaataca ttttataagg ctatagcggc catagatagc gattgctttg 151740
atgaatctgg gcaaagtaaa ttgaaaacat tttagaaaat aatcaccatt ctagatgaaa 151800
ttaagaacat tagtgattca tggaagaacg tcaaaatatc agcattaaca ggaattggga 151860
aaaagttgat tccaaccctc atggatgact gaggggttga agatttcagt ggaggaagta 151920
actactgatg ttgtgaaaac tgcaagagaa ctagaattag aagtggagcc tgaagatgtg 151980
gctgaaatat cattagttat tagagaaatg caaataaaaa acacaatgaa ataccacggc 152040
ccaattatta tattatataa aatgagggag atggatgata ccaagtgttg gtaaagatgt 152100
gtcggaggtg gaactctcat atgctcccgg tgagaatgca aagtccaaag cgatgcaacc 152160
atttgggaaa cagttcagca gtttcttgat gtgttaaata catacctacc atattctaca 152220
gcgattctat tcctaggtat ttatccagga gaaataagat catatgcatg ccaccatttg 152280
tacatggaat attcatagca gctttataaa aactggaaac cccaaactgg aagcaaccca 152340
aatacccatc aacatttgaa tagatttttt tcaaagttgt agtatattcc taaaatggaa 152400
tactacttag aaatacaaag gaatgaacca ctgatatgcc tacaatatgg atacattgca 152460
acataattat ggtgagtgaa agaagccaga caaaaaaaaa aagagtacat ggtatcttat 152520
ttatgtaaaa atctagaaaa tgaccactaa tatagagtga caaacaagtc agtggttatc 152580
agtggttacc tggggatcag gggtagtagt aggagggaaa aggacaaaag ggcacaaaaa 152640
aacttttggg gcagtggata tgttcattat cataatcatg gcgatggttt catcatgtgt 152700
caaaagttac caaattgcac actttaaaca taagcaagtt atgtcaatta tatctcaata 152760
aaactgttta taatatataa tgtaaatata taatatatat tttgcatagc aaaaaaacat 152820
actgaaaata attttttatt gataacctaa agaaaccagt tgccactcac ctataggcat 152880
ggggctaatt taattgctat ataaaaacgc tcttgtaaat caagatagaa gttaaaggat 152940
attaaaacag ttcacagaaa aggaaatacc aataattctt aagaatgaaa atatgctgga 153000
tgacttcaat tatgacaaga gaaatgcaaa ctaaagcaat ggggtttttg aaacttatct 153060
gattattaaa tatcaaagag tttgataaca ctctatgggt atgtgtacat ggaaactctc 153120
agtctcagtc attgatgtta gaaaaataaa ttgatacaaa cctctgtgga gataaataag 153180
gcaatttcaa tcaaaattaa agatgcatat gcctttgaat cattctagaa atttattcta 153240
cacatatctt acacatttgc aaaataatcc atcatcagga tattgatttc tgcaattgtt 153300
aaatagcaaa aaattgcaaa ccaccgacat acccatcagt ggaggtctgc ttcaagtatc 153360
atatctccgt taaacagcca tcaaaactgt gaagcttcac tctcatcact gatgcaggac 153420
atccctgata tctgatccta gaaataacag tacatctttc agaagagtat gaaatctgcc 153480
atcatgtggg ggcaaataca atggtttaca aaacaaagtt ttatctacct tccttgttct 153540
gtgtcttgga actgtttgaa gaacattggg attatctttt ctgtagaggt taaatagaat 153600
tgagttgtaa aaccatctgg gcctgataca tgttttatag gatatcttta gtaatttctt 153660
tttagtctgt tttatgatat gttgttctaa attagtttat tgcatcttyt ggagtaattt 153720
attcattgct atttaatttc ctcaagcatt tcaattgtgt tgccacttgg tagcaactga 153780
ttttttcctt tagtgatttt atggtcttct ctatcatctc ttcgtttttc ttttccttta 153840
tgcctgaact tttgtggttt ttctcctttt ttcttaatca agcacatgag aaatttatgt 153900
tttatttata ttttattatc agaaaactat ctttgtactc tttgttatct atttcattaa 153960
tctaagcttt tatagctatt aattcccttt tcttggctaa ctctattttt gttttctttt 154020
acttaagagt catagttcat ttatttgaag ttcttctact aaaggcattt ttaaaggcta 154080
taaattttcc tctgattgca gctttagctg tgacacgtag atctgattat gaaatatgtt 154140 cctttttcatt gctttcttga tagttttaat tttgtgtttt gatttttctc tttagagttc 154200
ttttaatgtc ttcttaattt ttaagcagta aatttttatc actgttattt atttctaatt 154260
tagtaggctt acagtgaaag gatgtagcct atgaagtctc cacttttttt aaaatgaaga 154320
ttttctttgt ctccaagtat gaaaataaca tcattatttt tgtaaatgct ccacagacct 154380
cagaaaatat cttctgtatt tgtataacac aaagttttat ttgtatacat ggacagacaa 154440
aatgtacatt gagatggatt gtgtatacat acttattcat tgcctcattt aggtctgctc 154500
tgcccttagt taaaaaaaaa aaaccctaat acatctgcca aattctgaga caggaaaatt 154560
aaatcttcct gtacaattat gtttctaaaa attgagtggc aggtttcatg gagtggtttg 154620
gagcacagcc tatatggcca accttcttta gggtcatagc ccagctctgc cattttctta 154680
tgtggcccta agcaagctac tgcattctct gtgcctcagt ttccacatct gtgaaatcag 154740
gatcctaact gcctgctccc aggactcctg tgttgactga gtgagttaga acatgtaagt 154800
gctcacccag gacccatatg cagcaaacag tcttgtgtct ctgtctgctg ccaaattggc 154860
ctcaggctct atcaatacca gatctgaata ggggctattc tttcttttag tgtccttaat 154920
gttgtattac tttccaatat tcacacttta actttacaga tgagtagaat ggaatagatg 154980
tgtttcagta cagaactttt ttcttatgtt tgcttgggct cccctcctct ctgttaccta 155040
tgttgataat ctaggatttg ttgtcttaca tttttcctga tgttcatata atattcaatg 155100
aaataaaata catgtgacat aatgaaggca ttatcattgt tttccaaact cacgggatca 155160
tatcatacct gctttctgca tcttgttttt ctcaatcagt aaaatagtaa aaatgcctct 155220
aaggctgctg aaacaatttt attttgattt aattctatct ctaattgaat tttatttcta 155280
tttcaattct attctaaaat ttataatctc tgcttaattt cctttggtgt acatactctg 155340
tgatgttctc tatcgcttaa aattcatttt gttcaagaac ataggttctt gaacctgttt 155400
ctatgtacag aacttttatt tctatgtgtt aactttccag gatgtattag tttgctagga 155460
ctgccataac aaaataccac aggctgggtg gcttagacag cagacatgta tttctcacaa 155520
ttctggagga tagaagtctg agatcaaggt gtcagcaagg ctgctttccc tgaggcctct 155580
ttccttgcct tgcagatggc cgccttcttc ctgtgtcatc acatgaccat tgctctgggc 155640
acttgcaccc tggtgtttct ctgtgtgtcc aaatatcctt ttctttaagg gcaccagtca 155700
cactggatta gggcccaccc taacagcctc attgtagctt catcacctct ttaaaggtcc 155760
tgtctccaaa catgctgagt cacgtgccga ggtattaaag accagggctt caactgcaaa 155820
ccttgtggga cacaattcag cccgtgacac aggaataggc ttgttaattt cagtgatgta 155880
gccaggttgt ttttctcgtt ttgtctgacc ttgaattcca caggcagggt tcctctttcc 155940
cggccggcat tcctgcccac cagtcctggc agagtgactt attgtcagcc aagtggggca 156000
gagtttctcc actgtacctc tattgaaatc tagtgccgga taattctttg ttgagggagg 156060
aagtcctgtc tattgcagga tgtttagcag catctccggc ctcagttatg accaccaaaa 156120
acatctccac atgttgctac atgtcccctg gagggcaaaa ttgcccccag ttgtgacctg 156180
ctgagctaaa gcagtccctc aggattgttt cttaaaacaa aacaaactgt ttatttggcc 156240
ataattttga actacagaaa aattacaagc acgagatata aaaacaccta catacccttc 156300
actaagattt accagtttac taattgttac attttgccac atttgcttta tcatttgaac 156360
ccctttctct acattatatt cacataacat gtttttctga aacatctgtg agttgcatac 156420
tccacagctc tttgccccta aacattttgc tgtgtatttc tgaaaaataa agatattatc 156480
tttgaaagca gtwatacagt tattgacttc kgcaattaaa mwtcaatatw atacttggac 156540
ctaatttaat gcstatggtt cccattttgt cagttgccat gacaatgtcc tttgtggcat 156600
wttttcctcc actgcaagat ccagttcagg gtcagtactg cctttagatg tgtctcttca 156660
gtcttgttta atctggaaca tttctagtct ctttctctgt tatgacactg atatttttta 156720
aagatacagt cctgccactt cttgggggag tctgatgttt cctcaggtta gatccacgtt 156780
gtgtactctg taagtgacct gatgtccttc tcagtgtatc acatcctgag gcacacagtg 156840
tatctgcccc ttattaacga tgttattttg atcaccaaat tgaggccgtt atccactttt 156900
ctaccttaca gttactatat tttgccttgc aaccaataaa caatcggggg agattcttta 156960
aggccatgca tataccctgc tacttgttaa aaaaaaaaaa aaagtctctc cagatttaaa 157020
tgcttttgga aaccaggctt tactgtggta gttgcaaaaa tgatcatttt ccaactctag 157080
cacccccttcc acgaaagtac agaaagaaaa aaaaatactg tccagttgga atggttacct 157140
cattgtggtt ttgatttgca ttttcctaat gatgctgagc atttttccac gtgcctagtg 157200
cccaattgtg tatcttcttt agtgaaatat ttattcagat cttttgcccg tttaaaaaaa 157260
tgagactttc aagcttttta tttttagaca ttcatatgca gtggtaagaa ataataggga 157320
tcccatgcac cctttagtta gtttccgtca gtggtagcat cttctaaaac catagcacaa 157380
tatgataacc aggatgtcaa cagcaagagt ccagatgcag agtgctcccg tcgccacggg 157440
gttcccatta tttgtccttt tacacggact ttctcccatc ccatccctcc aatccctggt 157500
gaccactcat ctgttctctg attctctagt tttgtctttt caaaaatgcc acgtaaatgg 157560
aatcacacaa tacacgatat cttagaaacg gggtcttttg gctcggcatc attctctgga 157620
ttcattccgg ttgttttgta tcgcgacagt tcattaaatc atagtgctga gtggagtttc 157680
acggtatgga catataccccc agtttattta accattccct catccaagga catgtgggtc 157740
attcccagtt tgggctatta caaatcagag taggctgaac aatggccccc aaagtagcca 157800
ggtcctaacg cctagaacct gtgactatcg ccttctatgg caaagggcac tctgcagatg 157860
tgtcaaatta aggaccttga gatggagaga tcatcctggg ttatctgaat gggcccggtg 157920
taatcacaag ggtccttata acagggaggc agaagaatga ctacagaaga gaaaaagggt 157980
tacgtggcca cggaagcagg ggcaggaaat ggcaatgtga tttgaggaag gggtcacaaa 158040
ccaaagaacg cttccagaag aaaaggcaag gaaagggaag ggatgctccc ctgaagcctc 158100
cagaaggaac cagccctgct gacacmttga tttttcgtcc cctaagactc ttttcagact 158160
tctggcctct agaactgtga gaaaaaaaaa aaaagcgtgt cttgttttaa gccactaagt 158220
ttgtggaaat gtattacagc agccatggga accttataca ttgataagga tgacatgaat 158280
attcttgtaa ggttcttgtg tgaacataag tttttatttc tttgggataa aagcccaagc 158340
ttgtaattgc tgagttgtgt ggcagttgca tgtttagttt tataagaaac taccaaactg 158400
attttccaga gtgactgcac catttcacat tccccattcc tgccagcaag gtctaagtga 158460
tctagtttct ctgcattctt gctggcattt gatgttcaca ctgtttttaa ttttctccat 158520
tcagataggt gtgtagtgag atctcattgt ggtttacatt tacatttcct cattaggatg 158580
atactgaaca tcttttcatg tgcctgtttg ccatttttgt attctatgca gtgaaattct 158640
tgttgatatc atttttccat ttcccaatta gactttttgt taactgtcga gttttgggag 158700
atgtttatat attctagata cttatcttaa gtcagaaaca gggtgcaaat atttattcat 158760
tgtagctttc attgtcatca tctcaacagg gtactttaca gagcaaacat tttaaatttt 158820
gatgagattc aatgtttcct ttttatggat tacacttctg atgtcaggtc taagaagtct 158880

-continued ttggccctgg accccaaata tcttctgcta tagctttttt ctaacagcct tgtggagata 158940
tagtttacat accatacaat tcacccattt aaagaatata attgaatggt ttttagtata 159000
ggcatacctc agagatattg tggttcggtt ccagtacact gcaatgaagc aaatattgca 159060
ataaagcaag tcacacaaat tttttggttt gccactgcat ataaaagtta tgtttatatt 159120
gtagtctatt aagtgtgcaa tagccccatg tctaagaaaa caatgtgcct accttaattg 159180
aaagacactt tattgctaaa aaatgctgac ccagaatgaa gtgagcacat gttgttggaa 159240
aaatggcact gatagacttg ctcagtgcag gcttaccaca cacatttaat tttttaaaaa 159300
cacaatatcc acaaagtgca aaaaagtgaa gtgtgcctgt gtatccccag agctgtgcaa 159360
ctgccactcc agtttgagaa catttttatc attccaaaaa gaaacccagt gccttttaaa 159420
tatcaccccc aaacccacta ttccatcccc ctcagcccta ggcaataact aatctttctc 159480
tctatgggtt tgcctattct ggacatttta tataagtgga atcatacaat gtatggtcct 159540
ttgtgactgg ttactttcac ttagcatcat gttttcaagg tttgtgcttc agtgcttctt 159600
ttttttcccc cgagacagag tctccctctg tcgcccaggc tggagtgcag tggcgcgatg 159660
tcggctcact gcaacctccg cctcccgggt tcaagcaatt cacccgcctc agcctcccaa 159720
gtaggtggga ttacgggcac atgccaccaa gcccggctaa tttttgtat tttagtagag 159780 acagggtttt accatgttgg ccgagatggt ctcgatctcc tgacctcgtg atccacccgc 159840
cttggcctcc caaagtgctg ggattacagg tgtgagccac agcacctggc cgataactat 159900
ctttttgaag aactgaccaa ttatttccaa agtgggtgcc tcattttaca ttctcaccac 159960
cagcatatga gcactgcgca agttctccat atcctcacca acacttgcta ttatcttttt 160020
tcaattatag ccatcttagt ggttgttaag cagtatctcc ttttgggtgt gatttgcatt 160080
tccctgtgac tactcacgtt gagcatcttt tcatgtgttt attaactata tgtcaaccct 160140
gaagaaattt ctattccgat ttttcatcca ttctttaagt tgggatattt gtctttttgt 160200
ttttgagttg aaggagttat ttatatatcc agtaacaagt cccctatcag atagattatt 160260
tgcaaatatt ttctcccatc tgtaggttgt cttttcactt tctttaaggt gtcttttgaa 160320
gcacaaaagc ttttaatttt tatgaagtcc aatatatcta ctttttttct tttgttcctt 160380
gttctttggt gttatatcta agaaacctct gccaaatcca aggtcataaa gatttaccct 160440
tatgtttacc ctaagaattt tatagcttta tctgttacgt atttatgtct ttgatccact 160500
ttgagttaat ttttatatat gatgtggagt ggaccaattg atttttctca tgtggatatc 160560
agttgtttca acactatttg ttcaaaagac tattctttcc gcattgaaca ttcttggcat 160620
ccttgtcaaa aatcagttga ccatagatat atggctccgt ttttacactc tgattctatt 160680
cccttgatct acatatctat ctcatgccag tatcacattt tctcgaatac tgttactttg 160740
tagtcaattt ggagatcagg aagtatgaag cctccaactt ttctttttca aaattgttgc 160800
tattctgggt cctttgcatt ttcatatgaa gttgaacatc agcttattat tctacaaaga 160860
aaccagctga gattctggta aggattgtgt tgagtttgta gatcagcacg attccgggag 160920
tgttgccatc ttaacaatat taagtcttcc agtctatgag catgtaatgt ctgtccattt 160980
atttgtatct tcttttcttt caacaatgtt ttgtaatttt cagaggataa gttttgtact 161040
tgttaaactt attcccaagg tattttattt tttctttatt atggtaaaaa tatacataaa 161100
atctactatt ttactcattt taagtatata gttatgtggc attaggtaaa ttcgcactgt 161160
tgtgctttat tctttttga tgttatacat ggaattgttt tcttaattat attttcagat 161220
tgttttttga cagtgtgtag aaatacaatt gatttttata tactgatttt gtctcctgca 161280
gccttactga actcattcgt tgtaattgtt tcacaatgga ttccttgggg ttttctggat 161340
acaacattag atacggtttg gatgtttggt ccctccaaat ctcattaaaa tgattcccaa 161400
tgttggaggt ggggtctggt ggggggtgtc tggatcatgg acggagccct cgtgaatggc 161460
ttggtaccat ccccgtggta atgagcgaat tcttactctg gtagtttatg ctaagagctg 161520
gttgtttaaa gaatctgcta cctccctcca ccttgctcct gctcttgcca tgtgatatgc 161580
ctgcccctct gcctttcgcc atgattgtaa gcttcttgag gccctcacca ggagcaggtg 161640
ctggtgccat atttcctgta tagcctgaag aactgtgagc caattaaaat cttctttata 161700
aattacccag cctcgggtgt tcctttatag taacacaaaa ctggaccagc acaaatttat 161760
gtcatctcca aatagttcta cttctttctt tcagtctgga ttctttttct tcccaaatta 161820
tcctggatgg aacactcaat aaatgttgaa tagaagtgga aagagcagat ctctttgtct 161880
cattcctgat cttaacgggg aaacattcag tcattcactg ttaagtatga tattatctgt 161940
gatttttttt tttttttttt tttttttttt gagacagagt ctcgctctgt cacccaggct 162000
ggaatgcagt ggtgtgatca cggctcactg caagctccac ctcccaggtt cacgccattc 162060
ttctgcctca gcctcccgag tagctgggac tacaggcgca tgctgccatg cctggctaat 162120
ttttttgtat ttttagtaaa gacggggttt caccatatta gccagtatgg tctcgatctc 162180
ctgacctcgt gatccacccg cctcggcctc ccaaagtgct gggattacag gtgtgaacca 162240
ctgcacccgg ccaactgtga tttttaatag atgcccttta tcaggttgag gatgttcctt 162300
tctattccta gtatattgag tagggctttt tctcccatca tggaagggtg ttgaatttta 162360
tcacccaaat gcttttctgt gtcttttatt ctatcattaa ttgctataga ctgaatgtgt 162420
gtgtttcctc aaaatgtata tgttgaaatc ctaaccccca atgttggtat taggaggtga 162480
ggcctttggg aagtggttag gtcatgaggg tggagacctc atggaatgga ttagtgccct 162540
tgtaaaagag acctcagtga gctccttttt ttcttccgtc atatgaggac acaagaagac 162600
aactgttcat gaaccagaaa gcgagtcctc tccagatgct gaatctgcca gtgccttgac 162660
cttggacttc caagcctgta aaattgcaaa aaataaattt ctgtgtttat aagccaccag 162720
ttcgtgatac tttgttataa cagtctgaac agactgacag aaatcgtggt gttttgtctt 162780
ttattctgtt gataatggtg tattacatta attgattttc agatgttaat tcaaccttgc 162840
attcctgaaa taagtcccat ttggttataa tgtataatcc tttttaaaca ttgcttgatt 162900
ttacttgcta gtattttgtt gagggttttg agggttttac atcattttca tcacagttat 162960
tgtaatgaaa tacaaaaatc aatagtattc ctatacactg tcaaaaacaa tctgaaaata 163020
agaaaacaat tctatttaca acatcaagaa agcataaagc acaatagcgt ggatttacct 163080
aatgccacag aactatatac ctaaaatggg taaaataaat tttataagtt ctcttttcat 163140
gtttttgtct ggttttggtg tcagggtgat actggactga aagaatgtat tggaaaaatt 163200
ttccttctct tctatttttt tgttgttgga agaggtcata aagaattgat attctttaga 163260
tatttgttag attcactcat ctggccctct tgggcttttc ttttcaacta gtgttctcat 163320
aactaattca atctctttaa cttattacag atccattcac attttctact tatttcttag 163380
tcagttttca tagttttcat ctttctagga atttgtcaat ttcatctaag ttttataatt 163440
tattggcaca aaattgttca tagtgttcct tcataatcct ttttatttct gtcaggttgg 163500
tagtatactt ccctcattca ttcctttttc cttttctttt tgagaaacag agtctctctc 163560
tgttgcccag gctggaatag agtggtgtaa tcatagctca ctgtaacctc gatctcctag 163620

-continued tctcaagtga tccttgcccc ttagcctatg acaggtgtgc accacaacac cagctgttat 163680
tcaaaaaata ttttgtagag atagggtctt gctttgttgt gcatgctatt cttgaactcc 163740
tggccacaag caattctcga actcctggcc acaagcaatt ctcctgcctt ggcctcccaa 163800
agtgctggga ttacaggtgt gagccactgc agctagcctc gtttttttgc tttaatttgt 163860
aaaactgtca ttcatttctg attttagtaa tttgagtttt ctctctcccc ctttgcctca 163920
tgcacttccc tctctgtctt tcctcctccc cctctttctt cctccccttc ttttcttctc 163980
cctctccctc tctcttacca atctatcaaa ggtttgttaa tttcaaagaa ccaaattttg 164040
gatttgttga ctttattatt tttatattct atattttatt tctactctaa tatttattat 164100
tttgtttttt ctacttgctt taggtttagt ttgctcttct ttttctagtt tcttgaggtg 164160
gagagttggc ttactgattt gaagccttat tttttgatat aggcattcat agctataaaa 164220
ttccatcttt acactgcttt aaatgtatcc cataagttct gttatgttgt atcttcattt 164280
tcattaatct caaagtacgt tccatttccc ttgtgaattc tttcacccat tgattattta 164340
agaatgtagt gttgtttaat ttccacatgt gtatgtttcc ctaatttctt tgctactgag 164400
ttctactttt atttcattat attcagaaaa agataccttg tattatttca atccttttaa 164460
atttatgcag gtttgtttcg tgacttagca tatggtcctt cttggagaat gtctcatgtg 164520
cacttgaaaa tactgtatat tcaatgttgg ttgttgggcg aagtgctcta taattacctt 164580
ttgagtctag ttggtttatg gtgttgctca tatcttctgt ttccttattg atcttctttc 164640
ttgtactaca cattattgaa agtggagtgt tgaagtctcc aactactatt gttgaattgg 164700
ctatttctct gttcagttct gtcagttttt gcttcttatg ttttagttct ctattgttag 164760
gtgaatatat gtttataatc attgtatctt ctcatgaatt gacattttat cattatgaga 164820
tattcatatt taacttcagt aacattctta atttaaaatc tcctttgact ttattatagc 164880
acttcaggtt acttatggtt gctgcttaca tgatatatct ttttccatcc ttttactttc 164940
agttggcatt tatcatctaa agtgtgcctc atatagatgg aatacagatg gatcctgttt 165000
ttcaaatctg gtctgataat tcctgccttt gattagattg tttaatccat tcacatttaa 165060
tattattatt gatataatta gatttatatc cacagtttta cttttggtct tttctatgta 165120
ctatttcttg ttcctctatt tctcctttgc tgctttcttt tccatctagt gactactttc 165180
taatataaat cttcatttct tttatgattc ttcaatattc tatttgttat tagtgtttgc 165240
tctagggctt accttatgta tcgtctcaaa atttacttca tatttatatt aatcctggtg 165300
agatacagaa gttattcctg tatgagttta ttcagtttta ccactttttg tggtattgtt 165360
acatatatta catctttatt atgcgctatt ataatgatca tactatataa tgatatatct 165420
ttaaagaagc tgaaaggaga gcaagtatat atttctagtt tctgttttat taacctcctt 165480
atatcatata tttgatccac ttttttggtt tttatggatt tgagttacca actggtggta 165540
tttccttact ctagaacagc tttgctccta tttacctcct tgctctttgc ttttggatat 165600
atgtgaactt cctgggagca cttccttttt gcctgaagaa cttcctctag tagttcttac 165660
aaaactggtc tgctaacaag gaattctgtt tttgtttatc tgggaatgct tttattttgc 165720
cttctttttg aaagaaactt ttctggacac agtattcttg gttggctttt tttttttttt 165780
tttttttttt tttttacttt gagcacttgg gatctgttac cccactactt tctgggtacc 165840
actgtttctg acgaaaagtc agctccacat ttgtctccct gacaccagaa caggggaggg 165900
tattaagcag agtgccacat agcctcacct cccaccattt catccaagaa tagtagttgg 165960
gtaatagttc aataactcac tctgaataat tgatagaaca acaagacaga aaatcaacaa 166020
gagttagtac tattattgtt gagttgtcta ttattgttca gttgtctgtt tctctcttca 166080
tttctgacag ttttatttca tatacttcag ggctgtgttt ttagctgtta taaattttta 166140
tttctttatg acttctgttt atgatttcta tttcttcctg ttaaattttc ccttttgtca 166200
ttgtaaaatg cttctcagta tctctaataa catggtttgt ttttaaagtc tattttgtct 166260
gattttattt attcttattt tatttttggg atggagtctc actctgttgc ccaggctgga 166320
gtgcagtggc gtgaccttgg ctcactgcaa cctctgcctc ccggattcaa gccgttctct 166380
tgcctcagca tcccaagtag ctgggactac aggcatttgc caccataccc agctaatttt 166440
tagtagagac agagtttcac catgttgacc aggctggtct tgaactcctg acctcgagtg 166500
atctgtctgc ctcagcctcc caaaatgctg ggattacagg tgtgagccac tgcacccagc 166560
caattttgtc tgattttagt acagtcactc tagctttctt attactgttt gcatgtcatc 166620
tttttccatc attttacttt caactatgtc tttgaatcta gaatgtgact cttatagacc 166680
atatatattt ggatcctgct tttaaggcag tctggcaatc tctgctcttt attgagtttt 166740
taattcactt atatgtaata taattattga tatggaagga tttatatcta ccatgttgtt 166800
atttattttc tatatgtctc atatcacttt tgttcctctc ttcctccttt actgccttct 166860
gcaggttgaa tagatatgtt ctagagtacc attctaattc ctttgttagt ttatttcccc 166920
catttttaaa gtgtaatctg gaggttacaa taagcagctt aagcaaaaac aatctgcttc 166980
aggttaataa tctactcaaa tatttttgtc tgccctattc tctccttctc agtactctta 167040
ttaacacata tgttgttact ccttaattcc acatatgttt tctactctta attacatata 167100
tgttacaact taattacaca tacattgtta cacatcctgt taggacaggg gttcccaacc 167160
ccagggccat ggactggtac cagtctgtgg cctattagaa actgggctac acagcaggag 167220
gtgagcagca ggcaagcaag cattactgcc tgagctctgc ctcctgtctg atcagtgatg 167280
gcattagatt ctcacagaga gcaaatccta ttgtgaactg agcatgtgag ggatctaggt 167340
tgtgcactcc gtatgagaat ctaactaaag cctcccccaa ctggctgtgg aaaaattgtc 167400
ttccacaaaa ctggtccctc atgccaaaaa ggttggggac cactatatta tggtatccaa 167460
tgggtatctc ttcattttc ttcattattt ttctttctat tcttcagtct gaatcatctt 167520
tatggatctg cgttgaagtt cattgattct ttcttctgcc aggtcaaatt tgcttagccg 167580
cactagtgag tttttcacct aagttattat atttcacaac tacagaattt ctatttggtt 167640
tctaatttct atctctatat tgatattatc tatttgatga gtctttgtca tcacacttgc 167700
attctttaat gtggtttctt ttggttcttt gaacatagtt ataatactta ctttgaaatc 167760
gcgccctaac atttggggcc cttcagagat aattcctatt tattgctcat tattcttgtt 167820
caagggtcac aattttctgt ttctttgcat atctcatttt ttttgttaaa aacttacttt 167880
agataatata tcgtagaaac tctggattct agttcttctc cctaaccagg gatgatttct 167940
gttactcatt tatttgtttg ctcgcttgtg tatgccttct ctgcatggat tctgcagagt 168000
ctgtgttctc ctgcagtgtg cagccactgg tgtctttgct cagttttgtt tgttttaatt 168060
cttatgtttg ttttgtaagc ctggcttcat tggtgtcacc cctggatcag cataacctag 168120
tggtcaagcc atgattagtc agacatttgt ttaaacatct tgagccagtg aatcttccac 168180
cctctgctga ggggatctat gtgtgggttg ggacattcaa agttcaggca ctttataact 168240
ctgtcctgta ttttactgtc tgcttgcaaa aggtctcaca gtcagccaag gataagtaga 168300
tagcaggaaa cctctctgat ctctcctgca agcatgtaca acttccatat ctccagaatt 168360

-continued ccttttaaaa tttttcttaa tctgtcgctt gcccaaccag tattgaaaca ttaggttgct 168420
gtgatgtggg ttgcctccaa ttatttgcca ctgaaatcct tgttgcttaa catagtgcat 168480
agggttttct atggaattca aaatcagatg agccttcttt gttgctggtc ctcaagccta 168540
ccgtgcccct gagcttgggt ggggagatgg cagccccacg ttaaatcata accctgctat 168600
tcttaggaag gcttaatatt ttttctttaa ttagcacttt tcaattttat atttctttgt 168660
ccagttttat cattgctttt cagggagtgg ttatatcaag gtgctcattc caccacctca 168720
gaagtggtcc ctatcttgtt aattttattt tttgaataca tataacatta acatacttcc 168780
aaaagtcaat actaaacaaa aggagctact gagagaaatc ttcctctcac ccatatctct 168840
tccatcctaa ttccccctac ccattatagg taaccagttt cagtgttttc tagtttatag 168900
tttgtgtgtg tttgctcttt ataagacatg attattttct catttcccaa aaaagtacta 168960
ttctgtatat gccctttttga actttgcttt tctcacctaa caacatctcc tagaaatcac 169020
tcaacatcca ttcacagaga tctttctcat tgcattgcta aagttgcata gtattcctta 169080
gtgtgactgt gctataacct ttcaaccaat ctcttatgct tgcatgtgta ggtggtttct 169140
agatggcagc tatgctcacc attctttggc tttcctacca tgtctctgag atacatctac 169200
tccataaatc gaatctaccc ccaagaggtg attctctgag ggtgccacct caaatcttag 169260
tcatttgcaa gagcctccac tatagctgct gctctggact acctatttct gacatgtgtt 169320
ctccatgttg acatttaata tagagtcttc tttttctggt gataattctg tctgtgctgc 169380
tttttagtct tctgtgcacc ctttaaattt tttaagtaac agaaaccatt tcaaaatgta 169440
caattcagtg tcacttagta catttacaat attgtgtttt ttgtgtcttt tctaagaatt 169500
tatttccaat ctcaagtcat aaagatttac tcctgttttc tactaagaaa tttatgcctt 169560
taactcttat tttttggtct ctgatacatt ttgagataat ttttatatgc tatgagttat 169620
gggtccaact tcattctttg atatatgagg atccagttgc cccagcacca tttgttaaaa 169680
gactactctt cccactgaat tcttgataca tttgttgaaa atgaattgat catatatgtg 169740
agtgtttatt tctacattct ctattatatt ccattggtct atatgtccat ccttgtgtcc 169800
tagagaccac attgtgtcag taccacattg ttttgattac tgcagctttg taaaagtttt 169860
gaaaatggca ggcctgagtc ttccaacttt gttctttttc aatatgattt tagattgttt 169920
ggggccctgg gaaaattcca tttacatttt aaaatcagtt tttacatttc tgcaaataaa 169980
aaggcccttg ggattttgat aagggttgca ttgaatctgt agatcactgg gtaatatcgc 170040
caacttaaca atatttaatc ttccaatctg tgaacacagg atgtatagtt ctatttattt 170100
aagtcttctt taatttttgt caacagtgtt ttgtagtctt tagtgcagaa gtctttcacc 170160
ttcttgtttt aatttattcc tagctatttt actctttttg atgctattgt aagtggaatt 170220
ttaaaaattg acttccttct tgggctgttc attcctggta tatagaggca caaatgattt 170280
tcttaaaata aatgttgaac atgtaccctg caattttgct ggacttgttt attagctcta 170340
ctagtttgtg gattctttga ttttctagat agaagatgtc attattgaat aaagagtttt 170400
actgcttcct ttccaatttg gatgctattc atttacctgt ttgtttattt atctgcctaa 170460
ttgtcatggt taaaactttc agtacattgt tcaatagcac tgggtaaagc atacagccat 170520
atcttactct ttgttatggg agaaattttt cagttttttt tctcattaag tatattagtt 170580
gtggattttt cacaaatcct ctttaacaca ttttgaaagt tccatgtttt tatcctgaaa 170640
ggttgtagaa ttttgtcaaa tgcttgttct gagtgaattg aaatgattgc atggattttt 170700
tatccttcat tgtattaatg tggtgtatta cattgattga tactcttgta ctgaaccacc 170760
cttgtattct tgagataaat tccatgtggt catgatatat aatccttttt aatatgctgc 170820
tgaatttggc ttactagtac tttgttaaat aaaagatttt agtatctagt ttgtcttttc 170880
ttgtggtata tttgtctggc tttggaatcc atgtaatact ggcctcatag aatgtattgc 170940
aaagtttttt ctcctctgtt ttttggaaga gtttgagagg gattggtgtg aattcttcaa 171000
gtgtttggta taattcaaca gtgacgccat ctgtgtagca ttttcttcat tggaaggttt 171060
ttggttactg attcaaactt tctacttgtt atgggtctgc tcataatttc aatttctgtt 171120
ttggtctgta ttagtatttt gtgaattcgt ccatcttatc taggttatat aatttgttgg 171180
tatacagtta ttcatagtat tcttttatca cactttttat ttctgtaaga tcagttatat 171240
cgttcccact tttgtttttt tttcttattt ttgttttttt ttgttgtgtt cctacttttg 171300
tttatgattt tagatatgtg caacttctct aattttttat tagtcattct agttaaaggt 171360
tttcaacttt gatcttttca aaaacaagca acttttggtt ttgttaaatt atctctgttg 171420
tttatttaag ctcgaattca gttttatctc cactcataca tattatttca ttctctcttt 171480
taactttagg tttacttcgt tcttctttct ctggttacgt aaggtataat attaggttat 171540
ggatccttct tctttttcag tgtgggcatt cacagctata atttttcctc tgagcacttc 171600
tttcactaca tcccataagt ctgagtatgt tgtgtcgtca ttttcacttt ttgaaagtat 171660
tttataattt cccttctgat gtcttctttg acacaataat ttttaaagag tgtgtagttt 171720
tatttccctg aatttgttaa tttttaggtt tttcttctgt tacagatttc tggcctcact 171780
atattgtagt tagagaagat attttgtatg atttctatat tttaaaattt attgagactc 171840
ttttgtggcc taacatatca tccctcctag ggaatgttcc atgtgcactt gagaagaatg 171900
tgtagttggg tggagtgtcc atatatgttt gtaggtctag ttggtttatg gtattgttca 171960
agtcctctct tttcttattg ggcttctgtc tggctgtaca ttatcttgtt gtgttttttt 172020
tttttaattt taaaaatatg catatttagt gtataaaaca tacagttaaa tcgttaacat 172080
agtgatgcaa attaatatgt ccatcatctc acagttattc ttttgtgtgt atgagtgaga 172140
aaagctatga tctactcaat tggcaaaaat tccaaatgca atatactaac tattctcatg 172200
ttctacatga gatctctaga cttgttcatc ctatatatct gctacttggt atcctttgac 172260
ctacatcttt ccattttctt cccccacacc ttgcccatgg taaccactag tttattctat 172320
ctctgtatat ttgacttttt tctttttaag attctacata taggtgagat tatttaaaac 172380
ttttcatttg tatatggctt atttaactta gcacaatgtc ttccagtttc atccatgtgg 172440
caagtggcag gatctccttt tttaatgcgg aataatattc cattgtagac atacacacca 172500
cagtttagtc atccatcaat ggacacgtaa gttttcatat cgtgactcat gcatataatg 172560
ccacaatgaa tataggagcg cagatatctt tatgaggtgg agatttcatt ttctttggga 172620
atatacctag aagagggatt agtgggtcag atgatagtat attttcaatt tctttaggag 172680
ccaccattct gtttttcatt atgactgcac caatctacag tcccaccaac actgtacaag 172740
agttccctaa ccctagccaa cacttaatag ctattctcat gagtgtgagg tgatatcgca 172800
tagtaatttt gatttgcatt tccctgacga ttagtgatgt taaatgtctt ttcatatatg 172860
tgtttgccat ttttataact tctttgcaaa aatgtctact cagttccact gcccattttt 172920
taattgggtt atctattttc ttgttattga gttgtatgca ttccttataa attttggata 172980
ttatcctctt ataagatata tggttggcaa atattttctt ctagtccata ggttgccttt 173040
tccttttgtt gactgtttcc gttcctgtgc agaagttttt tagtttgatg gtataccaat 173100

-continued tatttgtttt tgtagcctga gcttttggtg tgatctccaa aaaatcactg ccagagccat 173160
gtcgagcttt tcccctatgt tttcttctgg ttgtgggttt tggtcttatg tttaggtctt 173220
ttatccattt tgagtttatt tctatgtatg gtgtaaggca gcgatatcaa atcttttggc 173280
ttcccggggc cacactgtaa gaacaattgt cttaggccac acataaaata cactaacaat 173340
aacaacagct gatgggctaa aaaaatgcaa aaaaattcaa tgttttaaca aagtttacaa 173400
atttgtgttg ggcctcatta aagccatcct gggcttacat gtggtctgtg ggccatgggt 173460
tggacaagcc acagaactgg gtttcctaac gtcatttatg agagagacta tctttctgca 173520
ttgttttctt cgtgttcttg tggaaaattg gttgatcata tatctttgaa tttctttctg 173580
ggctctctat tctgttccac tggtctacat gtttgttttt tatgccagga ccatactgtt 173640
tgatcaatag ttttgtaaaa taaaccagaa agtatgaagt ctccctttgt ttttcagaac 173700
agaattttca gaatttcgtt ggctacttaa ggttcttgct attccaaatg aactttagaa 173760
tttaaaaaaa ttttccatgg gattttgata gggattttat tcaatctgta tattgatttg 173820
gatattattg acattttaac aatattattc agattcatga gcatgggata tctttccatt 173880
tatttgtatc ttgtttaatt tctttcatca atgattcata gttttcagtg tacaggtctt 173940
tcatcttttt ggctaaattt attcctaagc aatttttttg atgctatcat aaatgggatt 174000
gttttcttga tttctttttt ggccaggtca ttatttgtgt atagaaatgc aactactgtt 174060
ttatattgat tttatatcct acaactttac tgaactcatt tattagttct aacaggttgc 174120
tttgtcagag tcttcggggt tttctatatg taggatcatg tcatcttcat ataaagataa 174180
tattacttct tacttcctga tttgaatgtc tttcatttct ttttcttgtc tgtttggttg 174240
tactagtact tccagtacta tgttgagtag tagtagctag agtgggcatc cttgccttgt 174300
actggttcat agtagaaggg cttctgtttt ccctcattga ttataacgtt agctgtgggc 174360
ttttcataaa tggcattcgt tatattgagg agtgttcctt ctatacctga actgttagaa 174420
tttatcaaca aaggatgttc aacttcatca aatacttttt gtgtgtcaat tgagatgatc 174480
atgtggtttt catctttcag tctgttagta tcacattgat tgctacatgt atattaaata 174540
agatttgcat gccagaaatt aattccacat agacatgata tataatcttt ttgatgtatt 174600
gttaaattta gtctgccaat attttattaa ggatttttgc atcggtattc ttgggttatg 174660
ttggcctgta gtttcctttt cttgtgatgc ctttggctca cctgggtatc aaggtgatgc 174720
tggcctcata aaatgtgtta ggaagtattc cctttagctg catttttttt tttttggaag 174780
tattccctat agctgcattt ttttggaaga gtttaagaag tattggtatt ctttgaatat 174840
tgggtagtat tcagtcatga agctatctgg tcctgggctt ttctttgttt gaggttttgg 174900
ggttttttta acttttattt ttgatttaga gggtatatgt acaggtctat atgttgcatg 174960
gtatatggag tatactgcat gatgatgagg tttggagtgt ggataagcct atcacccagg 175020
tagtgagcat agtacccaat aggtaggttt tcagcccacc tctccattcc tcccccaagt 175080
agtccccagt gtctactgat catctttatg tccatgttta ctcagtgttt aggtcccact 175140
tgcaagtggt aacatgcagt atttggtttt ctgttcctgc attaatttgc ttaagatagt 175200
ggcctctagc tgcatccatg ttgctgcaaa ggacgtaagt tcattcatgt atatatatat 175260
attttttttt tttatttttt ttttagacgg agtttcgctc ttgttgccca ggctggaggg 175320
caatggcatg atctcggctc actgcagcct ccgcctaccg ggttcaagtg attctcctgc 175380
ctcagcctcc tgagtagctg ggattagagg catgcgccac cacgtccagc taattttgta 175440
gttttagtag agacagggtt tttccatgtt ggtcaggctg gtctcgaact cctgacctca 175500
ggtgatccac ccgccttggc ctcccaaagt gctgggatta caggtgagag ctaccgcacc 175560
tggccgaatt cattcatttt tatggctgca tagtattcca tggtgtacat gtaccacatt 175620
ttctttatcc aatccaccac tgatgggcat ctaagtggat tccatgtctt tgctgttgtg 175680
aatagtgctg tgatgaacat acaaatgcat gtgtcttttt gatagaacaa tttattgtcc 175740
tttgaatata tatccagtaa tggattgct gggtcagatg gtagttctgt ttttagttat 175800
ttgagaaaac tccaaactgc ttagcacagt ggctgaacta atttgtattt ctgccaacag 175860
tgtataagcg ttccctttc tctgcagcct tcccagcaac ttttattttt ttgacttttt 175920
aataattgcc attctgactg gtgtgagatg gcatcccatt atggtttggt gtttttttgt 175980
tgttgttgtt ttgttttgtt tttttttgtc tgttttttgc tttttgttt gtttgtttgt 176040
tttttgagaa agagtcttgc tctgtctccc aggctggagt gcagtggcgc aatctcggct 176100
cactgcaacc tccacctcct gggttcaagc aattctcctg tctcagactc ctgagtagct 176160
gggattacag gtgaccgcca ccatacctgg ctaattttg tgtttttagt agagacgggg 176220
tttcaccatg ttggccagga tggtctcgaa tacctgaccc cagatgatcc acgcacctca 176280
gcctcccaaa gtgctaggac tacaggcatg agccaccgtg cctggcctca ttatttgcat 176340
ttctgattat tagtgatcat gagaatgttt ttttgtttgg ctacttctgt atttctttt 176400
aagaaatgta tgttcctgtc ctttgccaat tcaattggat tattcgtttt ttgcttgttg 176460
attggtttaa gttccttatg gattctggac ataggacctt tgccagatga atagtttgca 176520
aatatttttt ctcccattct atatgttgtc tgtttactct gttgataatt tcttttgcta 176580
tgcagaagct ctttagttta ccactgtgat ctctttgcta ttggtctgtt caggctttct 176640
attcctgatt taatcttagc aggttggttt ttttctagga atttgtccat ttcctctagg 176700
ttatccaatt tgttgggata taattgttca taaaagtccc ttatgatcct ttttatttct 176760
gaagtacctg ttgtaatata ttctccattt tcatttctga ttttgtcctc tttcttagtc 176820
caagagtttg ttgattttat ttttcaaaaa tcaattcttt gtttcaaaaa ttgaagtctt 176880
agttttactg actttttcc cctatggttt ttctttctaa cttgtctctg ttctgatctt 176940
tattatttcc ttctgttaac tttggcttta gtttgttctt ctttttctaa ttccttgagg 177000
tacaattttg ggctatttga aatatctctt ctttttaat gtaggcaagg catttattgc 177060
tgtaaacttc cctcttagaa ctgcttttgc tgcatgtttt gcttttggta tgttgtgttc 177120
ccactgtcat ttgtctgaag atattttaa gtttctgttt tcatttcttc tttgactcta 177180
cccattactg aaagtacgtt attgaagtcc ctaagtatta ttgtagaact gtctttctca 177240
ctccaattct gtcagtatat tttcttatat tctggggctc tatattttgg tgtgtatacg 177300
tttccaattg cgaagtcttg agtaattttc catttctca gtatgtaatg tcctcctttg 177360
tctcctataa caatttttaa attcaagttt atttctttta ttagtataat tacctccagc 177420
tttctttagg ttactatttg tatgaaatat catttttcat tctttcactt tcaatctact 177480
tgtgtcttta gaccaaaagt gagtttgtta tatacagcat aggttgatgg ttttctttta 177540
aatccattct gccaacctct gctttttgga gaatttaatc gacttacatt taaagtactt 177600
acttataaaa aagaagttct gacattttgt gccttttctt ttgccttaca ttttttaaat 177660
acaacatttc ctcccttact gcctttttt gtgtttgatg attttctgat agtgtaccat 177720
tatgattctc tattcgattg tctgtatgtg tgtatgtgta ttttaaagac tttatatttt 177780
tagagcagtt ttagggttcc agcaaaattg agaggtaagt acagagattt cccgtatacc 177840

-continued cactgcaccc atacatacag agcttttccc attaccaact ctcccaccag agtggcacgt 177900
ttgttacaac ttatgaatct gcatttacac attattatca aagtccctag ttaacattag 177960
ggctcactgt tggggtgtac attctgtggg tttctacaaa tgtgtaacat gttgatatgg 178020
tttggctctg tgttcccacc caaatctcat cttgaactgt aatccccatg tgtcagggga 178080
ggggcctggt ggggggcaaa cttcccctt gctgttctca tgatagtgag ttctcatgag 178140
atctggttgt ttaaacgtgt gtggcacttc ccatctcact ttctttccct ctcctgttct 178200
gccatggtaa agatgtgcct gcttctcctt tgccttccgc catgatttta agtttctgag 178260
gcctgccagc catgcttact gtacagccta caaaactgtg agtcaattaa acctcttttc 178320
tcacaaatta cccagtctca ggtagttctt tatagcactg tgagaacgga ctaatatgca 178380
tgtatctacc attatagtat catacagata cgtatattta catatatttg tacattttca 178440
ctgccctaaa agtactctgt gcactgccta ttcaaccctt cttccccaac aacccttggc 178500
aaccactgaa ctttttactg cctccatagc attgcctttt ctaaaatgca atatgattgg 178560
aatcatacag tatgtagttt cttcagattg ccttatttca catagtaata tgttttttaa 178620
ttacctccat atcttttcat ggcttgatag ctcatttcta tttagtgatg aataatattt 178680
cattgcctgg atgtactaca gtttatctgt ctactcacct atggaaggac atctcggttg 178740
cttccaattt caacaatcac aaataaagct tctgtaaaca tctctgtgca gatttttatg 178800
tgaatataag tcttcacctc ctttgagtaa ataccaagga tgtgattgct gaactgcatg 178860
gtaagaatat gtttaatttt ataagaaacc actgatttcg atatactctg gattcttcgg 178920
gggatatgta tacacattca gaagtggaat tgatggatcc tatgataatt ccatttttaa 178980
ttctttgaag aaccaccaaa ctcttctcca ccagggctgc accactttac attcccatta 179040
atggtatatg tcaaagtggc tgtaccattt tgcattccca ccagcaatgg atgagtgttc 179100
ctgttgcccc acatattggc aagtatttgg tattgtcagt gttttgaatt ttggccattc 179160
taataagcgt gtagatatat cacatttctt gttttaattt ccatttccct aatgacgtaa 179220
gatgtggggc atcttttcat atacttagtt gccatctgta tatcttcatt ggtgagatgt 179280
ctgttaaggt cttcagtcca ttttgtaatc agattgtttg ttttctaatt gttatgtttt 179340
taaggttctt tatatatttt ggatgagtcc tttatcaggt atatctttta caagtattgt 179400
ctcccttctg tggcctgtcc tttcatcctc ttgacagtat gttttacaga gcagaaactt 179460
ttatttttaa caaagtctag cttatcaatt atttctttca tgaatcatgc ctttggtgtc 179520
atatctaaaa agccatcacc aaactaaaga tcatctagat ttcttcctat gttatcttct 179580
gggatttcta tttgttgttg atttccaaat cttttattgt ggcaaaatac acttaacata 179640
aaaattacca tcctaaccaa ttttagtgta caattcagtg aatgtattag atacgttcac 179700
aatgctgtgc aatcatcact atcatccatc tccataacac ttgtcatttg taattatgaa 179760
actctatatc cattaaacaa taattcccca acccccccac caccgccatc tcttggaaac 179820
caccttgtac tttctatgtc tctgatttga ctattctaca tacctcatat aagtggaaac 179880
atacagtact tctcttcttg tgactgctgt atttcattta acataatggc ctcgaggttc 179940
atccatgttg tggcatgtgt caaaatttct atttttttta aagctgaata atattacatt 180000
gtatgtatat accacatttt gcttatccat tcttccatgg acatttgggt tgcattgatg 180060
ttttaactgt tgtaaataat gccactacaa tcgtgggtat acaaatatat ctttgagact 180120
gcttttaatc cttctgggtg tatacacaga ggtggagttg atggatcaga taattctgtt 180180
tttaattttt gaaggaacac caaactgttt aacacagagg ctgtaccatt ttgcattccc 180240
actaacagtg cacaaggatt ccaatttctc catgtccctt ccagcagtgg ttattttctg 180300
tttatgtggg attttttga gacaagatct ggctctgtca cttaggctgg aatgcagtgg 180360
catgatcatg gcacactgca gcctcaacct agacctctgg gcttaggcta tcctcccacc 180420
ttaacctccc acgtagctga tactagagat gggtctcact atgttgccta ggctgtgttt 180480
attttttaa tagtagtcat ctgagtgtat gtaaggttgt ggttttgact tgtatttcct 180540
aatgactaga gatgttaaac aacttttcac gtactattat ccatttgtat atcttctttg 180600
gagatacgtc tgtccaagtc ctttgccctt tttttttttt ttttgagatg gagtctcact 180660
ctgttgccca agctgagtgc agtggtgcca tctcggctta ctgcaacctc tgcctcctgg 180720
gttcacatca ttctcctgcc tcccgagtag ctgggactac aggcgcccac caccacgcct 180780
ggctaatttt ttgtattttt agtagagacg gggtttcacc ctgttagcca ggatggtctc 180840
aatctcctga cttcatgatc ctcccgcctc agcctcccaa agtactggga ttacaggcgt 180900
gagccaccgt gcctggccct tttgcccatt tttcaggtgc attgtttttt ggtgatgact 180960
tttagaagtt ctctgtataa tctggacatt aatcccttat caggtatgtg atttgcaaat 181020
ttttctccca ttctgtaggt tgtcttattg cttagttgat attattttaa tgcacacaat 181080
gtaaattttt aaaatttatc tagttttact tttattgcct gtgcaagtac aatttatcta 181140
tttttacttt tattgcctgt gcctttggtg tcgcatacaa gaagcactgc caatgatgta 181200
aagtttttcc cctatgtttc cttataagac ttcatagttt taggactttg acccattttg 181260
agtaagtttt tgtacacagt gttaggtaag ggtctcaact tcattctctt ttatacatgg 181320
ttaggtaagg atctcaactt cattctcttg agttaatttt tgtgtatggt attaggtaag 181380
ggtctcaact tcagttatcc tggcaccatt tgttgaaaat acagcacttt ccctattgaa 181440
tggtcttggc actcttctca ggaatcattt gatcatgtat acaagggttt atttttgggc 181500
tctctattca attccattgg tctctacatc tttatgtcaa taccacatag ttttgattac 181560
tgtagcttcg taataagttg gggtttttgt ttgtttttca gacattctta ctctgttgcc 181620
cacgctggag tacagtggca ttatcactgc ttactgccac ctcaatctcc caggctcaag 181680
caatcctccc acctcggctt cttgagtagc tgggaataga agtgtgtacc attacacctg 181740
gccaattatt ttattttttg tagagatgag gtctccctgt gttccccagg ctggtctcaa 181800
actcctggac tcagaagtcc tcccacctca gccttcaaaa gtgctgagat tacaggtgta 181860
ggccattgta cctggcctgt agtaagtttt caaatcagaa agtgtgagtc ctccaatgtt 181920
gttcatcatt ttcaagaatg ttttagctat tcaaggtccc ttgagattcc atgtgaattt 181980
taggatgggg tttcttcttt ctgcaaataa catcattagg atttttattg ggattacctt 182040
ggatttgtag attgttttgt gtggtactga caccttaaca atattggcct tccaatccat 182100
gaacatagga ggtgttttcc ctttatgtct actttaattt ctttcagcat tgttttgtaa 182160
ttttcattgt acaagacttt cacctccttg gtaaagttgg ttcctaagtt tgttattctt 182220
gatgcttttt tcagctttta ttgaggtata attgacaaat taaaagtgca tatatttaag 182280
aacatatttg acctactgtg aaatgattac tacaatcaag ccaattaaca tataccttac 182340
atagttgcca tgtgtgtgcg tgtgtgtggt cagaatacct aagctatact ctcttagcaa 182400
attccaagta tagaatatat taactatagt caccaatctg gacgttatgt caagaactta 182460
ttcatctgat aactctatgt ttgtaccctt caacatttcc tatttcccct actccctgac 182520
ccctagtaac caccettcta ctctccgttt ctctgagttc aagcttttta gaattccata 182580
tgtaactggg atagtgcagt atttgtcttt ctgtgtctgg ctatttcact tagcataata 182640
tcctccaggt tcatctatgt tgtcataaat tgcatgattt cctgcttttt aaaggatgaa 182700
tatttcattg tgtgtgtgta tatatgtgtg tgtgtgtgtc tgtatgtata tgtatgtgat 182760
gtgtttattt gggaatttgg tgatacacac acacacacta ttttcttcct ttctttttga 182820
gacagggtct ccatctgtca tccaggcagg agtacagtgg cacaatcaca gttcactgta 182880
gcctcaacct catgggctca agtgatcctc ctgcctcagc ctcctgagta gctgggacca 182940
cagtcatgca cccccatgcc cagctaattt ttaaaatttt atgtagagat agggtatcac 183000
tatgtttcct aggctggtct caaactcctg tgttcaagct atccttcacc ttggccaccc 183060
ccaagtactg ggattacagg tacaagccac catgcctatg aatactatgt tgctcatttc 183120
ttgactactg taacactaca atgaacatgg gagtgcagat acctcttcaa gatactgact 183180
ttgttttcct tagatatacc cggaactgag actgctggat catatagcag ttccaatttt 183240
aatttttaa agaaaatcta tcgtgttttc cataatgact gtatcaattt acattcctaa 183300
caaaaatgta taagggacac cttttctcca catcctcacc aacacttgct atcttttgac 183360
tttttgataa tagcgattct aacagttatg aggtgatatc tcagtgtggt tttcatttgc 183420
atttccctga tgataagtga tgttaagcac ctttttatat acctgttgac catctgtatg 183480
tcttctttga ataaatgtct attcagtccc ttgtccatct taacaggtta ttaattgggt 183540
tattaagttt ttttgctagt tatatgagtt ccttatatat attggatatt aatagcttat 183600
cagatatatg gttggaaata ttttctcccg ctacatgtgc tgccttttca ttttgttgtt 183660
tcctttgttg tgcagacact tttttgtttg atgtagttct aatttatttt tgcgttttat 183720
tccttgtgct tttgatgtca catctaaaaa attgtcacaa aaaccaatgg caaggagctt 183780
ttccctgttt tataggtttt atggtttcag gtcatatgtt taaatcttat tcacttttct 183840
ctacagtgta gggtaaggtt ccaatttaat ttttttgcat gtggatatcc tggtttcaca 183900
gtgccattta ttcaagagag taccctttcc ccattgtgta ctcttggtgt ctttgtcaaa 183960
gattagttga ccataaatgt gtgggtttat ttctatgctt tctattctgt tccattggtt 184020
tatttctata ccagtaccat aactttgaaa tataattcaa aataagcatg tgtaatatct 184080
ttcactttgt tcttattgct caagtatgct ttagatcttt aaggtctttt gtagtttctt 184140
tcaaatttta ggattttttt tgtctatatc tgtgaaaaaa agtcactgga aatttgatag 184200
gcattgcctt gaatctgtag atcactttga gtagtatagc tatttcggca atatttattc 184260
tattgatcta tgaacaccag atatctttcc atttatttgt atcatcttag aatttgttca 184320
atgtttcata gttttcagtg tctaggtctt ttatctcctt ggttaaatgt atgcctaaat 184380
gttatgcagt ccaatttctc tatttttat tttatctgtg cctttcatat tatatccaaa 184440
tgaagtcaat accaaatcca atgtcatgca gtttttgccc catgttttct tctaagagtt 184500
ttatagtttt aggtcttaca tttaggtctg tggtccactt tgagttaatt tttgtatatg 184560
gagttaggta aaggtctcga cttcattctc tcacgtgagg atatccagtt ttcctggcac 184620
catttgttga aaagagaatc catttgccat tgaatggaca tggcatgctt gtcagaaatc 184680
atgcgttcat atatgaaagg atttatttgg gagctctcta ttctttttga tgctatttta 184740
aatgaaattg ttttcttaat ttgtttttca ggttgtttat tattagtgta tagatacgca 184800
aatgacttct gaatgctgat tttgtatcct gccactttac tgagttagat tattacttct 184860
aacaggtttt ttttgtggag tctgtagcat tttctacata tatgatgtca tctgcaaaca 184920
gagacaattt tacttccttc tttctgattt gagtgtattt atttattttt cttgcccaat 184980
tcctctggct aggacctcca gtactgtgtt gaatagaagt ggtgagaata acttgtacta 185040
ggtccctcat cttagaggag aggcattcag cttttcagca ttgagtatga tgttagctgt 185100
gggctattca tatatggcct ttattgtgtt gcagtacatt ccttctatac ctaatttgtt 185160
catagttttt atcatggaag gatgttgaat tatgtgaact gcattatttg cacttatcaa 185220
aatgattgta tgatttttat ctttgatttt attaaagtat cccatttctt gtatatgtac 185280
acttaactgt ccttatgtac taaggataaa tcccatgttt gtgatatatg atttttttaa 185340
tgtgctgtta aattcagttt gatcatattt tgttgaaaat ttttaaatgt atagtcataa 185400
aaaaatatca gccagttatt ttcttttctt atattgtcct tgtctggcct tagtatgagg 185460
gcaatgctag ccttgtaaaa taagttggga ttgttccctc tttgtttggg gggaatattt 185520
tgatcttata cttcccccgc tacattttat ttttgatgcc ccaaggtaca ccttttaata 185580
ttgcatatcc attgagaaat tatgaaaaca atagtaattt ttaattattt ttcttttaac 185640
ctttatacta gagttatgtg atttatatac taccattaca ctattagagt attcttaagt 185700
tgcccgtata tttatttatc agtgaatttt gtactttcat atgttttcat gttactaatt 185760
atcatccttc catttaagcc tgaataactc cctctggcat atcttgtaag gcaagagtag 185820
ttgctgataa actccttcaa cttttgttta cctgaggaag tcttgtatct gtttcatatc 185880
tgaaggacag ctttgctgtg taaagtattc ttagatggca gtttttatc tttcagaact 185940
ttgaatatat aatcctattg tttcctggcc tggaaagttt ttgctcagaa atccactgat 186000
agccttatgg aggttcctgc agatgtaaga actttattta tcttgccgct ttcaaaatta 186060
tcttgtcttc cattttttac attttgatgg caatatatct aggtgaaacc tcttttagat 186120
ggaaactaat tgtaattctt tgagcttcat gtacctagat gtccatcaat ctgggaagag 186180
ccccagatat gggaagtttt cagccattat ttctctgaat taactttcta ccctttacct 186240
ctctactttc cttctataaa tcctgtgtga acattaactc tcctgatggt gtcccataaa 186300
tcctgtaaac ttcccttgtt accttttcat tctttatttt tctcctctac tggttatttt 186360
caaataattt atcctccagt tgatgaattc ctccttctat ttgatcaagt ctgctgctga 186420
tgctttctat ttcacttttc atttcatgca ctatattctt cacctccaaa atgtttgttt 186480
ttttttagg atttctattt ctttattgaa tgtctccttt tgtgtattaa tgatttcatt 186540
aggttgtctc tctgttctct ggtagcacac tgaacttcct taaatcagtc gtttttaatt 186600
ttctgtaagg caattaatgt atcccaattt cttgggagtc agtccctgaa aattattgta 186660
tttctcaggt gggtgctatg tttccttggt ttttctgttt cttgttacaa tgaattgaaa 186720
tctgctcact tgatggagtg ttaagtaggt agggtgcagc agctgtagcc cagatgagga 186780
tataatggaa tactcttctt gcagctccat cagctgaggt cagcagtggc aaacattaca 186840
aaggtccttg gtggccaagg ctgagtgtcc tgatgctgtc gtgtaaatag agttgtgtta 186900
ataatatccc tttcagattg tttgtgatta atgtatagaa atgcaactga aagctgggcg 186960
cagtggctca cgcctgtaat cccagcactt tgggaggctg aggagggcag atcacaaggt 187020
caggagatcg agaccatcct ggctaacatg gtgaaacccc atctctacta aaaatacaaa 187080
aacattagcc aggcatagca gcgtgtgcct gtagtcccag ctacttggga ggctgaagca 187140
ggagaatggc gtgaactcgg gaggcagagc ttgcagtgag ccgagatcgc gccactacac 187200
tctagcctgg gcgacagacc aagactctgc ctcaaaaaaa aaaaaaaaaa aaaagaaatg 187260
caactgaatt ttgtgtactg acttactatc ctgctacttt gctgaattaa tttattcagt 187320
ttttgtggtg agttttcagg gatttctaca aatatgatca tatctatgaa caaacataat 187380
tttaattctt cctttctaaa tgatgccttt atttcttttc catattcttt ggctagaaag 187440
ccactactat gtttaatata atggctaaaa tgcgcatctt gctttattcc tgatcttaga 187500
ggaaaagctc ttagtctttt caccattatg atgctccttg tgggtttttc ttctaggagt 187560
ctttttcttt gtccttttat ttttagtcaa catgtaataa ttgtagatat ttatgggata 187620
tacacagtga tattgtgata catgtatata atgtgtcata atcaaatcag ggtaattagc 187680
atattcatca actcaaatat catttctctg ttttgtgagc agtcaaaatc ctccatcttt 187740
ctgtgcctaa tttcatttaa catattatcc aagttcatcc atgttgctgt gaatgacagg 187800
acttaatgct ttattatgac tgaataatat tccattgtgt atacatacca cattctttct 187860
ctgcatctgc tgatggagat ttaagttgat tccatatctt aactgttgtg aacagtactg 187920
caataaacat gagaatgcaa atatcttttt tatatactga tttcctttcc tttgagtcaa 187980
tacccggtag tggattgtca aactgtatga tagtctactt ttagtttttt tgacaaaaca 188040
ccacagtatt ttccataatg actcactaat ttatagtccc acaaatagtg tattatttcc 188100
cttttctctg catccttgcc agcatttgtt atgttttgtc tttttgaaaa cagccattct 188160
aactgaggtg aaataatgtc tcactgtggc tttgacttgc atttctgtga tgagagatgt 188220
tgagcatttt ttcacatacc tgttggccag ttgttctatt ttgcacattt ctaaatcaga 188280
taatctggtg ttttttgctg ttgaattgtt tgaattcctt gtatattccg gatattaatc 188340
ccttgtcaga tgaatatttt ctcccattct acaggatatc tcttaatagt ttattatttc 188400
cttttatgtg taggttttta gtttgataca gtcccatttg tctatttttg tttttgttgc 188460
ctgtgcttat aaagtcttac ccataaaatc ttcgctagac ccatatcctg aagggtttcc 188520
cttctgtttt cttctagtac tgtttgcttc aggtctcatg tttaagtctc taatcaattt 188580
tgagttgatt tttttatatg ctgagagata gtatagtttc attcttctgc atatgatatc 188640
ctgttttccc aacatgatgt gttcaacatg gtgtcctttc cccagagtgt gttcttggca 188700
cctttgtcaa aaaccagttg tctgtaaata aatttattta cttctgggtt ctctattctg 188760
ttccattggt ctatatgtct gttttatgcc cattgcatgc taatttggtt accattgttt 188820
tgtatacaag gggggattgct tccgagaccc cctgtatata ccaaaagcca tgtatattca 188880
agtcccagag tcagccctgt gtaatgcgca tatacaaaat gtcagtcatc tgtatacata 188940
gttttcactt ttgtgaatat tgcattctat ccttgttaga ttatggggaa aatccacgta 189000
taaatgaacc tatacagttc aaatctatgt tgttgaagag tcgactgtat tttgatgtca 189060
ggcagtgtag tgcctccagc ttcattctgc ctgctcagta ttgtttgtcc tatttgtggt 189120
cttttgtggt tccatgcaag tttaaggatt gtgtttttgc tatttcggtg aagattgtct 189180
ttggtatttt ttttttttta gatttctctt ttctctctct ctccctttttt tttattatac 189240
tttaagttct agggtacatg tgcacaacgt gcaggtttgt tacatatgta tacatgtgcc 189300
atgttggtgt gctgcactga ttaccttgtc atttacctta ggtatatctc ctaatgcttt 189360
ccctcccccc tccccccctcc ccccccaccc cacaacaggc cctggtgggt gatgttcccc 189420
ttcctacgtc caagtgttct cattgttcag ttcccaccta cgagtgagaa catgcggtgt 189480
ttggttttttc attcttgcta tagtttgctg agaatgatgg tttccagctt catccatgtc 189540
cctacaaagg acgtgaactc atcctttttt tatggctgca tagtattcca tggtgtgtat 189600
gtgccacatt ttcttaatcc agtctatcat tgatggacat ttgggttggt tccaagtctt 189660
tgctatcgtg aatagtgctg caataaacat acgtgtgcat gtgtctttat agcagcatga 189720
cttatagtcc tttgggtata tacccagtaa ggggatggct ggatcaaatg gtatttctag 189780
ttctagatcc ttgaggaatc accacactgt cttctacaat ggttgaacta gtttacagtc 189840
ccaccaacag tgtaaaagcg ttcctatttc tccacatctt ctccagcacc tgttgtttcc 189900
tgaattttta atgattgcca ttctaactgg tgtgagatgg tatctcattg tggtttttg 189960
atttgccttt ctctgatggc cagtgatgat gagcattttt tcatgtgtct tttggctgca 190020
taaatgtctt cttttgagaa gtgtctgttc ataacctttg cccacttttt gatagggttg 190080
tttgtttttt cttgtaaatt tgtttgagtt ctttgtagat tctggatatt agccttttat 190140
cagatgagta gattgcaaaa aatttctccc attctgtagg ttgcctattc actctgacgg 190200
tagtttcttt tgctgtgcag aagctcttta gtttaattag atcccatttg tcaattttgg 190260
cttttgttgc cattgctttt ggtgttttag acatgaagtc cttgcccatg cctatgtcct 190320
gaatggtatt gcctaggttt tcttctaggg tttttacggt tttaggtcta acatgtaagt 190380
ctttaatcca tcttgaatta atttttgtat aaggtgtaag gaagggatcc agtttcagct 190440
ttctacatat ggctagccag ttttcccagc accatttatt aaatagggaa tcctttcccc 190500
atttcttgtt tctgtcagct ttgtcaaaga tcagatgatt gtagatgtgt ggtattattt 190560
ctgagggctc tgttctgttc cattggtcta tatctctgtt ttggtaccag taccatgctg 190620
ttttggtgac tgtagccttg tagtatagtt tgaagtcagg tagcgtgatg cctccagctt 190680
tgttcttttg gcttaggatt gtcttggcaa tgcgggctct tttttggttc catatgaact 190740
ttaaagtagt ttttttccaa ttctgtgaag aaagtcattg gtagcttgat ggggatggca 190800
ttgaatttat aaattacctt gggcagtatg gccattttca tgatactgat tctccctatc 190860
catgagcatg gaatgttctt ccatttgttt gtatcctctt ttattttgtt cagcagtggt 190920
ttgtacttct ccttgaagag gtccttcaca tcccttgtaa gttggattcc taggtatttt 190980
attctctttg aagcaattgt gaatgggagt tcactcatga tttggctctc tgtttgtctg 191040
ttattggtgt ataagaatgc ttgtgatgtt ttgcacattg attttgtatc ctgagacttt 191100
gttgaagttg cttatcagct taaggagatt ttgggctgag atgatggggt tttctaaata 191160
tacaatcatg tcatctgcaa acagggacaa tttgacttcc tcttttccta attgaatatc 191220
ctttctttct ttctcccgcc tgattgcctt ggccagaact tccaacacta tgttgaatag 191280
gagtggtgag agagggcatc cctgtcttgt gccagttttc aaagggaatg cttccagttt 191340
ttgctcattc agtatgatat tggctgtggg tttgtcataa atagctctta ttattttgag 191400
atacatccca tcaataccta atttattgag agtttttagc atgaagggct gttgaatttt 191460
gtcaaaggcc ttttctgcat ctattgagat aatcatgtgg tttttgtctt tggttctgtt 191520
tatatgctgg ataatgttta ttgatttgca tatgttgaac cagccttgca tcccagggat 191580
gaagcccact tgatcatggt ggataagctt tttgatgtgc tgctggattc ggtttgccag 191640
tattttattg aggattttgg catcaatgtt catcagggat attggtctaa aattctcttt 191700
ttttgttgtg tctctgccag gctttggtat caggatgatg ctggcctcat aaaatgagtt 191760
agggaggatt ccctcttttt ctattgtttg gaatagtttc agaaggcata gtaccagctc 191820
ctccttgtac ctctggtaga attcggctgt gaatccgtct ggtcctggac tttttttggt 191880
tggtagacta ttaattattg cctaaatttc agagcctgtt attggtcttt tcagggattc 191940
aacttcttcc tggtttagtc ttggaagggt gtatgtctcc aggaatttat ccatttcttc 192000
tagattttct agtttatttg catagaggtg tttatagtat tctctgatgg tagtttgtat 192060
ttctgtggga tcggtggtga tatccccttt atcatttttt attgcatcta tttgattctt 192120
ctctcttctt tattagtctt gctagaggcc tatcaatttt gttgatcttt tcaaaaaaac 192180
cacctcctgg attcattgat tttttgaagg gttttttgtg tctctatctc cttcaattct 192240
tctctgatct tagttatttc ttgccttctg ctagcttttg aatgtgtttg ctcttgcttc 192300
tctagttctt ttaattgtga tgttagggca tcaattttag atttttcctg ctttctcttg 192360
tgggcattta gtgctataaa tttccctcta cacactgctt taaatgtgtc ccagagattc 192420
tggtatgttg tgtctttgtt ctcattggtt tcaaagaaca tctttatttc tctgccttca 192480
tttcgttatg tacccagtag tcattcagga gcaggtggtt cagtttccat gtcgttgagc 192540
ggttttgagt gagtttctta atcctgagtt ctagtttgat tgcactgtgg tctgagagac 192600
agtttgttat agtttctgtt cttttacatt tgctgaggag tgctttactt ccaattatgt 192660
ggtcaatttt ggaataagtg cgatgtgatg ctgagaagaa tgtatattct gttgatttgg 192720
gttggaatgt tctgtagatg tctattaggt ccacttggtg cagagctgag ttcaattcct 192780
ggatatcctt gttaacttcc ggtcttgttg atttgtctaa tgttaacagt ggggtgttaa 192840
agtctcccat tattattgtg tgggagtctg tctctttgta gatctctaag gacttgcttt 192900
atgaatctgg gtgctcctgt attgggtgca tatatattta agatagttag ctcttcttgt 192960
tgaattgatc cctttaccat tatgtaatga ccttgtctct tttgatcttt attggtttaa 193020
agtctgtttt atcagagact aggattgcaa cccctgcctt tttttatttt ccatttgctt 193080
ggtagatctt cctccatccc tttattttga gcctatgtgt gtctctgcac gtgagatggg 193140
tctcctgaat acagcacact gatgggtctt gactctttat ccaatttgcc agtctgtgtc 193200
ttttaattgg agcctttagc ctatttacat ttaaggttaa tattgttatg tgtgaatttg 193260
atccattatg atgttagctg gttattttgc tcgttagttg atgcagtttc ttcctagcat 193320
ctatggtctt tacaatttgt catgtttttg cagtggctgg taccaattgt tcctttccat 193380
gtttagtgct tccttcagga gctcttgtag ggcaggcctg gtggttataa catctctcag 193440
catttgcttg tctataaagg attttatttc tccttcactt atgaagctta gtttggctgg 193500
atatgaaatt ctgggttgaa aattcttttc tttaagaatg ttgaatattg gcccccactc 193560
tcttctggct tgtagagttt ctgctgagag atccgccgtt agtctgatgg gtttcccttt 193620
gtgggtaacc caacctttct ctctggctgc ccttaacatt ttttccttca tttcaacttt 193680
ggtgaatctg acaattatgt gtcttggagt tgctcttctt gaggagtatc tttgtggcat 193740
tctctgtatt tcctgaattt gaatgttggc ctgccttgct aggttgggga agttctcctg 193800
gataatatcc tgccttgcta ggttggggaa gttctcctgg ataatatcct gaagagtgtt 193860
ttccaacttg gttccattct ccctgtcatt ttcatgtaca ccagtcagat gtagatttgg 193920
tcttttcaca tagtcccata tttcttggag gctttgttcg tttgttttta ctctttttc 193980 tctgaacttc tcttctcact tcatttcatt catttgatct tcaatcaccg atatcctttc 194040
ttccagttga tcaaatcggc tactgaagct tgtgcatttg tcacgtagtt cttgtgccat 194100
ggttttctgc tccatcatgt catttaagga cttctctaca ctggttattc tagttagcca 194160
ttcgtctaat ctttttcaa ggtttttagc ttctttgctt tgggttcgaa cttcctcctt 194220
tagctcggag aagtttgatt gtctgaagcc ttcctctctc aacttgtcaa agtcattctc 194280
cgtccagctt tgttccattg ctggcgagtg gctgcgttcc tttggatggg gagaggtgct 194340
ctgagtttta gaattttctg cttttctgct gtttttccc catctttgtg gttttatcta 194400
cctttggtct ttgatgatgg tgacgtatag atggagtttt ggtgtggatg tcctttctgt 194460
ttgttagttt tccttctaac agtcaggacc ctcagctgca ggtctgttgg agtttgctgg 194520
aggtccactc cagaccctgt ttgcctgggt atcagcagca gaggctgcag aacagcgaat 194580
actgctgaac accaaatgtt gctgcctgat tgttcctctg gaagcttcgt ctcagaggag 194640
tacccagccg tgtgaggtgt cagtctgccc ctactgggga gtgcctccca gttaggctac 194700
tcgggggtca gggacccact tgaggaggca gtctatccat tcttagatct caaactccgt 194760
gctgggagaa ccactactct tttcaaagct gtgagacagg gacatttaag tctgcagagg 194820
tttctgctgc cttttgttcg gctatgctct gtccccagag gtggagtcta cagaggcagg 194880
caggcctcct tgagctgtgg tggactccac ccagttcgag cttcctggcc actttgttta 194940
cctactcaag cctcagcaat ggcaggctcc cccagcctcg ctgccgcctt gcagttcgat 195000
ctcagactgc tgtgctagca atgagcgagg ctccatgggc gtgggaccct ccgagccagg 195060
cgcgggatat aatctcctgg tgtgccgttt gctaagacca ttggaaaagc acagtattag 195120
ggtgggagtg atccagtttt ccaggtgcca tctgtcaccc cttccgttgg ctaggaaagg 195180
gaattccctg acccccttgtg cttcccaggt gaggcgatgc ctcgccctac ttcgtctcac 195240
actcagtggg ctgcacccac tgtcctgtac ccactgtctt gacgagcccc agtgagatga 195300
acccactacc tcagttggaa atgcagaaat cacccatctt ctgcgtcact cacgctggga 195360
gctatagact ggagctcctc ctattcggcc atcttggaac caccccactt actgcaatct 195420
ttaactccca ggctcaagtc attctccatc cttgacccct caagtagctg ggactacagg 195480
catgcaccac catgcctgga taacttctta attttttgta gagacagggt cgtgcattgt 195540
tgcccaggct ggtcttgaat tcctgggctc aagcgatcct tctgccttgg ccccccaaag 195600
cactgggatt tccttttttt tttttttttg accgatacat aatacttatg gggtacatgt 195660
gctattgtta catgcatcga atgtgtaatg atcaagtcag ggtatccatc accctcaatt 195720
tatcatctct atagttagga acatttcaag tcctcttttt tattttgaaa tatacattat 195780
attgttaaat atagtcaacc aactcttatc aaacattata aattatttat tctaactagc 195840
tgtgtatttt tacccactaa ccaacctctc ttcaccctcc agacatacct ttcacagcct 195900
ttggtatcta tccttctact ctctacctcc atgagatcaa cttttatagc tcccacatat 195960
gataataaca taagataatt atctttctgt gcctggctta aaataatgac ctccagctcc 196020
attcatgttg ctgcaaagga catgatttca ttcttctttg gtcaattagt attccattgt 196080
atatatttac ctcattttct ttttccattt atccactgat gtacacttag gttcctgagt 196140
ccatatcttt gctgttgtga atagtgctgc aataaacacg ggatgcagg tacattttta 196200
gtatactgat atcttttcct ttagataaat atccagtagt gagattgctg gattatgtca 196260
tatttctctt tttaggtttt tcagaaatca aactgttttc tatagtatta atttacattc 196320
ccaccaacag tgtataagag ttccctccac atcctctcca gcattggtta atttttgtct 196380
ttttaaaata gccattctca ctatggtttt ggcttgcatt tcccttataa ttactgatgt 196440
tgggcttttt tttttaaata tacctgttgg ctacttgtat gttttctttt gagaaatatc 196500
tatccatgtc ttttgctcac tttttattgg aattaatttg ttgtttacta ttgagttatt 196560
ggagttccta gtatattctg gtattagtac cttgtcagat gagtagtttg caaatatttt 196620
ctcccattca acaggctgtc tcttcactct ggtgattgtt tcccttgttg tgtacaagct 196680
ttatcattta atatagtccc atttgtctat ttttgttttt gtctgtgttt ttgaggtctt 196740
atccataaaa tctttcccta gaccaatgtc ctaaagtgtt tccccaatgt ctccttcatt 196800

-continued

```
aatagtgatg ttatagtttc atgcctcatg tttaagtctt taacccatct tgagttgatt 196860
ttagtatagc aagagataga aacggtttca tttttcacat ggatatctta ttttcccagc 196920
tccattaagt gaagagggtg ctcttttccc agtgtatgtt cttggcatct ttgtcaaaaa 196980
tcagttggct gtaaatacat ggatttactt ccaggttcta ctctgttcca ttggtctatc 197040
agtttttatt ccaataccat gctgctttta atgctatagc cttatatttt taaatcaggc 197100
agtgtgatgc atccaacttt gttatttttg ctcagaattg ctgtggctat tccagctctt 197160
ttttggttcc atctgaattt taggattttt tctatttcca tgaaaaatgg cattggtatt 197220
ttgagagaga ctgcattgaa tctgtagatt gctttgggta gtatggtcat tttaattttg 197280
ttaattctcc caatccatga gaatgggatg tttttgtgt gttcttttca atttctatca 197340
tcagactttt gtagttttcc ttgttagagg tttctcacct ctttggttaa actcattcct 197400
agattttttg tagtggttgt aaaagataat gccttcttga tttctttctc agctggttct 197460
ttattggtat atagaaataa gcctgatttt taaatcctgt aactgtaatc aatttattga 197520
tcagactgaa gagttttgat ttttgtattt catggtatga gttgtaatat ccccttttc 197580
atttttgatt ttattcatgt aggtcttctc tcttttcttc ttggatagtt tagccactgg 197640
ttattttgtt tcttttcaaa aaccgatttt gcatttcatt gatcctttat atttatttag 197700
tttcttgttt agttctgctc tgatcttcgt tatttctttc cttctactaa ttttatgttt 197760
agtatggttt gttcttgctt ttctggttcc ttcaggtgta tcattagatt atttaagatc 197820
ttttctacct tttttaatgg aggcatttat tacaataaac tttcctctta gcattgcttt 197880
tgcagtatcc cttaagtttc agaatgttgt gcttctattt tcacttgttt cagtaaattt 197940
tttatttctg ccttaatttc ttctttgacc cattggtcat tcaggaacat gttaatttcc 198000
atttatttat acagttttga atgctcctct tatttattta tagttttatg ctattgtggt 198060
ctgagaagat atgtgatatg aatccaattt aaaatatata tatatttaaa atcatactta 198120
gtgtcctaac atataatgta tcctggagag tgttccatgt actgatgaga agagtgtata 198180
ttctgcagct gttttatgaa ctggtctgta aatgtctgtt aggtccattt ggtataaagt 198240
gcagtttaaa tccaatgttt ctttgttaat tttttgtcta gatgatctgt ctaatactgg 198300
aaatggagaa ttgaagttcc caagattatt gtgttgaagt ctacctttcc cttcagattt 198360
gatgtttgcc ttatatatct gggtgctttg gtgttgggtg catatatgtt tagaattgtt 198420
atatcctctt ggtcaattga tccctctgtc actatataat gacttcgtct ctttttagtg 198480
tttttagctt aacctttgtt ttatctgatg aaagtatagc tactcctgtt tggtttttgt 198540
ttcctttgc atgtaatatc ttttcccatt cctttctttc aactatgtgt ctttacaggt 198600
gagatgcgtt tcttgtagat agcatttaga tgggtcatgt ttttaagtcc attcagccag 198660
tctgtctttt aagtagaaag tttaatctat ttatatgcaa ggttattgtt gatatgtgag 198720
ggcttattcc tgtcattaat tgatttctga ttattttgtg tgctttcatg aagttgtcct 198780
ttcacttctt cctgtaagac tcccttaagc atttttgta gtgccagtgt agtggcaatt 198840
aattccctga gcttttactt ttaagggaaa tactttattt ctccttcatt tctgacgaat 198900
ataactttgc taagtacagt attcctggct ggcaggtttt tggttttgtt ttttctttca 198960
gcactctgcg tatataatcc catcctcctg gcctgtaaag tttctgctga aaaatctgtt 199020
agtctgcagg ttgttccctt gtaagtgtct acaacctctt ttatcgctgg ttttatgatt 199080
ctctctttgt cttgggatgg gcaatttgct ataatgtgct gtggaaaaga cctttctgaa 199140
ttgtatctat ttagggttct gagattccta tatttggatc taaatctctt gggagattgg 199200
```

gaagtgttca ggtattattt cattaaatag gttttataat cttttggttt gctcttcacc 199260
ttctgggaca ctgaaggtgt caccttatgg catcctatag tcacatagcc tttgttcatt 199320
cttttctatt ttttctatat ttttgtctga gtcatttcaa aagacttatc ttcaaggtgt 199380
gaaattcttt cttctgcttg ttgtggtctg ttattgaagc tttcaaatat gttttttatt 199440
tcattcaatc tattattcaa ttccagaata tctgtttggt tctttttata tctatctctt 199500
gggcaaattt ctcattcata ccccgaattg tttttttctga tttctttgta tagtctatca 199560
gatcttcttt aatattatat tgaatttttc aaggtttcat caatttcttt ttcactggaa 199620
tctgttggag aattattgca ttccttagga gttgtcatgt tttgcctttt catgtttctt 199680
gtgtgcttac actggtatct gcacatctgg tgtaacagta gtttcttcca attttttgat 199740
ctgtctttcc taagagagtc ttgttcctga agatatatct atggtgttct ttgggcaggg 199800
cactttggtt ttgattctgg gtgcctgcag tagtgtgatc tccatggaat ttttttcagc 199860
tgtaaacagc accagtagtg tctgggagtt cctctgtagt ttaggatgca gttgttggtg 199920
gaggctgtgg taaagtctgg ctggggatag ggacaccagc tgggccagtc ctcaggcccc 199980
agtggcagca gtggctggcc ccgaatgctt atccttgggc ccaatggtag tgtatgctgg 200040
taccagtgtt agcaagtcca gggaaaccaa ttttgggcct ccaggcaact tgctcaggtg 200100
ccaatgatga cagagctggg ccacagggtg ggtaggtcct tgagctctga gcagcagata 200160
tggcttgggc aatggcagta gcagtggcag aacaatcttc tgcctcccaa ggtgtccatg 200220
ctggtattgg gatggctggg ataagctgga tgagcttgtc ccaaggccca caggtggcaa 200280
attcaagtga atgccagttg tggtggtaat ggtcagttgg gtagggcagt cctcaagccc 200340
ccaggagtgc tcaggtgcca acaatactgg atagggcagg gtgatcccta ggcccagaga 200400
tggtatgcgc tggcactggg agaaaagagg gtgggaccag gccaggtggg cctgtcctga 200460
ggccctccag taatgcaaga atgtactgac tgtggtaggc aggcacagga agatccctgt 200520
ataccctgct gaatgctcat gttggggcag cagcaactct attgcagccc tactcctggg 200580
gaagttgagt gggattgctt tcagtggcag cagctataaa caggcagttg ggcaatgcat 200640
gcttcggccc caggtggtga ctatgggcag ggtcaccttt cctcatggca gccttgcttc 200700
ggaggtagca gagtattgcc aatggctcat gctttggcct ggagggagca gtcaggagtg 200760
gcaaccagct ttgtgtaagg gatgtccatg gggctccagg gatgagatag agggatgtgg 200820
ggcccacagc agatgcagtc tggtgggggt tgggctatca aaatgggact ttcctgaagt 200880
tgcctgagga ttcaggggat gtgtgaattg cctgaggatt cagggtgatc tccctctctg 200940
ggagctgttc attgccattt cacagtctgt aggtagcctc ttgttagtct caaggcatct 201000
atggggtcag gggttctct gactaggatt tcaggagtct gctgtgggaa tgtggaccac 201060
taggggctca cttacttacc tttctgcaca tcgaggagtc tcttcatgat cccagccagt 201120
cccatagaag cagactgcct gactcccctc ttatcccttg cattgggttt ttcttattac 201180
ttctcagttg aattccagca ttctctcaga ggcgatctat ataaactgtg gttacctact 201240
tgctatattt tgtggaggag gtgagtgcca gatgcctcta gtcagccatc ttgaagcccc 201300
tgctgatatc tggataggga tttcatagca tctgtatatt gctataggta aatatgatca 201360
ttttaacatt tttctttcaa tccatgagca tgggatgtct caaaaaattt tgtagcctct 201420
tcaattactg ttatcagtat tttatagttt tcattgtgga aatctttcac ctccttggtt 201480
aagctttgct ttttttgta gctattgcaa atgggattgc tttcttcatt tctcttttgg 201540

-continued ctaatttgct gtttcacaga aatgctactg attttttggg ggaggcaggg gagtgcagac 201600
agggtctcac tctgttgccc aggctggggt gcaatggtgc aatttctgct cactgcaacc 201660
ttcacctccg aggttcaagt gatcctccca tctcagcctc ctgagtagct gaacttcagg 201720
tgcaggccac cacgcccagc tcatttttgt actgatgagg ttttgccatg ttgcccagga 201780
cagtctcaaa ctcctgggct caagcaatcc acccgcctca tcctttcaaa gtgctgaaat 201840
tacaagcatg agccatcatg tccacaccta ctaattttg tttgttgatt tttttatcct 201900
gcaactttat tgaattcctt taccagttct aaaagatttt ggtggaatct ttaggttttt 201960
ctatgtataa gattatgcca tctgcaaagg acaatatgac attctctttt ccaatttgga 202020
taccctttt cttttacttg cctaattgtt ctggtgagga cttttcttac tctgctgaat 202080
aagaatagtg aaagtgggca tccttgtctt gttctagttc taagagagaa ggtgtttagc 202140
ttttccccag gtggctgtgg gtttgtcata tatgaccttc attgagttat gttccttcta 202200
gacattatgt gatgagcttt ttttttatc atgaagagat tttgaatttt atcagatgct 202260
ttttctgcat ctattgagat gatcatgtat ttttttgtcc ttccttctgt taatgtgatg 202320
tatcacattt attgatttgt atatgttgaa ccatccttga atccctggga taaatcccac 202380
ttgattatgg tgtattatct ttttgatgtg cgattggatt cagattgcta gtttgtgtgt 202440
ctgtgtgtgt gttttgtttc tgaggattct gcatctatgt tcatcaggga gattggcctg 202500
tagttttctt ttttgctgtt attgtgtcct tatctggttt tggtatcaag atactgcttg 202560
cctcacagaa tgagttaggg agaattcctt tctcttcagt cttttggaat tgtctgagaa 202620
gaattcatgt tagttcttta aaggtttggt agaattcagt agaaaacccg tgcaatcctg 202680
aggttttctt tactgggaga ctttattact gatacaatct cattccttgt tattgctctg 202740
ttcagatttt ttttcttcct ggttcaatct tgggaggtta tatatgtcca ggaatttatc 202800
tctttcctct aggttttcta attgttgaca tatagttgtt cataatggtc tctaataatc 202860
ttttgtattt ctgtggtgtc cattgtaagt ctcctttttc atttctgatt ttatttattg 202920
ggtcttcttg gttagtctag ctaatggttt attgattttc tcttttcaaa aaatcagttt 202980
tttggctggg tttgttggct cacacctgta aacccagtac tttggaaggc caaggcaggc 203040
cgatcgcttg agtccaggag tttgagacca gcctgagcaa catggcaaac ccccatctct 203100
accaaaaaaa aaaaaaaaat tagcgaggtg tggtgctgca catctactca gaagctgagg 203160
caggaggatt gcttgagccc aggaagcaga ggttacagtg agccaagatc acaccactgc 203220
gctctagcct gggtgacaga gtgagaccgt gtctcggggg gtgggggga ggcctcattt 203280
cattgatctt ttgtcttttt taccttttat ctctatttca tttagatctg ctctgatctt 203340
tactatttat ttccttctaa ttttaggttt gatttgttct tgcttttcta gttccttgag 203400
atgcgtttat taggttattt gtttaaaaac tttctacctt attgatgtgg gtgtttattg 203460
aaataaatgt ccctcatagc acttcttttg ttgtacccta tacatttttg tatgctgtgt 203520
ttctattttc atttgtttca aagaattttt aaatttttaa aatcaatttc ttcatagaca 203580
cagtggtcat tcaggaacat gtagtttgat ttccgtgtat ctgttcaatt tcagaagttc 203640
ctcttgttat tgatttccag ttttattcca ttgtggtctg agaagatact tgataagatt 203700
ttgactttta aaaatttatt gagacccgtt ttgtgtccta acatatggta tatcctggag 203760
aatgtgctgt gtgctaacga agcagcagtt caaatctaat atttccttgt tgatattttt 203820
ccatccaaat gaattgtcca atgctgagta tgaaatgttg ccatccctaa ctattattgt 203880
attggggtct atctctttag cactaataat atttgtttaa tatacctggg tactccagtg 203940

-continued ttgttggttg catatataat tgttatatct tcttgctgaa ttgatccatt tataattata 204000
taatgacctc ctttgtctct tttttctttt tctttttttct tttttttttt tttttgactc 204060
agtatttttt gtctgtctac tcctgcatgc ttttggtgtc tgtttgtgtg gaatatcttt 204120
ttctatccat tcccttacag tctatgggtg tctttacagg tgaagtcagt ttcttatagg 204180
cagcatgtaa ttgggttttg ttttttttaat tcatttagcc agtatctatc tttcatttgg 204240
gaaatttaaa ttacctacat tcaagattgt tatcaatagg tgaggactta ctcctgtcat 204300
tttattgttt tctgactgat ttgtatactt ttgtttcctc tcattgtttt tctttgcaat 204360
tttttggttt tctgtagtga taatctttta ttccttttcc tttctcattt gtgtatctgc 204420
tctactagtg ttttatgctt ttgtagtttc atgatggtag atatcatcct cctacttcca 204480
gatgtagtac tcccttaagc atttcttgtg gggctgattt agtagtaatg aattccctca 204540
gtttttgctt gtctgaggga ggcaaaattt cttccctcat tctgcttcat ttctgaagga 204600
tagctttgct gggtatagta tttgtggcta gcaattttgt gagcttttcc ccaccttgca 204660
gcacttttaa tatggcattc aattccttcc tggcctagaa ggtttctgct gaaaaatctg 204720
ttaatctgct gttgattccc ttatatgtga cttcatgctt ctctcttgtt ttttaaattc 204780
tctctttgat ttttgacagt ttgatgaaaa tgtgcctcag agaggcccctt ttagggttga 204840 atctatttag ggatttgtga gcttccttta tctgttagtc tctttctctc ccaaactttg 204900
gcagttttca ggtattatct tcttaaatag attttctggt ccttatccca acacttcttc 204960
tggaactccc aaaatgtgaa atattgttag cttaatagtg tctcatatgt cacgcaggca 205020
ttcttcattc ttttttattg ttatttttta aatctgtctg gtttattgca aaacacctgt 205080
cttcaaattt agaaattatt tcttctgctt gacttagccg gcttttgaag ctttcaattg 205140 tatttttttat ttcattcatt taatttatca cctccaggat ttttgtttgg ttctttttca 205200
tatctaactc tgctggattt cccatttaga taatgaattg ttttccctga tatgtttgta 205260
ttgtctattt gtgttctctt gtatctcatt gggtttcctt aagatttcct ttactttgga 205320
gtctattatt ggagaattat tgtgttcttt tggcaagtca tgttttcttg ttttttttccc 205380 cccaagtttt ttgtgtcccc aagttgatat ctgcatatct ggaataacag agacttccaa 205440
ttttatggag tagccttagt aaggactttt cctgtacacg cgtctgtagt atcatttggg 205500
tagggtgctt tggctttggt tctggttcag tgcagaagtg tggtgtctct acaattaatt 205560
agactataat ccacatcagt ggtatctgca agttcatcag tggcttaggc tgcttggtgc 205620
ttaggatgtc tgtgaaggca agaaggctcc ttagaggtac ttactcctct atttttgctg 205680
atgttgctaa ctaccttcaa actttttgac aaagcatttt aagcctcttc tctgattctg 205740
tatgcagttt tgcagtgctg ggcaggggac tagaatgcta ttggaatttg gctcactttg 205800
ctacccacag gcaatttgaa ggtattcttt ctcctaatac tgctaacagc atgggtcatg 205860
tggttttatt tgcacttact gattttatgc ttttagggga ggatgagtga gatgatttat 205920
agtcagaggg gatgaggagc agcatgctat ttttctccaa gcctggctga aagtcttttt 205980
taaattatcc tttttttctta gtacccctttt ctaatctatc agtatgtctt atcaactctc 206040
tggatttgcc cacacctaat ctctccagct atctccctgg ttaaaaccac caccatttct 206100
ctgcctacat tgttgtccat acctcattac tggtctcttg atttccactc ttgcttcctg 206160
tactccattc ttcacataac agctcaaggg agttctttaa atgtacagtg gatcttgctg 206220
cttccctact caaatgttcc gacagcttcc tgtcaaccct gtcttgtgtc agtctcacag 206280
cacacacagc ttaattcagg aattaagctg tgctggtcac ttattgagaa agagcttcat 206340
ggtgggcagc tgggaagctg cacagaacac tcctcagagt tctacaagcg gctgagagag 206400
ctggggtatt tatctttcac tagtgagtgc tgccccggtg gtggctcact ttccattcct 206460
tttggcctgc cctgtgtgca gctcagcaag tgcctgaagt cagaggtagt gcttatgaaa 206520
gtatctggtg ggcttgcatt aagaagctgt cagtgtgaag aacgtgaatg ctaagggcat 206580
atgagtgtgt ccctgagaac atggatattg tgttctttac ctccatgtct ccagtgcctg 206640
ccatatagca ggtcctccaa gatttgctga tctgcctgcc ccacctgggg tctctgtctc 206700
tcccacagct cactgacatt agccacgtgg ccctctgttt cctgtaatag gccatttcct 206760
aagtaagcat catcctcatt tctatacgtt ttctctgatt actggaaatt cctcaagtgt 206820
tgaccatttt gattcctggg ccccttaaga gtccattagc attggaatgg agcccacagg 206880
accataccag acagatgcca ccacatcttt tcttgaagta gtgttcaggc tgagggggtc 206940
atagccgagg gtccctctgg ggccgcttgc tctcctccta ctcacagccc tcctgcagcc 207000
agcagcagtg gggagccaa gctgagttga ttacttttga catcagttgt taacataatt 207060
ttgatgttga gcctcccccc agttctgggg tggctctgac tgtgtccagg ctccaatttg 207120
agaagctatg gggagcctct cggccccagt tctggcctgg ctgggaggtg gcctgggaag 207180
ggacctgtgt ttctcaagcc cgcgccctcg gggcctgggg gtggggcccc agcagatgtc 207240
tggatttggt agccagggcc tggagccgga tgctgagaat gaggcctgca actcatttcc 207300
ccattaaaca ttctgagaac atctgcaccg gtttccaagg cttctccctc actaattgct 207360
ttgattattg tgtgaagtta agaactggca catttccgcg atgttgtgat gaaggtgaaa 207420
agatcgctct taattagatt aaaaacattt ttttcttcct gtgtaatttt gtcttgaaaa 207480
tcaaggccac ttttttgttt tcttcatcca aagacctcca gaaactttcc tccccacctc 207540
tccagaggtt tctggggaat gtcctgtgag ctcaactctt ggagaagata gtgcttaacc 207600
cagattccat tgtatattaa agtttcctag ggctgctctt gctgcctgga accttcccct 207660
gaaaatgtgt cttgggagac ctagacagtg acttcctgca gcatggagac ccgggtgggt 207720
cgattttagt tgtgtgggtg gctgtgttgc tctctttccg tttcctgggc tcactcacgc 207780
tcagggttga ccctgtcctg gctctgtcac tgcctgtctt cctcagcgcc cccgctactc 207840
agaccccacc cttgggcctg cagagacatt tccgttcact ctgagatttg tgtatgctga 207900
ggcttgctat acttattcta aggagaagtg tttggggtgt ggggtgtggt cctcagtatc 207960
ctaaacttag gttttggaaa gcccagcatc ctccctggga cttctcagga ttccggaagt 208020
catctttgac tgtgtcacat cactgtcatg cttgaggcaa atctattctg cacacctttg 208080
atccaatgtg agatccaaca tgttccataa tttgcatcaa acatcctcat acagcagggt 208140
gtggagagag gctcactgaa ggtttgggga gatgaggact tgcatcacag cagtagaaag 208200
ccaatgtccc accttaggaa atccctttcc aagagttccc tgtgctgttg cagggctaag 208260
gccagggcct tggcctcagg ccagcttctt tcccacaagc cttctccctg ccctctgccc 208320
tgaaaactag tgggggcagt gcagaccagt ttagctattt tgtaaccttg actgccccca 208380
ggcccatgtc cgtaggctca cacctcaccc ccaactttgt catgcacatt cctgaagact 208440
ctcttggtaa caaatgatgg aaccccaact caaacaagct taagcacaaa agggacattt 208500
tttggctcac acagctggac ccagctgttt cagacacagc tggaccccag agctgagatg 208560
atcttgctca cttgctctca ctctcccctc ttgcactccc cttctccctt cccgttccct 208620
cttttgttct ccctttccct tgctctctat ccattggccc catgggatgg ctgtatcctt 208680
aggcagctac tttctaaaag gggcaaaatg gccaccagct tgcattcaac agctcaggaa 208740
gcccagcaga acgaggtcat ctcttccagg attcctgcca gaatctaagg ccaggttctt 208800
attggcctca gctggggtac aagccatcct tggacctgca gctgtacctc cgatggctga 208860
ggcaaggtcc acagggaccc ctttggggat ggccagaggg tacctaaaca ctgcacacta 208920
ggagtgggaa aggaagagcc ccctaaggaa gatttgagaa gctgttccca gaagccaggc 208980
ctggctgctg gcaggcaaaa acaacaggtg tccactcaag caaggtattt tcctaagcgg 209040
aactgggtgc cagctgtgaa tatacatttt cactccattc ctcgccttgt tcctggcagc 209100
tgttgtggga atggctttta cactttccat ccatgtccct tacttctcgc ctctgagtgg 209160
agacacaggt ggtggcgggg ccactctggc tcagggtcta tgagccgggc atgggcagct 209220
ggcacaggct gtggggctgc ggctcagcaa tgtcacgcag ggcctggctg cagctgtccg 209280
gatgcccctg gggagggctt ctccttcaca gtgcaggatc cgcagggctt tggtgaatcc 209340
actgagaggg ggagatttct tgagggggcc agggaggggg cttctacttg caaaggatag 209400
ggagagcttc tgttcatcct tgtgaagtag gctggctcag ggaactcgcc tgtgccaaac 209460
cctggggaga catgggtgag gcagaaggca aggttcccgt gctgagcgcc aggcacacat 209520
aagccctgca gccgtacagg ggagggggca atctccggag ccctggaaag cttgtggaag 209580
agggcttggg ttacacctgg gagattaggc cggattttaa tcaatcagga ggggaagggc 209640
agggggtgag tggttgggtg aagttactag gaagggccca gacactggcg agagtctctt 209700
gagggcagag ggcagcagag atgggctgga gctttgagct ttgtcatagg ctggacttgg 209760
ggcttgaatg ctgacctaat ctgggcaggg aggggtctgg ggctcgatga gaaggcagag 209820
gaagtgagac cagaatttct tgggaacaga aagcctcaaa gactttcatg ataggagagc 209880
tctatgtagc ctcatgggca gctccaggcc aggtggaggg acatattctg gcaactctag 209940
gataagatgt gcaaggtcgt gggccagaga gcaaggcaca gatacaggag acttccacaa 210000
attattgttt cttgacttgg aaaagtatca tgcaaaatag aaaacacaga cacaataagg 210060
aaggaaatga aaatcaccca aagacaaagt taacatttgg atctgtttcc ttctagtctt 210120
ttttctgtgc ctgtattttt aaaaaaataa aattcaaatc cccctatcga gcaggaccac 210180
tgactagaaa ggaggatgct gtgctgagtt tgattcctgt tctcttgaga gggtgagact 210240
tggcagccag cgtccccagc tggggtagtc gccacgcccg aggctgcctt tgccatccca 210300
gacctcccac tttcctagaa aacaaaattg ttttgttctg ccctgaaaat ttaggcccag 210360
atcctggcct tgacaaagca aaggcagcca aagaattaaa gcatcaaaaa ccaggactgt 210420
cttaggaaag tgtgacttca ttgtcaccag gatgctgtgc tgtttgtccc cagggccagc 210480
cactctaggc agttcagcaa agggcacctg gcattgctcc ggtacctcct gcagagcctg 210540
gatatccaga tgaactgccc tttcaagtac accatgggct caaccttctc tgcagctgtg 210600
agttcaggct gtgaaatacc cacttcagag gtgggggtga caagcaagac ctgttagggc 210660
acagcacttg ccctcaagcc ctggcctgaa agaggcagca ccagtgtgtc tggaaagagc 210720
tgaatcycca cccacccacc cccagctccc ctccatgctc tcctagatgc ctgacctggc 210780
tacgaccaca ggtgaaaaca gggaagaggt ggcagctctg gtgactgcct ccctgtggtg 210840
gagaaagcac gccccacagt ctccaacaca caagccagca gacaataacc tctcctcttg 210900
aattggaaaa acaaatctgt ggaggccttc tctgcccctt gttataggggg ccccatatgc 210960 cgttcccagg attaaaccaa aaagcacaca ttcctctctg gcaggtgcag gtcccaccca 211020
ctctgggcag ccaactgatg tgcacatttt aatttcctaa aacaccagga cagaaccttc 211080
ctcaggggtc aggtggctca cccttggccc tcaggctttg gagatgggca cttgtcatca 211140
tgggtgtttg gaaagcaact ctacgttcta gcctgtgctc cattgttcyt tctacataca 211200
agtgatgcaa acatcaaaat atgtttttttc tttcttcctt cctttaaaaa aaattgaatc 211260
ctggatgaag ttttagctct gtcacttgac aactgcatta tataacctag ggtacttgaa 211320
tctcagcccc aaatctctaa aatgggggca gtaacatgct tctgccaggt cccagacctg 211380
tgggtctcca aatctgcaca ttcttcaagc cttacaggtc cttccctggt ctctctaagg 211440
atgtcatggg cacagagccc tttcactctg agcccttctc ctggctgtga ctaagtaatg 211500
tctgtgtggt ttcctgctgg aagtctgcca ctcgccccca cgggccatga gctcctgagt 211560
ttatttacat ttccctgatt gctagtcagg cgcaacacct ttccacatgc tcatcagcct 211620
tttggattcc tcttttgtga tgtgctactt tgtctattgc ccattttcta ttaagtcatt 211680 tatattttc ctattgattt gtaggagtcc tttgcatttt gtgggcactg tctttttaag 211740
gtgtattttg atgattgggt cttaactcta atgtcaaatt actcagtctt ctctctcatg 211800
gttattgctt cttttaaaaa aaaccatcct aatgctgatg tcattaagat attcttctat 211860
attcagtcat gtgaccttta tagttatgct tttcatagtt aggtcttcaa tcccctagaa 211920
tgacaagaat gaatttttgg tatatgatgt gaggtaatta agggtccaac ttaatgtttt 211980
tccagtgtgg gtatccaact gctcctgaac atttgattga aaagtccatg ctcttcccag 212040
gatgtgcagg ccacctctga tacacagcaa gcttccatat ttgtgtgggc tgtttcccaa 212100
tgctcaatcc tgtcccattg gcctatttgt ctctccctgt gtcaatacca cattgcccta 212160
atgaccactg ccttggaaga agtactgatg tttggtacag caagttctcc caccttgttc 212220
ttcttcaaga atattgccaa ttcttggctt tttgcacttc caagtcgcag ttagaatcag 212280
cttgccaaag ttctcacaca gaagccttga gatttttatt aagatttgga gagatttatt 212340
cagattttga gataatcttt tcagtattga gtcttctagt cattggaatg aaggcatatt 212400
tctccattta tatcttcttc attgtctctt actaaagttt tacaatttc tccagagttc 212460 ttgcatatcc ttagttagat aattaatatt cttttgtgct attgtataca ggttctgttt 212520
tctcttgtta cctcacattt tttatttaca gaagagaaac aaaaatagta ccgagtaccc 212580
acatcccttt caccagcttc ccctaatgtt agcatcttat ataaccatgg tacattgacc 212640
aaaactaaaa aattaacatt ggtacactat taagctagag ttgtaaattt atttggattt 212700
ccccagttta actactaatg tcctttttct gttccaagat cccatctagg atcgatcatt 212760
acatttattg tcatctctga tcggtgacgg gcttctcagt cttgttcttc attaacttga 212820
cacttttgaa gaataccagt caggtgtcat tgtccctcag tttgggtttg tctggtgttt 212880
tctcaggact agaccagggt tataggttta ggggaaggag gccagtgagg tgagatgctt 212940
tcctcattgt ggaacatgac atcaacatgg tttatcactg gtaatattaa ccttgagcca 213000
ctcgtttaaa gtggtgtcgg ccaggctcct ccactgtaag tgaatagctg tttttccctt 213060
tccatagctt agtctttaga agcgagtcac taagtatagc ccacactcaa ggtggggaag 213120
ggaggagttc aactctacct cctgcaggag agtatcaaaa aaaatctgca aatatgttaa 213180
aactaccaca gcaattaaaa tacatttcaa ggaagaaact gtgaagtttc tgagtttcac 213240
taactaattt cagcattcat tcatggatcg ttttcctgca gcaaatatta ccgtgatgta 213300
cttctatttt cctcattcct tctacatttt ttatttggaa ttcctttata aggaagattt 213360
gtccctctcc tccaattgtt tatttaattt tatcagtgtg gatttgggag tatttatttt 213420

-continued ttgagttata gtccaatatt atttattttg ttgctcaaat tgttcaagct gtggccactg 213480
gtgggttcat gtgtcctttt gatgtgcccc ccgccatcct tttcatttat ttttaagcat 213540
ttcttttcta gcacttgaca atacttcagg ctcatctttt attttcccta ccctagccct 213600
agaatcatcc attcatccag agagccctgg ctccctggag aatgaataga aaacctggat 213660
ctaggcacgg ggtatgctcg tggctactag ggtatcattg cttcagtctc ctctcagtgg 213720
acagagctag gaaatatatg tatgtatgta acctgagtac acatacatct ttacatatct 213780
gtatctatat aaagctaacc atgagttcat actgacattt ctgaccagag ttcatccttg 213840
ccccctcccc cacaacttat ttatagcttt ttctctgaca gctagaaacc tggctcccat 213900
tacctacagt tcatttactt atttgtgtaa ccctattgta cacgtagtac cctatgtgaa 213960
gcaaatttac ctactagatt agagtgttta ggacagactt ttgctttaac catagagtgt 214020
ccagtcaaaa cagtgttttt gaaagcaaca tatgccagct cctcctcctc ctttcctttc 214080
actgctatgt catttgtttg taacacgctc atcatagtct gcttttcatc gtagggtcct 214140
ccaacatccg ggttaatttt ttaaatttgc atacagtaaa atccactctt tgagattcag 214200
ttctgtgggt tttgacagat gtctggagtc atgtgtccac aatccagtat cattcacaga 214260
agttccatac ccctaaaaat accctggggt gagtcttttg aagtcaagta cttctcccct 214320
aaccactggc agctattgat ctgttttatg tccctgtagt tttgttttty tagaatgtcc 214380
tataaatggg atcctataat atgtattctt ttgcatctgg cttctttcac tgcttagcaa 214440
aatgcatttg agattcatcc atgttgttgc ataaatcatt agttaatttc tttttattgc 214500
tgggtggtat tccattgcat gaatatatac attttgttta tgcattcacc tgttgaagga 214560
catcttcatt gtttccagta tttggtaatt atgagcagag ttactataca catttatgta 214620
caggtttttg tgaacataaa aattcaattc acttgggtgg gaaaggaacc gataggtcat 214680
gtggtatgtg tatgtttaac ttaataagaa attgctaaac tatttcctaa agtcactgtg 214740
ccattttgca ttcccaccag taacatatga gagttctaca tgttccacat cctcaagagt 214800
ggttggtatt gtcaggtttt gaattttttt tttaatttat ggaatttcat tgtgattcta 214860
atttgcattt ccatatttat gttaattgtg tatcttttca tgtgcttatt tataatccat 214920
ttttaaaatt ggattgttca ctttattgtc aagttgtaag cattctttat atattctgag 214980
tgcaagtcct tgacctgata ggtgatatgc aaatattctt tccaagtctg tgctttgtct 215040
tttcattcca ttagcagtgt ctgttgcaca gcaaaagctt ttaattttga taaagtccaa 215100
tttgttgatt ctttttctct tacgagttaa acttttggtt tcgtatttca gaattcactg 215160
ccaaatccaa ggtcctggag atttctcttt atgttttctt caagatattt tatggtttta 215220
tgttttattt tagatttttt ttcagtaagt ttgtgtgtag taccctttaa attttcattt 215280
tctaattgtt gatcatctgt cctatcaggc atagatacta aatgcattaa aacttttaca 215340
cacatacata tgtatacata caacacattc aaatagtgaa attaggaata aatttaagag 215400
agaattgtat tacgctgatg tgggaaaacc ttcctttttt ataaagcaaa agatgtatca 215460
ctttaaaaac ataaaacatt ttctaggata aaagcaacat aattcaggtg aaaaaacaga 215520
ctggggaagc tatctatgcc tcatataaca aggagttaat gtctgtaatg tatagaaaat 215580
tcctacaaag tgataagcaa aagtgagcaa aggacatgaa caggcaattc tgcaagagga 215640
aacccaaaca gatgccaagc ccataaaagg tattcaacac agatggaaat aacagcaatg 215700
cctcagtttt catccatgct tgatagtccc tgcaaaaggt gctgacaacc ttcattcggg 215760

-continued cttcattcaa cacttcattc aggcatggat gtgggaaagc tgggggagcc tgaattgcta 215820
caacttcttg ggaaagcaat ctagcaacat ttattaaaat tactaaggac acaccctctc 215880
accctgctcc agtatgtcag cttttaagaa taaagatgaa tatggcatca tagtctgaat 215940
aattaagcag cttaaaacta taagagcctg aatgtccatg atatacagaa tggttagctg 216000
tggccaatct aaactgtgga ctattatgta atgactaaaa taattaaatc catgcctata 216060
tacctagaga aaaatgaaat gagcttatgt tacagagtga caggaacaga gtcacagtga 216120
catcccatgt gcataaaagc aactcccacc tggcatctgc tgctcggatg agcagagagg 216180
gtgggctagg gatctagttg gcagttaaca ctgatggacc ttgggggagg aaagccattg 216240
tgaatctttg aattattcca cttctcacag atgagtactt aatccttttg caataaaata 216300
tttaaatgaa gacaaatata agccaagagc aaatactgat agtgtcaaca gagagtgggg 216360
agtgataagg atcagtatcc tgagctcctg tgtcaaagtt gcagaggtgg gcccaggaat 216420
cataatgtga agccagctgt tggagggact cctgtgcctc attgggggta caactggttg 216480
atgtagcatc gtattttgag gaaggagttc tgtggctgcc cccacctccc aggcttgcca 216540
ttcctcatgg gtcagaggtc ctatcacccc atctttcctg acccactact ctgtcaatgt 216600
atgagtgtga caatgtatgg tggtgggagc tgttgtccct taccaggcct gtgcctgtca 216660
cctctgtttt attcttgacc caagtgtcag ttgtgaacat gggaagaggc ccagaacctg 216720
aggtggggag agtcttggac acctgagcac agccccaggc acagttacca ctccgaagat 216780
gattcactgg cctttattct cctcagacac tgaggtgtca ggcactttgg ggccatctta 216840
aacacccacc caccccaaca cccaactata aaactgattg tcagggctgg agcttccagg 216900
cacaagctcc actcctcacc tggccctggg agctcacagg cctggctcca cagcactggc 216960
aggttgggtg ggaggcctaa cgtgctgtcc ccacactttc tcctcagtaa ggaagagccc 217020
aacactgctg gaagtgagca tgccccattt catgagaacc aacagcttcg ccgaggacct 217080
ggacctggaa ggggagactc tgctgacacc catcacccac atctcacagt gagtgcctac 217140
atgtgcgtga agggctgggc tggaggggac tggagctcaa ggagtcagac ttggtgctgg 217200
ggaagccttg ctctctggcc agagtgctat ctactcgcct agtgcccacc acttgccgtc 217260
tgcctggccc caacacggag gcaccaggca agagaggaga gcaagggcac ttcccactga 217320
gcctgggaac atgatcctct tgttttgact tatggaaaac cagactgatc attttccact 217380
tgttttcatg ctttgagagt ctgagattgt ttttctctcc cccagccccc tcccctgccc 217440
cccaaaaaag agacgacttt gttttttagc atttccccat ggaaccctgg ccaaagccat 217500
ggggcagatg ccgggtgcag tctgccagtt gctgctgctg tcctcagggg ctccttcagg 217560
tggaggaaat ggctgatttt ccacgccttc cagttggcct tcccctgagg cacagctggc 217620
ctgggatgca tgcccgtcct cccccgccgt cacggcatgg ccaggccaat ccccggtgcc 217680
cggccacggt gtgattcccc tgcgacatgt gactccccgc tggggtgccc agcggtgaca 217740
gccgtgcagc ggggtcagtg gggcacccaa gtccattctg gccacagtcc cattctggct 217800
gctaacccgt tggggattcc ccttgataaa tgtctttgtg tcaagatctg tgagtgacac 217860
tcgcggccct tctgagggtc acttgtggaa actctccttc tctctaccaa catttttcta 217920
aagggtgttt tgttctttgg actctctggg ggtcaggagg ttgtcctgag ccatgtgtgt 217980
ctttgtcgta gtgaggccct gggcctcctg cctttgcagc cagccaggtg caaggcctgg 218040
ccttgcaaat cactgaggaa atcgggaccc atggtgctgg gggctgcagg tgtaaccaga 218100
gaactggcag ggttgggtag ccagaatgag gccacctcca gggaaggagt ggctatctta 218160

-continued aggggtaatt atgatcagac aggacctgcc cactgtcttt ccaggccccc ccagttcaca 218220
gagaggttgg cagtacctca tggtgggtag ggtgtgaaga ggctccaagg gagccagcag 218280
atcactggaa agcaggggtg actagtcatg gacaccctga gaatagggct ctgagcttct 218340
gggcccctcc tggctgggta aaaaggcagg agcagaggtg tgagcaggct ggtagccaga 218400
tgggctgccc aggtacaggt cagcaccaga aggcagaatg atggcttaca ctgtggccaa 218460
ggcctgtacc aagtcctgga tatgatggac ctccaaagtg atcagtgtta gtttagtggc 218520
tcatgttgtg tgcaatacag gtggcagtgc ctgtattgcc tcttggctgt cccctcagag 218580
aggggactgt cccttctcat ccttctggct gcttgcttct cctgttggag ctctcgctca 218640
ccttggttct cttggtcacg gaccagcatc cagacatgca aaaagtccta ctgggaggag 218700
agggccatca cccacagtcc atctagctgg gcagccaggc cttaccaact cttgggtctt 218760
gcaaggcccc tgcaggtgaa ggtggtgaga gaccaggcac ttatgtggat cacagccaaa 218820
cttgcagctg cccagtaaat caccactatg gggtgagggg ctgccagtgc tggtatcagc 218880
acatgccaag ctccctggag ccagaggtta cccacctgcc caagggtgac cccaagccag 218940
tgtggctgtg tcatctagga cactgggctg tttcttgttc cactccagga tgacagggcc 219000
tgagagacct gaacatccat ccccaagctc tctgcccact ttgggtctgg cacattacca 219060
ttctgcaaga tcctgcagcc ttttcaggtt ggcactccca tggcctccag tgataagtgg 219120
gcccaggcag gtcagagact ccagtcatta cccaaccagg tccctgccct gtaacttacc 219180
aaggcctctc tcagagcagg ctgttccaaa agtggctgct agatatgagc cagcctggga 219240
aggcaggaag gagcccaggc atggggcttg gggtgaggga tctgaagagg ggactgggag 219300
agggaaaaac aaggaggttg ctgcaaaggg gccaccttga ggcattgtgt tctggtcagg 219360
gaagactcag ggctgaggct tcaggggagc tgggttcctg catcctcaga agtcagggta 219420
cggtccctcc agagaggcct gaaggggaga gtgggcacgt acagtgtcag ggcctaggaa 219480
cccaggctcc tctgggatac aggctgggta gaggccccac tccatctggg ggagaaggct 219540
ggcagcagtg ggcaccctgt ttcctcaggg cccaaaccgc ctggcggcag gggtgtgggg 219600
gccgtgcagg tcttctgccc gcattggggc tgcattcctc cacctcctgc acagcccgcc 219660
cagtgatgcc cataattaaa ttcggctcca gctgctcagg gatgcagcga agctcctgtg 219720
ggcagcctgg ccccatggac cctgaactgg gaagagaggc acacgccctg gtgtgtgtga 219780
gggacaggga tgtgtgctgg ggtctcacag ggggcagagt gggtgggagg cagttaccaa 219840
aaaacatttc catttttctt cagcattcta ctgatgttaa atgtattacc atgctgggcc 219900
agttccagaa ttcaaattaa aaacataaat aaagacacat tttgtttcca tctcgagctc 219960
tccccgcccg cagggcccca gagaggtgag gtcactatag ccttgattac gggaaggtcc 220020
ctggggctgg gcgaagctcc tctttccggg gcctgttagc cagaggtggg gtggggggtg 220080
agcaggcctg atgcaagcta gggagtcatg acaagctgag gcacggggta cccaggagat 220140
aaagagtggc gtcgctgcac cccagcctat aggtgggccc tactgctcag cctcaggacc 220200
ctcaaccagc tctgggcggc caggactcag cctcgaacac acctttcagg cagaagctgt 220260
cttcctaggt tgaatggggc acaagagagt ccctgccagc ctcaaactcc ctgagcctgt 220320
gtctcccacc cagaaccata tgacagggct tctgagagaa aggtgggaag tagagactgt 220380
aggcctgcat gggcagttgg ggagcacccc catgacaaga ggagccctgt accccaagag 220440
ccaggatgag ttcctgggat tctgacccac tcactatcct ctgctcacca agggtcactg 220500

-continued gcacgacagt gggtggggac ggtgccatgc ctgtgtgcat ccctgtgcct tgcgtgtggt 220560
aacctgccat ctagaatgcc cttgtcaccc atctgcagcc accagatttc cattcatctt 220620
tccaacgtct gctcagtaaa ccccccagga cacacttagg ctgtacggct gtgtcctcct 220680
ttggctctca aagccctcag taccagttcc ctaagccttt cgaatggtgc caggagggag 220740
aagggcatgt atagccctct tggtctcttc ctccccagaa cccccaaagc cccaggcatg 220800
gagaagccct aggattgctg ctcactcaac cctgcctaag atgaagcaag gactgcagac 220860
acattgtgcc agtgctgagg cacagggcta ggggcctgag gatctgcggc tctgaacttg 220920
ggggctgtgt gcaggtgtgg cctgggtgag cttctccaag caaccctggg aggctgaaat 220980
catttttgtg aaatcctccc tcacactgca tccccaactg ccaagccagc caggactggc 221040
ctggaattca cacgtctgcc ccattggttg cacatggata cctgagatag acggcccaag 221100
aggacaggcc cataagccct gcagcctatg gctctgccca gcccagtcat gtggtttctc 221160
tgaagggccc ctgtctcttc tgttttggca tcttagatgg gcaagcccca gctcgaggtt 221220
aacagatacc gccctcagtc ccactctcca gagggacact cagggagcac ccggcccatt 221280
gagatgggca tgggggagga ccaggacccc cgaggctggg cagagggggt ggaaagaagg 221340
cagagggaaa gctgcagaga cccccaccag gtgactgtga gcacctccct ggcaagcatg 221400
tgcttgcctg gcctcttgtg acatgacagc ttcgcaaatc cttgagcaaa aacagccccg 221460
tgtgcgttaa ttagaatttc catgtcttca actttctcct ggaccctgca gaatctcacg 221520
ccaagacatt cgagttgctc ttttccagca aggccgctgt ggcctggctt tcatccacat 221580
cactactaat gtctcctgaa ttctgcattt gtcagcaagg acagggccag tctgtgctgt 221640
ctggaaataa gggcaaacgt cacaagggtg gccccaaatt tggcttcatg gaccaagggg 221700
ctagctcttt tgatgggacc agcttggcct gggacatttt ggagacatcc aggtccactg 221760
tgacctactc ccacagaccc cagggtacca ggcactgcag ctctgtgagt gtctaagctc 221820
ctcaccatat ttctctccct gtaaactttg gtgggaaagg acagaaagga cattctggga 221880
accagtgtcc agaaggatga gtgaggggct tgtcaagaac agatgagacc attttgtctt 221940
tctagaccag tgtcctgtct tctgcaaagc tccagaccac ctctgtctgc acgagatgcc 222000
aaggaagccc tctgggggcc cgcccgggag ggctgtacag ggctgcatga gtcataggat 222060
ccccgtcaga gccccacata gccccagcca ggctcaaacc cgtctctgaa atgcacgggg 222120
ggattaaatg ttcttctaat taaattaaaa ccgaggcgta atggctcagt gggaaagaga 222180
tgggattggg aatcagatgc cctcaatctg gcttccagcc tgccatcagc ccagctgtgg 222240
cggccccccg tggcccccta acctttccaa acttcacttc ctccgtctga gcacgtgagg 222300
aagaagcggc tggcctaggg ctgctgctat ggggagaggg ccgcactgtc taggtggatg 222360
gcccagaaga aagcagtgag gcttctcatt tcctctgcaa gggaaaggcc atccaaatca 222420
ccctgcccca gtgcactctg gccaggctca gccctctcca cttgtgaact cccagccatg 222480
atgctgctca ggtcctcagc caagcagatg gtgttggagg atgtgacaga gagaacattc 222540
acgccacaga ggtggctgga gggcaaagga cttcacaact gcactgatat tgtcatggag 222600
acacttctgg cagttggggc agggggtcgg ggcggggttg ggcgggggc acatcccata 222660 tagatctctt gtgtgctctg ctgatacctg aaaggggaga ttgaactgca gagcctctgg 222720
aggctgaagc acggaggtga cctagtcagg aagtctggaa gccgtgtccc cttaagtgag 222780
ggagtgggat ggggctgggc ctagcggccc tgaaggccag ggctatccac ctaattaggc 222840
tcacctgggc taccctggta tagggtggtg gtgttaaact tttagttaaa gggtaatgtg 222900
catgcacaca gattagtaca caggtctcaa gtgcgcagct tgaggcatct tcagtccctg 222960
ggacccatgt gtgcagcacc cggaggaagc aacagaaccc ccagaaagcc tctcaggctc 223020
ccatttcctg tcactgacct tgagattaac cacaggccta actgctagca gcaaggacca 223080
gctttgccca catttgaact ttatgcggtg ggaatgatgc aactcataca cctttgtgtc 223140
caatgtccct cactcaattt gatgtctggc agcctctcta tggggctgaa gggagagtgc 223200
tccctcatgc tccttgctga ctggtgctcc attgtgtgca tggcctacat cattcatcca 223260
ttctaccacc tgtggccagc aggcagtttc tggtgtaggt tgctgtttaa gaatattctg 223320
tacatgcttt tggtgagcat caggttgcgt ttctggggaa tatatgccta tgtgtggagc 223380
tgcagggtcc tgggtgggca tatgtttact cttagtgaat actacccagc agtctaccaa 223440
aggagtcatt ccaattttca ttcccacagg cagcattctg gctgctccac atcctaacac 223500
ttggcatttt ccgtcgtttc cttttcagcc atgatggtga atgtctagca gcatcaaatg 223560
gtgattttaa tttgcagtaa cctgttgact aatgaagttg agtccctttc catgttatca 223620
tttagtcaga tacatcattc tgtataaatt gcctacatct tctgcctgtt ttatgtttat 223680
ttatggtcct atatatcttt agatattctg gagtcatttg tcagagagag agatacacac 223740
actcacactc tctcacagac acacacattg caaatatcgc ctccccctct gcaggctgcc 223800
ttcttcctct cttgatggtg tcttttgatg aacagaaggt cttaattttc atgtggtcca 223860
gttaatcaaa catttcctct ctggrwwrgg ctgtttgtgt cctatttaag aaactttgac 223920
tactccaagg tcataaagat atkctggttt attctaaagc tttattagct cacctttccc 223980
atgtagatct gcactccatc tggattgat ttttgtgtcc aatgtgaggc cgaggtcaag 224040
gtccactctt cccctacttg gatatccagt ctagctcagc acccggcatg ggaaggcccg 224100
tcctctcccc actaccctgc cgtatcagtg tctttacaat cagctcactg gctacgtgtg 224160
gctctgtttc tggaccctat tgggtgccac tggtcagatt caagttgttc tttgtggcca 224220
ggaccttgct tccttctcac tgtagtttgc taacaggttt tgacagctgg tcctgctggc 224280
tctggctgct tctccttccc catcactggc tttgctgtct ttgcagggtt tctcctcacc 224340
atacatatgc cagttgccat ggaaagcctc ctctaggcgc agcagcctct agatgggcat 224400
gggagaatgg gtatccttat agttttgggg ctcctgaaac atggcatcat gtgtcccttg 224460
tttatttagg ttgactttca tatcttttac cttgccctgt agttttcagt gtggtggtca 224520
tgaacagctt gtcagattca ttccttgtca gctaatggtt tgatgtatgt tcgctgaatc 224580
cagggacaag gtctgtcagg gagccctggc cagcttgggt catttcatcc tgcccacagg 224640
acactggggc agtcacctaa tctctatcag cctcagtttc ctcttgtata cattgggagt 224700
atatctcaca gtattagtgt aaggccttga ggagatggtg ttaggcatcc agccacatac 224760
ctgactcggg gaaatgcctg aaaatattag ccagcataga atgtctcttt gtgatgggag 224820
atcctgtggg gacattcctt atttggcctg agagcttttg agactgccag gtcatgagtt 224880
accatgggat acaaatgggg tcacaacata tggctgtcag ctgctgtcct taataagatg 224940
tgcctagagg cctgagagtc ccaagctcca ggacagtctg gagtcaggtg gagggaaggg 225000
aagtctagag gtccccaagt cacaacctca aatctcggaa tggggttcag gagctgttgg 225060
ggtcccgtgg aggtacaggc ggaaacctag cactcactat tctgctctgg ggaggggggtt 225120
ggaggcagaa tcagtggact gtgtctcatg gcagtcacag gtgccccagt atgcatctgt 225180
catttgttct tatcactgtc gggcccatct gccaaggcaa gcacccacat taaagcagag 225240
tgaagagcag ggcgagctgt gtagctcacc tgcctttgac cctgcacgtg acgggcgagg 225300
gaagaggacc atggtaactt gtctctaggc aacccatagg tgcccaatgg agagataatc 225360
tcaaatatgg tagcagagtt cagactcagt ggctttcaga tggttagtat aggctgaaat 225420
tccaagagca ttaaccagac acctactatg tgtatttctt gtgttggggt taggagatac 225480
tgctgttggc tgagacacac agcccacatc cttggtaggt ccctcagaga gcatctagtg 225540
ggcctgtcct cccagctcac agaaggggaa attgaagcct caagaaggat agggacttgc 225600
cagtatcact gggagatagg agcagaagcc agggctcatt cccagacaca caatctctgg 225660
gggagcctgg atatgcatgg cagaggccag gatgaaccct gaagattggt aggaaggcag 225720
tgtagcagta acaagacaaa gggattctgt ggcccatgga gcaggaggga acagtctgca 225780
gatattatct gggcactggc cagtggctct tgtggctgcc ctctgcaata agaattcttc 225840
aagttcagcc tctatgtgca tcataaacct ggtgccacca gccaaggagg tcaaaggtcc 225900
tcactggcca gtgggccact gggaagcctc ctggattgcc tggacaaggc tgacctgccc 225960
tcccaggatg caaattggca ggcccagctt catgccttct tatggtgccc cagagcccct 226020
ggctaggcat tcatgcttta gatatgtggg ccctgttagg gacaatgtag gtgtcctggg 226080
caggggctgt atctgaggca cacatccttg gtagtgactg gctagcagga ggaagtctgg 226140
cagttagtct gtcaggcctg gttggtccca tgggaggcct gaggtgccat cttagaaata 226200
gggccttgtt aggagaaaag gaaagaaaaa taaaaggtag agagacagag gtagacagga 226260
gtccaggtct gacctcaaaa tccgatgtcc ccaccatccc cagcccctta gcctctgatc 226320
ttctccataa gtaatctttt cccatgtgtg gctgcagcct cagaggctcc ctctgaagat 226380
gacactggga atatcctgaa aaaggtacag gaacacctgg catgcctctc ccagggtact 226440
ctggatgtgc acccagagat tctcccactt tagcaggcag aagagcaacc cagcagggga 226500
tatacacaaa gatctgagaa agggattatt tttagggcca attcaaggga tttttcaaag 226560
gttaattttg actctgcctg acttatctcc taagtctttg gcactgagca tttatacaag 226620
atcagactgc actgcaccct aagtataaac cttgccacag cagtgtcctg tggtgccctg 226680
ctggggaaac tgaggcagag agcggggtga ctttgcaagg caatagaggg tacttgggaa 226740
gtagggtggt aggcaaggct tttcagagaa caaggagcta catacacata catgcatgca 226800
cataatcatt ctgacccagt cagggttctt cccccaaata aatccctgca accccactgt 226860
ggttataggt ctgagccttc tgccccaggg agccaagccc tggagaggag gtgggcagca 226920
ccaggcagcc agcctgtggg ccccgctatg cttcctcagg cagctagtct ctgtatctgg 226980
ggtagaaaga gtgggctaaa aagtcagcta gcacccctga cttcaagtcc tcgagtgtat 227040
gttgggcttg tctccctacc ctggcccggt ctgcactcaa gcccagtatc ctcccctggt 227100
ccctggtctg gactgagcag ctgtcttctg cccacagggg acctttcttc tcccacctaa 227160
tcctccctct ttgggccttt caaagttggg cttgtttttc agtgttttct ttaggttcat 227220
gtcctgattt gttaagttaa attgaattcc ttccagtcca aaatactcaa atgctttttt 227280
ctgcttttct ttttgaactg ccccacgaac ccccaccagct gggtgtgtgg gctccaggtg 227340
ggagctcaag ggggcctggt gtggtgggtg cagaagcagt gtggtggggc agccttcaca 227400
ggctgatatg attgagctca ggctggtatg ggttagggga tgagagtaca gaacagtcca 227460
ccccaggggc tctgaagagc ttcaattgag atatccttcc ctaakgtccc cacattccat 227520
ggcagtgcct akgasctctg tgctcccagg cctctccatt accagcctgt cttccacatt 227580
ggaaggtggc cttatcaaac cacatggcct gaattttgat tgggaaagca tccctgtagg 227640
tgtcaggtga tggaaggact ctgggtaaat ggaagcactg agaccagata tgataggacc 227700
ttgcccagtg gacacagcca gctgatggca gagccaaggc cagatgtcag gttccagact 227760
ccaagttcta tgcttttttg ctggtccagc atggcctgtc tcctccccgc aacagatcca 227820
accagtcccc ttcagaaggg ctggaccaag tgaccccaac tctgggttct gcctgggcat 227880
tttcttgagt gtcataccct agccacctga ctgtcagggg agcagtatgt ggcacttgag 227940
gccttgggct ggccatgcag gcccaccaca ggtggcaagg aatcatgaac cccagctgag 228000
tcccctgcag gccttgccta aaggagaagc cagtgaatca atgtgttact tgaacaaata 228060
tagggtctag ggctggccaa aagggacagt gaagttggct tctcaggcca cagtaggcct 228120
tcacggtact cagcaggaga ccccagcagg cagcatcagg gcaggggtgy tgaccatccc 228180
tgacccaagc acgaggatca gaatgggccc tggagccaag gccaaaagcc gaactgtgac 228240
taggcaagct gagtcccctg tagattctgg ggactgggtg atgcagactg caaagcctca 228300
gccaccttct cccctagaag aaatcttgag agaaacaatc ccacaggcta ccaggccagc 228360
ttttggaaac agtctcatta gcaaacaaag ggaagtgaca gagcagagat ccccttggcc 228420
tttgtttagc ccaccttctg cctaggcacc aggcctggag gttccaactt ggtgttgggc 228480
ctccttgagc cggaacacct gaaaagccat acagactcct gctcatcaca accacttgtt 228540
gatgctgaca gcctgtagaa agattgctct cagcctatcc cctccctggc catgcaggtg 228600
gaagacccta ttacttgggc taaagagaag ctaaacgtga ccagcctacc caccttgcta 228660
ctgctgatga ccaccctgac tcatgtccct tgtctgcata ggtgttttcc tataaatgtt 228720
taattcctga ggttgctgaa tctcagggct tggaaggccc agactggaca ggggaagggg 228780
tacagtccct tcttgctggt atgttgggaa gctctggtgc aaagggcagt gatggccctt 228840
caatcccagg cccacaagca ccacagccag gagagtcaag gttggatatg aagagggact 228900
tcctgaaagc aggcacagga agggatggga gctcagctca ccgggtgcta gacaagggag 228960
tgtgtctctt tccccatgag tgacagcagc cacaagggga tgcccagcat tgggggtggg 229020
gtggggggag ggccctccgt gctttctggc tctttgggcc tggggtgcag cccctcattt 229080
gtacttgctg gctgccccat gggggcttgg gctaggtctc cctgccggtg gggagggagg 229140
tgtggaagct ggtttgccgg ggccacccag tgtgggctca ggaagggaag gaatgtgacc 229200
aaggctgggt gtggctgggg agagcacagc cagttgtggg tttttcttgg ggcccagata 229260
gatgtgagca gagctggagg cccctctctc ccagcccccg gcacacacas taggacytyt 229320
cttcatcatg cagccgtaga gctggaggcc aaggacaccc tctggaaatc tgaattccat 229380
tcgmtcttgg caaagagcag cttcctgctt agggaaggtg catgcgtgcg tgtgtgtgtg 229440
cgcgcccgcg cgcacacgac cacagaggct ggggggaggc acgtggggag gagggctgcc 229500
tgtcgagatg tgtaagatgg ccccagtgtt actaggcact agatggcact tgcaaagccc 229560
attcggagga tttagacaaa tacctcgagt gagtgaatct gaagcatgct agttgtgttg 229620
ccttttaaat aggctctggc ttaaaacagt cacagcgaaa catgcctttg aattggaaag 229680
ccagaacttt ttgcaaaata atttgaaaag tttgttgaac cttaaacctt tcctgatgac 229740
tccttccttc tgaacttaac tcgttaaagt tgctccaatc ccagcccagt gccagaccag 229800
cttcctggaa actctcgcca actgctggcc tttggaaagg cttgtcaccc taatagctgt 229860
tttttaaaaa aaaaaaaaaa aaaaaaaaaa aagctcactg ggcaccttgg ctgcagggtc 229920
tgaaaagtcc tttgtgttag ctccagctgc agagtttttc caggcctcgc ttctggggct 229980
ractggagct gtttctcttc gtttcctctt acagtggcgg gcactcagcc ggcttcttcc 230040
cgcctgactt ctctgccaga gcccaggtgg gggacgggga tgccaagggc agagcccctg 230100
gagaggctag tgtgggcatg tcctgagtgg acagacctga aggtgggttc actagcctct 230160
ttctcccatc cttcacccta ttagaggtag tgctctagcg gggaaagatt agggcccctc 230220
taggtcaata ttgtgtcatt tccccagaat agccagggcc aaaccagctc ccaagcagta 230280
ctgtttcaga agtgaagata actcacctct cccaaaagca gagttttggc aatataaaac 230340
atgaaagtgg gatgggatct aagtcatatt tttttaatga gtttaaaaca cgtgtgtgca 230400
ttagaaaaca tttaaacaca gatattgggc aaattaattg aaaaatatat tgtcattttg 230460
cgttaaaata aaagatgatc tgaaaatgga aaaaagttac ataaaaacgt aaatatttca 230520
tgagacatag cagtcacaac atgccataca catttcttcc agaatcactc cactggaaat 230580
tctgtaataa gacatacgta acagtttcac ttcctaggag atcccaattg ctcytcagat 230640
agggtggaga gcacccctta ttagagggtg gttgggctct ytaggagccc gcccagggcc 230700
tgccctgact ctggctctgc ctttccctgt caaaaacctc tttgtgctgg agcagcccct 230760
gctccacaga gtgacatgaa ccagagactc acagcactgt gtgcggggag ctgctgcccg 230820
cagggcatac cagccacgtg catgcagggc tgcacactgc cctaccgtgc atccactgcc 230880
tggccaacac ctgccttctg gggagccaat cgtgctttat gtattcaagg gttgtgctac 230940
aaaaatcata caacagtctt tacacacatg gtaaaaccaa ttcagagtac aaaaggggtg 231000
aaaaataaca ctctccccac ccaaccctaa ttcccaagtt tccttcccta aaggttacca 231060
ctcaacactt tcytattgca tctttccaga cgtattttat ataaacaaat atacgtgtgt 231120
ctgtgtgtgc atgtacttag tagatacggc tcctttttat acaaatggta gcatactgta 231180
tgtattttty tacactttgc ctytgacttc ttccataggt atgccatact tctttttgag 231240
ctgtacatac aatgctgatt tattatggtg cagtacatct gagaagcatt tttattgcaa 231300
aatgtgtgtt tacatgtata cagacacacg tgtgaacagg tgatggctct gaacagtgta 231360
gttgaagtgc tgttttctca tggttgggct tccagtataa ttggaaggag catagtctct 231420
gtgttcagct agagatttag cccaatgggc tgggcttttc ccagatagga catgctcact 231480
gttctgctca gattgttagc tgtagtcttt ctggcatcag ttccatttct ggtgaacact 231540
tggacttggc aaaaggcata gaggtagtgg tacaggaaag gtctaagaag gctaaggacc 231600
atcatactgg gtattcaaca gccagctctc caaagaggcc tctaagaaat gggtagcttc 231660
acagattcac agatagatag ttcattaagg tcttgagtat ttccaaggga gcactaactg 231720
gactacagcc tggcaggaga taaccaagtc atatgcatag tggctttggg tacgatggtc 231780
tgctgtatga agcaacccta ggacatttga agagaatgga gtgatggcca gtgtattgtg 231840
ctgggatcta ccacaggggt catgttgtaa tgacacctgt cagctttgac tggggagccc 231900
tttcatttct tagtaagtgt tcagccccag tgtgcaccac ttaaaaggaa gacactggta 231960
tgttctggag atggatctgt attaagacat ctagcaaatc tccttttcat taacagctgc 232020
agagtttcat tgtgccatga tttatggaac agatcctctg ttgatggata tgtagggcag 232080
ctaaaaaaca gcagccatta accattcaaa tatattcact actgaaatga ccacttatga 232140
aattagtttc cctgaaacat ccctccctat tgaacactgt tgtttctccc tatccatctt 232200
atccctactt gtatctctgc tgactgacct ctttggctgt ctcttgtcaa ccaaagacaa 232260
tataaagcac acacaaagta aagaggaact tataaagagg aactgtaaat cttgtcaaaa 232320
taggagattt catcaagtta aagaaaatga tgtcaaatga tttctcaaat agagactggg 232380
cagagtagac cagttagtta atcagttgaa gaggaaacca agatcgatgc ctagataagc 232440
atttcagagg acagcagggg agatgataat tgatgcaggt ggcctcttgg tcaagcagtg 232500
aaaccatgcc atacttctac aaaaaatgat cctctctgtg gaagtgctgc caacatcctc 232560
tgccaagtat aaaagatgcc ctcagatgtt accatataat gctttacaaa agacaaacca 232620
aaatcccctc tggatttgtt tttttctaaa acgtgtacat aattgtaact ctaacaactg 232680
ttattgcata tgagataaaa taatatttta actactgtta tttttcaaat taacttccca 232740
atcaaatatc tctattgtaa aattttggtc tccgttttca gtggatttac tttaagagat 232800
cctccctttc cccccatttc cagcaggatt aaaatgttca tttatgttgt gatagatact 232860
gccaaataag ggctgtacca tttacatcac tttgactgca caaatgcact ttcttccccc 232920
acccttacca agtgtatact caggttttta tcttcattca tttcatagat gagaaatggt 232980
acactggagc tttaatttac atttcttttg ttggaaatga ggtttttatc tttccaaatg 233040
cttaaaatca tttgtttttt ctttcttgtg aactatttct tcataccctt tggactttgt 233100
aaaatacctt gtcttactga tttgtagaaa cttgctttgt catattcatt gaaaatattt 233160
tatcctcatt ttccttaggt gttttggctt tttctataat atttttctgg tggcagaatt 233220
tttttaattt cacatagtca gctgtgtcag tcttttatgg tttgaggtcc ttatcttaaa 233280
ttctgaaata acctctcatc ctgaaattgt tttaataaat tcttccatgt tttcttctat 233340 catttttat ttcattttt acatttaaat ccttgcttta tcgggatttt gacagagtaa 233400
ttaaatccaa tttggtttcc catatatttg tccagttgtc caacactatt tatttgagta 233460
catcatcatc tctctactaa tttcaactgc tacctttatc atatttcaaa ctctcattta 233520
atttgtgtcc atttctagac tctattctgg actgctgatg ggcctgttga taggccagag 233580
ctcagttatt ttaattatgt aactttatga tgcacttatc tgtgtagcag gactccccct 233640
catctccatt acttaagagc caataatggg aagctcattt tcacaaatgc agtcaaccag 233700
gggaattcat ggcatggcct aagatctaaa cactcttaag atttaaacac aggattagct 233760
cttgagttag acaggaagct ggggtgtttg ggactgaggc ttcatcgtgg cagctaataa 233820
tgtcagggag catgagcact tgtttcttcc aaggctcact tcaaggaagg cagaatccag 233880
gtcgggggtg cacaggagtt gccagctgga cccaaggacc atttcgtata catgtatgat 233940
catactttca gggcatcttg gaaaaactga atttgctaac tcaatagaga acaaaagagc 234000
aaataggcct aattcaagaa tttttaaaaa cccgcaataa gaaacataat ctaaaacttg 234060
tagcccagcc cctcctccat accaaccacc aaaaaaaccc actaacacca taaagtgtca 234120
tagctagagc tagagtgctg ttataagctg tgcaggccaa aatggtttca tggcatgagt 234180
tgggcagcag cgactcagtt tccatgtctg agttaggcca cctgtaacaa tgcagcccca 234240
tccatgtgaa gctggtccag aggactacag ctgcctgtcc cacccttggc tgtgctctcc 234300
tttactaatc catagccaaa gacaggggct aataacaggg tctggagtct gaactcatat 234360
cctaattcca ctactttcta cctgctacac cttgagtgag tcacttagtc tcagtttctt 234420
tatttgtaaa atgggaatca taagagtacc ttcctcagag ggttgttagg aggattacac 234480
aaattaataa tataaagtat gcagaaaagt gcctgtccta tagtagtgac acagtgttac 234540
ttaaatgtat tgctatacct catgatggcc attccatcca ttgtaatcat gtgtaccatg 234600
caattcacag tgcctgacaa agctgatggg gaggcgagtt ggaatgaata gtatcagcat 234660
cagaaaaaat acaagtgcat cctcataaga ttatttagga tgcataggat cccagattag 234720

-continued

```
atttttttta aatcagccgt tctctgtatt cttgtccaga tgctgtggac agtgatgatg 234780
ggaaaatagt ccctgctgca cactagggcc tgttaggcca gttgagggct agaggagcac 234840
aaggggccag actgctgcta cttctgaatt ttataggaca tgcatttttt tcatataaac 234900
ttagaactag cacgcctaat ttttttttta tttttatttt ttttgaggca gagtctcact 234960
ttgtcaccta ggcgggaatg cagtggcaca gtctcggctt actgcaacct ctacctcctg 235020
ggttcaagca attctcctgc cttagcctcc ctagtagctg ggactacaga catctgccac 235080
catgactggc taattttttt ttttattaga gacagggttt caccatgttg gccaggctgg 235140
tctcaaactc ctgacctcaa gtgatctgcc cgcctcagcc tcctaaagtg ctgggattac 235200
gggcgtgagc caatgcacct ggcctcagct tgcctaatta aaaaaaaaaa aaaaaaaagt 235260
tgtctatctg tgtgtatatt catatcccat tggcatttgt tattgaaact tcattcaatt 235320
tagattaact gatgaagaat tgccttcccc acctcaaaaa aaaaagtctt tccagccaca 235380
aatagaagca gtttacccac atgttcaaat ccattgcaac atccttccat atttttttag 235440
atctttgtat ggattttgga cattctaaaa ttcatttctg ggtattttta ggaggactac 235500
tgattttttt ttaatttggg catttttttaa aataaatttt tattttgaga taattgtaca 235560
tttctcatgc agttctaaga aacaacacag agaaatctta catactcctt tacctagtct 235620
cccccgatag taacatcttg caaaactgta gtacaatatt ctgaccagga tattgcattg 235680
atagtctcac tacaggacat ttctaactct tcaagaatcc ctcatgtccc ccttttatag 235740
ctaccccaa ttccctccca ccctaccctg tccttagccc ctgacaacta ctaacctatt 235800
cttcatttct ttatcattcc aagaaaatta tataaatgga accacatagc aaatcacctt 235860
tttgggatcg gctcttttca ctcagcacaa ttccctgaag attcacccag gttattgtgt 235920
gtatccttgc attttggtat gacccaattt gggtttgtat ttttaaagct gatggacact 235980
atttactagt gttttcaaga ttgcactgac catcataggt gaaataggta tgtgttcttt 236040
tattatgaaa gcctcctcag atgtggacat tagtgaaatg tgggctccaa aaagagactt 236100
tggaagattt cactaatgat gtggttattt tttaaataga tgccccccaa aaaagcacct 236160
atgaaaaaat tcttacatag caattctact tctgaatgct aagagggttt ggaaaaagtc 236220
atttttgcag tgtttgtgtt ctatgaagag tgggtagaag gaagcaggag agtattcctg 236280
cctccccagg agagagcttc actttctccc tatatcttcc tgtcctacca gcccacctgg 236340
ttctctgtct ctctccaact gtgaccgtct tttccttgta gctccctgct cactccatgt 236400
ggaggatggc tcttggggct ggggtgacta aaggcaaaga atggggatcc ctgtgacagc 236460
tctaggggat tttgggacca gataacctta atggcctcag gctccctaga tgagaaatgg 236520
gacttagtaa agtcaaactg gtccaggtta agccagccca tgatgcctgg aaggaactta 236580
cccttttcta gagtaacttc ccttttcagg aagtttctag cttgcttgct cactcgctct 236640
ccccaccccc acccaacctc ccccaaccta tctctccctc tctcaggaga aggtgctccc 236700
tcacccttaa agaccaggct gccgttgctt cccatgtgtc tgttcctcta ttcagtattg 236760
tgggcactga tcacacacca gggcactgtg ggggccctgg gacctgggag gaccagaatg 236820
ggtacagtcc ctgccttctc aggttatggt catatcatcc atgctcccca aacatcaagg 236880
tactccaaag gaggcccagc actaccatct aggtggggag aaaacacacc ggccataatg 236940
aacacacgtt taggctgaag aataatcttc aaatgatact actacttaca cttcctgttt 237000
gccaggcaaa tatagacatc atttcactaa tcctcacagc agcttttaac acaagaatat 237060
tatcactcct gttttataga taatctccta agggttgagg gattgagtct agggcccagg 237120
```

gtcacaaagc tagggagccg tggatctgca ggagatgtcc cagctcatca aatattcttt 237180
cagtattaaa catatcaagc tctctcctga ccttctctcc ccttccccag gccaggactg 237240
tcttatcctg tggttcttag ctgaaatgtc ccttcctcag aggagccaat ttctaaagct 237300
taagactggg ctgtaaaaaa tcacatacct cccctcccat tcttaatgtg taactgtgtg 237360
tttatttgtg gtaaagggtt tactggctgg ctccttctat cacattcaag gagcatgagg 237420
gtataggctg gctgtttcta ttcagtgttt tatcttcagt gcttaatcca tatggagcct 237480
gtcacggacc ctcagtgaat gtttgacgag tgagtgagtg agtgagtgag tgagtgagtg 237540
agtgagtact tgtgcccagg tcaaaccagg tgctaggacc ctggcagggg ttccataagg 237600
ctatgctggg gttcaggcaa cccaaggctg gtctggagag tgtaaggctt gagagctctt 237660
cttcaggctc agtcatccct gcttccccag ggctcatgtc cacatgctat tgtccataga 237720
agctggggtc caaagttgac cagaatatct ctagtcataa agaatctctt cccattgagc 237780
ccactcatct ctgttgacat tctagaaatg cagggaaatc tgggcaccat gaaatgcagt 237840
gacttgcagt gatcctcctg gggccttgta tagaagagac catctcagtt ttgtagacca 237900
ggaaactgag gcttggggat agcagatgtt cccagacaga aaatggtggc acctggagag 237960
gtgctcaggt ctgtgtggaa gaaaggacag gagtccttct gccacccaga ctgtgcattc 238020
agacatctcc cttgtgctgt gcagccttag ttctgcctcc tgagagaggt gaccttctcc 238080
cacttcttac aggcaaggct cttgctagcc tgaggaccag gagccttcag attttcttgt 238140
tcccaggata tatcgcacca actcaggagg tgtggggatg ggctagcatt aggaatgggt 238200
attagcatct gcattaaaag gctcccactg acagctcatg cattgtgatg gaactagagg 238260
tgagatacag agcaggagtc catggcacct ccagaacctg tcagcctgag tatgggcaat 238320
ggcgttttag tttgcaaaac cagacacata gaggccaggt ttcccccgct caacactagg 238380
ccactgtgcc tgccactgct gtctgcaaat gcaggttcct ggggctctgg gtggtttgtc 238440
caatggctaa gctttcccca ggaatgggta actggaaaaa tgtaggaatt acatatgatt 238500
ccatcaatga cagttttcct attaaaacat aacttgttaa agcatagagc ttagttcaga 238560
gtaaacattt ctaaaaaaga ggtagaagcc cctacctact gactggcatc acaaacactg 238620
ccctgaaatg ccaactcatt tcaaatactg ctctagacaa ctgggccctg catctgctgc 238680
aaggaacatc ccttactttc ccatctcaat acaactgtga aaagcctagc ctgggactca 238740
ggcctttcct tactccctct ggttacctag ctttagctct gaggcagccc agatgacatg 238800
ggcctctaag gctggctgct cttactctat accccaaaat cccagccact agcttgcaga 238860
atggctttgt tggattcccc tccctggccc cacactcact gctacatctc tcttccaaat 238920
cataaatgca aaagatggcc aaaggtgcat gctctgtgac acgtttcata gtcagacaaa 238980
accggctgac tgcttttact tttttttttt tttcatttag aagaatttcc ttggcaactc 239040
cgtctctcct tagtcaacat cagctaactt catcctcccc ctttatcaag acattgttta 239100
gagtaaataa ttcattaact ggtacagcaa tttcagaacc ctttcacata gtttcttaag 239160
gggaccgttt cccttgaaga atggggtaca ccagaggact taggaagaga agcgcccact 239220
ggggcttggt cagactctgc caggagacag gcagctgtct gttaactgac cctacccagt 239280
accttctggg attggattaa caaaagggga gttggttagg ctggagcatt gcaactcatt 239340
tcttccctgc agtctctctc ctgaggtggc ccaggtatgt gtttgaggcc tgggacttgc 239400
tgccagcatg agacaagctc cagtggggtc catccccctg attcctcagt gccccagcac 239460
cacctctttc atttgaaaac gtgttctttt ggcaaaaaga ctatgctcca gaactttctg 239520
gctgagttct ccttctattc ctcctattcc actgttaggt gttggaaaag caatatattt 239580
gatgctttct ccatgtccca taaatgactt tctggcagag gagagtgact gtcctttgtc 239640
tgtggccctg gatttgaggc taagccttcc ttgaagaagg aacaggaaag aaaggcttgt 239700
tggatgtgca gggagctagt ggccaactga gcacttgctc aggcggaggg gcctggagag 239760
aacccagggt aggtctgcct gggagaaaag gggtaaggga ggactgcctc ccagccttcc 239820
ctccccactg gtctgggcac attccaaggc ttgaggtctc ctagtcaagg cctcctgtta 239880
ttggcttcct ccagggagtc tgctgagaca aaagttttag attctttcac tacatcataa 239940
ggtaggtaag tttgtgtccc tgatccatgc agcatgttat ctttgtacct ggtaaggagt 240000
gaaatggctt ccaattttac ggactggttg cttttcattc atatcttctt gccatccctg 240060
tctcatgggt gagcacattt cctggattta aaatgtatgg gacagcctgt gagaattaca 240120
gattccaggg aagggcccct tttggcacgg ggggtctgac ggtcagagct aatcaggtgt 240180
ggaagaagct gcctggagag gatccccatc tgcatggaat gccccctteg tggggatggc 240240
tggcacagct cacacacgga ggcactactt cagtcctccc attaccaaac tccagggcac 240300
acgtgccact gtgtcttgcc cacaaacatg cacacagagt atcgatctgt ctgatgtttc 240360
agggacccag ccatgtcatg gagggtacat gggcaggtac catctctgcc tggtacatgg 240420
gcaggggata gatgtgtttc catgggtctc cttcacatag aattgtcacc tgaacgagaa 240480
gcccttatcc agaagcccag tgcaactccc atctcacagg ccaccagcaa gttgctcaca 240540
tccagacagg agacgctagt cctacaggtg cagtgggagg atctgcagat gactacagct 240600
cttggccctt ccatacagca catgacagga agctaggagg gttgcagctg gctgttgcca 240660
ttccactcag ggttgagggg acaagcccac acaggtacca gaagttcagg ggtcccatgt 240720
ggacttcagg ccttcggtct gggaccccag ggagggtgct ctgacagtcc gccgaaatgg 240780
ccagcaggca ggcatcctcc caggtggcag tgagaaaggg ccctgcacag tcagcgttcc 240840
tgagaatgcg attcctacta gaacgaggct gtttcccagg ctgcctcctg cttcacccag 240900
gactcagacc acaactagac tagggaagaa cttgttctcc acggatgagc ctgaccaagt 240960
tctgggccca ctctcccatc ctcctgctgg gtcacacgga tgaggcctgt acactctggg 241020
cctcagactc cacaccaaga agagtcaggg gggctcactc taagccccgc cagctcgcac 241080
catctgatgg ggcaggggca ggggaaggac agggccagca ttgagtaggc ctgagttgat 241140
ggcaaagtgt aggcctttgc cctgtctcgc cccettgctt ctggggtttg cttcgcyttt 241200
ctgagagcac agcaatgcct actcatcytg cccaaaaccc tgctccaacc tagctgtgtg 241260
acctttaggc cttgggatag cacacagcaa atgtctgcca ccccagtact gccactggct 241320
tgggaggcca gaccacagac cacactagtg tcacctggcc cgtcccacct gttccaagct 241380
gggggaggag tatgctcact tgggcttatc agcagagcca gggtacccca acccctgact 241440
aggatattgt ggatacctat gcccagagcc cctccactgc caagtttcca caattgtttt 241500
gaaataattc ccaacagata cccccaccct cacccagtgt tgagtctcac tcccgtcacg 241560
gaaatgacag ctcccagccc tgggcaatgt gctcctgcaa ggacagctgt ggtgactaga 241620
atggcagctt ggctactagc acttttcaca tgagcgtggc tgccctcagg cccaggctgc 241680
acagagcatg gccgctggat caagtgtggg tcccagttgg atgacaaacc catgttcaag 241740
gctgggaagt cctactcggc cccacttcta cccaggacca gtagctttca attgtaaatg 241800
tgcatcccct gtgatacact atgatgcaca agcagcccct gctcacccct aaagagcagc 241860
acaagtaact cagagccact gtcccctctg gccagaggcc ctggtttgtg tctgcccagt 241920
gaccagcctg aagatagagg caacccaatc caggtccatg caggtctccg tgatgcggag 241980
catgcccagc ttaccatcct gatgcagagg caaggacaac actgggccct gacttgctaa 242040
gatgggagca agagcttagg gctaaaactc agcagtccca gctctggggg acaaggaccc 242100
acaaagtgat gcaagatatc ctgagttggg tgtgacaagt acaccttgac acacaaactg 242160
cacagggagg ggaggaatyt gagccagctt cctccacaaa gcacagaagt ctgccaaaag 242220
cccaggctgg atagggagca tcacactgtt gggaaatgtg caattttcac tcagccagca 242280
tcactaccag ctccgggctt ctctcctctg gcctcccacc ttgcagcttt gagatcccag 242340
gcctctcagg gctctggctg agggctgtga gccagaggct gaggtagcca ggtctgcctt 242400
gggctgtcac tcagggctga gctctgctga aggatctggg aggtcagtag gcacctgtgt 242460
ccacccagct gtccatacag atccctgcct gcacaagagc tgctgcagca tttcaatagg 242520
gccatcccag gcaccctagg acttgagacc agcctcctct gtatggtccc ttccctggtg 242580
cacctaccac agcccactct gatgaccccc tgtcaaggag gtgtgactga gaaaggaagg 242640
ggcagagatc ccttctccat tcctctcagg cccctgtaaa aattgggacc tgtccttgcc 242700
agccaggtct cagggagctc agggttcagt gttggaatgg gtctgggccc agatttcaag 242760
ccagtaacca gcaaatcatg gggagactga gaagaggagc cccttagcag gcctaaccac 242820
acccctaggc cacccagcct ggccccccctc ctctgcccca actggctcca ggccaaactc 242880
tggttcctga ggagcctcaa aggctggact tggggtgtcc cgcggaaatc ctggtgggat 242940
ggaaaatccc cagcagttgt gaggctgcac ttctcccacc cgctgtgggt cagccaggcc 243000
gctgcttcct gcttcccttt gatgtctcct cgtgcgaggg aggggtcagc acccctctag 243060
gcttgggcag gcacacactc cactcagctg cagccatgga gttggtgctt ctagggcctg 243120
ggtatgctgg agtcaggcag gggacctggt gggggtgggg atacaggctg aggtggagag 243180
accccacgca gctccctagg cctctgcaga cagctcccaa gcaagggggc aggaggggct 243240
gcactgagcc caccaaaggt tgtagccact catacagggc tgtttgatct gagagggagg 243300
cgccatgacc tctgtttaga caaggaaaat gaagactctg gaaaatctaa gcacgtcaca 243360
cacacagctt ccatgggggt cttcctctcg tgtctgggga acttccccgt agaggtttca 243420
ataactgcca tcctttgctg atcctctgtg taggcactgg gccccagccc ctgcctgtgc 243480
catcactatt tcacaggaga acaccacact gaggctctgc ctctggttgc cctgctctgg 243540
gtgatgaggt agaggtcaca cagccaggcc agtggcccta gtgtcaaggt tccacaccac 243600
agcctcatag cagccagtgc tcgctcactg aggccaggca ctcatcttgt gctgtgcctg 243660
ggtgagctct ggacctgcct cctaaacata gggctgcctg cttcgttcat ttccacacac 243720
cacgtgccta ggcccagctg gggctggcat acaaattggg tggcccggct ctgagctgct 243780
gctggttact gtggcagttt ccacctatac cacacctata tacttgccct cccccacaca 243840
cagcccacct ggcccatccc acaaagagag atggcactcc aggtggagag ggctgggcca 243900
gaggtcatgc agcaaggtca ggttggaagc tgaggtgggg ctagggccac cccacacagg 243960
cctgtctcac aggctgtcac ccactgggcc tagggctctg agagtagggg tctgatctgg 244020
agagcagggg agcctgcagg tccctgggtt ggaatcctgg agccctgggc tgcagggttt 244080
tgaggggcag ttacctcctc ctccccggtg gcacatccgg cctggaagtt gggtagtctg 244140
gcccaaggcc tgccctggtg tgaaagcctg agaccctaag gagagctaca ggtggctcaa 244200

-continued gggcctgctc ctcctccttt tctgtgcaaa cagctcagct tgctgacttt gatgcagtgg 244260
tttaggccaa gctttgaagt cagcccttgg aggacgttcc tatcagcctt tgcacagata 244320
tctcccactc caaccctaag actcaatgcc acctcaggac tgcccctatc cgcagagctt 244380
gaggccttta ggtcagcctt gggaagaggt gcttgagtgg ggtggaagaa gcccactctt 244440
gggaaatggg gagcataggg gaggaggaag acactgcctt ggaatgacac tcccagagac 244500
ctctgctctg cctacctgca ttctgctgaa ggttttgggt caccttgttt tatggtccct 244560
gtcccagcat gaagcttgca caggaagaac agaatgaatg atgtggaaat ctgttagcag 244620
tggtgtcttc cagattctca aggatccggg tattttagga acaaaacaag ccagcaggtg 244680
cagaggtcac aagcctcctg agagggccag ggcagagtga gtagctgcag gggcagctgt 244740
cctttgcacc tgggcctaga gtgccagaga cttagtctca tttgtttaca ggagactgat 244800
gggttcctga gcagcctagg aggggagggg aagcactgcg ttctcagtgt ggtgcttggc 244860
cctcccaggt gcctggttgt ggcctgccac ttagcaccca cccctgccta tccagcccca 244920
tccctgggga aggttcccac ctgctccaac ctctggtact cccaggctgc ctcacccaac 244980
gatgacagtg actagcctca gagcctggct gcttggaaga cctttgccca agcagagaac 245040
tgttgaggaa ggtgagcctt ccgagggcca gccctgcctc tcctcccctc tcctagcctg 245100
cttctgtctg ggctgaaggc acagcaggga caatcgctct tccggggtta gaactggggg 245160
agcagggaca aaaagcgggc agccctcccc agcatgacag gatgtggaag gctggtctct 245220
ccagagactg ggctaaactc tgctgtgtca agtgcctggt gacctcaagc aagtcattcc 245280
atgtggctga gctgctcctt gctgcatctg cacatatgtg tagtgtcttc ctccctgtag 245340
gattgtcaca aggattaaat gatgtcaagt ctgaggctgc cctgcagctg ctgtttccac 245400
tacttggcat ggaacatgtg ccagaccaaa agagctatct ctctccctgc gaaaggctgg 245460
ggtcctggga gctagagctg ggttaagata agagcagaga ctgggtcctg ggaacagcca 245520
ctgggcccag tcgggggggt ctcagcacct atcacaaaga aagtgccact gggcctaggg 245580
aaggacaaga agtaacatgt caaagatggg acagaaccca cctcctggca gggagtgggg 245640
cacacatatg tgcatgttca tatatgtgtc agaatgcgta tttgtcagtg tatgtgtgtc 245700
agtgcacata ggtatagggg ctgtctctca gaattcctga gggctttcca tttgatccca 245760
gtggttgaag atggagtatg atcccaaatc ccttaggtgg atgtggcctg gcagggggtc 245820
agcaggaggg aggtccctgt ctccttggct tccagcttcc aggctctggc actcccactg 245880
ttaggaacag gtacctttag ggacacagga gtgtaagcca ctgtttccgt ctgggttttg 245940
tcatgtgtag gtcccagcgg ctttaagcca acctgaaagg ttcatttggg agtcacgggt 246000
atgtgtcaac aaaagcccac cagaccatca atgaagtggg caaaagctct gggtgaactc 246060
ttggctcagg tatcaggata tgctgggtga gggaaataat ggaggcacct ttgttctaga 246120
tgcctgcaga ttcctgacaa cagtaggggt ggaggctgtg cagacctggt gcagagtctg 246180
tgctggcctc tggcctctca cagccttggg aggggtgctc agagctcagc tgtgtttaaa 246240
aattagcaag tggaggagtt agaggatctg cagttaaccc cttgagtctc ggaaggctgt 246300
ttgagccact aatcaggaag gagagctgac aagaaaaagg cgatgtctca cccctgagct 246360
acaatccact gcacttacag tgaccaccca tcctgacatc ttgggctcag gcctctgggt 246420
ctgggcatag aagcccagga actgctgtct gtggggagtc cactgaagct ccctgccccc 246480
actgagtctc tgatgttgac agcctctttg ttttttcatc tcagcctatt caaggccatt 246540
tttcagcttg cttggctttg cattaaagtt ggggggattt ctctatcctg aggttatgaa 246600
atacctcagc aaggacgagg cctccctgag ggagtcaacc tagcttgttc cctgcacgta 246660
ctgtggggag gtcctcttta ccgccacagt tccaagggtg aaacagagaa ccaggtgggg 246720
aaggggtctc tccccatctg tccaggggag aggcagccca cagggagcca cacaggcagg 246780
ggacattcca ctagggccat ttgcaggcca gtggccatcc actgccagca atcagagaat 246840
cacaagcact ggatccaatg tgacctctgc caggaccatg acccctaggt cctcttttcc 246900
atccctccag ttctcctggc tttcttgcca tctttctggc tctatcctca gtctccttgg 246960
caggttttcc cttctggcat ggccactaaa tgccagtgcc tttctctatg caaaccattt 247020
ccctaagctg ttccctcagc accaagggct tccagaccac ctgtgaggcc ctgacccccc 247080
aaatgtctct ccaacccagc cagacccaca ttccagtcac ctgcccccac ctcctctcca 247140
cagcctccat cattttatag cccactctac tgaaggcccc tgtcctttca gtgtcaccca 247200
tcctttcagt ggcacaagtc agaagttctg ggtcatttc cgatacaccc gcttcctcac 247260
cacctgccca tcacctcaag cccatcacca agccaggctt acttcaccca tccatagttc 247320
tagaggttcc ctgcttccct ccatccctat tgccactgtc ctgataggcc accatttctc 247380
tgtactgcag gcatctccta actggcattc tcacatcccc tgccccattc caatcaatta 247440
tctactcagt ggacagaaat cctttcaaag tttagagacc tgtgggtctt gcttaatcct 247500
gcagctgcct ttctggtagt tcagatgctt ggcttctttc catcccaggt gctcacaggc 247560
tccctaccac cagagggccc ttggcctgcc cctgccactt tccccaaggg agtttttcag 247620
accccaggct agttccagtg ggttcctgct atacacctgc tgtgctccca ggcctcagca 247680
ctcccctcag ggtgcaaacg gtccttcaac attagttagt ctttctcccc tttgtccact 247740
aaccctggga gggtaggcag gtccctgctc ctatcaaatc cctccctctg ggccagggtc 247800
tagtacctgc tgagtgtttg acaaatattt cttgaatgac tgcatcccta acatgaggca 247860
atgatcattc ccctgcctgt tagacataat tcactgcctg ggaaggcact gtgctgtgta 247920
gatgcagcaa gctggctaaa atcaactgta gcatggccta tgtcccaagc aggttgtcct 247980
gcccatacgc tcaataatga ggcccactga actctcctgg tttccagaag cctcataagc 248040
aagcacgctc agtgaaggaa caggaagtcc tttctggagc agggggagag aaaggcatcc 248100
agttagccat agaggggaat ggctccttac tctttaagag tcatttgccc caagactact 248160
ttctgtcaat caccagatag ccctcagtct acactctgtg atccactcat gaatatctgg 248220
tctggctctg cgttccagtc agacccttt ctgagaggac cacaagtcat agcccagggc 248280
tacctgtaca gctaccaggc ttaacaactc agatgcacac cctccacaac tgctcttagc 248340
acccacaggc ctgggccctc tctccctgcc ctgaagccaa ccagaccctg ggtgggggcc 248400
gagtctggcc aagcagcagt gtgtggagct gggcctgggc ctaagctggg aataagcttg 248460
ttttgccagg cgctggcccc ccatcgagtc cccattctct aatgctaatt gctacaatta 248520
gcaggagaaa ggcctttag atccatttct tctcctggct gaggcccggg ctgctaggga 248580
ggttgagccc aaggcttttc ggaggagcag ggattcttcc ataaatgagg ccacatttaa 248640
attgcaaaca agagcttcgc ccagccgtag gaaaggctct gggagaaagg cttttagttc 248700
cgcagacaga gcagccagag actgggtgcg ctccagcctc atgggccttc ctggctggtg 248760
tgactggaac cctgggttat acaggctcct gccagtaacc tggacatgct ggggccggcc 248820
agttcagagg agcatggcac aggctgataa aggcaccgga aggaaaggca gtattagagg 248880
ccaccccttg ccctcccatc caggcctgct ctgagggaaa ccctactcgt cctcctcctg 248940
gagtgtactg caaacctgga tccggtatcc gctgagaacc actcattcat cagtctgcac 249000
taactggaga aggtgagcag gcccagcccg gcctctctag gccacctcca acttggtcaa 249060
gccacaggtg cccatgccat agatggctga gggacggcag ctgacacgta gttccaacta 249120
aacctctggg tggcagccca taggttgtgg gactggaagt gcttgccaaa caaattatac 249180
tgctgaccag ggaagagggt actctgattg gccaggcctg ggccagggtc tttctcaccg 249240
aggtggtgag gctataggtg ttagatgtgg caggatgcaa gccagggcct gctgccttta 249300
aagagccaca gcagagacac catcccagtc ccaagagctg ttctaaggaa gtggttgtca 249360
tctgcggtgc cccccagggg acatatggca atgtctggag atatttttgg ctatcatgac 249420
tatgggagaa ttactaatat caactaggta gagaccaggc agggtgctaa acatcttaca 249480
atataaatga cagcccctca caacaaagat acatcctgtc ccaagcatta ccagtgtggc 249540
tggctaagaa accctggttg caaggggtca gattttgaca tgctatttgc tttctcactg 249600
agttgtgaaa atggaggcac actttcctgg cctggcctct tccttcgttc aataaatgaa 249660
tgaaaccatt caacagaaat ctgtgacaca cccaccatgt gcggacccta tacggaagac 249720
agatatgctc tcttggggcc tctcttccgg tggaagagat aggcagccaa caaataagta 249780
gatgtctaag gaactagaaa agcgtagcct gtgctttgca gagactcgaa aggtagtcgt 249840
cagctagtga gtgactgaag gggatgacag atatggcagg tcagagcaaa atttcctgtg 249900
agatttaaat aagaagaagg aattgtcaag ggaagatcac cagaaaagac aagccaggca 249960
gaggtggtga aggccttggg gcaggaggga tacttggcag atttaacaaa gaagaagaag 250020
gctggcagag ccaaagctca gtgagggagg acagtggtca gagaggtaag cagggcagat 250080
cttgtaaaaa cctgatggaa tttgaatttt atttcctaga aatagaagcc actagagggt 250140
atctggcagg agagtcatgg aggcacattc attcgttggt tcttggcttt tgggactctg 250200
cacagagttg atcacagccc tcagcctatg aaacactgtc accctgtaag ggtctgcata 250260
aagtcaccgc tctcttcctc tccatgcttt tccacttcat ctctagcctc tatccttgct 250320
ctcctcccta cacaaacagc ttctccaggg taatttattt atatcattgt gtgtgtgtgt 250380
gtgcactcac gagcactccc tagtactgcg tgtctgggtg gtgtgtaatt ttaatttaaa 250440
tacacagtca tgtactgagg ccctctttct gtttggcatt tgtgtcactc agcactgtgt 250500
ttccacgcgt ctctatcttg tgaagtgtac atctagtccc ctgctcctaa ccacagtgac 250560
cagctccaac tgcccacccc tatgggccat gctgccctga gcatgcacac acacagcctc 250620
tcgttgttct gggtgagaac tgctccagca tgtttactta ggagggaaac tgctgggcca 250680
caggtataaa atattttatt tgaggaagaa gtgttggcca gctcttcaga acgtctgtgc 250740
ctgtctccgt ccccacctgc agcacacagg gaggcttgtt ccctgccttc tgccaacact 250800
tggccttatc ctactttcta atgcttctcc tatgaagaat agctgttgct ttcatttaca 250860
tttctctgat aactgattag cttgggcaaa ttttcatctg tttgttaacc ctcctgcaaa 250920
ctggcaatct tcctaccttt ttcttaatga tttgtggtgc tttctggtat attttagctg 250980
ttgttccctc ctcagcttta attgtttcaa atatcttgta atgagtcatg gcaaagttac 251040
attcatgagt gtaaaagtga aaaacgcaaa ttgtttcctt agtattatta tgaaaacagt 251100
cctgaccctt gccatgatgg atttatttaa cagaaatcct taatccataa tcattaatgc 251160
attcaagttc atacatttta gtcttgaggt ttgtgctttc tggatcctgt ttaagaaccc 251220
cacggccacc ctggccctgg agattattca ttttttctcc tattaaacaa atggcaacta 251280
ccttttgctt tcaaatattt agtccatttg gagtctactt ttcctagggg ctcagttagg 251340
aatccatatt cctattcctc cattttaggg ctggctttcc aacatcatct tctgaacagt 251400
ccccactgat atgtggtgcc acctttatca catgtcccct tcctctagac ttggagttac 251460
ctctgagctc tcttctgggc ctctgtcatc acaccgctct gattgctgaa gttggcgtgt 251520
gccctggtat ctgccagcag aagtcctctg ctctcctttt caaaagttca gttggcattt 251580
acaaatattt ttcttccaca tacattttag aatatgtttg ttaaattact caagccctcc 251640
aactggaagt ttgagtggag tcctgttgaa cttaacagat ttggaaaatc ctgacgtcat 251700
tctaatgcca agttgccctg ttcaagaaaa taaaatgtct ctgcatatgg aaagatctcc 251760
ctctatatcc tccaatagag ttttaaaatt ttttccataa aagtcgtcgt ctttgttaat 251820
tcctagactg gtataaattt tgctgctatt ctgattgctg tcctaatctc tattatgctt 251880
ttttttagtc agttgctatt ggcataaaga aatgtggttt gtttttgttt tttgttttga 251940
gtacactgat cttatatcca aaacctctct gaaatctgaa atctctcttt agttgttaag 252000
ttccttaatt ttttttttcc atgtagccca gtaattttca aagtgtagtc tggggattcc 252060
agagagcccc ccagaccctt tcaggaaagg tcaaaaacat tttcataata atactcgaca 252120
ttatttgcct tttctttcat tctcacaaag ataaagagtt ttccagaggc agcacaccat 252180
gaccccagtg gaatatgtgc ttgtatagtt ctgctttaaa catttcttag ttttaacttc 252240
taagatggta actatcaaca gatagaatct ctatcaagaa aagccctttg ggggtttcaa 252300
taacttttaa gaatacaaca agtcgtaaca ccaaaatgtt tgagaacctt tatggagacc 252360
atcaacccta tgagctacac taagttttat cacttcctac ctgatcctca catccccatt 252420
tctttttctt gtattagggt atggccagga tgacatcctt ggcctactcc ttatcttaaa 252480
gagaatgata cacttttaat ttctctatca agtttactga aaagttaagt tttggtttat 252540
aacttgtatc aagttgaaga agttcctctc tagtcctggc ttgctaagtg gtgtactcca 252600
ctaccccaaa atcacacata ggcgttaaac tttatcacat cattttttc tgcctctatt 252660
gagggaacca tatggttttt ctcctgtagc ctcttaatgt gaattacatg gataaagttt 252720
ctgatattgg atcatctttg cattcctaag agcaatccca cttgtttaag aattgttgtt 252780
taatacatat tattggattc agttagctag cattgtacaa ggaacttctg catctacatt 252840
cataagggaa attctttata gtttcttgt gctttctatc tgaatttgga catgctctga 252900
ttcgcaattt taaaaaatcc ctctagctgg agcataaatc ctgaaacaga cccacttttc 252960
tcctcagcat gttaggaaac acattaaaat acacccataa tcaagcaact caatccttaa 253020
atttttctcc tactgagtat ctggaaaaca ggtgcagaaa tggatcattt gagacaccat 253080
agaaatctgg ttaatcctgc ctgcctgctt tccttcaagt actgactgag taaggctgtg 253140
tatcaggctc ttggctgggt acagagcagg cagcagaaaa caaaacagag ttcctcgctg 253200
ggagcttttg gtctagcaaa aggggcacca cagtaaagaa agaactggta aatgcacatc 253260
aaatgtggat attatcagga aagtttttat actttgtgat aatctaagac agaactattc 253320
tacctggatg aattattctc tttcataacc agaacagtgc tgtgggaagg cactcttact 253380
ctcaatttta tataaaaggc tatttgacct gctcagggac cacagtgggg tactgggatc 253440
tgaacatagt ggtggccctt caagcctact acccagactg agactgcatc tgatcaactc 253500
tcatctccaa tatgaccaag agacttctac cactacctct cacctggcag gtgatcacca 253560
cccccaactc agactgcaac ctttacttcg cccccctaatt cctgactcag aatccccacc 253620
tagaggcaga acttcgactt caattcctga ctcccatacc ccactgagac ctctaacccc 253680

-continued aatcccaatc tcttaactca gagcccccca ttcagaacct ctacccaaag acagactcca 253740
gaccctgact ccagtcgcca actcggacct cccttggatc tcaactcaga gccatgatgc 253800
agactccaga ccgggattca ggtccccaac tcagactccc gatcctctgt ccctaatgag 253860
gccctaccta aaaccaccat gcggactcca gacccggact gactgggacc ccaactactc 253920
agatcccaac tcaggcaaac tcccagccag gatgtggacc ctagacccga attctgatcc 253980
caactaggat acctaactca gaaccacaac ggggattccc acctccgatc ctaattcggg 254040
ccctgactca gaaccactaa gtggatttcc gactccggtc ccaattcggg ctttgactca 254100
aaaccacaac atggattccc aacttccatc ccaatagcgc ggactcagaa ccacgatgcg 254160
gattccagac tccaatccca attcagccca ctctgaacca ccatgagaac tatagacccg 254220
gaatccgatc cttgggacgc ggccaggaac tcggacctcg accctggcca cgctgtccat 254280
aaggtgcaga tgggagcgca ctgcccaggc caggctgcac tgctgacgcc tgtgatctgg 254340
gacggccgcg gggcacacag ctcacctcag caacgccagt gatcacccgt cccgcgccgt 254400
ccgcccaggt ccgtgctgac cgtgttcaaa ccctcccaga gagatgggga gggccgcgct 254460
gaggagagtc tgggagaacc gcactgagga gccgccggga gagtgccgcg ctgaggagcc 254520
cccggggaga gtgccgcgct gaggaggccc agggaggacc gcgcggagga gaaccatgct 254580
gaggagcccc cggggagaac agaaccgcgg cgagaggccc ccggagagaa ccgcgccgaa 254640
gaacccccgg ggagaaccgc gccgaagaac ccccggggag aaccgcgccg aagaaccccc 254700
ggggagaacc gcgccgaaaa gccccgggtg ccccgaggag aacggcgccg aggagtcccc 254760
ggggagaact gcgccgagga gcccccagaa gagcgccgcg ctgaggagcc ccgaggagaa 254820
ccgcgccgag ggcgcgccg gggagaacca cgatgactga cgcaccgagg aggaccgcgc 254880
tgaggggcgc accgggagaa tcgtgctgag gagccccggg gaggaccacg ctgagaggca 254940
ccccggcaga atcgcgctga ggggcgccct ggcaggatct tgctgaggag ctccctggag 255000
gtccgtgctg aggcgacgcg gcgaccgttc tgcctggaga ctgcggcagc gctccgactg 255060
cccccgccgc tgccgacgtg gcgaccgccc cccacctgct gattgggcgg cagcagggga 255120
aggcttgcgg cgggctgctg cacggattgg ctgggtgcgg aaagtgatgt gccgtgtcct 255180
gtcattggcc gaaagagtct ggttttgatg ccacccgggc tcagattggc ccagcgggtc 255240
cagcgccgca tgaggcactg gctgggtgtg aggtggcgcg agccgccgcc ctccctgccc 255300
ccacccgtcg tccctgagca ccaccggggg ccggggccag cgccagcctc agcgttggca 255360
tcgccggggt gagccggaga cacgggccag ttctctgcgt gatgtgttca ccacccccggg 255420
gtgaccgcgt gaggacagcg gccgcacccc gacactgctg tgggccctcg gtgtggaggc 255480
ctgtgggcgt ccaggccacg cccgagacca gcccctccgc cggcgccgct gcagcgaccc 255540
tcgaacccgg gcaaggtctc caccgccgtg gcaccgggtg cgggaggcgt tttccccccct 255600
cccagcgggt ccatgcaggg gatcgggatg ttctgaagcc cccactgctg tgcctggaac 255660
acccgtgtct gccgctcacc cctgaggact tgggacctca gggggtgagt ggcaggggtg 255720
gccgggacat gccaggccac ccacctggca aagggcagcg ccgagggcgc cccgcgcctg 255780
ccagcgcccg gccgggcccg ccctgcccac ctcccatccc ccatccgggc gtgacacttg 255840
accgcgtctg ccggcccctc cccttgtccg tcccctccgc gccgctggcg cgcgccttct 255900
gaatgccaag cattgccata aactccgggg acaaaagcct gggtcacaaa agccccctct 255960
agaagttcac accctgaggc ttccctggca aggctggggg ccgtttggcc cttccatgtg 256020
gactgcaaaa acagtgttgg aatgcaggac tctgggtatg ttctcgaaag ttgttacaac 256080
cccaacccag ggttgacctc aaacacagga ggaaggggga ggctggagcc agccaagaga 256140
gccagccgtc cccccaccaa ggcacgcaag gaggccattc atcttcactg cctctgccga 256200
aaatatacgt ctacgggaga gccaggaatc tctctccaag ggtgaccggg ttgggggttt 256260
tgttgttctt cagcccagaa gagaaagaga aaatggtgtc attttttcag gcagcaagtg 256320
attcctttca ggccttcagc aacgacgccc agatgagtcc actccctgcc tcctgctcag 256380
cccacaggca atctgggcac aagtgacaca tcccctgggc gcctgtccct tcgcactggc 256440
ccagggagtt catgtgtctg atcagagggc gcagtccacc ctcactatct agctgggaag 256500
tttttgtcat ctgcctgtcc gagaggcagc tgtgcaacca gtgccatcac tcagagccag 256560
tgctcaggtg caccccagac tcagggtttc acgctataat gtcactgtct tgaaattctt 256620
gatagttatt atctttgaac ttgtgtttta gaagtgaagt ctgaggggaa aatggagctt 256680
ggaacttcag ctcccaagtg gctttcccac cttcctgcct cctcaggaca gattatcagc 256740
tgcctgtctg cctgcttcct ctgtgcccag cctctctctt gacatccaaa ggatcacaac 256800
tcccactcag tgaccactat tattctctgc ccctgaccaa aaagagcagg gcagggctgg 256860
agtcctgacc ctggcctgga ctctgcaatg cagagatacc tgcaagtctc atttccccgc 256920
ctgtaggatg gaggtgatgc tgacagcctc ttggagccat tgagatagga aacgagagag 256980
attatgtgag aagacagggt caggaatgtt gagttgaggg tggcctcagg cccctgtcct 257040
gctccttttt gctgcttggg gtgcagctca attccagcct cactgtggcc cccaggcctc 257100
ctctggcctt cctcagcctt cctcaggagg ccagaatcct cccctgatca ccctccctgc 257160
atgtccattt ctacctcccc aggaggtcag gggagcagga tcccaggtct tcagagtcat 257220
ttcacagatt tcaccagaat aaaagtccca ctcatgtggg gtttacattc tggtgggaaa 257280
gacagatttt cgaaacgtgg ccatttttct ttgggccttt gttagctgca tcagatggag 257340
gaggtagcct ggtggactcc ttcagtcctc gctcttggac acagagctgt ctcccagcct 257400
ttgttgttgt tttctccaag gatgtcgaac acaggctgaa aagctcccta aatcaatttc 257460
acttaaaatg gtgtccaccc tcctactaaa gagtgacaaa gggtgttggt taggattttt 257520
atcttgaaaa ctgatttgta aagtcatgaa aattgagctt atttggtctt acacttaaca 257580
aaactgtggg ttctaattgt gggcctggat ggggacatat cttacaagta gttgattcat 257640
ttatatagat tttcatgttc tgggcttgcc tccaccctct acctaaccct ggaacctcag 257700
accccaagct cctgggcact tggatttttc cctgacaaat tccccgcctg tgatattcca 257760
tgggcacctc accttgtgtg cttgtgtgag gtctccttga gtactcttag cagtggggtt 257820
gccaggccaa ggagcctgtc actattgttt gtgaccagct caccagacgt ggtcaggaag 257880
gacagttctg tgtcctatgt cctctgctcc tcacccccctc gccacacacg gggtgctgtc 257940
aatcagccag cgccgcctgc cagcccagcg cacctgttgt gtgcccccac tcccgcctcc 258000
tctagtcctt tgggggaaga gtggagagga aaacaggccg agactgagag gggtttgttg 258060
tctcgtcggg cgacaagaga cacgtgggaa ttggctagag aagcatgtga ggctgggcgg 258120
actccaggcc agccccagag gcagatgggg gctgccaggc aggctgggag gtgagcccag 258180
ggctggcctt gggcaccatg gcagaattct gggaggggc tgcagtcacg gccagctccc 258240
tttctgaatt gttctgtggg ttgtggaagg ctttgaaatt tggcgcctgc accttgtcac 258300
cttcttggga ctcaaggctg caggggtggg tgtgagacag agagcctggg cacctggtgg 258360
ccactccctg agctccccac gtgacagagg gcaggtccca ttctcctttt gtgtctggtt 258420

-continued tgcctcatct gtacatggta ggggctgagc tagcgttcct tgcactccct ccagctttac 258480
tctttggggt tcaaaaggtt cccttgcaag cctgtgcacc cgagagcacg cacgcacaca 258540
cgcactcaca gctgaagaga attaggctca aaacgtccac tcggcttttc tcttgattcc 258600
aaggtattta gagtgggggt gggggattag gggaggaagt tgctgagcta attcttttgc 258660
atttgccagc acagaagtgc agatggggcc cagagccccg gcggtgtccc aggggaaaca 258720
ccagtcctct tctgcagtgc aaggcaggag aaagaactgc tgtgggagcc cctcacccaa 258780
gcagcaggat gtgtggcagg ccctggccaa ggagttctgt gggcctcaat tctctcccta 258840
ccctgccccc accctcggag tctaagggtg gaaccatctt cagacccagc caggttccca 258900
agttgctgct tccctcggaa gctgagaggc ccagggccac gtggcagcct ccgcagtcca 258960
tctgaagaaa ggccccaccc cacgctgctc tcaggagtgg acaggaacgt gggggagtgg 259020
gggtggttag gacctcaggg ttatccctga gtggctgatg cattgccagg aagcctgctc 259080
ttaaggtcag cccttgcagt tggcagtctg tggcccctcc tcggtcccct tcagtgaggc 259140
tttttgcatg cattggtcca cacacccacc actgcagctg tcctgggtaa gggctctgtg 259200
atcctgcaac gcccaccttc ttccttcact ggtcataggt ttctgctgac cctgcagccc 259260
atgtccttgt tccagaatct tccgcctcct gtggcctgtg tgtcgcctgc acctgcattc 259320
cactggggct tcccttccaa cttgatggtt tcaggtacat gggcctgttg tcaactctgt 259380
tcccactgag cccatgagac ggctattcct ttgagacatg tttacttgac ttcctgcccc 259440
aggtctctgc tgtacccaca ggtggcatgg actcatgtcc ccacccaaat cacatcccca 259500
ccaggatggg caggctctgg gtccttttgg gccttgtagg ctgtcgtcag aggggaggaa 259560
cagtggggag tctctaggag gttttcggca aggcagtgcc aaggatcaga tctcccttct 259620
agaaaggtca ctctggctgc tgaacagaga gagaactgaa gagaggcagc agggtgaggg 259680
ggaagactac gggggacttg ccgtcaccca gtgagagaga tgggagggtt ggagaaagcg 259740
agcatctgtg gaggtgtgag aagtgccagg ctgggctccc tcaggcggca actttgtcta 259800
gacttctggc tgaggacagg gaggagctta aggtagccct cagcatccaa caggggtagc 259860
agcctagtgc atgtatgacc acgagcgagc ccaagggaag gacgggtttg gagggtttct 259920
gaagatctgg cttggatata gtggggtcag accctatccc tccacccagc tgcagtgaca 259980
actctgtggc tctggggcac tgtcaccctg tggcatggcc tgtttgtggt gtccattgcc 260040
gtcttagcta cccaaggccc agggagaggc acacggctca ggctgacaga gtgtgacaga 260100
tgcaggtcct gctccctcag ggaatccccc attccaggac agtctcagcc cccatgcaag 260160
agcagcctca gcatgggctg ctcggggaat gccctcagac aacagtgctg tgttagggtc 260220
actcccagcc tgtcctcaca ggcagatttg cgttcctgca tttggggtca gtgataacgt 260280
gaggccagac gggtgggggg tctggagttc aggcggtctc catgagtggc agcacggggt 260340
gtgggccagt tcccattggg agggcagctg tgctgtgtgt gtatatgttt gggcattgct 260400
cagccaagcc ttgattagcc gaacccaact ctcccagagc ccccacttcg acgcgggtta 260460
actcagcagc tgtctcctga gcacctgctt ggggcctggt tgggtgccag gcacgggggg 260520
gtgggaaaat gaagtgaact gggcctgcca gacccattgc ctgcagggcc ttttctacca 260580
ccaccttcca gaggcagctt cctcccacaa agcatcccaa gctcggggtg tgtgcccccc 260640
ttcctgtgca ggcctgccac ttccacagct gcccccccagc caagaacaat cccctcagcc 260700
tgccagggaa aagtgggccc aggcctttga ggacattgcc acagccaggg ccaacctggg 260760
aagttgtttc tgattatctc ttgagtcctg ggagaggtgt taacaaaaag ccccatccct 260820
gtcgctctgg tggttatagt ttgttttacg cattaaaagg ccctggatcg gtatttgtag 260880
tgagaacaga tatttgcaga gagcctactc cattcccagc tctgtacttg tagagggtga 260940
ggctgctgaa atgaaaccca ccaggcctct ggtgagcagt gggtgcagag ttattggcag 261000
taaaggtcct tagagaacct gaagagaata ttctaatcaa gctaggcagg ctcagaagat 261060
ggatgtaatt tggaggaaaa agacaagaat gggaaagaaa gggaaaccta cctggggtac 261120
cgtgtggctg tggtggtttt agtatgtgtc tacaaggcct ttgacaatcc gttcttccgg 261180
aagtggcact taattcccct ctaattaagt tttggctgga ctgtgatttg cttctttcaa 261240
ataaaatatg gaagaagtga cagagcatga cttccaagac taggccttgc agcctccctg 261300
ccctctcact gggatcactg attctggggg aagccagcca ccatggtgtg aggacactag 261360
cagccctctg gagaggtcct gtggtgagga actgaggcct cctataaatg gcctcctgta 261420
tgagcttggg agtggatcct ccagccccag tcaaacctct gatgagacag cagccctggt 261480
ctacaccttg actgcagcct cacaggagat cagaaccacc cagccaagcc acccccagat 261540
ccctcgccca cagaaaccat gtgggatgat aaatgtgggc tgctttagga atgaagctgt 261600
agggtgactt gtcacacagc aaaggccagc tgacagagcc acccactctc accaggctta 261660
gtctgaccct tgtcaggggc agcaaagtgg gctcagccta cctgttggct tttactgatg 261720
gttggtggct cccaggagaa agagtactgt gcccaggtag catgcccacc ccaggcatac 261780
atagcatgtc tttgctcttg cagagtttga actctgccca ccagaccagt ggctcttaac 261840
ctaggctcct cgtgagaacc actccccggt gcaggtccca ctcccagaaa ggagagcggt 261900
tttgactcct gcagtctcta aggcagcaga gagctgtggc attttgggtg gagtgggtgg 261960
agagggtgcg tgatgggtgg gagaaactga cagttggaat gtgatttagg aaatgtaacg 262020
ggtgactttt ctccccaaga gaacaccaaa tccatttcct tgggacatgg ataaggctaa 262080
gggcagcacc cacaaggacc aggagcgggg ttctcaacag ccatttctgt cccaaatttg 262140
ttttctatgc ccaggaatgt caaagggccc tcttggggtc agccacagag aagggggagc 262200
aggtgtgatg gggtggtgat gggatgctgt aggtggatga gaagtagcac caaagctcac 262260
tactgttttt ctcttatccc tgggtcttgg ggacaggcct gtgccagaag cagggattgc 262320
ttctgctgta acgtccactg gaataaaaag cagacattgc agtgttgaga aattccttta 262380
gccctcagga ggcaagttac agaacaggac agaactgccc tagtcaggcc ctgcctgggc 262440
acagagctgc caccactctt ccaagagccc tccctttggg gactgtgcc cccaccccac 262500
ccccaggcag cccctgcctc caaccttact cctagctggt gttctgggcc gtcagttcat 262560
aggtccagct ctgagacctg ccaggctctc agagcagcct ggacccagga gagcgataaa 262620
tggatgtgca ctggcacact ccaagcaggg aggctttgtt tatctcccaa ttagtcctgt 262680
agcacttagt atgtcaggca tggttctgag ggcttcatcc acactaccac ccactgtaga 262740
gatgggaaaa ctgaggcata gcaaggtcaa gggattgggc aggccttagg atgtagaagc 262800
tactagagct gggctgcacc tgggtatcct ggagccaggg tctatccctc cccctctgcc 262860
acacggcctt ggtgtgaggg acacagcccc tgtttgcaga ggcagctcct ttcatggagc 262920
atgggggaca gggcaggtgt gccttggccc acatttggct tcttgagcgc cgaacctgca 262980
tgtgccaccc cccagagttc ctgtgtgtgg ccgggtgaat gtgcacaggt cgaggaggtg 263040
gtgtgggcag ccaacctccc aaagcaccag gcccctcagg gctgttcccc tgtttcccaa 263100
gatttcccaa acagatggcc aagatcgggg gcccccagga gaccacgctc atgaattgtt 263160
ccacttgaac acaacattgt tttttatgga actgggctgg ggagtcctct gtgactcttt 263220
cctcagtagg gagagagctc ctgaacccac cgtgcacact tcttcagcag ccgctttgga 263280
gacttgactt tgacactctt ctcaacagga tccctttcct cactggtgtc tgcggcccgg 263340
gccgctggca tggctgagcg gaacttggca aagcagtgaa ttgggagctc acttaggcac 263400
gtggtcctga ggctccttgc tggcgtttct gttttgctcc ctgctccttt cttttctttg 263460
taacttctct tcagggcacc cacagccccc gaggagggtg gggctgagga ggctggaggt 263520
ggagcccagg cttatccccc tggtgggcca ggcaggcagc aaagggacca accccaagag 263580
ggtcggtgcg gagacccctg gggtgcacag ggtgggcagt gaccagaaga ctcaccccag 263640
ggcctctaat tttgaccctt gatctgggtc taagcacctc tgagcaagag gtgagggttt 263700
caggcagcct cagctcttag gaggcagaag atacagttta tacgcgggtt ggggggggcg 263760
gtccatttcc atctccctgt tctctcccca ggccaatggc cagggctaaa gccctccttg 263820
ggacatgtca atagcagcaa acattttaaa gatgtgacat gttcgaagcc tggcaacagg 263880
ggcagctcca gctgtgcgag aacatggctg gatttacgtc tgcggcaaag cacccggtca 263940
cctttctctg cttggagtgc aatctttttt tggaagccct gctggaaaat ctgaatcttg 264000
tgagccatca gctgtttata atcagagaag catatgttta aaagagctga ggggccttat 264060
aaactccgtg tgcaaattac ctttggggct gcctgctcca ccgcccctcc ctgaggctgc 264120
catcactggc gaacggctga gtgtgctgca cagaattcgc tgtaaccctg ttgtggcacg 264180
gggtctgttt agctttagtc acgtcagctt ggccctggag cgtgggagcc tccatctctc 264240
ctgcacggct tccaggcccc ccccacccc accccccagc cccagctgca gaggacttct 264300
ggctccctgt tcctgggctt tcagcatgag aaatatcaaa cctgggaacc gtgcagcaag 264360
aagcgggcag aggctcagac gccaggacct gcgggggctt cctggaattg ggagccactc 264420
tcggtgtctg ctctggtgct acggtcctgc agggccggtt ttttttattt tgtatttttt 264480
ggtgttcatt tttgtttttg taacagcttt attaagataa aattcacata ccatacaatt 264540
cacccattta aagtgtacga ttcaacggtt tttagtacgt tcagagttgc gcaaccatca 264600
cactatctag ttccagaaca ttttcagtgc ccctaaaagc aaccctgcat tctttagccg 264660
tcactcccca cttcccttct ctcattcccc agccccagtc agccacggct ctgctttcta 264720
tctccacggg tttgcctgtt ctgaacattt cacatagctg gaatcacaca ctaagcagac 264780
ttttgtggct gacttctttc acttagccta aggttttcga ggttcattca tgctgtagca 264840
tgtatcagtg tttcattcct ttttagggcc aaataatatg ccattttatg gatattatca 264900
cattttattt atccattcat tcattgaaca cttgggccat ttttactttt tagctattag 264960
tgaataatac tgccaggaac atttgggtat gagtttttat tgtggacata gattttcatt 265020
tttcttgagt attcacagag gagtagaaac gctgggtcat atggtgactc catatttaac 265080
cttttgagga tctgccagac tgttttccaa tgtggcagca ccattttgca ttcccaccag 265140
tagtgtatgt gagttcctat ctctccacat tctcaccaac acttgttact gtctgccgtt 265200
ttcattttag ccatcttagt gggtgtgaag tgatatctcc tagtggtttt gatttgcatt 265260
tccccgatga ctaatgatgt tgagcatctt attagccatt tgtatctctt ctttgaagaa 265320
gtatgtattc aaattctttg cccaaatttt aattgggttg tgtttttatt atttagtaga 265380
gttctttata gtctagatat aagtttttta tattctagat tcaagttcct tatcagatat 265440
attttcttcc tttttgtggg ttgtcttttc actttcttga tcatgtcctt tgactcacaa 265500
aggtttttaa ttttgatgaa gttcaattta tctgtttctt tctttggatg cttatgtttt 265560
tggtgtcata actaaataac aacatgtaat ctgaggtcaa aaagatttac ccctatattt 265620
tcttccaaga attttatagt tttggctctt acacttaggt ctttcatccg ctttcagtta 265680
gtttaacata tggtgtgagg taggggtcta actttattct ttgtcatgtg gatagacagt 265740
tatcccaaca ccatttgttg aaaagactct tctttcctca gtgaaggatg ttgataccct 265800
tgtcaaaaat cagttgacag taaatatgaa ggtttatttc tggattctca attttattct 265860
attgatttgt ttgtctatcc ttatgccagt actatatcgt cttgattgtt atagctttgt 265920
agtgagtttt aaaattggaa agtgggtttt ccaactttgt ttttcttttt caagattatt 265980
ttggctattc tgggtccctt gaatttccat atgaatttta caatcagctt gtcaatttct 266040
gcaaagaaac catctgggat accaataggg attgcattga atctgtaggt caacttgggg 266100
agtattgcca tcttaacaat gtgttaagtc ttccaatcca agagcatgta tttcattgta 266160
tttggatttt taaaaatttg gttcaagaat atctcatagt tttcagtata gtttttgcac 266220
tactttgtaa atcctacagg gttttgtgtg acagtgactg gcagccatac ttcctcccca 266280
tgtactgggt tctgcccatc ctccagccca tctcccttgg agtctctccc cgactccagg 266340
gctcatggcc cctttcaggc ccttggcttc tggtaatgct tctttgtggt ctcctgtctt 266400
gcgcactaat tgttgcccaa gtctttgcac atcctgcatc ctgcctggag tgttctctct 266460
cctccctttt ctgtgagccg tcatgaaaca cctcctgtgg gcttactgag ccaccatctt 266520
atccaagtgc tctgtggcag cttgtggaat cttctcaacc ttgggtgtcg cctgcccaga 266580
acggggctct cggaggccag ggtgactcca ctatcccacc aacctctgta ccccacggcc 266640
atgcacaagg cacagggtcc cacagagggt ctgtgggtac aatggagcta tttcccagtc 266700
agacctcaca atcggtaaac tgtgcttaaa ctaagtgagg tatcttaagg ctttaccacc 266760
agggaaatag aactttggca gcttacaaag gagttttatt tttcaaattt cctttcaact 266820
cgagggtctc aaatccactc agcagactta ggagggaggg tcctggcact gcttctgagg 266880
agggtgcctt tgaggggagg cagagttggc tcacgggaaa ggctggccct gaggcatggc 266940
aggtggcagg tggctggggc tgctcacctg ctcacctgtg tccatcccct tgggcagcac 267000
acagccaagt ccttttggac caaattggat cactgccaaa tggtatgccc agccttgctg 267060
aatctctacc catctgtaaa aaggagaaat cgtttctgtg ctccctgcct cccagagagc 267120
cagggagagg ccaggatcca aggaggtaac ggctttctag ccctttggaa acctgagtgg 267180
ggttttgtgc ttgcatctca tttaagccat gaacacttgc cggctctcta ttcatccaca 267240
ccccctgcat ttattgagtg ccttctgggt gcccggccct ctactagatg tgggagttac 267300
cgtgtgggat ggactgacac tggtgacccc tgcctggggg aagcagactc tagctgggca 267360
gcctggcctc aggagatcat cacaaccctc gctggggctg gggtgcaaat ggggcaggaa 267420
caggagtccg gcctggggga tgttagactc accagccatc ccctggaaag ctgtggggag 267480
actcagagca gagcccccag taatcatagt gaggtattta gggatagagt ggagatctcg 267540
cccacatatt cccgaagcca ccaggccaga caccgcccca gctgaatgca tgctggcggc 267600
ccaaatgtta gacactcttc tctcttaggt ggtttgagga gacttagggg cttccatatt 267660
ccccttggaa catgaagaag gggctggcta aggcccccat ccctgctcag gcctacagga 267720
gagccctgtg gacactccag cctcagcctt ccttgccatc cgcaaccaca ccagtggctg 267780
gaaagccaga gtcccctggc tcctgcactt tttctgcacg ggactccctc acagcctctg 267840
ggttgggagc acacatggca tctcctagag agtttggggg ctggacacag ggaggaggca 267900
gcatgggaaa tggaaggact gcagccccca cctccctcca aggcagttgt cagagcaaga 267960
tcagctccct ggaagacacc cgggttgtaa acagggtggg gcaggggtcc tggtaagtat 268020
gaggaaccag agacctggta agtatgagga accacccctt ggcatggggc acccagaagg 268080
cagcaggcta acgactcccc atgaaattaa caactttgtg aagcatttgg tatttggggg 268140
attttacatt agggttaatg agcctctgaa atgagatccc ggagaggggc caggaccatg 268200
ctgggatgtg gcttccgtgg actgagcagc ctggagcccc tacttgcttg gtgtcccgag 268260
ccagccggac atgcatcccg ctctctccgc tccctggaaa cgttccctga atcacattgt 268320
tcactgcgct tctcaggcct tctgggctct tcctctgctg ctcgccataa aaactctcca 268380
gtcatctttt ccgctgtggt ttttattgtt ttattttatt attccagcta tattacgttg 268440
ggaagagcta cagaaatggt ttcttctccc ccagattcca gaacaagtca cagccattgt 268500
agattttgat taatcgccat ccccattatt cttcactttc tccagctgaa tttttcccac 268560
tgtgggaagg gggtctggag gacaggcacc cttgttggcc gtggataggt ttctgttctc 268620
cctcgaccca cccagcaaga gaaaaaaagtg agctgacatt atgggtcggc ccctgttctg 268680
gaggccacag ccacaggctc tgcgggcctc tggccgagct gggttgcagg agaagccaag 268740
tgccgggtga aggcctgggg aggaatctgg gttctcttgg ctgctggtaa gattatccat 268800
taaatccata ttcctcactg tagagttcat ggattcagag gatataccgt attctggccg 268860
tcttacatta ctgcaatatt gcttccagat gggcaaacgc gcgctcggag cctggccctg 268920
cagacacgat ggcccagcac gccgctcact gccgcgcctt tgttctctgc ttcctgctcg 268980
gttcctgcta actcagggag ctccaggtgg ctgccactca ggggtgtgtg gggggcgcct 269040
tggggcaccc aggcctgcag ccctccccca cacaggcagt ctccacagag atagagcgcc 269100
aaggatgcgg gccaggactc tttccgagcc tctcctgttg ctggggcctg ctccctgaag 269160
ggcacagtcc tgggcaggcg cagtgcccag gctggagagg tcctgcgtct ccatctcatc 269220
cacaggataa gtcaaatggg agcattccag cattccgcat ctcatggggg ggttgggcct 269280
cacctccctg gcagcccact cacctcacat ggcctgagcc gcaaggtcag ccccctccca 269340
ggcccgtgag aggcagcggg cactatgggc gagctgcctg ctgggccaca ggctctggta 269400
ctctcctggg ttggggctcc cggggtaggg ctaagtgtgg tggcagtgga gtcagggcag 269460
ctggacagcc cctctgccat cagtgagaac tgtcttctct ctgcttcccc tgtgcacttc 269520
tgaatcccca gggctgggca cagggctgtg acgccatagg tgctctagat agatggagga 269580
gctcacagct gcagggagtg ttgggtggac atatggggtg tggggggcga ggccaggctt 269640
cacagaggtg gaatctcaaa ggaggaagcg gcatgccagg tggcggacat agcacctgca 269700
aacgcctggg aggtgaaggc accagctgta gccagcatcc cagaaaggga cacgaagccc 269760
ttggggccgg ggtggtaggg gtaggagagc atcttgaggg tggctgcagc atcgtcgtca 269820
tctttcaaat ggtggcatcc cttccccaag caagggaatg atgcagacag aggtgccttt 269880
cagaaagaat ggaggtcctg gggacctgac ttctgggtcc ctcaggacac atgctctcca 269940
gctcgtcagt gttacctgga tactctaatg ggggcacaaa gccggggggg agcctgcagg 270000
aggggcctag ccagggccag gtgtcacaca agcagagctc cagggtgcag ctgggcagat 270060
tgccggtggt tggtgctggt gaggagtagc agggtggggt ccggcggtaa tgccactgat 270120
gatacttggc gaggatgacc gcaagtgtct tgacccaaac atgagatgcc cctcacccat 270180
cctcccatga acctcagcat gggcacccca tgccacccgc tccatttaca gccaaggagc 270240
ctcagtagag acacagctag aaagtggcca gctggggttt ggtgctgagc ctctgtctga 270300

-continued ctctctgctc tctggagagc tcaagggaac ctgtaaagac ctgcgggctg tgtcatggag 270360
ggcccttacc ccggaggagc caggaaggtg gacagagcag gaaggagtgg ggcaggaggg 270420
ggctttgcag attacccaga ccctttgttg gccagtgtgg gaatgggggg aggccaggga 270480
ggaacccctg cagcctggct caggcagggg catgtgtgaa ggcccagggg gaagagagca 270540
gccaggtaga cttcgtttcc agccggagtg tacctgggga tgcctgtgcc caagccttcc 270600
tcttccacca cccctgctgg ggtcccctgg gacccatcct tccaagcccc tgccagcctt 270660
ggaacctgtg actccccagg tggtcaaaca cagaaggacc tcttggggga aggggaacca 270720
gcaaaggggg tatggggagc cctctggggc accctcatat cacaccctgt ccctctggcc 270780
acattccagc tggccctgcc tgtgagggtt gaccagctgg agcagcccca catcccacat 270840
ccccgcagcc ttgcgctggt ctaaatgcct cccagcctcc tgaggttgag ggtggccaca 270900
ccagccagag cttgggtgat tgagtgggta gagggggtgg ccagagtggg aaccatggtg 270960
atgcaaacca taaacctgtc ccccacgtca cctccaaacc ctttgggctg gcctcttggt 271020
gaggaatggc cctgggagag gctgccctgc ctttgacctc tcatgcactg agagtaatgg 271080
gcaagcgctg tctgcagagc actgacccca ccgccggggt cggagcccct attcctagcc 271140
tcccttgagc gttttggttg ccggatcctc attaatggct gtttgtatca cttaacaatt 271200
tttcactttt ggaggggtcg tgaataaccc caaagcaaca tgtaccctct ccgggccagg 271260
ctcaagcggt cctctcacta gggaaagaag tcagaaaaaa gctccaagct gaagcgccca 271320
cacctaccct ctgcatcaga tgtgctgcgg ctctcaagga accctctagg gcacagcttt 271380
ggggagtgga gctgcgtggt cagctggcca agccacagtg ggaaaaggtg gcccattggc 271440
cagaacacag tccccaagcc tcctcagcta ggctctcgag gaatggctgg gtgtcctttc 271500
tcagcagaaa agccttgtcc ccagcctcca gggccaggct ccagcttccc aggcgtgtgc 271560
ttcccaccca ggctcttgtg ggttggcttg ccaagcggtg ttaggacacg cagcttcagt 271620
tctgcagggc ctggtggaat tccattccct gcctcccaga aatcttatct tgagggccgc 271680
tcagctacag taggccccaa gccccagaga ctccagattc cccactacgg aaggcagccg 271740
tgaaaggcac gggcagcgcg gtgcttctcc ttcaggaggt ggaactgggt ggcccgcatt 271800
gaacaggcca ggagcactgg tgttctggat ccaaagcaac catctcttcc cacatttgga 271860
gggagccgag ggcaggcagg agccaggacc cagtgcatcc tgaatactgg gtgactggca 271920
gacatcactc tggcccaagg ccaggcctgc agtaggagct ctgtgcatat cccctatgtg 271980
agtacaggaa cctcagtggt gcctgtggag ctgttcagtg ggccctgtat tcgccagcac 272040
agccatggtc ctgctgagtg acaaacagcc ccccagatgt cctgccctct ggtgctgctt 272100
gtccaccatg aagtggccgg ggctctgctc agggacccag gtgctcttgc agacaaccca 272160
agtcttcctt cctactcctg gcagggcagg caattccact gatggctgca gtgcgacaca 272220
gactgggcct ggcatggtgt ccctcagacc ccacggcttg gtcgggtcac ctgggccatt 272280
tcaaaggctg ttggggagca ggaatcacaa gctggatgtc agcttgaggg ttaccccaga 272340
gtgagagcct cgacagccag gccctcccag gcttctgtga tcgcagccca cacctctgcg 272400
cacagtatgc caatgttccc caaaatctac atactgagaa ggtagacagc aaagccacag 272460
ggagacttct gggtagccca ggtggaattc ttccctccct gtttcccagt tttccaccct 272520
tttccctggc tttcttccag aaccttttaa tgaaagtgcc tctgccccac cagggcctgg 272580
cttaggatgg gtgagggaga ggagctccgg gaggtcacgg ccccacccag gaacgttcct 272640

-continued gtcccaatcc tcccatcccc atattcagga aagttcccca ggcccgtatg aactggcttc 272700
ttaattttgt tttaaacaca agctttcaga agagcagaaa cggaaagaca gatggcagga 272760
ggtgccgcag ggcagcactg gggagcctga gatagagagc gggtagacag gaaagcagct 272820
cacagcggct ggagagcagg gagcacacgc ctgtccaaga ccttgggcca gaggaacccc 272880
ctctcccccg atggcccact cgccccaggg tctccaggtt tgagcccccc ggggtattag 272940
cccagcattt taggggctgc cgtggtcatg gagtaaagac tacacctggc atggcttcct 273000
tggtttctga aggctgcgaa agctgcgtct gtcgcagaag tgaaccttgt tttgttttgt 273060
tgatgggtgt agtctcaggg catgttcaat gtctgtggag ctgcctcttc tggaagagcc 273120
gggttgacac ccgcgtgccc cgtcctggct taaacacttt gaggccctcc ctgccctcgg 273180
gggagctgag agccccactg cagcccagag gccctcccct gacagctgcc ttcctctgct 273240
ccgtccttcc ccacatcccc ctcacacacc ttgtgcttgc tctgggcttc aggggcctga 273300
gccccaggta gacccccaca cttagggtgc ctcaccacac tccatcccta gccccagact 273360
ggcttccctg catctggctg accccctcct cacctgcctg tttccacctc agggcccctc 273420
ctgaagccgg aacttgatcc ccgcagcacc agcccctccc cgtagcctca tggggcacag 273480
ctctgaggat gtggatgagc agaggggagg acagggatga tgaaccccag gaattggctt 273540
ccagtggatg caaggctgac tcgtacatgt catggaggat agttcgggca tctgagctag 273600
ctgaggctcc ttggagcaca tgcatggcct ggactgtcca gaagtcgtct acgtgctttg 273660
tgtagacgca tgactcccca gctggctccg tactagatga cctgggctag ggccacttat 273720
atctgtcagg ggaagggcag ttgcagttag gaccacacta aaaggttaat gtccacgctg 273780
gtgttgacca agccctggac cctgctgtgc caggcactcc catcagcatc caggtgccca 273840
ttttactaca gggatctgag agctggctag gcaggcatcc cgggtcatta ctgggcctgt 273900
aagggccttc atgtctgcac cctccctgcc atgcacctta aggtcaggaa gtccattcaa 273960
atgcagattc ctgggctatt ccaagagtta ctgaatcccc accctggggt gaaggcttgg 274020
cgtctgccag ggaccataga ccacagatac tcatctacgc ttgtgacccc cctcccgccc 274080
ctgagtgtgt gctggggcag gaggccctgt ggcaagtgga gccccaaccg cagagcacca 274140
tctccagccg tgtgctctcg ggtgcagagc tgacctccca agtctcaggc ttcttgtctc 274200
tcaagttggg ggtaacaatg gctatgtaca taagattagg agaacacaca gaaggtggtg 274260
ctggctaaag ccattatcac aggctggtgc ctatagtccc agcactttgg gaggccaggc 274320
gttagagacc agcctgggca gtataacgag actctgtctc taccaaaaaa aaaaaaaaaa 274380
aaagagccat acaaggtggt gcgtgcctgt ggtcccagct gtttgggggc tgagatggga 274440
ggatcgcctg agcctgggag gtcaagagtg cagtgagcca tgatgactgt gattgacgtg 274500
ttgaccaggc actcaaaaac aaacaaacaa acaaaaaaaa aaaaaaacca ttatcacccc 274560
ctgcacacaa atcccagagt tcagagaaca cagatcaaaa taagaagtca gagaatcctc 274620
tccagctgaa aaccctcatt tgttatcacc caaatgctgc ctgctggctg gcgagccttg 274680
ctggtggtgg aaggcccagc agtagcaaag gaaaccaggg caggacagtg taggaagtcc 274740
tgccctcgga tcatttgggg aaattggcac ctgtgtttct caccacacag tgttgggttg 274800
gagaatgggc ctgggtgcag agcttcggag ccaaacaccg tgctggtttc agagaaacaa 274860
acagccctga tgtagctgtg gcccttggag gtgtccgaat agtccatcat tttcagtgac 274920
agaaagacgg aaatggacac agatcaaacc tgcatcacag atgtatagct aggtcagcga 274980
accactcaaa agaccccagg gtctgacccc ttgcacgcct gggcggaggt ggagccgctt 275040
caccatacat gcaaatgtag caaactgcaa aatgtcccaa aacaagtccc ttactgtccg 275100
tgtccctcca tgccagctca ctggaggggc tcctgctgaa agaggtgggg ttcagttccc 275160
aaacccactg gagggttgca aggagacgct tctagtatgt tagacagcac agtcttccaa 275220
atggactgtg ggcatgatgg atgtgtaaag aatcgagaag ccaagtgccc ttgccatttg 275280
ttatctttaa aaagtatcgg tgggctcatg gggcttgag tgtcctggca gctctcctca 275340
tccatcctat gtgtacactc aggcacgtac tccctggctc agccgccttc tggggcccgg 275400
ctacagtcag gcctccttcg tgctgagcat gtgctggccc tgcctgggga cagctgaagg 275460
ccaggaggaa gctgctggcc tcaagaaggc ctctcgaagc agaggcagcc ccctcgaagc 275520
tcacctggcc tctctctcta aggggagagg gacccagggc tgaccagagc aagcagtgtg 275580
ccattaaccc ctacctgtcc agaactctga gctcctgtgg gtccttctct gagtgtccta 275640
tgttgggggt gtcagcctgg gtgtcaaggc tgaagagggg agcctccttg gccactgaaa 275700
cggaaacagc attagccacc accagcccct tccccctttt gcagggcggc tcccagaacc 275760
taggagtcca tgctacctgt ggggttcata gtgtgtccct ctcagccaat gggaagtcgt 275820
gcccttggat catttggggc aaatggtcct cgttttcttc attatatggt gttgagttgg 275880
ggaacggcct tgctgggagt tggggcctgg cctggacctc gaggccactg gggacttggc 275940
tacctgaggg agatgaggtt gttcccaggg tttcctcatc ccaggggctc tcagatttcc 276000
agggactcgg gcaggcacag ctttccaggc cagagccatg gacggtccct ggacacctgc 276060
agcagccagg ccccagatgc aagaaagggt atttgtttct taaagcttgt aaagagtttc 276120
taaaaggtgg ggaggggatt ggtgggggcc tgtctcatgt tttccattct ggacgccggg 276180
gggacatgtt gctggggcca gaccaactcc agggagacaa ctcgacaagt tacgaaacat 276240
ccagcagcat ccacgactaa tttcttcccc ctgtttgtcc taccgtggag gtcgagttaa 276300
aaggcagcac ttcgggggtt gaaaagctac ccgcaggggt ctgctcgtga gggacccccg 276360
ggcctctgca gcctttgttc agaggcagct aataagccga ctcccgctgg gcgctttgta 276420
gcgaggccgc tgttcccagt cccagctcag cctccctgcc tcagagggct ggcagatcag 276480
caaattgctg tctccagctc gcaagagggg caggtccagg gatgtgtttc acccccaagg 276540
tgtgagtgga atcagcaaat tgtatcaaga aatatttcta gggatttaca ttccggcggt 276600
cagcagcctt tgggaggctt tactccgcct gcaggggtgg gaggcctcgc gtagagttgg 276660
tgggggcagc agagcctggg tgtttcagga ggacccactc actctgggcc acttctgatg 276720
ctgcagatca tgccaggcag gcctccggcc gtttgtctct tccgacagca gcggtggtga 276780
tggtcccctc ggcctgcctg gcctgcagca gccctggctg gaggctgacc gagcctccga 276840
ggaggttcac ctggagctgt ctgtccatcc atccatctgt cccttggccc ctttaagagg 276900
ccttgtcccc tttgccagtg cagggagacc ccaccgtgga cttctcattg ggacttccag 276960
tgagacccaa ctccactgcc tggggatacc ctcaccccaa gcccaaggag cctgtcccta 277020
cgcacacccc ctgcccctgg gaggcacatg ccgagctttc ctgtcctcca tttggtggcc 277080
gcctcacctc catggggtcg cagggcccac acagacagcc tactatggtc ctggcaggca 277140
cagggtatgg gaagccctgt gcccctggga tcaagcttgg atcctgaggt cctgagcttg 277200
gtgagtcagg gctggggagc cacaaagcca gcatgctcct gccttttggg ggtcccaggt 277260
gatgtgtcat cttaccaggt gttgacaggt ggagagaggt aggctgggtg aagataggaa 277320
aggactatgg gaggccaggg cgggcctcgg gtgcatgcct ctctgtggca gtgacatttg 277380
tacagaacga ggcaaggcca gcccatcctg ggagctgagt gctggaccat gggggctgca 277440
gcctggaact gagcccagag actgcagcat tcagaggtca gggatcaagg aggacctcac 277500
aaaggagatc gggaaggtgg aggcttggtc acccccagga ggagcttttt ctaaggaagg 277560
agaggccagc atgtcagcca cggctggtgg gtcccactga agctgagaat agaactggca 277620
gtggggtttg gccacatgga ggtcctaggg gagctgatga gagcgatgcc gtagccaggg 277680
tcggcagtgg cggaccgaga gtgcttccct tctcacgtgg ttgggagtca tgacctgttt 277740
agtaaatagg ctatggcagc ctcttggaac ttagtgaggt ggctaagctg cccctagata 277800
gctgtgccct gtgaccaaga ccttcctccc tccttccctc taccccacca ggctcagcca 277860
actgacacca gggccctgtg aggcagtatc tgagccaccc ttctgagtgg gagctatggc 277920
aagtgctgcc ttagcggagt gggggtgggg gcatgtgtca ctcccaggac caactggcag 277980
atgaaggtct ttgggcactg cagctgccac ctggggtgcc tcggggcagg ctcacctcac 278040
acccttgtgg gccagctgcg gcccaaaagc ctcctggcct ccattcccgt gccagggtgg 278100
tctgagcgga gaggacaggg gggatcccag acggatcctg aaaacaggct ccgccttcct 278160
ctgtggctct gccttcctct tggctccgcc ttcctccgtg gtggcctgag aggggtgtgg 278220
tgctgcttgt ccgtggtgct ccacacacct gccacagctg cttaccccac tccctgccgc 278280
cctggacaag gtgcccacgg ccctgtccca tttaccgttg gggcaagtga gggacgagga 278340
ggctccgcag cctcccccgg gacactgcaa ccctcaagac tcctagcaag cccctccgtc 278400
tcagagcctt ggtgtcccca tctgtaaagt gggatgtgac aatacccttc ttgctgaatg 278460
ggcagggaga gaggagctgt taggtgagac caggtggtac ttggcagctg tggcacgtgg 278520
aagccctaca caggcagccc cacacctggt ccgctgttct gtccttactg tagcagtggg 278580
cctggaggca gtggcattta gagaggaccc tgaagtccaa agaggggatg ccagcctcaa 278640
actcagcagc tcgaagtagc aacagcctcg aatccctcac acctagcggt tggctgggca 278700
ggtggactgg tccgagctga gtggtctagg atggccttgc tcccggagaa gacccttggc 278760
agacagcctc tcctctacta gctagtgggg cctcactaac cgctggtggc cgcagggttc 278820
ccagccactc ggtgcacatg tactccagcc tctctgtgtc ccatttgctc atgacatggt 278880
ggtcaaagca agtcacggat tccaggggga cttcgggacg aggaagtcac acgttggggg 278940
atgtgccgca gggatggggc atctcagcct ttgtatctgc cgtgggcgtg gaggcattta 279000
ctcttttcac cgggggagca gaaatcagaa catggctctc tgtgtctgac acagagccct 279060
gtactccatc tatgcagccc ccaccacctc tgcacacagc cctccggtg gtgcctgggg 279120 gcccaggctt ttgatagaga atcacatctg gaccaggacg ttctggtaag atcgccaggg 279180
ggccgcgaca aggagaccag gaaggaaaga cagaaagaaa aacatgcaca gatccaggct 279240
cagatgatat acagtcctcc tcccggctca ggacccctttt gcggtgtcac ctttcggcat 279300
gtaaccactt attctgtcag ggaggagagc cctcccgctc caccaggtga cggccctaaa 279360
tcctcaggag tgacagcgtc ctcccgcccg gattgggttt ctgcacagtg gaatggagct 279420
ggcagccagg gtccctgtcc cgccagccct aggcctcgaa ccctccctgg caagctaaca 279480
ctgcccttgg aggaaggagg gtgggagggc aaagagagag aagtggtggg tggcagcgag 279540
caggctgtcc tgcaaggccg tggctgcact gagggcagaa ggggccttgt cacctaggaa 279600
ggaccccact aggaacccct tcccgcggaa acacagcttc tccccttggg tgccattgca 279660
gctgcaccca agccttgccc ttccctctca cttcgctccc caggaggcga cactgtgatt 279720
gtcctgggct cacagaggag gacgtgggga cctgcccaag gagacacagg caacagaacc 279780
agggctcaga gttgggggaa ggggccagtt cacccacaga gggtggagtc actgggctga 279840
agcttctggc catcgtatgg agctggaaca aggcactgga aggtaccagg cctcagcgtt 279900
ctcaactgtg aaatgggaac acggtggtct ctgtcacagg gtagagatga ctgatccagt 279960
aacctggaca gggtgccgag ggcagggtct ggtgtggcta tcaggagcca ctggattgga 280020
acttggtgtg ccaccagggt ccctgtccgt ttaagaaaag cctgtgggcc caatagagaa 280080
gcacagggtc tgagaagcat cagacaatga ctcctaaaca agctcacgtc ttgaagcagt 280140
gctggacccg tttcagctcc aggggagagc cagggcaggg tggggcaggc acggattcct 280200
gacgtggaga caggaggaag ccgacggcca tctgtgctca gacccagtgg tgagcctaag 280260
acaagttccc agaatccatc cgggacagac ggctggactt gtgaaacact ccagggtcgg 280320
gggctcagcc acgggaccag cgcttgccag aaatgttccc agctttttttg agttcgtgag 280380 tggctggtgg atacttagtg gtttggcttt cgggttcctg ccttccaaaa caggagaggc 280440
aacttggcct gctttttcct cagaagagcc cactttttgc gtggaggtga cctgccattt 280500
gtccggttgg gggtccccaa tcgtcttcga gctactgata tagaacctct gcgtttagct 280560
gtggtttagg aagtgcattc acgtgaagtc gccaagttca aagggctgcc cctggaaccc 280620
aagtcagact tgccctcgcc cccttcccga acgtaccctt tccatgaggc tgggcgccct 280680
gccctgcctt cagtgccaaa gccccaggcc cacaggctgt gcactccagc cgagggcagc 280740
ctggggaagg tacgagagat cactgggctt tgtgaaacct gtcagcttgt gtgaaagcta 280800
tctcccccag gccccacccc cgccccccacc caaagcacag gtcacctgcc tggttaatca 280860
tcctgggctc tgagagctcc ctggggcccc acaggccaag cgttttctga cttggagagg 280920
caggaggcca actccccgct cctcagattc tgctgaacta actgaaaccc taaccttcgg 280980
gcttccccac taatttgtga taaggcctcg ccaagaaaaa cagcaggcta aagacccctg 281040
atttcttcat gaattccaga gcacttggtt cactccggca gagaaggggc cccaggcagc 281100
catgcataca gagccacctc tgcgtgggtg aagggctggg gacggcctct tgggagccca 281160
ctaaggagga ccacctgcct gctccaggca gattgcttcc agctggccag ggcagaggag 281220
caggccaagg gtgggtcccg ggcagtggcc cagagaagct gagctcgctc acgagatgtg 281280
tgctgacgtg gcaagatggg cgggagtctt catgaaggag tggctgcctg gccccctgac 281340
ctgaggatcc tagggcccct ggatgggttt gggggaactg cagcatcctc agatcacaga 281400
cggtgtgtcg agtgagggtg gtgctcttcc tgggccagca gtaggtttcc aaaagggcac 281460
agacacagct caggagatgg atgctgccct gtcagagtgg ggaaactgag gccccaggcg 281520
gagacaccac ccactgcagg ttccagccgt cccccacccc acccctgccc caccatggct 281580
gatgtgaggg aggtggccag aagtccagag ggacactggg tgggaccccg gtgaagatct 281640
ggtggactga ggccagagaa aaaggggatg acccattcct agcagggagg aatagtagtt 281700
tatattttcc cccaaaattt tatttttctg cattggcctg aataggagct gactttaata 281760
cgggggaaat agtgatttta aagccggctt tcccatggaa tgtgcttctc ctgtgactgt 281820
gcccatctcc tcactgcttg gcagagaggt atcccccgtg ccccactggc atgggcgcca 281880
ggtctgccct tccagaggcc cctcccaagt agctcccagc agaacacttg aagcccaaaa 281940
gcagtgagaa agggaacaca tttgcctcca atcctgactc tccaagccct gtccctgccc 282000
ccaggtgaag ggttggccct gggcatggag gtcggcagca gggaggggac acttaagcca 282060
cttggttggg ggtttgtgct atgccctttc ctctgccctg ttaggtttgc ttctacctct 282120
taggtcctgt gatatatctg cccctgtagg agcgagacag acataagcca gacttcagga 282180
aggagcagcc atggggcagt ggggctctgg agcaacagag gcctcaaaag ctcagcgtct 282240
acagatgtta gggacaagga ggcagcttgg gggatgtgct cgggccctgg aggcagacac 282300
atcagggtct gaatcccagc tcaggggccc agggcagctc aagccctctc tgaggttctg 282360
tttcttcatc tgtaaaacag ggacaatcac ggtagctacg tgtggggcgc aggacggcac 282420
ccaaggatca ttcctgtgtg agtcaggtgt cagggaccac caggccttgt gcaggaacat 282480
ggggtagtgt ccctgggga aatcctaccc cagactcgag gaataaagag gaggaggagg 282540
ttgcctgagc ttaacagaat gatggctgtc tgacatgagg ctcacaactg gccccagcag 282600
ctccacggca gggagcagga gcagacaccc cggatccgct ctcctccctc cttgcctcct 282660
gccaggggtc cagttggcta gacccaatct gaagccctgg gccaggagct tgtggacata 282720
acctgcagag atcagcctcc tagggcagag tgagctgaat ggagaagggc tgtatgcaga 282780
agggcgagca gacagagccc aggattccac aacggtgtca atgtacaaca ccaagcacct 282840
ggcctggtgt gggctcgtct tgcactatga aggggcaggg acgtggccag gcattcgttc 282900
ctctgtgggc actgtggggc tttgctgtgg aggcagaggg agcatctgat ggcccccggg 282960
gccgcgctag tcaaagcgct tcatttccat catatgtggt gcaaaatcta accctcttac 283020
cctgcgtgag gttcatgtga ccgctcccgc tcacctccca gcctcattgc ctccctgttc 283080
ccctcctccc tccccagcca ctctggcctt ctcctcgtcc ttcagctcct tccagagtgt 283140
tcttgcccag ggcctttgca caaatccctt ccaggacttc tgatggttct gtcctcccct 283200
cacacaggcc tcacctcttt tgccccctcc acctctggag cggccactcg cccacccttc 283260
tgccctgact tctctgtggc ttcccaaggc tcttcctggc acctcgtagg gtaagtccga 283320
ccccaggtgg ctgtgctctg aggccagggc caggactctt gttcacagtg ctatgcctga 283380
cccggcgcca gccctcaggg gaccacagcc ggctgaacgc caactggtta gctgcttttt 283440
ctataggacc taccgagcgt ttgactctag aaccgggggt tggtgcttgg tgacaagagc 283500
taggctggct tcctactaat tctgcagcct ctggcttgct agcctcccgc ccactagggt 283560
ccaggtcact tcctctagga gattctaaaa cactctggca cagcccacca gcagagccgg 283620
gccttgggag cgtgagggca cggggcctga gcctactgca tcctcccaga agctggccta 283680
caggacggag gctcagggtg gccagttggg catggggttc tgctggccca gagtgccagg 283740
gggacaggaa gtccctgagg gctccagctg caggaggagc atctcaggag gagctgaggc 283800
cggagcagag cgtcctcctg gtcctggcag cccttggccc ctcagcaccc cagagggccg 283860
gccgcagtgg atgctgctga accaccagaa acttaatcta ttattacaca gaaacttctg 283920
tgcagtcagg ggtttgaagt ccccagaagt gtttgcctga tttggggcag atagcggggt 283980
gattaatgct cgtgataagg tgttgattgg ttctgggagc cactgcagac acaggggctg 284040
ttgtgcatgc agggctggca actgtagtca cagaacaata gcccgtttat gtagcacact 284100
cccacccccc gcctgcccca ggcgggcaca aagggcgctc gggccaggaa cccatgagct 284160
gggctgtccc ggggccgagg gtccagacct gttgccgaga agctgcttag caaggcctag 284220
gggcaagggc tggtctggcc tagctctttc tcccttgagc cccctgccac agggctaggg 284280
ccatgctgtg ggctcgagtg actgccctgg acgtgacaaa tctctgtgcc tcggtgccca 284340
cacctataca atgggggtaa taaagtcccc acattgtagc actgccaggt ggattaaatg 284400
aaagaagata gtgaagtcct taaagtgaga tgtgttggca tttactccac aaatactgaa 284460
tgcctgctcc aggtgccagg gacagcagtg acaatacaaa actgatatga aattccaaag 284520
ggatgtccac caatgggaga cgtataaggg ctctgcatcc atggattcaa ccaactgtgg 284580
atggaaaatg tttggaaaga aagttgcatc tgtgctgaac atctgaactt gtacaggctt 284640
tttgtcttgt cgttattccc taaacaatag agtgggtcac gcagcatttg tgttgttagg 284700
tatcgtaagt ggtctggaga tgggaggatg tatgtggcct ccatgtcagt atcacaccat 284760
ttcgtatcgg gggcttgagt acctgtggat ttgggtacct gcgggaggtc cccatgggtg 284820
ctgagggaca gctgcacttt agtatttatc tacagagtgc ttggaaggga aaacaaagac 284880
aggcagggct ggtttgggga aggggcctgt tgtggatggg gtcgtggagg accttacagt 284940
gtccccaaag cgaggtgaat ctcatggtgt cagggctaag agcattgtgg agagagggta 285000
cagccacagc aaaggccctg aagtggggat gggcccacag gctggcagga cagcaaggag 285060
acccatgtgc tgggaccccg agagctaggg cacgtgaagc cctggctggc cccgagtgcg 285120
gtgtggttgg cgcagatggc aacagggtca ctctggctgc agagccaaga atggaccact 285180
gaggggctgg gacagacctg gcagaccagg agggaggccg ctgcactagt ccaggcggag 285240
gatggcagct ggaccaggag ggcgaggagg aagtagtaga ttcaggactg ttttgagagg 285300
gaccatttta gcttcttacg gctgctgtaa tgaattccca caaacttagt ggctttaagt 285360
gacacgttta ttatctaaca gctctggagg tcagatgtcc gacatgggct acattcaagg 285420
agccagcaga gctggttccc actggaagct caaagggagg ccccgcctcc cttggcttgt 285480
ggcctttccc cacggccccc ttgtctctgc ttctgtcctg cgctcttcac aacctccctt 285540
cctccctctt tctcttatgg ggagtgcagg ggtgatctgg aggagccggt caatagcagc 285600
gtggtggggt ctggcagaga cagactgcag gggggcctggg aggccccagg aggcaggtgg 285660
actttgtccc taggcatcca gtgcagaggt gagacctgta tggccacaga gtctccctat 285720
ccaggcccca ttaccctggg ggaggcggat tatggtatga actgctgcag gtggtccaag 285780
aggggctgcc cctgggagac gcagggttct tcagtaatgg tggtttcgaa gggcagagga 285840
gggaagaatg gagggatggg ggacagacgc tggagccgtt ttggtggcag gcctctgtgg 285900
ctgtggccag aagcagggct gggcaccagg ccagttggac cagaggctgc ccccagctga 285960
accaactaca gaaatgagag ccccggccca gcctcctccc agccgccgct ctctgggagc 286020
ccagctttgc tcatagaaaa ggaaggccct tgttgccctg cattgggagc aaacacttcc 286080
tttggcctca cagctcaacc ttggacccaa aggtcctcag ggacctgggg gaaagagagg 286140
gcagccaggc acctctgttc acggcagggg ctgcgttgcc cagcctggca gagggaggca 286200
gcccctaggt acagtcccct gtgcccactc gagggggtgc tgaattcctc aaggcctgag 286260
tcagacctgg tgcagcttca taaagccaag ggtggcaggc ggaatccaag gggcctcacc 286320
gcccatgcac cccactgttg catggagaga acaatgccca aatgccctcg tcccacagtc 286380
ggcatgccag acccctcggg aattcaggcc ttgatgagtc tggcacattc cggctgtgtg 286440
tcagcgggag aggcctggga aagggagcca gcactgcagg ccgcccacca cacgcccact 286500
cgggcaccgg acacagggaa ggcggacacc cagggcggcc atctctcggg acaggaggtg 286560
cggctccacg ttctcaccca ggagagggct ttcctcccat gtcagagtcc ccttcgctgc 286620
ttgaggcaag ccctccggaa cagacccatc ttttgggga ccctgtggtc atggagatca 286680
ggttcctaga atcaccccca gcagcgcaca caggagggcc tgaggcccag agaaaggcgc 286740
ctgaagcaag ggaggggagg gctggtccag agtccctgtc ccctctgcca gccacccagg 286800
aggctcctat ggccccatct cccagctctt ccgggtggaa gacagtggtg ggtaactcac 286860

-continued tcagctagag cgtctgatca caccactgca gcggctgctc acagccttca ccatcaggac 286920
cacaattctg agggcccttt ggatgaagcc atctcacaga gctgtctcct gcagagagga 286980
gaggagaggg aggccgcctt gccagcaggg gaccagcgag gtgtggcctg caagccgtgg 287040
gctcctgtgt tccttcctcc cccttcagag gaatgggagg aaaccaggct tgagttcctg 287100
atttttgccc tttagggttt ttaaattgtg ggagagccag gagtgcctgc gtggtggcct 287160
ctgtcgactc catttgctct gaagcggggc tgcggccagg cagtgcctct cagccttctg 287220
tttggtgggt gaggacgatg cttggtcttg cctcaggagc attgctggca cctctcatgt 287280
gctcctgggc ctctccccaa ccctcacctt ggcatccccc aatatccaaa caatagtcca 287340
caaaacaagc tgccccgtgg gcactgcgaa gaccctcggg gccagagcca ctccctcagg 287400
gtgctgaggc caccagctgg ggcctcctct ttccacacta ttcctgacgc ctgggctggg 287460
caggggactc ctggcttcgt ttcttccctc gcctttgctg ggccatcttt cagaccttgc 287520
ctggtacctt ctctccccgt gccaaggcct ggaggtgatg tggatgcagc cgggcagtga 287580
ggagcgcagg cgaatgttac agcaggcgcg agcgaagggg cccgaggcac cggtgcttcc 287640
gacggggccc gagggccgtc tgacctttcc ggccacgggg cagcagttgc gtgagcagga 287700
acaatcgccc cagtgtgcaa ggcacaagcg gccttttctt cctcaccggg ccggcgcaca 287760
cagctcccag cctggcttcc cttgaacaaa catatttatt gtggccgcca ccgaggcctc 287820
gccttgcagc cggagcctgg gggcctctgt cccacccact ggggcccagg gaggggaccc 287880
ctgccctggc ggtctcccct gccccatggg ccccagcccc atcttgcctg aggcaggggt 287940
ggctctggtc ccacccaccc tctggaggcc cagaaactcg aggctcctgc tgggggctgg 288000
tgaccaccca caggcagcaa gccagccagg gtcctgggaa gagggggttc tgggacacag 288060
ccacacctga gcccatcctc cacctggagc cagcccctta ccttctggag cctcagtttc 288120
cccctctgta aaataggagg catcacccag ccttgcacgt ctccagtgtc cctcagaacg 288180
gctctggccc cgcagctggg gtctgaagag cagagccctg agctctgaga tccactccca 288240
cccccacccc cacccccagg cctctctctg ccttccctag tgctcctttg tgtgtccaga 288300
gggaaggggc atcctccatc agcactgacc ccactcaggc ctctcagctg cactcaacac 288360
aggggctccc cacactcgcc ctccttcgct gcgaccccga ccctcacttt cccacaaacc 288420
ctcagtctcc tttgctcagc ttccttccag acaggctggc ccaggccctc cccacggctt 288480
ggcttccctg ggcggtgtca ggcagggaca gcagccatag gtggtacccc tagtgagggg 288540
gactcattct agttgcaaag atacaggtag agcataggga ccccaaagag tagcagggga 288600
cccccgaggt tgctgctggc agctcctagg gagacagtcg ggcacggtgg gcaccttgag 288660
aggaagaaca gccaggcctg ggcagccctg gggggaggagc caggccaagt gtgctgccct 288720
cttggcctca gatctgaagc tatagagcct cctggagggc agaggcagtg gagaggggtc 288780
tagcgggcag gagggggact tcaggccttc cacacacaca cacacacaca cacactcaca 288840
cacacactct ctctctctct ctctctctct ctctctctct ctctctctcg ctctttctct 288900
ctccccccta cttcagggcc ttcgcgcccg ctgttcccct gccctgccag gcgcaccacc 288960
cccgaaacat gcacacgctc tcctcttccc tgcttaatcc tcttgagtct tcaggcctca 289020
acccacgctt cccctgaaca tcctcctcag agcagttgcg cgctctaaat caggaccacc 289080
ttgcggttct cccagcccca gccttgcctt tctagtggtt ctggcctctg atcacaggca 289140
cagtttcagg cttgtctagc gctggcaggg gtggtcctgc tccggcccca gggcccgcag 289200
gtgtgtgtga gaggtgcatg gtggacgtcc aaagaataaa cgaatgaacc atccaaagca 289260

-continued caggccagag gcagattggg agggtcaggt cctaagaggc ctcaggccgg agcccagctg 289320
cagagcaggg caggggtggc caaaaggcgc ctagaaggct ggactttccg tgaggtggcg 289380
gggagcacca agggtagagg caggggagca atggatgggt tgaatgagga agcttcacag 289440
ccccccggcc accgcaggtc gggggagcac tgtccccggg gccccgcagc cagctgtgct 289500
gggcaaggca ggacgggatc cttggtgatg ggcagaatgt ggggagcagg gtaggacggg 289560
ccccttggct gagagccaga tgtggggagc ggggctgtcg aggctgatct caggatgctt 289620
gctgcggctg ctgggtgggg gataacaggg gttttccgag gccctgaagg actggagagt 289680
aggagcaggt ctcgggggta gcttcctgaa gagatgagtc aggtcccagg cacattcagt 289740
gccagccagg gaggtgagag gtaatcctgg aagctgctat gtagacagaa gcgagggcaa 289800
gaccaccgct cctccgccat aaaccgtgtt ggatgggcct cctgcctcct ccagcctcag 289860
tttcccccac tgtgaaatag ggatgacctc ctgtgctggg gcctggctgt ggcttcccag 289920
gccccggctg ggaccaccgc agaggtgatg tctccaggag gcttctgggc cagcagcatg 289980
ttccagtgcg acacatgtgc cccggagtgg ccgcgtgccc agccggctgt gcacgctgcc 290040
ccaggctggt ggggtaagcg cctcggaggg cacactaaca agaggcacat gtgccaggga 290100
agccctgcct tgtcatcacc tgtgccgtag ctgtcagcgc gcatctggct tacattgaac 290160
tcccccataa aacgtgtgaa acctgacagc agcgccgcag caggacaggg agggactgtg 290220
tgtgagagcc agggaagggc tgctcagggg gctctccttg atggtgaccc cctatgagac 290280
gccacttgcc ctgaggccct gggggacagc ctggcccctg gatggccaga gatgcctggg 290340
gccctggggt gggaggtggg gacaggctaa tggcaattga cgccctgccc ggtggaggtg 290400
ggccatggcc gcccccacct cccctcccgc aagcttctcc ccttccttca gagcccaacc 290460
actgcttgct ccttcccacc cctcctaggc cagggatgcc tgaagccaca ctccactgca 290520
ttcagccacc gtcctgaagt gcccctcacc cacccatcca caccccgcag gcatcctagg 290580
gcctggccca ccaccctctc cctcctcacc attttctgtt gagcacactt gaggagcact 290640
tggaggagct gggggatgac atgagtccac tccgctgtca ccaccaagac cacagtgggg 290700
cagtttaaac agcaggcatt catcccctca cagccctgga ggctggagtc caaggtcaag 290760
gtgctgcagg gctgggtcct cctgcagcct ctctccgtgg cttgtagaca tcaccttccc 290820
cggtgttctc atggggccat ccctctgtgt gtgcccgagt caccttctcc tctcataagg 290880
accccagtca ggtgggatta gggctcaccc ttataccccc attctgcttt aattacttct 290940
tataagaccc catctccaga cacacagtca cagtcagagg caggaggagg tgggtgagag 291000
gaccccacgc ccttcctcca gtgtgtctgg agccccttcc ctgtgtacaa agggacagag 291060
aagcgagggg gctccttggc cctccagtat gtgtgtgcag aaggcccatg agctgcctgg 291120
ggttgggggg tggtccttat acatacttta gatgccagag ggggctcatt gggcagaacc 291180
tacctgggaa ggggcccagg cttcctgcct gcccttcagt ttaccctgtg ctcccaaatc 291240
tgaaagaagc ctttcctaac cagcagtcca ggggattaga ggactgggac cagttgaaac 291300
tccattctaa gtcttgggga cctaatggga ttaaaggcga ccgagcttgg gccgtatctg 291360
ggatctgggg cccaccgggg gctgtgaata gttggagccc tggagtgccg agggcccatg 291420
tcccacgcct ctggggagtc tggatttttt ggagtcttcc tgagacttgt gaccagtggg 291480
cttgggagag cctgaggggc ctctggggtt agacggtggc ccccgtgcct ggagagaagg 291540
tgcactttgg ggatgggagg cgctaggtgc caatggccct aggaggggc tttggagctg 291600 gacccttgag ggagtcaatg ccagctcatc gccatagcgg cttgcttagg gccgtccctc 291660
ccacccccca gttacacagc ctgcaaaccc caacctagcc ccttccaggt gtcccttgtg 291720
atcttccgcc actgacatag gtgtggccca gagcaaaggg cggcttccca tttcacctgc 291780
gcatctgcag ctggtatgtg gctgccctgg tgggttcctg gctggctggc atgcgccctg 291840
cgcctctgct gggcctggtg gggcctaagg gtgaaaactc ggtcaagata agatgcccac 291900
ggctcaggga ccccacagtc acaggtgggg agtggcgcag agcctgggcc tgcctcgggc 291960
taccctgaag tgccagccga gggtggctga ggaagcccag tcccgacccc caccgcctgc 292020
cttcccaaga catcctgagt gcccctcgcc agcactccct gctcggggat cccattattc 292080
caggaggagg agccaggggt accactttcc attagtgggt ccagaagaga tcccagcggg 292140
aaggggcagc cttcagggta gggcagcgga ttagggagga ctcccccagg agaggaggag 292200
gcaggcaggg aaattctggg gggagtgtat tccacagggt aagcagaggc tggatcccga 292260
gagcatctgg acttgttccc agggcaccca gcacagaagt gaaggggtgc cggtggagag 292320
ggagagcccc gggcagctgc tgccgtgtgg gtggatgtcc ggccactgcc cagccacctc 292380
tctgtcccag gaagctgctc tcctggggca tgtgcacctc aagtgggtgc agcaggccca 292440
gacccacggg ggcccctgga ggcctgctgg atgcccgcga gctgcaagga gttaattcct 292500
ggccttgtgg gctggcaaac tctgactcac agagcaataa aattcttgtg ttttaaaaat 292560
cagtatatta gcttaatttt atagatttca gaagtgctac ttgaaaataa aagtctccta 292620
attatattta tgatcccaac gtgagtgaat ttgactccgt tcacggcgaa gaagctttgt 292680
gtaaaatgcc gggaagcctt cgtgctgact cggccctcgc agaccataaa acacggctgg 292740
tgggtccgag cccggcaggg atatggggtc acagcaaagt ccctattaat gccatgtcca 292800
cctcgctgcc agggagagtg gggctgcagc agggtgcgac cgtcacagcc ctaactctgt 292860
gatggatgcc tgctgttgtg atcatggaca tgaggatgtg aggtggtcat aatacaggag 292920
tgggctggag gcagggaaag gggttggtgc cccctgccca ggggaggcac acctgggggc 292980
acagaatgac actgggtcct ctcagcttca tccatttcct gctccaggca gggccctggg 293040
cctgggctgc agggattcaa gggagaacca caccctcctc cactgctggg aggggccgag 293100
cctggcctgg actgctggcc ccaggagcct gggcctgtgg tcagggcagg aaatggagaa 293160
gatgaacgag gaaaggagaa actgctccaa atggtgggga gggaggagag acgagggcag 293220
aagtgagccc ctggctcggt gggggtgggc tgtggagtgt gggggcacag cgggttcctt 293280
actgagccca gggggaggca gggtctggag tgtgggggca cagcgggttc cttggccatg 293340
ggggtgggca gacgtgttat catgaagccg ggagatcaag gaaggctctc tgagggaggt 293400
gacatttgta ccaagcaagg aaagaggcag aagatccttc ttccaggcta agcgccatgt 293460
gagaatgcag caggtcgggg ccactggcac tagcgtgtgt gacaagggaa tctcaggctt 293520
ctgctcacct ctgctggggg cagagaccct ggccagagcc atggccaacc tccccccact 293580
cccagccagg cctagagcag agtgcccttg gaggctggag gaggccaagt cagcctgtcc 293640
catccctcct gggcccccga gtcaccagga gatgcagggc ttagcctgga gaggggcctg 293700
tgcggttcct gggtgttcag gggtggggtg gatgtctgct tttcctgggg gccccacagc 293760
tgggccaggc tgtcctccca gcagaacgtg ggctgcagca ctggccacac agacagaccc 293820
tggggggatt gtccttctgc cacctgggca ttggcacact ggccttccgc agacactcag 293880
caggccaaag agtgggctat catcagacgc tggccccagg cctgccctgt tgttgcgggt 293940
gcagtgaggt gcctgcggcc aggtgggtga gcgaggtgca ggctgtcact caccagcagg 294000
gttggggctt ggggggaccc tggtacaggt ggagtccagg ggtctgcaga ggatggctcg 294060
agccctgcta ccaccatgct gctttgaaaa aggactgact tctctgctgc ctccgcctcc 294120
ctgtgaagtg ggactgacat cccctgtcct ggggtggcct tgagtgtgtg cagtgcgtct 294180
ggcacaggca ggtaccccac atgtgtgccc agcatgtctg ggagggccag ggtcgcagca 294240
gggcccccac ccatcctggc tggctcatac ttggccactg gccacaggtg acaccaaccc 294300
agcccctgtg tgaggtactg agagcccatc acacagatgg accaaccaaa gccacagatg 294360
acaggtggca ggcccgagat tgcctgaggt cacatggtaa cacatgtgca cccggcagtt 294420
gtttctgccc tatctgtggt tcccagccat ttggatgtca cagccccatc aaaggtccgc 294480
tacatattcc cccaccccca aaggtggatg gacataggtg ggcaacattt ttattacgca 294540
aaaaaggaca tttcgtagaa caacattact ctaatgaaat accaccattt cattctagaa 294600
aggctgagga ctccatctca gaccaggggc tggtggtgtc ctggtttttt aacaagaact 294660
tgttctcact ctgccccagc gtttgtcagc ccagccatgg ctcctatcca cggcactggg 294720
cccgcagagc tccaggagct gacatgctcc gtcttaaggc aggtcggctg ctccgaggac 294780
tgccggccct gtcagtatgg tgtccttgcc cagctggtat tggccaagtt gaccgtgtcc 294840
aggggacaga gagaggggag gggcaggttg ttggaagcct ttctgcagat gtagcttgga 294900
gcagtgtcct aagggaggcc agcccctatg ggtcgggaca gaggcctcac cagtgggatc 294960
cagtcactgg ggctgaggcc tgggtgtgca ggtggggtgg tgagccatgc ggcagtagcc 295020
cctggggact agagcaggct ccttgtggag ctgtgcggag ctggccggcc tggtccccgt 295080
ggcttcaccc tgagcgtgct gctgcctagg ccctgaacag acagaggcaa gccctgcatg 295140
gcgcccaggg tgccagtgac tctggttgct ctcaaaccat gagaaacgtt agaacgtctt 295200
tacccctctg tgagatgggc tggcctggc ctctgaggag cctccaggaa tggcaggagg 295260
gagggtgggg gatggggagt gggtgctgct gcccatcgac gctgctgggc aactaacaaa 295320
ttcagcaaat tcttcttttt attgtgtatg ttcgacaact gccttcactt aaagtcactt 295380
ttttctggct ctccaaatat acttagataa ggaaacagag tctatttaag gaacaatgtt 295440
aagcaaacaa tagtacaggt gttcaaagat atggaatgag tgacagatgg ggcgagggac 295500
cccgatgcag ccccacccag aggacagcgc acgcgggctt tgaagtcctt cctggcaggc 295560
cccgaatgtg agcgggtgga cccaggcctc ctgggggcct cagctcagct ggagccaggg 295620
tctctggagg ggcctgggtt agtttcctgt ggctgctgga acaagtcgcc aaaattttgg 295680
tggcctaaaa tcaaggtgtc ctcagggctg gtcccttctg gaggctctag ggagagtccc 295740
tgtcctgcag tttcctgctc ctaggggcgc ccacatccct tggatcatgg cccctccttc 295800
accctcaaag gcggctgcgg ctcatggcat cctcacatca cagactctgt gcgtcccctg 295860
cggccacgtc tcctcctctg actctgatcc cctgcctctt tcccgtatca ggacccttgt 295920
catcacattg ggccacccag agaacccagg attttctccc cattgcacga tcagctgctt 295980
ggctgcctga attccatgca gccttgattc cccttcaaag gaaatcaagt ggcaaagggg 296040
aattgagtga cgcatgcgtg agttccaagg attagggcat agactccttt gggggcgccc 296100
tggggtgggg ggtgttcctg tgtctccctg cagcccctgc ttggacacat gaccagctca 296160
ggcagtgctg cctccggggg aagtcaagag tctctggtga gtctcagaca ggcctcagag 296220
tgtctcaggg tggcctcaga gacaggggag gcccctatga gctggaggga gtgtgaggac 296280
agggcctcct gtgagagggc aggtttgact tttactctgc cgctgagtga ctgtgtggcc 296340
caggcagtca ccccagagag gtctgactgg cgcttgccgg ggtggctgtg tgcagcaggc 296400
attggggccc tggagatatt tgctctttct ttttgtttta ttatccagac ttgcaaggcc 296460
ctgtgtgccc cctcggggct gcacacgtgt acgcacaaac gcatgcccag tgtgacccct 296520
gtccacacct ggtgcctgtc ccctgtgccc ctgtttatcc cttctaccta cagcctatcc 296580
cctacccagg cccagccctc ccagctcacc ctcttccaac ccaggcctga gctctgttcg 296640
ggtctctatc ctcctgccct ttagcctcct ctcttactga tagaacattc cagagcattc 296700
caccaccact ggcctgcaat tatcacccca tcgctgtgag tgggggcagg ctgaggaagc 296760
tgtgctcggg ccggagcaca gccggcctcc ttgcaggggc agctgcgggc gcgcagacag 296820
ctggggctgg gagcctcttc cagggatcct ccgcctgtgg ttttcctcct tgaccttctt 296880
aggagggtcc agttccttct cctggccaag gccccactct ctgccacccc aggcagggcc 296940
agggtgggtc accatctgca gaagccctca ggggccccca gcagcgcccc tcctatcccc 297000
ctgccccagg gcgggctgcc gccttgtaac ccccagaact cttggctctc atgtatatga 297060
gtcagcgttg actgtttaac ctgttgcaag acactctgct gggtgctgcg acatggttag 297120
gttttctcca cattagaagg tagaaggaag aaaaataagt tctgaaagaa acagacttgc 297180
cctgcctctg ccctgacctt gaggtgaaca gaggttttgc acagaacgac catccctgca 297240
gcgggtggct tggggggtac caccatgatt tgagaccctg ggtggtgctg gccagaatca 297300
gcctctatga gatgggcagg gcagtccagg gcaggggaag ccctgtgccc caagatcaga 297360
tacatcagct acaatgagag gcatcaggcg gcctcaggcc ctcaagccgg tccccatgtg 297420
cccatttgca gtctgtctca tactcacggc cacctggcca ctgcaccctg atacagcagt 297480
ggggccttca tgcctgtggg gtgtctgcct gcccagctgt gcccactcat gtggtggatt 297540
catcccaatg ctggtcctgg gggccctggg ctccccccgg ccctttctcg aggcagttta 297600
cactttgcag ctgaatcaat caggggcaga aatgcctggc aggggaatgt ttaccgattt 297660
ggttttctgg ggctgaggat gctcggtgtt tgtccaggct ctgtcctgct ggctcctcta 297720
aagctttgca aacaagagcc tcggagagaa ggaggccttc ccctccccat gtgctgaatt 297780
cggggcggtc ctgacagcca tgcgcggggg cccgctgtgg cctcctctgc acggctgctg 297840
agggaatgca ggtcaaacaa agtaggccag cggcttaggg accccgagta agcaggcaga 297900
cccacaggaa atccagtgct ccgagccccc acacctgtgg tgtggcagcc acccagcaag 297960
actggaccga gaggccacgt gggcagccac ccttgccagg tgggcacagg gagtgcaggt 298020
ggtttgttct tgcctcagat ccaggagagc agctttttttg cctgaaccca ctcgtgaatt 298080
tttcatattt ttggagagct ccttgtgagg acagccggcc tgagcaggct ttgatgaaca 298140
ttagagcagg tggccacaat tggcagatc tgggcctgga gacccagttg tcatgtttga 298200
gagggaaggg gcattcccag aaatcacagg gatgactggt gtgagcccac cgcccaccta 298260
gactcccgta ccatgcgggg cccctcattg actccgaggg tcttcaaggc cctgtgctcc 298320
tccagaaggt ggggtctgag gtgctgctgg gtgtctctct tcacctcttc agaagcattc 298380
atgaggtaag accccacccc ttcaggccct ggcacaggcc tcagagcagg cccaccaccc 298440
aactcactgg ttcacttagg ggtagaaatt atcccagctt ttacccagag ctcagggccc 298500
aagatgtcag tttgcctgcc ggctgttgct ctgactgtgg cctccctccc agctccccgg 298560
catgcagctc ccagagggag aacttgagca gggaagggaa ggggctcgaa tccctacgcc 298620
agtccctgca tggccctatg gggacttgcg tctccccgga ggagagcagc cctgcgcagc 298680
cctctcttac tgattcctgg agtctgcaca gctacatagg gtcagattca cgacctccca 298740
gctttaacca gccttcttga ttagccgcca tctaaggccc aactgtgctt cgtgacaggc 298800
ctttgagcct aaaaggagtt gcccccagca atgacatcgg atgcctgttt agtcagcgga 298860
ctgcctcaga aaggaatctc acaggcagcg ggttcttctg gtagggtggg atatttcagc 298920
gggaggtaaa caggtgttgt cacagaacgg cagactgggg cctcccctgg tgggccttga 298980
gggtgctggc ctgcagacct gctcctgccc gttctggcct gatccggggc ctcttgactg 299040
caggtctctc gtgggctctc agccccaggt gcctgccctc acccacgtag cttgggacat 299100
catcagccca ttgccggtac ccatggtacc ttcaccaccc tcttggccgc attctgaaaa 299160
tcaatgttta gtccctcctt gaacttaaaa agtcaaactt aaaaagagat tattacaggg 299220
agctggggac tcaggcttgc accctgcctg tttaggataa aaggccaccg tgtgtccact 299280
ctagtgtctc tgctcaaaca ggagacgatg tggcatcggg aacaccaatg cggcactcag 299340
agaaggctct tagccagctg gcccctgatg ggctcactgg ctgcaccagc ttgtgtagca 299400
gctgagctcc tgcagagcct tctgggaggg aagaatgtgt ttcttgctcc agtactgcag 299460
agcatgtgat acctgcaggg gtgcaagagg tgcctgagag caggcatagc caagacttgt 299520
ttgcggttgc tcctgacgca gagccggcac atgaggtggc gttccctcac tctctcattc 299580
attcatttat tcgccagtgt ttcctgggcc ccatgccatg ccaggtacct tactaggccc 299640
tggggataaa aaagaggaca aaagagatga gaccttcatc ctagagctta ggatgtgaac 299700
tgcgtccttc tttaaatgga aatttctaaa ttacggtgta ccgaatgcat ccacccttgg 299760
cctcgtcaca tgtgctgttg ggcagtattt tcctacattt tcttctgtga aatttataat 299820
tcagcctttg tcattcaggc ctgtcgtcgt gtccaggtgc acctttgcat tcggaagaat 299880
ccagattcct tttcctccgt ggagtgactc cccttcccca cctgccctgc agccattcca 299940
tcctgtctat ggtggtcgat ggtgtcatct ttgtggtcta gtgtgttccc gagtatacaa 300000
gggtgtgtga tcggggctcc ctctttgcac tgatagtctg ctggtcggaa ggacaatggc 300060
ggcaccccaa gacctgatgc tctggtttag aaacgggttc taatgcccag aagagctcct 300120
aaacccctat ttataataat ctctttttaa gtttgactta tctgtttggg acctttattc 300180
ctccatgcca actttaaagt taagtttatt gcatttctta aaaatttcaa ctggaagttt 300240
gcttgggatt gcctcgaatt tgcaggttaa atttgggaaa aactggagtc tctctcatgt 300300
tgcgttttct cctccaagaa caaggagtct ctctgcattg agtcaggccc tcttggacct 300360
ctgttgccat cttttcctga aagggctggt ggggtcttgc ttccattatt cctggatgag 300420
accttctttc ccctgctatt ttggaatttt ttctcccagg agtttattgc tggtataaag 300480
aaatgccatt gatttggggg ggttgatctc acacctgaca accatgtcat actttctatc 300540
agctctattg attgatcttt tgatcctgct gattgtctaa gtggatcggt cctatcagga 300600
ggagtcagcg tgaccacagg cccccattcc ccagccccta atgttcttgc ctcatgtctt 300660
caggtgcggg gctggcaagc tggggttacc tgacacttgt catccttctg ctgggcctca 300720
gcacccggcg gagcaggggc ttcctctgac acgatacagg gatttgctga cggttccttg 300780
tctgctcact aagcgtgcct tggagaaggc cgctcagcga gggccgcctt caggcctgag 300840
cccggggcca ggaccaggag caggcggcag cagcaaggca gctcatcctc ggctgcctct 300900
tctccctcac tactatttgg tttttgtttt gttttgtttt gttttttgag atggagtctc 300960
attctgtcac ccaggctgga gtgcagtggt gcgatctcag ctcactgcaa actccacctc 301020
ccgggttcaa gcgattgtct cacctcagcc tcctgagtag ctgggactac aggtgtgcgc 301080

-continued caccacacct agctaatttt tgtatttttg gtagaggtgg ggtttcacca tgctggccag 301140
gctgatctcg aactcctggc ctcaagtgat ccatccgcct cggcctccca aagtgctggg 301200
attataggca tgaggcacca tgcccagcct cttgccgtca ttttttttat tttaaataaa 301260
ctttgatttt agaatagttt tggaattaca aaattcttac acaggtggca ccaagagtcc 301320
ccaggtgccc ttcccccagc agccctatta tcagcatctc acattagtat gcatttgtca 301380
caaggaaaca acagtgctac atgactgtta actgagtcca tgcttgatgc agatttcctc 301440
agtttcccta ctgtcttttt tctctccccg ggccccaccc agggtcccat gtgacattcc 301500
tcatccgtct ccctgggctc ctctgggcgg tgactgtttc ccaggctctc cttgttggtg 301560
gtgacctgga cggttcagag gaggacaggt caggtgtttg tagggtgtcc cttactagga 301620
tccgtctgct gctgtcctca cgattcgact gggctgtggg tgtgaggagg gagagcacag 301680
agggaaatgc ccttctcatc gccctgttcc gagggcccat cctgtcggtg tggctcgtca 301740
tgggcgatgc tgtctctgtc tcctggctct gaggccatgg ctgtcaatct cttcaactgt 301800
gatttgttct tttccccctt tgcagactgt ccttggaccc gccagcattt ggctctgggg 301860
ccctagagag accctgggat gtggatcaca ctggtgaccc ctgtgagccc cactggggac 301920
agatccagga agggacctcc tgggaatgag gtctggcctc tgcctggatc aaagccatgg 301980
cccccattcc ccggggatag ggaagctgtg caggcagcct gggtaatggg ccaccgcccc 302040
aggcaggcgt gggaatccac acatggccct tctcaaagac gggtgctgtc cctggggctc 302100
tggcggggtc ctggagcctc tctcattggg cacatccgag cccagcctgg cccatggtgg 302160
aaatgcaaat ctaattagtc tggcattgag cccgtcttaa aagtattaac agagccttaa 302220
actgtgctgt tggacgggga tgaagaaacg ccttagaaag aaattaccgg atggtgacaa 302280
agccccaatt tattagtctt ctccaatggg gactgtgcaa aggacattaa ttactttaat 302340
gggacttatt ttgcttcgtt gcccaaagta attggtttat taacctctcc ttccctttag 302400
ggagggaggg agggaaagac tggggcctgg gggtggcccc gggaggggct cgtccagcct 302460
tctgctcctc tgcccagcgg tgcagccttg caccctgggg cagccggtgc ttggtccctg 302520
ctggcctggg ctggggctgc cccagtgccc actgatctat tcttgttcac taggcatcca 302580
ccgtgtgcca gtcactggaa tacggccatg agaaagacag gaccctcaag aaacaacctg 302640
ttccctgaag gccataagtt cactgttgtc acaggtgccc agaggaaagg aagatggctt 302700
tgggggtgga cacgtctggg caggcttctt gcagaaaggc cacaggctag gatggtggga 302760
aggcaagaga atgccgggaa agggaggact ggttgcccac agggagtggg ggtcatgggg 302820
gcaggttcca gagatcagaa ggaggtggtg ggaagaggca cgcagggtga ggctggctgg 302880
aggcaggtga ggcagcccag cctcaggagc caggaaccag cttccccggg ctttaccaga 302940
tggggagcga taagggctgt gtttcaaaac aatccctctg gcgtgaagca agccgtcttg 303000
aaaacagacc agaaccggct gcttccacca ccagcagaat acttcaagaa gaccactcgg 303060
gcctagggct ctgcaagcaa tatctgattt tcagaaaacc atggctcacc cacactctac 303120
cctaggaaag ggcaggttcc cagggctggg cttgtggcca gtgcagcact atcctcagtg 303180
gcctgggaca cccagaactg gccaggaaag acccctacac agacccccag ctctgcagtc 303240
agccctgtct ccttgtgtcc ccagacctcg ggcgagggag aagcaagttc ccctcaggaa 303300
tgctggtgaa gctggcatgc cccacccccc tagctcaccc tgggtccacg cagggcctgc 303360
tcccagagtg aatcccagag gtgtgcctgc cccacctgtc ccagtaaggg tggttgtgtg 303420
tgttgggtag atgtggtgag gtgtgctggt ggggagggtc catatcagat gcccctgggt 303480
acctccccag gcagggccct cagcacctga tgccaaacca ggctccactc ttcctccagg 303540
tgagcccgag ggcccagctg ggcgtccacg tggaggtgtg gggcccgggt gggacaagcc 303600
tggcaaccag gacccagcat gaaactgcag gtgcaggagc cccagccagc ctggaatgtg 303660
ggggctcaga ggccacccag agcccacagc agggactccc cacgccaggc ccggctggat 303720
cacagagctt agggtccagc cagctgctgc tgcccctccc tctgggcctc aagaccatct 303780
gtcacgtgac aggggcaggc taggcctttc ttgaactcac tgtgagctac agagactgtg 303840
ttctggccag gtgaatggtg cccctggggg ccaagatccc cacctctggt ctggcagctg 303900
ggtgtgcagg ggcagcccca gacctccaga gtgccctctt cccctctttg cggttgtcac 303960
cctgtccttg agtctaactg gggctgtgct gcctttgacg tgagctattc aaaatggcgg 304020
gaggggcgag gcctctggag caaggaaaga gagtggtggc tgtgtccagc aagtccctgt 304080
tgccactgat agcataaaaa gtaactctga aacctggtgg ccctacagtt gacacacatg 304140
gggccgcagg aggaaggagg ctcaggctag gccaaacatc agagacctca ggtctgtctc 304200
ctttaccaaa tggggggctg ttccgccagc accccagtag ggaggatgag aggatgccat 304260
gatttccagg gtggtgtcag aacctgtctg ccagggctct gcagggaggg gtttggggtt 304320
gagattggga gacctagaaa tcgaggggtg tcgggggcct cggctggggg gcaagcacag 304380
atgaggatgg aagcagctca gtgtcactca gtctgcactg ggaatggggg atcccaaggc 304440
cagggctctg cctggtgcca actgtgtgac cctgggcacg ctgctgagcc tctctgggcc 304500
ccagttccct tattcgtaca acgggaatga tcgaggagtt aacatgtgtt taaaagcacc 304560
gaggcttggc cgggcgtgct gcctcacgcc tgtaatctca gcactttggg aggccgaggc 304620
gggcggatca cgaggtcagg agatcgagac cacggcgaaa ccctgtctct actaaaaata 304680
caaaaaaaaa aaaaaaaaaa aaattgtccg ggcgcggtgg cgggcgcctg tggtcccagc 304740
tactcaggag gctgaggcag gagaatggcg tgaacccagg aggcagagct tgcagtgagc 304800
caagattgcg ccactgcact ccagcctggg caacagagcg agactccatc tcaaaaaaaa 304860
tatatatatt agctggatgt ggtggtggac gcctgtaatc ccagctactc aggaggctga 304920
ggcggggaaa cacttgaacc cgtgagttga gatcatgcca ctgcactcca gcctgggcaa 304980
cagagtgaga ctctgtctcc aaaaaaaaaa aataaaaagt acaggggctc tacacggcgc 305040
cctgagaatt gtgtgtaaat gagtgaaaat ggggtgagag ggagggagtg ggaacagcca 305100
agaggccagg aagcagagcc tgggtgcagg ggcatcttgc tggtgaagct ggggagagac 305160
ctgcgcaacc ccacctgagt gaggcactgt gggcccagag tccaggtcag cgccaggggc 305220
agcaggggct ggatctccgg ggaagttgag gaatgacatg tattccaggg aagaattggg 305280
ccggaggctg aaacaggacg acagagccct cagcccaggg cggaggacat gggagacggg 305340
ggtatagctg ttgggcttgt ggctggcctg gcctaaccag ttgggggaat ccatgggagg 305400
ctttagccct gctctgtgaa ctgctgggcc ttccttaggg gccctgggga gccttcccag 305460
cagaatgtcc aggctcctgc tggcccaagc tccaagttct ctggctccca gggtctgtgt 305520
ggaatccacc ggtttcaccc cacgtctttt cctctcctgc ctggtaaccc tctctgcaga 305580
ggccctggct ggaccagttg ctttgcaatt cacaaggctt tggaaggcag tgctcacaaa 305640
tcacttttct agacgaagac cagtaagaag cccatgtcat tcttctgaga cattaggggt 305700
tttctctccc ttgttttaat caaccagttc ccaataagtc atttcagtca ggccattacc 305760
aatggctcat aatctcctgg gctgctgggc gaaatgggat cccctggctc tttcactgaa 305820

-continued aacacttttc ttgttttctt tctccggcat gctggaagcc ggccaactcg ccagttccat 305880
taacttaatg agggctgaca gcctgcgaca aacgtcctca taatctcccc aggatttaaa 305940
cggggtcctc cccagctgcc tgcctacacc ccaacctcga ggctctttac ctctgtctgt 306000
gcacccaccc agcccctcct gggaaaaagc caggacaaag atgtatttct tcgctagctc 306060
cttcctggcg gctctgtgca ggcagcctca gacctgtagg ccctctgccc aatttgggtc 306120
acccacagcc cccgcacccc acagcaattt cttgggagct gatcatcccc aaagcttgga 306180
actacaaggc agtgactggt tttgccgggc tccgctcgtc cctctgagcg gagggtcacc 306240
ctggtcacca tgaaaacttt atcctcatcc acacctttct ttctccaact agcatgggaa 306300
tcagtttagg gtcctcccac accctcatcc aaaccctcat ctcccacccc ccacttgcag 306360
agaaagcccc atgctctcag cagaaacgga cgccagcgtt taggagcggg tgggctcccg 306420
gaagggggct ctatgggaaa ggggaggcaa ggctgagcag ctgcccaaag tgagcatctg 306480
tcccacgttc cacccccagg aaaccctctc tcctgacgcg gggacttgcg tctcagtgca 306540
gagggcagtg gagggacagt gcagctccga aatgagcatc tgagttcact gctggtgggc 306600
accatcccgg ccaacaggcc actagtgtgt tctccctctt tcaaacgggg cggcgaccct 306660
cgtctgacag gcggctgttc tgagagcggt ggctgtccca gggaagccct cggtgagcgt 306720
agcgttacca tggtttttaa attaaagcat ctgcagatgc gctgtgtccc tgcaagggca 306780
ggcagatcgg gaccccaggg actggtcccc atagccaagg tgttcagccg ccctgtcccc 306840
tacacagagt gcctctccca ctggctcagg gtgagggcaa aatggcactt gcagaacatg 306900
aggcccggcc agctttgccc tattccccc atagcatggc tgaccttcct ctgagcccct 306960
cgtggatgcc cacacacggc aagacgtttc ctcaaagatg ctcttctgca aagctgcact 307020
ttctcggttg ccgctgccac cttggcacct ctctggggta ccttgtactg ccctgtcctc 307080
cccacgccct gaggggccgt cctaggcagc actcaccctg gtcatccctg tttccaccac 307140
aagactgttt gtagccgagc ttgggagttg tgttgtgtag tgttgacttg agttgcatcg 307200
tgttgtgttg acttgagctg aactgtgctg agtgttactg agttgaggtg actgggttga 307260
ttttagcttc acaggtgatc tgaacccagc tgagtggctt ccatggagct gatctgaacc 307320
cagctgagtg gcttccatgg agctgatctg aacccagttg agtggcttcc atgaagctga 307380
tccggactaa gctaaactga gtttcattga gcagcttgtt tagctggtgt gtgccaggtg 307440
gtctctcggg gggtccgatg ggatacctag tgtcttaatc tgttcagtct gctataacca 307500
aataccttag acctggtgat tcatacttag gaattcattg ttctggagac tgggaagcac 307560
agggtcaggg cgccagcaga tctggtgtct ggtaaggggt ctgtctgatt catggaagtc 307620
agcgggctgt gtcctcacgt ggcagaagag gcaaaaataa ggtgcaaaca agctccctca 307680
ggcctccttt ccaagggcac gcatcctctt cctgaaggct ctgccctcac ggccgaatca 307740
cctctcaaat gcgccatctc ctaacaccat cagggctgcg ggttagcttt cgacataggg 307800
actttgggaa gacacacaca ttcagactac agcaccttgc tcctggggaa acagaggaaa 307860
ctggttcctt tctttcggtt ctgggttatg tcaaaatgag ttccctttgc tgaatctgtt 307920
tcagccacct ctcccgagga tcctcgcaca atttcactgc cagccaggaa ggtctgccct 307980
ggctggtctg ggcttgagga ccagcacggg atcgttctcc tctgtgggtc gctgatatga 308040
aaacaatctc acaaagacgt aagaaccaca catgcttagt gtcatgtgtg atgcatcaac 308100
ccagggggag gagagaacgt gcattcacgc agaactctct cagccacaag ctctgtttct 308160
gttgcatttg ggccaggttg cggggagcct ggcaggccac ccggccagtg tggatgtcat 308220
tacatgagca gtaggaagcc atacagtatc tgaggcgggg gagtcacgag atcttcagtc 308280
tgtccctcgg aaagcccctc ctgccgccac tcagggggat gggttggaag gggtgaggct 308340
ggagcccaaa tagggagttc agaggcctcc gtgtctgccc agggaaggag ggaggccagc 308400
ttcagctgct gtcctgaggg ttcctgcctg ggtccctgat ccccctgaga aagggctccc 308460
tcccagaaaa ggcatgtgcc ctgggcagag ccaggaaagc tggggatgtc tcaaagcctc 308520
cctacctgct ctgtgtcccc tccctctgga gcctgcctct ctcccgagca aagtacctgc 308580
cacctgggag tgatctggga cagtcagatg cacctttga agtatacacc tcagtggctt 308640
ttggtatrtt cagagtcatg caacttcacg actctctaac tttagagcat tttcatcacc 308700
ctcaaaatgt cccttgcatc ccaggtacaa agccatacca ggccccatgg ggatggcttg 308760
tgactgctgc acatcctgcc cctggacctt actctagttc ttctttcatc cactggtgta 308820
ttcctttggc cggggacaca cacatttgag aaacttccca gcttccctct atctgaggct 308880
cactccatta caacacaagg aactgagaca tctgtggctg gtttttttg ttgttgttgt 308940
ttttccaaat tgtatatctg ataagggatg tgtatccaga atatacaaag aggtcttaca 309000
actcaataat gcattgaccc aattaaaaaa tgggcaaagg acttgagcag acatttctcc 309060
aaagagcaga tacaaatggc aaatgatcac aggaacacat gcacatgaac acacgcycag 309120
cctcagcagt cattaaagag atgcagatca aaaccacagt gaggtttaca cccagtagga 309180
tgactaaaac aaaaaagaca ataacaagtg ttggcaagga tgtggactgc cagagcgagg 309240
ctagccatgc catgtatctg gaggagggcc ctggaggggt gtgcccattg catgtctgtg 309300
tgttcccatg cagtgggcac aggcagtggt gccagaaaga gcctctgctg ggctttctca 309360
ccaccccagc ctctcacctg cagcccaggc atcctccagt gggtttttca gggaacttaa 309420
catgatgagt ctaaaatttc tatggctgaa taaagaactg aataaaaata accaagaaga 309480
tcaaggaagg gccctgcctt ccagatatca ggatgtggaa gaggctatac taactaagat 309540
gttgcagtgt aggcacaagg gtagacaatt agcccattat cccagtggac aagacagaga 309600
gccctgaaga gatccataca aatgtgggac attggcatgt gaccaaggag gtgttgcagg 309660
ttgctggaat caatcatcct ccagaaggaa aaagctagag ttgggccccc acctcatgca 309720
atctataaaa actgactcca ggtggatcta ggaattaaat gttaaaagca aaccttaaaa 309780
ctcttactgg ataatatacg tttattagta tcttttataa ctcggcatag ggaaatattt 309840
attttacaag acacaaaagc attgactatg aaagaaaaac attggtcaat tcgattttac 309900
aaaataagaa tccctcatca tccaaagata ccttaaagaa cgtgacaagt tgcagactgg 309960
cgattgcact agttttctgg cactggttta acaggtgacc cccaacacac atcagaataa 310020
cagacgttta ctctctttca cttctgtcgg tcagaggtcc aaccccaggt ctgatggggc 310080
tggagggcgt cattagggct agaggtccta ggggaggatc tgtgtccttg cctttttcag 310140
cttctagggg ttgtctgcat tccttggcct ttagcccctt cctctatctt cagagccatc 310200
atgttcctcc tctctgacat ttttttcgt aatcacagct ctctctgacc acagccagga 310260
aagagcctcc actgtttgtt gttgttgttt ttgttgttgt tgttgttgtt gtatggtttt 310320
gctctgtgac cygggttgga gtgcactggc gcaatcatag tttactgtaa ccttgaactc 310380
cctggctcaa acgattcttc cacctcaact tcctgagtag ctgggactac acgcacgtgc 310440
caccgcgcct ggctaatttt gtttaatttt gtgtagaggt ggagtctctc tatgttgcct 310500
aaactggtct tgaactcctg gccttaagtg agcctcccac ctcacccttg gccttccaaa 310560

-continued gcactgggat tataggcatg agccactgtg cctggccagg gccttcactt ttaaagactt 310620
gtggttaatt gggcccacct ggacaattca atatgatttc cccatctcag tgttcatgac 310680
cttaattaca gatacaaagt ccctttttcca tataacgtaa catattcata ggttctagga 310740
catctttggg ggagccctta ttctgcctac caaagaaatg gatattcaca atacaatgaa 310800
ttgataaaga attggtgtat gtataactaa tacataacat gtataatgta tttatatatg 310860
tgtgtgtata accaataaaa tcactaatag aaactaaaat aacgaatcaa taaatataca 310920
aattatcaga cagaaaaatg gccaaagaca aagacttgtt ctgcccttca tggtcgagga 310980
acacatgtgg ccagtgagta tgtgaaggca ccatttacag aaaccattta caccactcca 311040
ttggcataaa ccacagtctg accattggga gcggtggcag ggatgtaggg cccagggtct 311100
ctcctacatt gctgatggga gtgtacagtg ggactaccac tttaaaaggg tggcatcacc 311160
tccaaggtgg tgaattcaca tacctgttga cccagcagtc ccatatctgg gcatacacca 311220
aaagggaact ctggtgtgtg gacgagtgag aatgaacagg agtgtgtgtt gcaacgctgt 311280
tcacaagctc cacgtgcaac cagccacttg cctcccagca ggagggagag tgagtaaaca 311340
tggaatgccc atacaaaaga gaattttaaa ctaattaaag caaacaagcc agagtgacag 311400
acaaccatgt gggaaggctt ggcaatataa taccaaggaa aagcccactg cattcttatc 311460
aagtttaaat tactaaaatt aaaraaaaar aaaraaaaaa catgactttt gggacacata 311520
tagtttcaat aatattatat taaaaaagaa agcaagggag agaggaacac aggattcagg 311580
ttgatggtta cccaggatag gggagacaag gatacagttg gggtggagct gtcagggtcc 311640
agcatttatt ttgtgttttg tttgtttgtt tttgtagaga tgtggtttgg ccgtgttgcc 311700
caggctggtc ttgaactcct gagctcaaag caatccgccc accttggcct cccaaagtgc 311760
tggaattaca ggtgtgagcc accacacctg gccgtctagc gtttattttg aataacgagt 311820
ccttgggagc tttctacatt gtttttaaaa actaattata tgacatttta taagaaaatt 311880
atattagcac aaccgggaga gatttattct aggtaatgca aggctagtta acattcaaaa 311940
cttaattaat gtgatctatt atggaacttt cccaacttga tcaagagcat cttaraaaaa 312000
aaaaaaaaaa aaaaaaaaaa accccacagc taacatcaca tcacacttaa tagtgaagaa 312060
cagaatactt tccccctaaa ataaaaaara aggcaagggt atctgttctc accacttcta 312120
ttcaatatag tactggaagt tccagccact gcaataagac aagacaaaga aatgggacat 312180
gtagattaga aaggaggatc taaaactgtt tctatttgca aagatagaat tgtctatata 312240
gaaaatccca aggaatctac aataaaaata tctggaactt aggagttcag cacacaaaaa 312300
tcacttgcat ttctatacac taacaatgaa cctgtgaaaa ccaaaattag aaacaatacc 312360
atttacaatt gcgctaaaga aattaaaata cttaggtata aatttaacaa aacatgtaaa 312420
gatgtatata ctaaaaacta caatatgcca atgaaagaaa tcaagaccta aatcaatgga 312480
gagatattcc atgttcatga actggaaaac tcaaaatagt aaacatttca gttctcctta 312540
gaattaccta taaatatagc ataattccta acaagaatcc tagcaagatt tcttatggac 312600
atggacaaac ttgttctaaa atctatatgg aaaggcacat gctgtagatt aaaacaattt 312660
tgaaaaagaa ttcagtggga gaaatcactc taccaatttt aaggcctact atacagtaag 312720
gaatcaatat gatttgatat tggaggaata agcatgtagc tcaacagaac agaacgagga 312780
atccagaaat agacacacgc aaacatgcct gactaatttt aagacaaaga tgcaaaattc 312840
agcggaggaa gactcctctt tcaacacacg gtacaggagc agttggtcat tcataggcca 312900
aataaataaa ttaaaaccct gacctaagtc tcacacttta tataaaaatt aactcaagag 312960
ccaccttgga cttaaatatg aagtgtacaa ctctgaaacc tttagaaaaa catagaggag 313020
atagtattta ggatttagga agggcaaaca gttctcacat tggatgctaa aagcatgatc 313080
tgtttaagga aaattgatga aatggacccc attaaaactt aaaacacttg ttttgtgaaa 313140
gccccagtga aggggataaa aatgcaaact atagacttgg agaaaatatg tgcaagccac 313200
atatttgaca cctggcatct agaacatgaa gtactctcaa aactcaacag taaaaaacag 313260
cctgtccaac tagaagatgg gcaaaagaca cgaagagaca tttcaccaaa gaaaataaat 313320
agggaagaag tacaccaaaa gatgatcaac ttcgttagca aagatggaaa tgcagattaa 313380
aaccacagtg agcggtcact acgcacctat cagaatggct aaaatgaaaa gtaatgatga 313440
caccaaatgt tggcgaggat gtggagaaac gggattgccc atctgttgct gctgggaatg 313500
taaactgatg cagcactcgg ggaaaataat gtggtcgttt cttataaaag tcagcatgcg 313560
actaccacac atcccggcaa ctgaactcct cctgggcatt tatcccaaag aaacgaagac 313620
tcatattcat acacaaaact aaatgaaaat ttatagaagc tttattccta actagctgaa 313680
agctgagaac aatctatgta tcattcaaca ggggaacagg caaacagtgg tgcatcccta 313740
ccctgaaaca ctacccagca gtagaaagga acccactatt ggtacaacct aagcggatct 313800
tacgggaatt gtgctgagga gaaaaagcct cccccgaaag gtcgcatgct gtgtgattcc 313860
gtatagataa cattctcaaa gtccaggctg tagggatgga gatcagatgg tggttcctgg 313920
ggttgggaat ggtgagggtg ggagtgactt gcacaggaga cgcagagggg gtctttctgg 313980
tggggaggac ttccattcct cgttgctgtg tgaatctgca cgtgtgaaca caaggcagag 314040
ccacgcacac tgtaccaatg tcaatctcct ggcgttgatc tgttactcca cccatgcaag 314100
gtgtgaccgt cgcgaactca cgtagagggc atacaggacc tcttggtact tttttttttt 314160
ttccaacttc ctaggagtct ataattgttt caaaataaaa agaagcaaaa caacacactg 314220
ggaggtgcag gaaaccacac acgtgatgtg cttgtgtctg ctgacataag tgctcaagga 314280
agagtctgga aggcctgcaa ggccctcatg cctacgaggt ggctgctagg gggatgtgac 314340
gtagagtgac ttcagtttcc ctcttcatgt ctcctgggtc ctccagcact ctgggtttcc 314400
tctgccaaga cccccaccca tctgcctctc ttcatctcac aagcctgcat gtgtgcagag 314460
ggcaggggtc cccaggggat gttccttccc caaggcgctg tggccactta gagggtcccc 314520
caagctcggg cctttgaaga cagctctgtg tctcctagga cgcacaggtg tgggacctca 314580
ctgcgcggga gggagttgca aagagcgaca ccccagcatg tgggaaggaa gggagcgagc 314640
tcttatttcc ttattttctt tccatctcca ctcccaggca aagctgataa attcttcctt 314700
attccagagt tagaggatcc tccagaaggg gccgagagct tgtccaggca gggtggatac 314760
aaggggcttg catctgactt aactgtctgg ctgggggaga ggggacagag gtcctgggag 314820
gggctgaagg ctcagggaca caggtgaggc cagcccctcc tccaccctgg gcatctccag 314880
gcccagcccc accctgagct gtactggacc caagccccag gaccccctgg agtcacctcc 314940
agccctccca catgccagcc cctaccctgg gcctcaggat ctgcctggat ggaggccagg 315000
ccgctgagct gctgggaatc tgttccacag gtgggaaggt cggcccgcca tgggcagccc 315060
agtccgggaa acttcctgcc tctgctttcc cacagtgtcc ttcgatggcc cccagtgacg 315120
tgtgttgaat gtggcgctgg ccccttgggc agcccagcag cccccacccc agccagccca 315180
gcctgggcag cactgggggc tcctggcttt gaatttgacc tatccagaaa caacggctcc 315240
ttcagtgggc tcagcccctg agaccactca gcctgggctg tgtgcccagc ggcacttcat 315300
gtacgtggac ggggcaggcg ggcaggcrgg cgtggaggag ctaatgggta agttaggcag 315360
cacattaaca aatgaaccag cggatggggg tggggagctc atctcattca tctacaaatt 315420
attaacaata acttgttcat taatgaatga acaggtgaga tacaggtcag tgggtgcacg 315480
aatgagtgag gagatgaatg aagcgggtct tttctcagca gctgacccac ggccaagccc 315540
ccgctgggca gcacgtccct tcctcctctc ccaagctggg tggtgcgggc agggagaggg 315600
tccatccgcc cttcagtagg tgaggaagcc acrggcctgg agggtggccc agcccaggca 315660
ggagggcacc agccccgggc cctcagtgcc ttcctgcaac cagggtccag gggtcacttc 315720
cttcacggcc cagtgagccc aaggcctccg tcctgccccc tgtctcttac cagctcgctc 315780
ctgcatcagt gctactgaaa tgggaaaggt ttccttgtcc cccttgcagg acatgtgaca 315840
ggggtgtggc tcgcttcttc agtgccccac tactcaaagt tctaggggag catacagtcg 315900
gacaggttgt ggggctccga ccccacagca gcgtctaggg gtgaatgttt acagctgaag 315960
ccccatgggt gtgtgttaca gggtgctctt tagtttagcc gtccatagac agcttgcgtt 316020
agtcagctca gttagacccc ctgccttacg gcaagggcag aggtctttct gtatcccgag 316080
gttcttgcct tggcgtactg gaagaatcag atcacacgtg ggcttggaga atgagtgcaa 316140
ggttttattg agtggaggta gctctcagca gatgggggag caagaaggga gatggagtgg 316200
gagggtggtt ttcccctggc atcaggcggc tcagcagcct gggctctcct gcgtccaccc 316260
cagccaaacc cttcatcgtt cctccggtca atggtctgcc ggcctgtcgg tgcctgttgg 316320
tgcctgtcgg tgtgctccta cgctggtgtg ttcctctcga cctaccctca acgtccagcc 316380
gcttgtgtct tcttctgccg atgtgttcct cttgatgtcc agccgcttgt gtgtctgccc 316440
actaaggtct cgagattttt ataggcacgg gatgggagca tggcaggcca gggtgttctc 316500
gggaaatgca acatttgggc agaaacaccg aaatgtctgt cctcacctgg gtccgtgcac 316560
ataggccgta gggtggaacc ctagccaggg acccgccctt ctcctcccag cacttccctg 316620
cccctcttcc gtatcactac caggaaaggc cacttggccc catcccaggc ctcgcccaag 316680
acagagagag agacaccacc ccctgcaaag gagcaagccg ggcccttctc tctgagacca 316740
cagggtggac tgtgttcagc agaaaagcca ggtagccagc gctgtcacca gagcagtggc 316800
tgacccacag catggcctgg acagagctgg gggcctgggc tggcaccctc agccctggct 316860
gcttgcagtc ccggccggct gtttgcctgt gaaggctccg gctgtgttct agggagttgg 316920
caggagggga ggcccgcagc agcttctagc ggcctgtgaa gcagccacgg ggcatggccc 316980
tctgtgcaga acaggatctg aggagccccg agtgttctca ctggatgtgg ggccgcatcc 317040
agaccttggc ggtcatggcc acaggctccc aaggccctaa gtgacagcca gtggtagacc 317100
cttcacggtc aggcacctat gactccccgt tccctgcctg ctcccaggct gtttggggtg 317160
atggaaagag gccaggacgt gaggccaggg taatagttcc tctcgtgtgt caggcctggg 317220
aggggggcct tcatgagacc atcacggaga tcttggggcc tccaatttgt caaatagttt 317280
tctgttacag ttcatactgt ttgcgttcct ttaaagacgt ctttgcccat cccaggtcgt 317340
gaaaatatta tccaactttc ttcgacaggc ccgattgcct catagttagg cctgtgactc 317400
tccctgggtt aactttgtga ccggtgtgtg gtaaggatca tggttgacat actttcacag 317460
gtgcatccac attgttccag caccatttat tgaaaagcgt atccttccgc cagctcgacg 317520
gcaaaggcgt cttttctatg aaccagtggc cacaggaggg tttgtgtgtc taatgtccta 317580
ttccacgggt ccccaggcca cagaccggta cccatccata gactgttagg aacaggaccg 317640
tgcagcagga ggtgagcggt tggcaagtga acgtgatcac ctgagctccg cctcctgtca 317700

-continued gatcagtggt ggcattagat tctcgcagga gcgcgaaccc tgttgtgaat gcacatgtga 317760
ggggtctagg ctgtgtactc cttatgagaa tctaatgcct gctggtctga actggaacag 317820
tttcatcctg aaaccatctc cccccacccc accccgtcca cggaaaaagt gtcttccacg 317880
aaactggtcc ctggtgccaa aaaggttggg gaaccactgc cctattccgt cagacccccca 317940
ctgttcatct gtctgcccac acgctcttaa tcaagccctg tggcctcatg aaaccctagg 318000
agtgtcagac ctctgacttt gttgttcttc aagatcgtct tggctattct tggcccttca 318060
cgttgttagg aatattttag aatcaccttg tcggtttcca ataaataaac waacaaacaa 318120
aaagcactgt gatattgatt ggaatcatat ttaatccaca cctcaatttg cagaaaatta 318180
acatcttata aatattgagt cttcttatac atgaacatac tatatcccca agtcaagtta 318240
gggcttcttt atctgtctct ccaatgctca gtgcttttct gtgtagcagt cttacacatc 318300
ttwaaacaga tttattttrg agytgggtac gatggctcac acctgtaata ccaactactt 318360
gggaggctga agtgagagga tcacttgagc ccaggagttt gaaaccagcc tgggcaaaat 318420
aacaagaccc catcttagaa gaaaaaaaaa aaaaataaga aagaaagaaa taaagaaaga 318480
ttgtgaaagc aagacagtaa agaagaaaca aaaaactttt ttgaaagatt tattcttaag 318540
tttctggtca agtttatggt tattgatgct attgtaattg atatgtttta ttttctaatt 318600
gttactagca tatagaaata tacatataca tattttaaag acagggtctc tgcattccag 318660
gctcagagct tacagcagcc ttgagctcct gggctcaagc agtccgccca tctcagcctc 318720
ctgagtagca agaagcacag gtacacacca ccaagcctgg ctatttttta aatttatttt 318780
ttctacagat ggggtctcac tatgttgccc aggctgatct caaactcctg ggctcaagtg 318840
atcctcccac cccaccctcc caaaacactg ggattgcaga tgtgagccac tctgtcaggc 318900
ctagaaatat aattattata tatcatcctt aaaaccggcg ttcttgttaa attcatgtat 318960
tccaacagtt tatctgagga ttcttaggga tttttttttac atgtatggtt atgtcatttg 319020
caaataacaa atgttttatt ttttcctgtc caatccttgt accttttatc tcccttttcc 319080
taccttttta acataccagc tgggactttc tggacaatgt gaaatagaaa cgataacatc 319140
cttgccttgc ttcctgtctc aggaggaaag cgtatcacat ttcactatta agtatgatgt 319200
ctgcttaggg tttgggtttt tttgttttag tttttgtctt ttttttttta ggtaatggag 319260
tttctattcc tagtttgctg agagttgtgt ttttaattat gaacaggtct cgctttatca 319320
aatgctttct tacaatctgt tgtgttgatt ctatttttttc tgacttattc tgttgatgtg 319380
aagagtgacg ctgcttggtc cttagagggt aaactcagca tgcacaagtg gattaaacca 319440
cattcgagca tgtgtttggg cacagtgcta catgcagctt gctggtggtg gttaggatat 319500
ttgcacgtat gttcacgaga gagattaacc tgtgattttt tttttctttc ttgaaatatc 319560
cttgtcagat tttgatatca aggttatgct gccttatgaa aatacttgta taaaattgac 319620
attatttttt ccttaaacat ttggaagaat ttactggtga tgtcgtctag atacagagtt 319680
ttctttgcca gaagatcatt aaaattccaa atttaactta tttaattaat attgggcaat 319740
ttggattatt tttgtttttg tgtctacttt tacatactgt gtttttaaat aatttgtata 319800
ttttatctaa atcatcaaaa gtatttttgt ttgtaatgtc ctctgaataa atgtttctgc 319860
acctctaggt ctatagtgac attccatctt taactcctga tggcggtcat ttgtgtcccc 319920
tcccccatct gatcagtctt cccaaaagtg tgtctgtttt attagtctct tctgagaacc 319980
aaattttggc tttgttgatt ttccttaaat aatgttcatt ttttatctca tagactgtgc 320040
tcttaacttt atctcttccc tcctactatc tttggtagga ggcaaatggt aatttgccat 320100
ttttttaacc rcttgagatg gatttcagcc tttcctctgc tctgagatat gcatttaaag 320160
ccacgaggtt cactgtctgt gcttatttca ctgtactttc agtacctatt tggctatgaa 320220
ttttaatacc ttacattttt attactattt aatttaaact gttgtttgat tctcattata 320280
tatttttctt tgacccctgg gttatttaga ttgtttaata tccaaaatac atggagattc 320340
cctagttatc tctttttatg gatttctaat ttaattgtac tgtagtcaga gagcataata 320400
aatatgattt gcctgctttg aaatttgttg gaacttgctt ctgaagtctt gcatatggtc 320460
tcttttggta catgttctgt gtgcactagg gaagcttatg tagtctccag ttgtagggag 320520
cagtgttctg tatatgtcaa gttgctaatc aggctgttca aatttgtctc tgacttgaca 320580
aagctttgac tgcttttcta tcagttactg acgaggtgtg ttcaaatctc ccaccatttt 320640
ctcttttagc ttttagttct gccagtttgc tttatgtatt ttaaggttat gtttttaggt 320700
gcatacaaat ttagaattga tctcgtcctg ctgaattgac acttttataa ataggacata 320760
ttcttcttta gtaatactta aagtctgcta ttggttttcc tttactagtt ttcatttggc 320820
tacaccatga cctatctttt tctatccttt cccaacatgt ttttgtatct ttatatttta 320880
aagtggattt atatagttgt ttttaatcat gacaatcttg atcttttaat tagactatta 320940
atccacttat aatgtatgca atctaccatc ttatgcttct ttttcatttg tttcatctct 321000
tcctttaagt ctattttctt ttcatgctcc aagctggcta ttttctttgg gttcacagct 321060
attcttttct actctgtcgt ccctgctatc caactcacct attgcattct tcatttccat 321120
tatggtcctt actttctgg aacttccttt ttatgtatct ataaatttta tttctctggt 321180
aaaattgtct atcttttcat ctattttctt gaacctattt atcatggtta ttttgaagtc 321240
ttcatctaaa tattctgaag caaagcacaa tcatctgtta gctcacaaat ctatgggtca 321300
gcaatctggg ctgcccagtt gggtggtctc acttggattc gatgacatgg cagtacttgc 321360
atggtgatgt ggtggtggct gagtggtctc tgttgtcctc acgtgtctgg agccactggg 321420
ttgtcagcca gggtctctca gctctccttc acgcggctgt tccagcaggc tagctcagac 321480
ttgtccatga gccaacagaa ttctaagagg gtaagagtag atgccacaag gtccttgagg 321540
ctgagcttca gaagacatga tcatttccac catggtggag atagactcta gcctgcaatg 321600
ggaggaacca caatggattg tgcccatctt taattaatca cagtctgccc tctggccata 321660
acttttcgca ttctccccta tgcaaaattc actcaccccc ctcccgacga tacctaaaat 321720
tctcacccaa ttacatgtgg catcatgctc aaagtccgac atcttgtgat ctgccccttc 321780
cagcctctgt ccaattcctt gtcccaaaat taatgctgta agttttagga tattgatatg 321840
acattaccta tttcttagtc cttatttctg tatcagttac ctattgttgc gtagcaaact 321900
agacctaaat ttagtggctt caaatatttt ctttgggccg ggcatggtgg ctcatgcctg 321960
taatcccagc acttttggag gccaaggcgg acagatcatg aggtcaagag atcaacacca 322020
tcctagccaa catgatcaaa ccctgtctct actaaaaata caaaaattag ctgggcatgg 322080
tggtgtgcac ctgctactca ggaggctgag gcagaaaaat cacttgaacc cgggaggcgg 322140
aggctgcagt gagccgaggt tgtgccactg cactccagcc tggcaataga gcgagactcc 322200
atctatatgt gtgtgtgtgt gtgtattttt ttttttcttt gcttagctag gaggttggac 322260
ttggttcagc taggaggttg ttctgttggt gctggctgtt agctgaggcc tctctcttct 322320
ccatgtggcc tctctaatca gcaagcttgt ttgcagggcc acattccaaa aggacatgaa 322380
ttatataccg tgtacattcc ccagtactct ttcatcagtg aagtcacaag gtgaccccaa 322440
attcaagtaa taggaaaaca gactccatct cttaatggaa ggagctgcaa gtatttaagg 322500
ctgttggaag taccacacct ttagatctgt atgatctctc ttttcccttg ccttttagtc 322560
tttcgtgtat aaaattgtag atgctcgagg gtattatctc cctacagata attttatttt 322620
cttctgccac gcgcaaagca ccttactcca gtaggggatt gagagaggtg gggttaatgt 322680
gatggaaagt tggcattgct tagtttctgg ggctgccttc tagatagctt ctaaacccca 322740
aagcttctct ccacagtgcc atgcgtctac tgagtactct gcttagcttt taccccttca 322800
gcaactgctt tttgctcagt ttctgtgatt ctcacccacc cgtgtggctt aggaattcac 322860
aagtgtttcc agaggaagtt gtgtgaaagg tggctagagg accagaatct ttttccctcg 322920
tgtcctggct gtcctgtggc cctggactcc acatttttat cactagccca ctgggccccc 322980
accctgttgg gtgtcagtgc tccccaaact gacaagtgcc ctgaggagga aacgctcgga 323040
tgcaggcgca gctcagttca tttcctttct atgtgggatc ctcaccttct atgtctttct 323100
tggtctccaa agcctcacac agctgttcct tgctgttggc atcacttagt ctcgcagtcc 323160
ctggtgtttc catcaggaaa gtcaggcagg cgttagcttc actgccagga gggaatctcc 323220
tgtggcctcc atggcgctgt gttttcttcc agtctttttt ctatgcacag acacatcatc 323280
ccctttgttt ccttttgtga tgctgtttct aaaaggatct ttatttctag aagaaacttt 323340
aggaggcaaa aacagcgcag ccccccttaac agagtggctc tggtggcaac tttcccttgt 323400
taatttgtcc tgtagcccct actttcccaa gcgcttgctg tttgtggggc tacaggacac 323460
agcagctgaa aggggctgtg ggcatcgcca gcatgtaccc tcttatccca tttgctgaca 323520
aggatcctga aggcccaagc atagaaagaa gttgctatgg ctgccatgtg tcagcagcat 323580
agccatggcc aactcagggc cctgactcct acctgacccc cttctgaatg acactcaagg 323640
taagggtccc cttcccactc acaggtgagg tgaaacattt caccttgaaa agcctcttgc 323700
ccccagcctc ccctcgagcc cacactggga catggcctaa gtatctccat cccatggagt 323760
tgaacactct ccttgtttct ggaaggatcc agtctgcgtg ctcctcaggc agtgcagggg 323820
cagtgagggg atgaccagca cagggtggcc actcacaatc tcctctcctc tctccactgc 323880
aggctgcggg aacaccatcg ggccaccatt aaggtcattc gacgcatgca gtactttgtg 323940
gccaagaaga aattccaggt aagccctgtg ctgagccttc ctgccctcag cctgcccctc 324000
gcagcctgat gcagctgccc acacctctcc tgggttctct cctgcccata gtggagggtg 324060
tcaaggcctc cgcccccaag ccacacaggc aggcctatct gagacctgac agtgcctacc 324120
ccaccgaacc ccagacagca ggcccctcag aggacctatc cttggaggcc cggcctggaa 324180
ccagggacac atgcagtgtc ttcttcacca agtagaaggc agcagccgtg tagctcactc 324240
agtcctcccg tggggtgggt cgtgcaaggc agcattagtg agagatgtga gggtgacatc 324300
agaatgactc agagatggtg cggagcctgc cctgagtcac caagctggga aggcaggtcc 324360
cccagacccc ccagccctgt cctccactgg ctcagtgctc tcattccctg ctcctccacc 324420
ctctgtgagt tgggaggatg gagggaggct gggccctgct ctgtaagagg tggggtcccc 324480
ttggccaggt gaggctggag ctccggggct tccataagct gccctaactt ctccaggggc 324540
atgtcccccc tacagaagcc ccttagagcc cccagagtcc atgccccgca gagaatgcca 324600
ttgatggcag gcatgtctcc cctcctgcct tggggacatt cctcggatga aggcggtggt 324660
ggggggtact gagtcctggc ttggaaatac atgtgtaggt gtgggaaccc cgtatcctct 324720
gtgatgggtg atccagaagg caaaaatcac aaagcaggga aggctggggg gtgacttgcc 324780
tgagtccctt ggagcggagg gcgtgtgacg tgcttgagtg agtgcgtgtc tgccggagca 324840
gggcggggtg gggcttctga gctgggggcc cctggcacct cagccacagc ctcaccagtc 324900
ataaggcaca gcccaggaag gctcagcaat gtccgccgac caccaggacc cacagtcggt 324960
ggcatcccag cccaccaaga cttatcctgg agccactgag ctccctgcta gggtctggtc 325020
agggcttatg gggcctttg tcaagaggtc gttgggtcgg gctgggaaga tcatcttgac 325080
ttcaggagcc tgagatgagc caagataatg cacagcccat ccagacggac tgacagtggc 325140
attcaagtct ggtccccctg cagccatgtc tttcacacca ggccacacct tccactccag 325200
gccccaggat tgacacaggc ccgcccacag tctccttggt ggagccccca cccatctggg 325260
ccctggagcc acctcagcct ccagacttca cagggcggtc tgggtgcaga ccctggcaca 325320
ggcagccctg ggcaagttct tccccagctg tgaggggaat gagagcctaa gggtttggca 325380
taagatcata tgcacgtgcc tcacccgggc cttgccccca gcaaccccag gccagcaccc 325440
gctaggctcg tcgtcactct gagccccaag agcagccctc ggccaggccc ttgccaagag 325500
cagtatgcgg gccctcgttc tggccaccgg gccaccatct ccaggggggt ttcgcatgca 325560
cagccctccc acagtggtgt ttctcagctg gccctcccac ctgcatcccc ccagggaagg 325620
gggtggttca tgactcaact gaaccaagtt gtgtcaaagc tcccagcagt gcctgggacc 325680
tcttgcagtc aaaataaaag ccatggcaaa tgccactgct ggccagtgcc cggagatctg 325740
cctggcatgt tctaggggag atctgacagc ccctgtggac cagggtgtct ccattctggg 325800
accgtctcct ctctctggtg ctggcatgga gggccttgct ggagcaggga gctcactcgg 325860
gggcaatgga agagagaggc cagcctcctg gcagcaccag tgctctccca gacagggaag 325920
gggctgcgtg aaccccttg ggactcagat ctgggcaggg cagtcccccg agggcagagg 325980
agaccatggg aagggccagg gtgtgtcagt tcgctggaga acagcatggt cgtgacagcc 326040
gaagcagctg acgtcacccc agcagtagag cagagggaca cagggagcct cccagggtgg 326100
ggctggtgtc tggcctgagg gtgcagagca ggtcccagca gggcagagcc agagcccacc 326160
aaggcttgca gaactgcgcc acttgggcat cctgggggct gcttccaagg tctgggggaa 326220
cccagcagag catgcagacc ctgatggctc ctgggcaggc ctagctccag gggtggtgtg 326280
ggcagcttcc agctcaggtc aagagatcat ccagccatcc ctttctccat cagccaggaa 326340
ggacactggc attgaggttg atatcaagga tatcccatcg tgataataac taccatggct 326400
tccagtcttg tggtgaaacc tcagatgcgt agcctcctgg ccaagcgtct gcaatttcat 326460
gttgttggag cattcgttga atacctggga gttgcagctc tctgtaagtt tgatgtggct 326520
gaaccaagaa aaaaagcaca cgatttctac agatattatg atgccgtcaa agattttgag 326580
gtgatgagga aggctggcat ctttcagagt gcaaagtgat tttggaatat aaagaatttc 326640
tttgggttga attacctaga agcttgtcag tgacctgtgt tcctgaactg tgaaacatga 326700
atatatgggc caagaaatgg tttctcttgg taaataagca attaacaaat acaaaaagag 326760
agagagggag agggacagag agagagagag agatcatctg cgccagcccc agcaggccct 326820
gtcgctgagc cacaggtgaa aaagctggtc cctggggagg aacacagtga gccctgcact 326880
cccttccaga caggagggag tgggtcccct ttcctgtctt aggacacagg ccgggaccct 326940
gagaatggcc caggaggctt cctgaagcag actgggaaac ccccacccca ctgtctgctt 327000
ctccactgct ccctggccct gggagccttg cagaaacctg gcaacagcag gatcctcgca 327060
gggcacagag gctcctgcac aaagccgctg ggctccctc cgacctcacc agctggctct 327120
tattgctggg agcagcatgg aggggtgggg ccagggtgag gggagcagta gcccgtggca 327180
gtgaggagct gtgtgtggct ccaggggctc ccctagccca cctctcagga tgcttccctt 327240
cctcgacgcc tgcctgtctg cttgcttgca ccccacccca cccccgctgg cctcaggggc 327300
tgctgacatg gcaggtgacc cctctgccta ccttgctggc tgataagtcc ttggccaacc 327360
acccctgtgt ctggcccaag gagccggagc ctctccaccc ttcaagtgtg ccttgaactc 327420
cctgtccacc atcagtcagt ctggacaggc ctgcattatc tcggctcatc tcaggctcct 327480
gaagtcagga tgatctttcc agcccaaccc cagaggacca ctggacaaag gcccccgtga 327540
gccctaaccg tatcctagca ggcatctcag tggctccagg ataagtctct gtgggctggg 327600
atgccaccgg gccgtgggtc ctcatggtct gcgggcattg ctgagccttc ttgggctatg 327660
ccctacacca ggtaaggctg tggctgaagg tgcagggagc tctctgctga taggcccacc 327720
cagccctgct cctgcagacg tgcacacact caggtacata atacttcctt gcccacaaca 327780
ggcctgtttg gaagcactcg catctgcaga ggctgctaac acacacacct acacccacct 327840
ggtcacagtg gcccagagac tcctagggct tggttttccc ctgccctgcc tcccttcacc 327900
tgcccacacc gcacccagat ggctggaggt gccccatgct tcagcttcac agagctctgt 327960
ggtctgcagg aggctcacca ccatgactca tgccatgttc aatgtgttct gaagagaggc 328020
ttcggccaca gctggctgtg actctggctc tggcatggtg ctggcttagg attccctgac 328080
ctttctcaac tcccatccta tgtcatcctc actccctccc ttaaggcaga gcaaggcagg 328140
gctcagcatc ccatcttaga gaagagagcg tagaatctcc atcatacaga agggacatac 328200
agaagggaga aacagagttc aacaacccgt cctacagaaa ggaagatcaa ggctcagtat 328260
cccatcttat agaagagaga ggcagggctc agcatcccat cttgcagaaa ggagcttaga 328320
atctccatta tacagaaagg agaaacagag ctcagcaact catcttacag aaaggaggat 328380
caaggcttag catcccatct tatagaagag agagacaggg ctcagcgtcc aatcttacag 328440
aaaggaggat caaggctcgg catcccatct tatagaagat accaacaggg ctcagcatcc 328500
catcttacag aaaggaggat cagggctcag catcccatct tacagaaagg aggatcaggg 328560
ctcagcatcc catcttacag aagggagctc agcattttca tcctatagga aggagaaaca 328620
tcccatcttc caaaaggggg gatcagggct cagcatccca tcttacagaa aggaagatca 328680
aggctcagta ttccatctta cagaaaggag ctcagtatct ccatcttaca ggagggagaa 328740
acagggctca atatcccatc ttacagaaag gagaacaggg ctcagcattc catcttacag 328800
aagggagctt agcatctcca tcttacagga gatgctacca ggtacaagag atgctaccag 328860
atgctaacag ggctcagcaa cccaccttac agaaggggag gattgaggct cagcatccca 328920
tcttaaagaa gagagagaca gggttcagca tcccatatta cagaaggggg aatcaaggct 328980
cagcatccca tcttatagaa gacagagaca gggttcagca tcccatctta cagaaaagag 329040
aattaagact caacatccca tttcatagaa gagaactcag catctccatc ttataggaag 329100
gagaaacagg gctcagcatc ccttttacg gaagagagag acagggctca gcattttatc 329160
ttacagaaga gagaagaagg acttagcatt cccatattac aggagaaact gagacctgag 329220
gatgttatta ctagcctgta cataagtacg gtttttacgg gccagagggt ctgcctagag 329280
tccaacccca tgcctgcctc tatcacagtt cttggtgtgt catttctggg caatgccggc 329340
gatcctggtg cccagtgtgg ccccaggagc agcaggccct tccttccatg gggcacagct 329400
gtgttgtgag gacacgggcc ccatcccagc cctcctgatc tcaggatctc ccgttcaggg 329460
cccagagagt ggctagtgtt gccagtgagg gccctacctg cttgtgtcag gtggaagagg 329520

-continued aaccccctga acttctgagg cccagccttt ggtagggagg aggtctctgc cctgtcttgg 329580
gattcctggg gtccaaaaca atgttgggcg ggctgtaaga actccaccaa gcctccggca 329640
ttggtggcag aacccctggg catgtcagaa gtgtgtctag agctgaaagt gggtacatgg 329700
agacctgacc tcagggtctc cccatctggg aacttgctgc ttcccagggt agaagtggct 329760
gcatcctcag attaaggtca ccctggtctc aggagtagga ccccaaagag aggtagcagg 329820
tgggcaggga gggcatgttc ccagacccag cccgggccct caacggtacc tgagcttcct 329880
cctttctcat cctgggcctc aattgcctcc ctctgacttg ggctggccct gccccaccct 329940
tccccaccaa gccgcttggc tcgtctcttg ggccttgcaa attcccccagc aaaaggcagg 330000
aaagccacta gctcagtgct aaggtggcta tttgagcact aatgatgact accctgggcc 330060
tcacccggtc acccagtggc ctctcgggat agaggcagtc tgttgtccta tgtgctggct 330120
tgcctgcagg gccaaggcct tcctaggcca tcaaacccct gctcagcctg gctgctccac 330180
ctgagtgagg cccttgggag caaggccaca aatgtggctt ggggtttcct gatatcatga 330240
gatgctttgt tttctctgtt gtggtttcaa gatgtcacct gagtcccact tataggctta 330300
gagctggcaa caagcctggg agccctgggg tcccctgccc tgcctcacat ggccccagcc 330360
ccactgtggg agcccaagca gatgctcgtc acccacagca agtgctgcag gctaaggccg 330420
tcatctgggg ccacccctgc tgcctggcac aaactgccag gaacgatgca gaggagaccc 330480
gctccctacc ctgaggacag tggcggctgc agccagtgag catgtcaagg gtcagtctgg 330540
ggcccaggta ggtagtgggc atgcagagct gtgcctcctg gtcagtgcct ggcactgtgc 330600
tgctccttga ccccttgggg gggccagctc ttcctgaagc cattgagaac cagaactggt 330660
agcctggggt ggtggggggt ggaagggagg agacagcagg cccctgccgg tgagtagaca 330720
ggaagctggg acccagagag gccgagctga tggcccagga ctacccagag acccatggcc 330780
aagctgatgg ggacaagctt cgctactgtg cacgcttgga accaggctta tgccatcacc 330840
acataggcga gctcccaggt cttcacaagc ctcccgaggg cagacactgt cactgcctgc 330900
actttgagcc acatggctgg ggcacaggga ggagaagtga tgcgtgtctt tttgtcccgc 330960
agcaagcgcg gaagccttac gatgtgcggg acgtcattga gcagtactcg cagggccacc 331020
tcaacctcat ggtgcgcatc aaggagctgc agaggaggtg ggcacggcca aacggcagcg 331080
gggagggtgc ccgggtcctg cccagcccgg ccccagctgc atgatcagcg gtgccggagg 331140
agggaggggc tgagaccctg agttcttgcc tctcaaccac ccccttctcc tcaccacccc 331200
cacccctgca gagggagggc agctggccac ggccacggtt cacagccagc ccaccaggca 331260
gctctacctt gttccccgcc cggatctgag atgatggggg aattggggta ggggaggcgc 331320
gtaggggagg caaacacccg cctccgtccc tgctcaggta gcaacaccag cttcacactc 331380
cccacaactt caggacactc ggcagccagc ccacccgcct tccctgtcac ctctgagcaa 331440
ggggccaggc ccagccctgg gaagacactg cctggtgcca ggccccaccg cacgggtctc 331500
ccccagactg gcctggagct ggagaccctg actgtgggga gctaatgtgt tcccatggag 331560
ctagcaccat cctcccgggc ctgcacagac tcagagcagc tgtgcctccg agatgggctc 331620
gcctgggaac tagctccgtg tgttacaggg catggctggg agcccgtgtc catcctggcc 331680
acaggcgagg ggtcaggctg ccttgcccat ggctgatcca ctgcctccca ctcctacccc 331740
cagggaggaa gtctgagagg cagcccaccg actccccctt tccgagatcc ctgctcagcc 331800
ccctcgggag catggccctc tggggggttg ggagtgacct ggcaggcctt agggtcgggg 331860
gtgtccccag agtgggtgga cagtccactg tcttgccggg cacgtcaagc tgtctgtccc 331920
acagacgaca gtgcatctgc gcagtgccag ggccaggtgt gaactggtgt ctgtgtcctt 331980
ctctccaggc tggaccagtc cattgggaag ccctcactgt tcatctccgt ctcaggtggg 332040
tttctgtgtc agttactctg ggcccagcag cctgcaatgg actctcccgc acctctgccc 332100
tcctggctct ccccatgatg tcagaatggg ccattgcacc tccaaagtgc atgacatgaa 332160
atgaaagcca gggagtaagg ggaggtagac cccaccctta gcaaagtggc tccaaagtac 332220
gttttacaaa ggaatattca ggtttcataa gaacctacct gggtcccttt aaattccagg 332280
gcgttgaggt taggctctag gtgtggaaac atgaacccag ggcaactttg cagaaggggg 332340
tgatcctggg gtggggtttg ggtggggtga gctgccagcc cagaattcaa gagactatgg 332400
gtgggggcct tgcagggctc aagttgagag ggacagaagc acctggctgc agcctggggg 332460
ctggttttct ggctccttga ccaaattcct tgggtcccct ggacacgggg ctgtgagtca 332520
ttccggggaa tgacagggaa aaggcacatt ccctggggtt tccctagccc agatgccaac 332580
agcagccacg gctcatagtg tgggctggtg taacgggggc agtggaatgg ctgtgccccc 332640
agcctggagt caggcctgtg tcgccctggg agtggaatgg catgggcttg cacagctggc 332700
agtgtggcca gcttaggcag ccccctaggg ctctcagagg tcagaggtgg agagcgtgga 332760
gcaggatgga gcccaggtcc ccagctgcag ccatgcccgg ccaccgtacc acccctggta 332820
tttttgtcat agcatgcttt ttaaaaatgt cctagtaggt ttaggcattt tgactctcag 332880
ctacctcccc cagccctacc accccacttc ccaagcccag ctggggtccc cggcccaccc 332940
cagcacttgg ccctgatttg ggtgttttat cccccataga aaagagcaag gatcgcggca 333000
gcaacacgat cggcgcccgc ctgaaccgag tagaagacaa ggtaggctca cgcgccggcc 333060
tgcggtggtt ctggttagcg tcctggggcc agcaggcacc tccctgtggt ctgcgtgtga 333120
acgtgaagct cctgcaggcc tccccacctt cccgccagtg cctactgcag cctgcccagc 333180
aactcccaag aggggcccag gcccactgcc cacctggcgg ggcattggtc ccccatggaa 333240
ggagccaggc caggctggtt tctcatcctc tgacaagtgg cgtctttact ggcaggtggc 333300
accaagtgcc ccctccccc agctctttcc cgctgcctct cgtagtctgc tttgtgctct 333360
gcgagcctcc tggctgtgtc ctgagtggag ggtggcagaa gctggcctca catcccagcc 333420
ttctcctggg cccagctgtc tggggcctcc acttggggcc agccgagggc tcagggaggt 333480
gcagggccca gctgggatgg gttcatggga agagaggcat cttctgttca ccccgaaccc 333540
accaggcccc cactccccac caggctctgt gcccatcact cggtccctca ggccggagcc 333600
tctcccccag gcaccctggg agctgccggg ggatctgggc ggtggggagg gcctttctcg 333660
ggcccatggc tgagcccacc actgcccttt gaagtctctg tggtttgaag cgggctgtta 333720
tcttgccgaa cagcaagtcc gtctacatgg actttatctg aaagtagctg agaggctaaa 333780
aatagaggag tttcagttgg gcagggagtg cgtctgccgc ccggtttccc tggcaacgcc 333840
tggctctggc ctgcttccat ctcggctgca gccgggcagg cggggcaggc acagcccggc 333900
ccaggctcct gctcctgccc cacccgtcct ggcccccagg acctgcagcg tcaccctctc 333960
cccacctggc accatctgcc catggcctgg ggcggccgtg gggccctgag accagcaaat 334020
tgggtcatgc agaaagagcg aaggctggtg ttcaggtgcc tggccccatg ggctgtgtg 334080 accacagtac cctgagtccc atgggcctgg ccaccctctg tcagcacaga cctgagcagg 334140
gctggtgcag acctttgcca ggcagatggc ccagtgggag atagcgccca tctggcagga 334200
caggaagcaa gacccgggag aggtcagctc acaggattgg caagctcaga ggcccagaag 334260

-continued ccttggcctc tctgctgccc ggggaacacg gtgtttccct ggctttctct ttgcgcaagg 334320
gctgggtgac tcctggctgg cacacccagt acagcagggc cgggtaccct gtgttgttgg 334380
catggccagg agtttctaga catcaaggaa agccgtggta gagacaggga gtggcaccca 334440
gttccccagc ctccactcct gcttccatct cggctgcagc caggcaggcg gggcgtgaac 334500
atccctgacg tgcaggagtg tcggtggccc tttctggaca gcacaggctg gggacagccc 334560
ccgcctttcc ccgccactcc ctgccaagct ctggttccat tgcctacact actgtcccag 334620
acctttctta cggctctgcc cctgctccat gggacaggcc accctctaag cccagacctg 334680
gagtctggca tcctgcgggg gtgatggtgg gtggcagaca gggcctcctg aagtgcaatg 334740
gccccttcct gacgtgcaca gcagccgtcc agcagcctgc tggggcctgg gaacaaggac 334800
acagtcctca gtcagccaag gtcggtgtgg gggcctgcag aggggccagc gctggccttg 334860
aaggcacaaa attatgcacc caatttcttc acatctgagc aacaaaggga agcattttcc 334920
ggagtccctg atccctaggg caaggtttaa gaacaaggct ggggccacat cctggtgccc 334980
tgtcaggctc tgagccgggg ccacgaggat tctggtagat tctgcatgca cagccctggt 335040
gggccctggc tccctgccgt tacattcgag tcctctgcct ggggtctctg aggtggtgag 335100
tggcacccac agtcgacact aaatctcagc cccgctgagg ggtctacctg gaacctggct 335160
gcccatcaag gagttgacag agctgtgctg acctaggtgg gtaggtggta gcctacccgg 335220
tccttgccct gccactgact ggtgcacccc tcagggacag accctaggaa agggcctggc 335280
tgggcctgga gggcttggtg gcacagcctg gctcgagttt tctccgttat cagtgcagcc 335340
atcgggaccg taaatacccc aagcgcaatc ctgctgactt cgggaagtag gggcaggaaa 335400
tccagcagcc gcccggccct cggaggccca gcaggcgtgc agcggtgcca atgcccgccg 335460
gccccgccaa ccccagccag agcccctggc cttccctacc agcaccctcc cccacctcat 335520
cccgctggtc tggctgcctg ccggaaggga gtcaaggccc cagcctccaa ctgttttctc 335580
agctcagctc agcccctcag ctgggctgtg cagtgagtcc caccccaggc cagcttgcct 335640
agccatagga tgagaggtct ccgggatgca cagctggctg gcacccctcc agggaggcct 335700
agagtgtccc cctgcaggga gttcaccagt gcaggccagc tgagcttgtt cagggctgcc 335760
tcagtttccc tggcagggag ccctcttctt ccttggtgtc ctggccaggg acccacattg 335820
gagagagggg tctgggggtc tcccttctcg tcacagtcct gcggcctcgt caaaactctt 335880
gcttgacagt gcagtgtctg ctccaacaca gacctcccaa ctaccttgca ggacgtcccc 335940
attccaggga tcccttccac ccctgtgcct gtcctggtgg cttaggttct gcctcactcc 336000
agggtgtgga gagcagaaac ccacccacac ccgcagatcc aggggcctcc tcacagcgag 336060
tctacttcct gcgggcctcc ctcccctgtc aaatgagagg gtttgactcc tgcttgtgtc 336120
cttagggtca aaagtcacaa aagctgcctc atgccctttc tgttttcatc ttagattatt 336180
gtcttcttta tcctggagag gactcttatt tgctcaaatg cccacataaa tcctctttta 336240
cagatgggga aaccgaggct cagagaggct gagtggtcgc ctgaggtcac acagctagtt 336300
aggtgaagag ctggtcccaa ggaggacaca gacaggggtg ggagatgagg tagagagagc 336360
aaggaggggt ttcatatcac ccaaagtccg tatggagagg ctgaggaggg ttgaggccag 336420
gggcaggctg ggggcaccag cagcagggcc cagggccttc agtgtgggcc agggaccaat 336480
gcaggcggtc gggagaggtc cggagagagc tggccctgcc cactccccct ctggccccac 336540
tgggcttcct gaagtcccac acagggctgg cagtctgtgt gggggctgca taccccagac 336600
attctgagga atcgatggca gaggccgctc cagccctcct cccccagcaa gtattcttag 336660
cttggtctcc aggacctgcc acactgttta cgttgggccc tgtttatttt gcaagctaag 336720
ctcatactgc ttttgctgat atgaggagca cagtgggctg ggagagtttc tttcttctct 336780
gtttttgccg gaaatgttca tggctgagag ccggacacag gggagtcctg ggtttccatg 336840
ccgcagttca gaaagcgttg ggcgggaagg ggcccccacc acctgacact cctttcactg 336900
cctccggtcg cagaatccag gcctccagga tgagaatgcc ccccaaccca ggactcccaa 336960
aaccacaccc tgcccatgcc tttaccaagc ttcgtgcatg accccaacct ccaggatgca 337020
ggcaggccca gcctcccaga attgggtgtt tgcccccaga cactgctacc ctttccctca 337080
ttccagtgtg actcctccat caaccaggcc acaagctgga ccccaaggct tttttgtctt 337140
gggcagttcc ccgagctgca cccccagagc cgccgtgctg ctgttcatcc tctcccttta 337200
gcccaacccc tgctgagttc aggcctttat catctcttac ttggattatt tttccagcca 337260
tataataagt ctccggcctc tcctcacacc caccaatcct tcacattgta tattatttct 337320
taaacactgc tgaaatctca cttactaata tttaatatat cagaattttt gtgccagtat 337380
ttatgtgtga gatacataca tgacataatt ttcctgtctt gtatggtctt catcaggctt 337440
tggtgtcaaa tgtatgtgag cctcacagac taacttaaga agtgttccct cttttcctat 337500
attgggatat tttgtataag attagaattt tattttcctc aaatgtttgg tggaatttaa 337560
aggtaaagac atctaggcct ggtgttttct ttgtgggaag attcatcatt cctgattcaa 337620
tcgctctaat aattatggac tgttcaggtt ttctatttct tcttgtatca gttttgataa 337680
gttatatatt ctaggaattt atacatttca ttttagtttc catgttcatt ggcatttatt 337740
ataattttaa tgtccgtcca ttagcattta gtcccatttt ttattctcaa tattatttat 337800
ttgtgccttc actgttttcc cccttagtgg tcaaacttga cactattccc ctgtcttatt 337860
aaatgtttcg tggacttctg gctttgctga tcctctctat tgtgattttg ttttgtttca 337920
ttcacttctg tttattttat tccttctatt tacttggcct taatatactg ttctttctct 337980
aacctctcta aattaagaag aggataattc ttaattttca ggcttcctaa atttcctttt 338040
cgttttaatt tttctaacca ctgtcaatct catggctttc taaattttta aggtatgcat 338100
ttaaggttat aaatttttcc tttaaatatc atccaaacta catctcccac attttgatat 338160
atggcattta attttaatct tcattcactt tagtattttt ctaatctcca ttatgatctc 338220
ttgtttatcc taggagttct gtagcaatgt ggtttttgtc attgttataa ttgtagcaca 338280
gctttctcat aatgttgccc tcttgtcaga gaaagcaatc catatgatat taatccttta 338340
gaatgttttg aaatatgatt tacggcaaaa atgtggtcaa tttttgtaaa tgtgccttct 338400
gtacttgaaa acaaggtata ttctgacatt gttgggtgca gtgttatgtt catatccact 338460
ggaacaagct tgttagttgg tctgttcaaa tcttctatat tctcattgga atgtttttat 338520
ctgcttgatc tattattact gagaaggcat agggcaaatt tctgtttaac tttctaagaa 338580
acttctaaac tgtttccaaa ggatttatac cattttgctt tctcaccagt aaagtataaa 338640
ggttccactt tctccacagc cttgcaaata catggtcttt tctattttag cccttttagt 338700
gagtatgtaa tggtatctca ttgtggtttt gatttgcatt tccctaatga ctaatgatgt 338760
tgagccactt ttcatgtgct tattagccat tcatagtctt ctttggtgaa atgtttattc 338820
aactctcttg cccattttct aattaagtag tctgttctat tattgagttg caaggggttt 338880
ttatatgttc tggatacaag tcctttatca gatctatgac ttgcaaatat tttctcccat 338940
tctgtggctg tcttttcatt tccttaatca catcttttaa atcacaaaag tttttaattt 339000
taatgaagtc caatttgtct tttcttatat ggctcaggct tttgatgttt tatctaagaa 339060
ctctgcctaa tccaaagcca taaacatttt ctcctgtttt gttttgggtt tttttccttc 339120
tagaagttgt atagaattag ctcttacatt tcggtctata tttactttga ggtaattttg 339180
gggtatgata tgaagtaaag tctagatttg ttttgtttta ttcttactta tggatatcca 339240
attgccccag aacatttgtt gaaaataccc catttcctcc tttgaattat catggcttct 339300
tggtcaaaaa tcaattgacc ataaatttat aggtttattt ctggattatc aattctatta 339360
tgttggtcta tatgcctttc tgtaagtcta tatgcctttc tgtaaaccca tactatactg 339420
tcttgattat tgtaggttta cagtaagttt taaaattaaa ttatgtaagt tttctaattt 339480
tgttcatctt tttacaaatt gtttctgtct attctaagtc ctatgaattt ccatataaat 339540
tttaggttca acctgtcaat taaaaaagaa gggcctgctg ggattttgat aggcattgtg 339600
ttgaatctat agatccattt ggggaaaatt gacaacttaa caaaattgag tattgtaatc 339660
aatgaacatg gtatatccct ccatttattt gatctacttt aatttctttc agtgatattt 339720
tgcagtttgg ggcatataaa tttggtactt cttttgttac atttactcct aaatatttta 339780
tttgtcatgc tagtgttaat ggaattgttt tcttaatttc attttgaatt aattgttcat 339840
tactagtata tagaagtaac attaaatttt tatatcaatc ttgtaaactg acttttctat 339900
tcttggcttt agccattttt gttgttgcta ttgatttctt aagattttct acatatagga 339960
tcatgtcttg tggcaataaa gacaattttt acttctttcc agtcagatgc ctttaatttc 340020
tttgttttgc ctaattgcac tggcttgaac ttcaaaaaaa atattgacta gaagtgctag 340080
agcagatctt ctggggaaaa tcactcaatc aatttccatt agctctgagt tttccataga 340140
tgccttttat catgttgaga atatttcctt ctatttttag tgtgttgaga gctctcatta 340200
tgaatggata ttggattttg tcaaatgctc tttctgtgtc tagtgagatg gtcctgtggt 340260
ttttattcct tattctactg atttggtata atacattaat tttcaggtgt taaaccaatc 340320
tcacatttct ggaatatatc ctacctgggc atgatatata atccttttta tatgatgctg 340380
gatttggttt gctaatattt tgttaagaat gtttgtgtct tcaacctagg aaagctgatt 340440
gaaagaaaaa aaaaagaatg tactttatat tcataaagga tactggtgtg gttttctttt 340500
ctgactttga tgtcagattt ttaaatcctt ttctttttaa tcctacaacc gtaggatttc 340560
aggtttgtct tttgtaaaca ctgtattact gagtttttaa aaaatcattt aatacattta 340620
tatttaatat aatttctaat agatttggat tgaattctag cagtgtattt tgtgctttcc 340680
acttgtacta aatctgtaat atttattttt ctcctctttc ttgcctctca ttagattatt 340740
acttctcatt ctacttttct ctctactggt tttgaagtta tgtattctac taccatcctt 340800
ggaaaggtta acctagaaca ttttaaatga atatatatca gaagtaattg ctatatctac 340860
ccatatctgt aataaaatag ggatcctaga acactttaac ttcaattatt ctccccctga 340920
cttagtactt tgctgttgta tattttagtt gaactgtgat taattttttaa ctcactaatt 340980
ggtagtgttt tatacaatca atatttgttt aaatttactc acccatttgc ctctttgtca 341040
tttgttattt cttttttatc tcagatctta catctgggat tacctttttta tgtgactgag 341100
ggattcattt aaattttctt cagtgaaaaa ctctcagatt ttgtccgcaa atgaccattt 341160
tactgtcatg ttaaaaaata tttccaccaa ttataaaatt ataggcctta ggttatcaaa 341220
attctttttt cttagcacat taaaaatgtt attgaactat cctttggctt ccactgttac 341280
cattgagaat gaagatgatg aattgttgct ccttggaaga caatctgtct tttttctccg 341340
gcggccttta agatctttcc tttgactcta gtctgcattt tcactaggat atgttaatag 341400
gtttcttttt ttctgcctga gctaccttac tcagtggttt ggtgtctttc atcagttcta 341460
gattattctc agttaatact tcgtaagatt tcacttcagt ctcattatct ccttctgaaa 341520
tttttattgg ccagtagtag accacctcac tccccttcat atctcttaac cttttttttt 341580
ttttaaatca ctttgtctct ctgtactgta ttctggaatc catcttccag ttcactagtt 341640
gtttctttga ctgtgtttaa tctgctgtta aaactgttca gtgaatttta aacttcaatt 341700
attattattt tatttataaa agttctgttg ggttcttatt catatctgat aagtcatttt 341760
aatcgtatct tcctctttac ttgcctgttc aaactaatat attttcttga agtgtattaa 341820
atatggctat tctatattga gcttctctta attccagtat ctaaagtatt tctgagttca 341880
cctccctgtt tgatttttttc ttctgctgac tctcattcat ggtgtttcat ttcgtttctg 341940 ttttttttt tttttttca ttgtaaactt atatatctta aaatttatct gtgggaattt 342000
ttgaagtctg gtgtgaagtt ggggtcctca gggaggaatc atgtttaccc cttccattgc 342060
cacatatgtg ggtgtactgc cagcctggac ttttaattct aggctcaaag ttttctaggc 342120
cacttaggta gtatgaattc aagcctccaa gctgagcatg gactaacttg tgaacatgac 342180
tttccaggac agaacttgtt ctccttctct tagcagtaat gcagttttct ttacaatctt 342240
ctcagggagt aggagatttt tcattggccc tcacaatgaa agcagagccc tttgagggtc 342300
ccagctttgt gtaagtctct gctatgagac ttcctggggc aggcctgggc tttgacacat 342360
aatcatctat tcctggtgaa accaaagctc aagttcatct cactcatcaa ataccttcag 342420
ggcccctatt acctctgggg ttccactttc actgagtttt cagcctctaa cctcccttac 342480
ttcctggtca gctcatccat gctagccaca gatatcattt taaattttct aatagccact 342540
tttttaattt aaaagaaata agtaaaattg attacaataa tatattttat ttaacccaat 342600
agatccaaaa tatcatttca atatataatt aatattttta aaactcttaa aattgttgac 342660
attcttcttt ttcatactgg gtcttcaaaa gccactgcat attttacaca tttcaattta 342720
gacaccgagt tttcatgaga acgacttggt ctgtatttag atttcataaa atttaccatt 342780
gaaaaaggag attcccatgc ctaagtcatt tcaaacatac tgaagggttt tctaataacc 342840
gaatgaagga tctatcttta aattttaatt ttaatttatt aaaatgaaaa gaaaattcca 342900
ttcctggatc tcagtcacca cttttttaag tgctgtgcca cacagattca gctatgggac 342960
agcgctgctt tggacgggca tggccgtgcg cgcgtgtggg gaggtgagtg tggctccccc 343020
aacgtttacc caggccagcc ccaaggaaat gctcagtgag tgcccataga atgtgttgaa 343080
tgtggatggc agggaccata cgggatagca cactccagta gttgccaact catggcccca 343140
gtgcccctct ccaccccatg cccccaacag agatgcatcc ctgcagaccc ctcctgggct 343200
ccttctccac agcatcctcc ccaagttccc ctgcctcgag tccccagagc tcatgaccca 343260
cgcctccccg aggtccctaa ggaatgtccg cttgggattc tggttctttt ccggttctct 343320
gcagccaggt ctgttccctg gcgtagttcg caactggaag gtgctgctca gcagactgtg 343380
agaagtgtgt gtcggtgcag gcaggacaca cttccaggct gtcccagagg ccagggagca 343440
ccttgccact gaagggctgg ttgcatcaga aagttaggca gcctggactg ccctggcagc 343500
cccagacctg cctctcctcg gcagctcccc ctcccctctg caccaccccc cgccccccac 343560
acccaaccca acactcctct ctctgctgct gggctgctct tgagtgacag ggccgtaaat 343620
aggcaaaggc gggggctctg actgatcaaa gggctccctt tagaagccgt cattagtttg 343680
ctattctggg aactggttat tttaaggtta gtgtattttt tctttcctga ggagccgtct 343740

-continued tagtggatgg cggagtccgg aggggctgcc cttcagtcaa accacacaag ccctgttttg 343800
tctggggttc caaagataaa cctataatga aagcagcgtt tgacgctgag caccgccacc 343860
ctgttcctgc acaggggtgg gtgtgtctgc cagggagtcc ctgtgcccag caagctccgg 343920
ggaggcttgc aggaggcccc tggggccagg ttgagtctgc tcccagggag cctgaggtgg 343980
gaggtcttca gacctggcat tctcacagcc atcatggctt gcctggccag ggaccgaggc 344040
cccgtaccct cccccaactt caggctaccc ccaaaggcca cccctggaac caggctcagc 344100
aggcacctct gaaccgcagc ccagctctgc ccagcacctt ctttggaaag acagtggacc 344160
caccagtggc caggggaatg cacaacccta aagtcaaaat gtaaggaaat gatgataccc 344220
tgtgctggca tgggtgcgga agagcagacg ctcttctgtc ttactaggag gtgggaatta 344280
atgaaagtaa caactcctgg aagggactct agcactgcct gtgaaaacta gaaacccgtc 344340
atcactccta ggaaagaaaa gcaccagggt cgggctttgc atgcaagctt tgtcatgtga 344400
caagctcaaa gccatctgtt tgtccataga gaagcgtggt atatactgag acacctcgac 344460
gccgcagccc cagtgcccgc cacagacgag cttttgccgg cagtcattgc tcgggaggga 344520
tattattgat gtgttgctca gtaagaaacc aaagttgcca aggaacgtga tcgcatctct 344580
gtgcagccac agcacccagg acgcagctgg gaagggaggc caggggacag ctgcgctccg 344640
ggatgctggg gccgtcggcc tccccccttcc caggcccagc tcctgggcac tgggaccacc 344700
gtgggcttgg ctctgagatc caccatgagt tctcgctttg tccaagattg agatgcgcca 344760
ggtagttggt gtgctcattt cgaggtgttt ctttttcccc ccagtaaagt gatgtcacgt 344820
ggaggtgagt gtgatgggaa agggaacctc agaaacaagg tcccaccttg gtcctctggt 344880
ctcccctggg aggaccaccc ccaatcctaa catcctgtga ggtcctcccc actcagaggc 344940
tcctctctgt gccacccatc ctcggatagg ttgccatgag gttgccagag gctggcaaag 345000
ggcacttgtc agctgcagat tccagccctg ccctgggact tggaggggat catatccctt 345060
tgaccaccag gtcatgaccc ccagatcata tcccaatgac cctctgccat accatgagcc 345120
caaatgaccc tcaacctgcc acagagacag cccccactaa ctgccactgg gtgatgggac 345180
cgtggagagt gcccagctca gaggagaagc ctgtctgatg tggctcccgt cctcctctgc 345240
tggggttgtc tacactgtcc ccactcggtg acaccaggag ctggcattgc ctctggttct 345300
actgctctgg acagccctgg cagcagtgcc ctagcctggc ccagcaccta ctgagacagc 345360
cgggccaagc cccatcctgc aggtgcagtc tcactttgtc actcttggtt acccatggga 345420
ccctgaaccc catagggaggg gctcatcact cagggtcctc atccaggtgt ggcccatcca 345480
cacccagcat ccagctgtgc acacagggcc acacacagac ccctttccca tccccccttc 345540
ccatcccaca cagggcaaaa gcctgacctc ctctcacgcc tttggagcca gtggctgggg 345600
tgcaagctct gccccctaca cgcgatggct gtgagactcg gcgagtcacg tgggctctca 345660
gcgcctcagc ctcctggccc ccagtggagg ggacaggcac cattatgccg atcgctcgcg 345720
tgcaaaggcc ctgtggcgtg ggcagtgtca caagctcctg gcccaggagg cctgcttggc 345780
tgatggcaga gctcagaggg tgtgagcatg aggatggcat caggggtctc tctgcaagtt 345840
caagttccgc ctcaacccta ctacgtggcc ctggccaggc ctcctgaatc caggtcttgc 345900
tttccccagc tatccagcgg cttcctgctt ctcttaccct cagcaatccc ccaagaactg 345960
ttcttttccc cacactagcg tctctctttc ttggggtgtt tctctcttag cctgcctgtg 346020
ggggacagtt gccaccctca agcctctcct gaatgactct atttataggc ctccaatatt 346080
ggccagagag gaaatttaag tctttttaaa aattcagctc aagtgtgtgt caacttctgt 346140
gagtgcaact gcttcagaga gaggctggga taggacagca ggcggcaggg gcgtgtcagg 346200
tgcccgagca ggacggtggc cggagcccgc agcggccgag ccctcactgg gcaccgtgtg 346260
cggatctata atcgacagca tcaattgcgg gagtccggct gggctggccg cctgcagggg 346320
ccagggcgtg agggcggtgc ggagccttgt ctgtgcggca aaccctgcct ggctgccctg 346380
gccaacctca gaaaaacatg tattttggtc aaaatgggcc ccttttcaaa cttgtcaccc 346440
cgtgggtcag ggcacagcct gcccccagcc ggttctgcat attaagcagt ggcttggtca 346500
ccatcaaaaa tagatgtccc gacccgagcc tcccctccct cccggggagg ggacctggcc 346560
gtgccggctg ggctgggaaa ccgcgggcgg ggaaggaagg acggggcgaa ccggcggcac 346620
aggcccagca cgtcccgggc cctccccgtc aggtgtggac cccgaggttg tgcgggggct 346680
tggcggcagc tgcgggtggg ggtggggggc ccgggcctcc cgggctcggg ttctggcccc 346740
aggtcagagg tggcgctggc ggcaggtgga tgcccaggtc ctcgccgcgc cgctccgggc 346800
ggtgggaccg gcttcctgcc ctggctccga gcccgcaggt ggggcttccg cctcactttg 346860
gacggtggcg tccacaaaat ggctgacgcg gcgcacggcc gtccctgcac ggagccggtg 346920
tttactttgc cgcgcgaaca gcctttcgtt gcccgggttc cgagtgctcc agaggcagat 346980
ggaaattttt gtggattaaa cacggggccg aggcgcgctg ggctgtttgg gttggcaacc 347040
tgagccctcc ccaccccgtt ccgcgtccgc tgcttcccgc cctggtccgg cgcttccatt 347100
catgccttcc cgggtccctc cgccacccct gcaggcccgg cgtcccctcc cgcactcccg 347160
cggcctccag gggtggccc tgcaggccca gagcagcgtg ggcctgaacc cctctccacg 347220
tgtggaagac gctgcagcaa taggaagggg ctgctccttt gagggccctt ctcaaacctg 347280
gagcccctct ggccgccaga tctttgtctg tgaaacagca gccagtgtgt ggaccaggca 347340
ggagtggatg gggtgtgtgc ccacaagtcc agcacccaga aaacccccag cacacggtcc 347400
cttttacagt ggcctctgct ctcaggaagg tggaaagcgc caggtggata ggagggacgg 347460
ggccgtgacc cctccctctg cccaagagaa actctctccc tcaggtcaga cccaggcctt 347520
tcaagaagag gttgcagggt gtgcgggctg ccaggaaaag gtctgtgcgg gtgagggagc 347580
gcatcctatg gatatctaga ggaagagcgt tctgggcgga gggcacagcg gttgtggggt 347640
gcgggctgag gcagtgcctg gaccaccttg gcaacagcag gaggcactgg ccagagccac 347700
ggacaagggg gagcctgggg gcgcagacca ccctgtgagg cctcaattag aggagatggg 347760
ggcttggggc cccggagggc tgagatccag ctcatggctt tggcagcatt gttcttgcac 347820
gttcaggatt agccgagtaa ggtgagcctg acagcggggc cagcacgcag ccccctgccc 347880
ctcgcccccct ccctgccccc agtcccccac ataggtgtca aagtgcacag caccccctct 347940
cttccccgcc ccccgggagc cgcaggtcag gcacacaaga gccatctgtg tgggcggcaa 348000
ggtggctgcc tgtctgctgc ccgcaaaggg atgcttgtcc agcagggtga acaccccgtc 348060
agggcaggag ctgctgagga gatgctgatg cctgggtgac tcatgctacc tggccaccca 348120
tcctcgctgg gctacaaatg ggttcagcct catgggcatc aggcagggcc cgcctgggtg 348180
cacccgacaa acacaagggc tcttgttcta aggctctgtg atagcccctc ttactgagag 348240
ggaccatatc caataacggg tggaaattgc actagcaggg tcatgtgagg gctccgagct 348300
ttctccagaa cccaggaata tcctcaaaac tgaggctggg cacagtggct cacacctgta 348360
atcccagctc tttaggaggc caagacgggg ggatggcttg aggccaagcg tgatggtgtg 348420
tgcctgtggt cccggctgct cagcaggctg agttagaaga atcgcttgag cccaggagtt 348480
caaggctgca gtgagccatg atcacaccac tgcactctag cctgggcaac acagtgagat 348540
cctatctcta aaaataaaag taagaagtat ttttttttta actgaggccc ttctggaggg 348600
atggagggac cagaagtcac aaggagcaga aaggaaaaaa gcaaaggaat ccttctgaag 348660
cactgtgggc atttattcat tcaccttgtg ccactgcctg ggctgcagt gtgagtaggg 348720 tgggctggcc cctgctcctt agaatgtaca gccccatggc tgggcagggg gacgcacata 348780
gtgacccgta attacatatc tgtctgtgtg aaggagaaag tactcggttt tcccagtcag 348840
tggagtcagg agcccagagc caaccaggag tgagtgagga ggaggagggt gacacagggt 348900
ggaagagtgt ccagtgtgtg cagccttgca aaggccctag ggcacgaggg cacatcctcc 348960
tgaggccatg agagcaggtg aggcagagct ggtgagcgag ggatggcccg gccgggccaa 349020
ggatccaggg gtggctccgg cttcgtggga ggagggttac aggcaggtga ggatgcagtt 349080
ccaggagtgg tgaggggctg ctgtgggatg agggagagca tcagcacttt ggactagggt 349140
ggaggccttg gggccagccc ccagtctgcc agccccaccg atgagaacaa gcagactgag 349200
gggagaaagg ttggagaagg accccgagct tctgctgtga gcccccacgt ggggatgctt 349260
tgctcggagg ggtgctgagg taggagggtc aggagggtct ggagctgtat ttggacttgg 349320
caggcaacca aaaccccagt gcttagaggt caagtggaaa agaaaagagg aagaagatgg 349380
gggagtgaga gagatgggaa ggcagtgagg gaagccttgg ggaggccgtg gtcaggggcg 349440
gcacagggga gaagcaggct catgtgactc agccctgagc ccagccgggc ccccaaagac 349500
gctggacctt aaagacacaa agatgtgatg catgtgtgtt cacagattag cggggagcag 349560
atgccgcatg gaggggcgtc agggagtaca ccgccttccc aggtgagggt gtcctggagg 349620
aggcacaagt tctgctgggc tggactggac ccagcaagag agcctgagcc tggaggaccc 349680
ctctggcccc catctcccac tttcagcttc agctctgaag ccaccaccca gaaccacata 349740
cctgttcttc ccaagtttgc tctccctagc ggagggaaag acgggaggtc cacagattac 349800
cttgtctctt gaaagcaaga tgccaccagt ggggaccaat gtacagagac caggcccagc 349860
ctagagtggg tatagctcat cacaccccca gaagctgtgc ggggaggaag gcaagcaggc 349920
agcacagtca agacctgagt ttgatgactc agagggtcct ctgcctgtgg ttggcggggg 349980
tccaaggggt cttcccatct aactcgccac ctcctcccac gtcccactca actccacccc 350040
acagcagcca agaagccagg gcatcacttg accttccgct gcgtcagtct ccgcatctcg 350100
cctcccctac ccccgacctc tcgggtgctg tagggatgag gtaggagtgg tggctatgaa 350160
ctggaggcct tcgcctcggg ctggagctca gagcagtccc tgctgctgcc agacctgcag 350220
ttggggcact gcacccatgt ctggggaggc cacggacagg gccccagggt ctcaggtgac 350280
ctgtcttgtg tatcccactt cgtttctctc tttccctaaa ggtgaagttc tggagcaaaa 350340
agagcctgag ctgtgagccg aggggctcct cctcctccaa actgacaccc agtcacagag 350400
caattgctaa agacacagtc atgcttgggc ccagagtggg ccccacggag cttcccccaa 350460
cccagcctgg cttgagcagg cccctgatct aaaccaccct accccacacc cactggggct 350520
cacctggggt ttggccagca tccctagaaa tcagaagccc gcccctaatt ctgccagctt 350580
ctggctttcc gttgccatgg tgacacccag cccccagcta cagatcccgc caactcttcc 350640
ctgccatttt gcaagaaaca atatttttct gctccacaaa cttggcggga ccctgccttt 350700
ccccgggtcc atgaggaacc ccacgggttc cttgccctgg agtctctcca gctctcatcc 350760
cctgagtgcc tccacaagca ggggtcccat ggggcggggg ccgggggaac agggggtaag 350820
tgtggccaac cccttgcaca gggcttggag atggaggccc ctccccaggt gagaccggcc 350880

```
tttggccccc tgccccactc acacagggac accctttgtg tttttccaca tctgagagcc 350940
accgacattt cttagatgac gttttcttga acccaccgtg cttggtgccc gttaagtact 351000
tctactgcag cagcctagaa ccgacacgtg tgaaaccatt ggcttatggc gcgatgcact 351060
tcctcccggc atgcatgaaa acataaacgt aaataccaaa atacacaggg actattcgga 351120
caccacctga aatcattcca tgtcccacca gaagccagca cggcccctgg ccccctgcca 351180
ggtgacgctg ccccatggca gccacagtgc tgatgaagct ctgtttgaga tcaccgcccg 351240
gctaaggcca aggcggccac gtcagttctc acggctcctc ccaaactgag gagcatggag 351300
gaccctgggc attgatggca gggtggcagg aagcacccat cgctttcctc tcccggatct 351360
tcccagcacc cttccacctt cagcctttat accccgagac caggcgaggc ctcccactgc 351420
cgacccaggc ctatcatggg gcctgagaag tagtcctcat ttcctcactc tcacaccccg 351480
acacaccctt tccatgggga aggaaaacgt gccccgaagg ggcctgtgtc caggttcctg 351540
cccactcagc ccctcggggc cgtgtctccc tgcgtcagag ctgggcctga agataatggg 351600
cccactgagg tgcaggcggt ggacagaccc gggaagacct cgtgggtttc ccaggaagac 351660
agagactggg agccattctt cccggcggca gcggctctcg gcctgtcctt gtccccacac 351720
aagcccccac tgctgcgccg tccctcctgc gccacctgac agatgtggcg gtgagaaaac 351780
gatggggcag ggaaacgttc gccattcggt gccaataaag gccgccttta tcccgaccgt 351840
aaatggtttc tgtgtggagt gagactgtgc ctgtcccggg cctaaccccc caagggccag 351900
agaggcgaaa ttagatccgt ggggagagat tttacaacgt atgggctggt ggcaagtggc 351960
ggcaaaccgt ccccacgggg ccacaatggg gcattgttca cggcctcacc tgggctgtct 352020
ccagcacccc aggatttacg aggactcggc ccagagcctc gatgccggcc gctccgggca 352080
gacctggagg gggtggcggg ggggaggccc tgtgaagagg aggacagtgc tgggggctgg 352140
gccacggaga ggccgggcag cgctggcccc agcccccagc tcccagctcc ccagagacag 352200
ccagccagga acgggcccca acctgcctgc agaccaagcg gtcacatcgc gaatgagtcc 352260
tcatgctgtg cgtcccccac tgggcagcca gaggtgtgcc taacggggcc aggaggctga 352320
agacaacctt tccttgggct ctcagcgatg ccagctccag ctgctgtgtc atcaaggtcg 352380
ggcttggctg gcctcttcct agcagacctt ccaaaacccc gcagactccc gtggctgtac 352440
cagccctgca cctcctggcc acctgcccct gcgtacccac cacccttgct cgggagctcg 352500
agggcccttt ccccactagc atctgaccgc cttcttgtat gtcttgaagg ttctttgcct 352560
tctctgtgca gcagggccct ttacagtgta gtctggcccc tcctcctccc ccgggccccg 352620
tacttcctcc attctgcccc ttctcaggtg tgcgggacct ttttacagcc ccctgcttgt 352680
gcctgcactc cctcccctgg gagcctgcct caccctgacc acatggcctt cggcacccag 352740
cttgagtgtc ccatcctgtg aagccagccg gttcccccag gcacagggga tacctcttcc 352800
ctttgggcac ctgccctgcg tactgtgcca gcctccaggt tggcccaggc agcccaggct 352860
gctcagggtc atggccaacc cagggcaccg cggtgggcag atgcagcccc tttccaggcc 352920
aacttcagcc ctctcaccct cacaggggac ccaagtgcac agccatccac agcggccttg 352980
ggacaatact gagtcttgag ttaggggtgt ctctcctcaa ccctgagagc agccccttttt 353040
cccaccctca gtgcccccac ttgtggccca ggcccaagca agcctgcatg gtgcaaaccc 353100
acatggcagc ccagggccca ggaatggctg tccaagagga aggggctgga ccgtccacgc 353160
cctgggttcc caaccaccct tcccctcctg gtcacctttc ggcttggcat caggagggct 353220
```

-continued

```
tgaagaagac tcctcagccc cacctgcaga cctagctagt tgccaaccac ctggggttgt 353280
gcccagtcct cagaactcac ctgcccatgg tcatccgagc cgttcccaca aaagccttcc 353340
ttgggatcct cagccgtctg gggggcctcc ttactggggt cacctcaaaa acagctgtag 353400
aggggtttgc ggcagcagca gcagacgttt ttaaactaat tcattggtga tggcaaaatt 353460
atgccgagtt ccctgaaaaa aaaaaaaaat acccactcta tttcctcatt aacataattg 353520
caaacagaac gaattttctt gatttcgtgt aaacaacagc ttgaaatagt ttataatcct 353580
tgcaggtatc aaattaagtt cttacttatg gtctggaaat taattaccct tgcagcgaga 353640
caaatgtgaa aactgtgtat ttttgacaag aaaatgaagc agctattggg gaaaatgtaa 353700
cttaatcgta gcagagaaaa ttgtttataa attggtcgcg ttgtttgaac tctcgcctct 353760
gtggctcagg gctgggttga tctatgcatg tacatttgcc taatttggga caggggaagg 353820
ggctggagga gcaggaacag gacgggggaa ggagaggaag aagaggaagg agagcagagg 353880
gtacccgcgt gaagggtacc cacgaggaag gggacattag acaagaatgc aggtggtcag 353940
gcggcactta cctggcaggt gaaatctaaa caggcacctt caaaggagga caaagcagct 354000
cccttgggta actaggaaga ggacaccagc tggcgagggg caaagcaaag gacctgggac 354060
aggcacgtgc ctggaacaga aagggagcca gtgtgtctgc atcaaagtga gtgagagagc 354120
agcgcaggag agaaactctc agaggcaggc aggggccgga ccacgggggc ggtggtgctc 354180
agattccatg tggctgtcca tccatggtgg gccaggaggt cactgttgtg gtgacaacca 354240
gcgctctttg gaatggactg aagtggaatg tgatgtttaa cttctgtagc tgtaagttcg 354300
agtgtgtgtg tgtgtgtgtg tgtgtgtggt gtggtgtgta gcatgcttgc atgcctggac 354360
acagtgtgtg ttggcatgtg tggtgtggtg tgtttgtatg tgagggcagt gtgtgtgttt 354420
tgttgtatgt ggtgtgtctt ctacgtgtga gtgtggtgtg tgttgtgtct gcatgtatcg 354480
tgtgtgtggt gtttgtgtgt gtgagtgtgg tgtgtatatg ttgtatccaa gacagccaaa 354540
gggaagttcc aaggggctcg tgcactcggt gtccagggag cagcatctgt gctgtctgca 354600
ggtagtcacc gttctccatc ctgttacagc aaataccctc ctctgcattt ttcccttgtg 354660
tttgatttgc caggagcaga atttctgggt tggaatcggg aacatttaga ggagcttctc 354720
agtagagttg tacagagtgg aaatgagtcg gcaggctgca tggggggttc cagtcacagc 354780
acagagggtg tgtgttttcg gtgcctgccc tcctgagctc caagtgtccc acgcctgccc 354840
gtcagtcctc atgtctacct gggcgacccc attttgaaga tgcagaactg aggtccggag 354900
aggcctgggt agctgcctaa gggtggggta gaagcatggt gccggctcag ccaccctcag 354960
gtctccaggc tcccagccaa gggctccgat aaggctgctg ggacctgggg gctgtgagca 355020
gatgcagacg tccacagttc ccagggctct gaccctgccc tgtctccaga gcccacagcc 355080
ccacccaaaa ggccaggagg tcacagatct gggatccttt cccgccacct tcaagaaggg 355140
aataaagcca cttcctgctc catcccagtg gcctgagggt gtgggaggga cagaggcctc 355200
ccccagcagg gtaaccctgc aaagaggggg ctgacagccg ttcctgcttc ctactgggca 355260
gaggctatag aggaggtttc cagcgcctca gtgcaggcag ctgagcccag accccctgggc 355320
tgtccttgga accactccca gcccctgcca gctttgtagc ctctttcttc cccaccccac 355380
ttgcctcacc tcggcccaaa cctgggtact cccagctgca gccctcccca ctttgcctgc 355440
tctgaggctg tgtagggccc agggagtggg ggaaggggcc tgggtcccgc acaggattga 355500
ggtggcgttt acagaaccgg gggccagagc agctgtggcc gtgaaggttc caagcttgaa 355560
gtggaaaggg ttttgatgcc aaggtccaac gcccagctta tcattgtgta aatctgggca 355620
```

ccacacatag cctctctgtg actcagtttc ttcaacccta aaatggggac atgcttgcgg 355680
gggttcagga gatccccatt gagcacggag aagagcaggt gctgtccact cagtgaccat 355740
ctgccgtcac cattccccaa gttatgggag aattcagcta tggtaagagc agagaacagg 355800
atggcgctgg ggcaggagga gaaggtgtgg ctggcaggca ctcatgagga cagggtctca 355860
gagcccattc tagagaatgt tccagaaggc atggggaggc aggagaccag gtgtgcccag 355920
ggtggggaca ctggtaatgg gaggtgccag agctggtgac agaagcaatg gaggtgggtg 355980
cagggctggg gcagggccag gcagtggctc ctggggtgct ggtggcccag acagactaga 356040
gatggtggaa gggtagagtg cagtcaggtt tggagtgggt ccactctttg cacagaccag 356100
ccccctagag gctccccagt tccaacagga tactgggctc catggctgtc acgtggagct 356160
gtctgtaggt ggactggctt ctgacccact cggggtgccg gaccctgccc tgtgcctgta 356220
ggggcgggca ctcacctgcc cttgcagtcc cctctagctc tccagcttcc tgctggccag 356280
tcgtatcagc tggctcagca gcaaaggctt cagaccaggg gacttaggtg agagaaattt 356340
attcctcaca gttctggagg ctggaagtcc gagagcaagg ttgtggaagg gtcggctcct 356400
ggtgagggcc ctcttcctgg ctcataggct gggcccttcc tctgtgctta cacatccctg 356460
gtgctgccgc cttctcttgc aaagacgtga gtcctatggg accaaggccc tgccttcaca 356520
gtctccttta atatttatca cctcctaaag gcctcgtctc caaacacagt cacattgggg 356580
attagggctt caacatgtga atttaggagg gcacagttca gttcataaca caagtcctcc 356640
gtcgggccac tggagcctgg ggagatgccc ccactgcatg ctgaagggca ggaagtgagg 356700
gaggggagag cttgttgcgg gggtgtcctt gcctctcagg gccacgccca ctgcctgcgc 356760
cagggaagac cagcagtgac agggatggtg tccccgcagc ccctgggtta acactgcctc 356820
ctcccttgct cttcttggca gcacagacct cagaaggctg gagccccggg caggcccaag 356880
cacagaaaaa gccagagcag ggtctggggt ctttgcctcc agtagggtgt tgggggagct 356940
ttgtattctc tgtggctgga ggcgatttcg ccagctgcgg agcggggcgc ggtgggcaca 357000
ttcacccaga ctcacaccgg cccaggacgt gctgagggtg ttggggccca tccaccctcc 357060
actccgcttt tccaggggtc aggcaggggg aggccacagg gtgcccagct tcagccacac 357120
ccgccttctg acaatgcgaa gcccacctgg tctgtgagct gtcgcctctg tcctcacagt 357180
gacagagctg gctttgaggg cagcaggaca ggggtttagc cctggctccg gccctgtcgc 357240
cagccggcag cactggggcc accagcacag cctcccagcc ctcaccagta ttaactgtca 357300
tcccaagggg gccactgagg cagcggggag cctgccctgg aatgtgccat cctcgggcgc 357360
aggcagccct tcatgggcct gcccaatgtc tattaattaa gccccctgga gactccagga 357420
gctgggggcc ttggctcagt gccctctcat aaagttctgc tctctgggga ccgtggctct 357480
ggcagccacc ctgcctctca ggagccagcc tagtgcctcc tgggtcccca gggtataggg 357540
ccagacccca aggcttagtg gcaagaggcc cagcagatgc tcattctccc ggtcaaaccc 357600
ctagatgaca ctcactgggg aacagagggg ctgggtccag gaaggaggcg tttgcagggc 357660
ggggttgtct cctgaagact gcgagctaga ggggagaagc cactgcatgc tcccagccct 357720
tcacctcaca gtcccggaat ggggaagctg agtggccacc caccccttgga cgttccctga 357780
gcatttcccc actcagagtc cagaagcccc cagccccagc agaccctaca gcgctacctg 357840
caaaggccag accggccagc cagggaggtg ggctagacag tgccctggcc accacagggc 357900
aacccctcag ctccacttcg ccacccagag gagctggccc tggccactct ctcagagcag 357960
gaggtgacat gaagggaagg tggcaggatg ggagtgccca tcagccggaa ggccacggga 358020
gtcaatggtg aggggcagag tgagcaaggg gctcagggta gcccagaaaa cccagccggg 358080
cccccccccc cacgggcacc caggaaccgc cctggctttg ctggaggacc tgccatggct 358140
ttgccagaag accctgggac tgtctggagc atcctcccaa ggactcgccc ctagtcagga 358200
aaaaataggg ccccggagtc agcaagggct tcctgggggc ccaggtcagc ctggacggtg 358260
gcaggactcg gcgaggtggg gatggggctt ggaggatgtg gcagagttcc catggtgtgt 358320
gtagaatgat attccctcca gaccacggtg ccttctgggc tctggagaat gcacctgtgt 358380
tcccaggagc tttaggggta cccaggtggt gtgatgggga gcaggagcca gttgttccca 358440
aacctcgccc tttctccctg caggcactgg cagagctggg ggtgatgggg cttcagtgga 358500
gcccgccagg actggggaca caagcctagg cctgtaccgt ctgcagcccc atctccaggt 358560
cccggcctgc cccagcctgc ccacccccag cctgtccccc aaatgcccag ggctgtggcc 358620
tgcccagact tgccagggag ctcctgtgcc cttcttttct cctggcctct cagaagcact 358680
ccctgatcct ctccccactt ccctcctccc ctctcatccc cacctcgggc ccaccagctc 358740
ccaccctgct atgcccatgg accccagggt cagcttttat gcacactcag gtactcagga 358800
caccccacac cagccattgg atggggccgc ctctgccacc tgctccagcc acctggcaga 358860
tcccactcgg ctcacacaga gccttggcca gcatgtggcc gcagccccaa ctgcagcgga 358920
aggtatcggg gagtcgaagg cagaggggaa aggacgggat ggcgggtgaa ccacacgggg 358980
aggagcctgg agctccttct gcattttctt aggaagtgct gcagggaccc actggattct 359040
ctacagcgcc cagtagccca ttagaagata cagaggcagc aatattcaca gggccagaaa 359100
caactgcagt tcacccatgc tgtgcaccag ctcccacacc acccatgcca cgtgcctgct 359160
ctccaccgag ccctgcaaat gcctcggcac atcagcaagc acaggcctcc tgcaacgtca 359220
ttttgcagaa gggaaactga ggcacaaaat actccactgc caccaagtca cccaactcag 359280
tggtagagct gagatctgaa tgcaggccgc ctggtcaagc ccatctgtga actagaaccc 359340
cgccgccctg ggcagaaaca aggctgtatt gacggtgctg ggagagatga ggggagggag 359400
ggatggaggc cggaacagag ccggctgctc ccctcagagg gctgggtgtc accccagttt 359460
tgtctgtggg tttgtggaga gcatcactga aatttctaac ttgacagagt ggttccaggg 359520
ctcatataga agcataaaga ggtgaaaata gctgatattt ctaaaggcaa aagctaacga 359580
gtggggttgc actgcccagc gtgaagctgc agccaccatt ctccacactc tcctggccct 359640
tggcacagga tgagccttgc agacggaggc gacaccaagg ccttcccctg cgcccacacc 359700
cagcgtctgg agctgctgga aatatgtgtc ccccaccatga aactgatgct gctgttcatc 359760
ccattttgtg tatgaggaga ctgaggcacg ggcccacagt tgccagctgg gatttgtccc 359820
aggccacctg gctcaggtca ccggaacatg tgacaacaca tgtggtcagg gagaggcagc 359880
accacagtca gatacaatgc tgacagggac ggcagagttc cacaggcaat gaggccccccg 359940
gggtaaaaat gaagcagttt gaaaacaaaa ccaggaagag tgtctggcca tcccgggcct 360000
gagtttctgc ccatgggcag ctgccggaca agccctctgg tgtgtcagcg ggtcaggctg 360060
agccagacgt ggagatgagg ctgagagccg gaagcaaggg ctttgtctct agaagacgca 360120
ggggtggttc acaggccgct ggggacccag gtcacagagc ctttccccca gctccagcct 360180
ggctggggag agcaaaggct gcagctgcac agggcccctc cctgcctgcc caaagctgct 360240
accagacagc aagctgggga gaaaactgca gccgacgacg gagagggacg acattttgca 360300
agtgaaaact caaatctatg agaaaagcac tcgccccgca gtaggaaagc aggcaaagaa 360360
ctagaaagac aatttacaaa aggatctgaa ggtcctcact gcactcatcc tgtaaggtgg 360420
acttggggcc tcatctggcc ccgctgcctg tttttgtaaa taaagtttta atagcacata 360480
gccacgccca ccggtggaca catcgtccct ggctaacctt acaccacctt ggcagagttg 360540
agtcgttgta acagagatcg tgtgaccaac gaagccagaa cgatttactc tctggccctt 360600
tagagaaaag cgtgctagcc cttgctctaa gagtttcagt gaagagacgc aagatgcaga 360660
aatgaaccta attgtgtggt cttccgtgct ggggaagccg aggagaaatg gaagtatgag 360720
ccggttccct gctccagaaa tcgctctgat gacacgtatc acggggatta aaaaacattc 360780
ctcccccctt gacctcataa tcctccttcc aggattctct ccctaaagaa caaatcagag 360840
ttatgcacaa acaagctaat cacagcctta tttataatag tgagaaattg gaaacagacc 360900
gcatgtgcag catttgcggg atgttggttc ttgttatgca cattagggac aattatgcag 360960
ctttcagtca tccctcagtg acccaggaaa atgccccatg tacaaggtta ctggagacaa 361020
acatggtccc agtttctggg gtgggaggtg gtgcccaaaa catcacctta cagaaaatgc 361080
ccggaaacgt gtctctggag ggtggactta gagatatgtt tttgaaacag attttttcat 361140
atttttcaaa atttctcccg taagtggttc ttacctccat aacagaaaaa gagtaaacaa 361200
tcaatgtgga gtgaggaaga agagagggga gggagagagg aagggaggga ggtacgcagg 361260
gaggcagcaa ggggacttcc ctgctgagga cgctagcccc tccgtaattt gtctgtcctt 361320
cccagcctgc ctggggccac atgggccact gtgcccagtg aagcctggct tccttgtctg 361380
tggtgccagc catgtgggag ggtaggcgac ccgccttggg ctgtgtaacg caggcttgcc 361440
tcttccttac cccggttgtg ccagtggcta ggcaccaggt aacctgtctg tgctccccac 361500
cgagcagctg ggccgtgtct gctttccgag gaggctgcag gtaacccttc tctaacctgc 361560
tcagccccca gctccatctt ccacctgtcc tgggggatcc ccattcattc tctccgtggg 361620
catcatcaga ggctcagctg taccagacca ctgcccggga gtacgttcgg gctcaggttt 361680
cccttgaggg tggcccccac ctgacccctc cccgcccctc tcttgtgccc tgagagaata 361740
gcgtgccccc agagacagta aaagcctggc ttgcgtgctg gctccggtga cacacaaagg 361800
cctctgcttc tccactctca ggccagcccg agagggacgg caccaccggg acagcaccag 361860
cgggggcatg gggaggggtg acaggttggg cggggtccct ggggctgggg cgtagcccct 361920
ctctgcaggc cccacagtct gtgaccgtgc agggagggtg ctgggagtct cggctctttc 361980
ggaaggcgcc agtgtttcct tgtcacagaa tgaagtaaat gggacgatga aggggcagtg 362040
tttaaatggc tgctttagcc cgtttggaag tctgctaatt attctcttga ggaaagaaat 362100
gcaggttcat tattataatg agctttgggc aaaatatttc atcgagcctg acaagccgca 362160
gcgacgcctc gaacgtggcc ggctctgaaa ggcctcctat tctgctggaa gctaattggc 362220
ccggggtctt cccagccctg tgctgtttgt gtgctatttt aattcgctta tgaaaagccc 362280
ccgctttgat gtccgggacc agataaggcc gggaggggac cctccatgga gagcgggact 362340
gtgccgcccg cggtcgctgc actgggcctc ctcgcccccc cactccgggc ccggggccag 362400
cgcgatgtca tgaggtaact gaacaaacag tcctgctgaa aaatatgctt ttgtttcact 362460
aataaatccc tcctcggaac actcccgggc cgggccctcc tcgggcccag cctaccaggc 362520
cttcccgccc agtgcctccg caacccgcgc caggacagcc ggcggtgggc acaggcgggc 362580
gaggggcacc cccacccccct ccagggcccc ccttccctca gcctcctccc cacccacccg 362640
agctgcctgc ctttcccgca ctctcctccc tgacttcctc ccacctaccg gcctcttccg 362700
acctctctct gcctctttcc cccatcacga tactccagtg gccaccttcc ctgcccacca 362760
tgcctcctgg cccccaatcc ggtcaccaac ttgaggctgc ccctgacaag ccctggctgc 362820
agcatgaggg aagcagcggt agagaaggcc aagtttgggc accttgcaca gcctcctgga 362880
gcctcggttt ccacatctgt aaggatgaga caggaacggt ctctctgggg gcagggccgg 362940
tggtacctgg agccctcccc actgagcacc tggcccagtg cccggcacgt ggcaagtgaa 363000
ggcggctgct tcccgcccct ctcatggaca ccactgtggg caccacttgg gcaccctgtg 363060
ggcttatttt ccctgcccac tgccaagcac cagaccaaga tctgatgcca tctgcccagg 363120
gcattgaggg tgaacccatc caggctggcc cgccttccag ccctccccca gcacccacca 363180
agcccctgcg atatcccagt ggaagataat ggaggtgtta cggggatggg ctagaactcg 363240
gtcctggcat cacagagcta ccccggtcaa aaatatacca tgtaattaca gaccaggaaa 363300
attactgtgc aggagcaaag cagggcactg tgccggagag gaacaggggt ggtcagggaa 363360
gacctccgag ggaggggcat ttgaaaatag cattcagagt tgctattaat aggctctgat 363420
gcagaactga gcagagaaga aaacaaaaga ggaccataat atctccacag agaactatca 363480
ttaatttttt aaatgggagt cctcaggtag gttggttgat tgagtgattg attgattgat 363540
aatcttggtt ctatttgaat ttctagaaaa ttccaacagt acagaaaggt ctgaaatgaa 363600
aggtaaatac cttcatgacc atgccccctt tccctaggat accccttgtt atcctagaaa 363660
tacccatcct tagtgtgagg agagcagcat tccagacgct tctctgtatg ttgcatagaa 363720
aaaggatggt tagatacatg ggcagattaa tggatggaca gattgttgta tggaggatta 363780
ggggagggat aaatggatgg atggatgaac acatggacaa tgggtgggta gatgggtgaa 363840
tagatgggtg gacagatgga aggatggatg gatatatgga tgcatggaga gacagagaaa 363900
tagatgcaga gatggaggga gggagggaag gagggatgga taaatggagg aatggaggaa 363960
tggatggatg gaggggtggg taggtgggtg ggtaggtggg tggccagaca atggatgtgt 364020
gagtgagtag atgaatgagt gggcagacag acagacacac catcagaagc aaatataaat 364080
atggaatcaa gggatgcctg cagcttttga attgttgatt tttttctttt tttaagaaga 364140
aaccaaagta aaacagaagg aattgctgaa ttcagataaa tgtttcttca ccaaaagaga 364200
aattcatttc taaatgtcac tttcaggtta aggaaaataa aatgtgggac gctggactca 364260
tcgtgggttt ttgcggtctt ctctcagctt tgtgtggtag ccagcgacgc tgcaaccccg 364320
cccccgcagc ctcctggtgc agcacgtgtt catttatggg ttgttgttac cgtggcattg 364380
gtccaggttt gtgatacttg tgcacagctt gggggctctg cttccctctg tttgttcgtc 364440
ttggtgctgt gtatgaaggt ggcaacagac tccccatagt cctctcacca cagacacctc 364500
ttctcagttc ttcgtttcca gttggactca tctcctgact ggttgggttt ctgcctcggt 364560
cgctgactcc agaaggcccc acggctcatg cctgcttccc tgctatcctc ctgtgcactg 364620
ttggccttta tcatctccac cacgtgctca acactccagg ccagagccct tctctcaaat 364680 ccccttttggt tctagccatg tttccctgag ctcttccctc tctgtctcta attgatgtgt 364740
tttcctccca aaccctcctt ccttgcataa ttctgcaact gaccttttt ctggccatcc 364800 tagattgggt ttactgttcc ctggtactca gacctgctta atgctcattt cttcagtttt 364860
ctggggaagc ctcaggggcc ttactgataa gaactgtgtg gaaggtaagc attcaaagtt 364920
cttacatggt gaaaatatct tcattcaacc atggtgccct attgatagtt taagtgggta 364980
tagaatttgg agctgaatgt aattttcctt cagaattttg aagacctcgt cctatggttt 365040
tctagcatcc agacttacta ttcagaagtc ttatacttgc tttagtctca tacttttgta 365100
agtggccttt cttttcttcc tggaaatgtt tagtatctac catctggact caggggtttc 365160
aatttcccag agaagttccc tgtggatggc tttgttcatt gactgttctg ggcacttggt 365220
gggctctttg gaaactttag tccttgagct ctggaaaggt ctctgtatga tttctcatca 365280
tggaggccac catctctgtt ctctctttct gaaattcctt ttaagtcaga ctgaagacat 365340
ttttaatgac actttgatgt ctcaactttc ttccccttt ttatggcatt atattcttaa 365400
ctttatctct tcagagttct aggaaatgtt tttagcagtc ctgtttttaa tatcccagag 365460
cacacgcttg ctctctgacc gtggtcatgg cattccgccc tcatttgatg ggcacgacag 365520
ctcctaggat ctttctggag actccagata catcttatat cttaagttct gcttaattcc 365580
ttgatcttct gtttatgttt ggccagccag gcccctctct ctcatgttct gaatgttttt 365640
caatgtttgc tcgggatctg tgcatggatg ggcctgctgg catttaggat gtgttgacaa 365700
tgactgggg aggtgcctgt cattacactg aggaacccca tatgttagag ctctgaggct 365760
gctgcatctg agagcttggg ctcgaggtac agggctggca gccgggagtc ccacctgtag 365820
gacgctctgc tgtggcagag ggacaggaca tggacctcat gctcagcccc ttcccatcgt 365880
cttggtgctg tgggcctgat gtgtgcctcc acaaggactc ccgccttccc agcatggcat 365940
tcagagcagc agatggctta gactcacccc cgcccagtct tggcaccctt acagccccgg 366000
cgagacccgg gtgggcgtgg accctagcgt ccccttcaccc tcaggctgtg cacctccgca 366060
gtgccgtgtc ctgtctggag cctgtcacac ccctgtacag ctaccccaat ccaaatggag 366120
cctcccccag gaagcccctg gtgggaatcc gtccccacga cccctgtccg gcttccctgg 366180
ctcattgtcc ctgttacaac ccagatttcc cttatcgcaa ctggtcctag cctgtgacct 366240
cctggggtgg ggaatcatct ctgcaaacac agctcctcca cccttatcag tgctttgtga 366300
aggcagcaga acgttctcct gagccagtgt ctgggtcact tgagcaatgg ctgccaagtc 366360
catgggcctg cacgcatgag gctgtgcctg tgtctgtgcc gctggagacc ttcttgaggt 366420
tcactgccct aaaggccgca tgaggggaca gaaggtgaac acagggccct gcttggtctg 366480
acaagcccag gcggggccct tgccgagcgt cagggtggct ggcagccacc ttctgtgatc 366540
gtcctccttc tgggctgcgg tctagggctg cacattcagg atggggatgt cccagtgggc 366600
gcgcagcaca agggtcagca gacccctggc tggaggaggt cagtgtgggg ggctgcgtgg 366660
gagacggtgc agcagtgggc ctgggagctg agcaacggtg gctgggatgg gtggagacca 366720
ccaaagagga ggggccggcg aaagccaggc ttcctgcagg ctcaagcctg gaaaacggtg 366780
ctcagtgagc aacacattcc cgttctacag tttcctgagc tcccgagtgc ccgccgcagg 366840
atgacagtgg gacagtcctc acaggggcat gctcaggccc tgccccaggc agaccccacg 366900
ccctggcacg cagccccacc ggctgtgccg cctctcgttc ctgtcctcct ggcaccgccg 366960
gccacccctc agcccagccc tcatggttct ctaagccgcc gcctcctcag gaagcctccc 367020
aggcacccat gctccctgca ctgaccccca gaccccagct ttggccatgc actcccagac 367080
ggctggtccc cacacaaact ttctgtttca aggaacagaa acacccctga aacttgtcta 367140
agaaggaaat gtgtcaactc acatacatga aaagcctgag tccctcctca aagtcctccc 367200
ctccctcctt ctctctcctt ccttctttcc cccttccctc cttccctccc tctctgcttc 367260
cttctctcct tcctccctga gacctgggac gccgaggagg gttccgttcc ctccccacc 367320
ctggcagtgc tcgggggctc cagttgaaaa tgatgggga cacatttgca tcacagcctg 367380
cccggccggc tctgtggccc ctgatcttcc tactgcagcc tctgccgggg ccggaagggc 367440
atttccggga ggcgggaaca gcatgtatga aggcagagct ccttcccgga gaggagggcc 367500
agccccgtcc ccaggggctc ccggctttct ctctccccct acattcctgt ctccatgcag 367560
cagccagagg gactttaaaa cataaaccag accacagcac tgcctgctca agccccccat 367620
ggcctccctc ttccctagga agcaatccag gcacccttcc atggccgtgg gccccacgcc 367680
cccgaggccc cacgcccccg gggccccatg cctgcccttg caacatcccc ttcctgactc 367740
cacccagcct cctgggggct tccgcctcaa ggcctctgtg cctgtgtgag tggcaccctg 367800
gggttgtgcc atggccagcc ctcaaaccat ctgaagtctg ctgttggcac ctgccctctc 367860
ctggctgcaa agctgccccc tcatggcctc aggtctctgc cccagcctcc aatccctcat 367920
tactgcccca gcctgtgcct gtgcctggag gctgtggcct ggctctccag ctggaacaga 367980
agctctgaga agacagagct ggccagcacc atctctcctg tgagaaccct gtgcctagaa 368040
cggagcctgg tacagaggaa gaacccgaca gactgtgagc cctgtcttcc tcttggcacc 368100
atgagtcacc tgtcaaactg aggggctggc agagctggag ggagttccat cccagcccca 368160
aggtgcctgg agtagcttat ggaggtcact gatggcctca ggatgccagc aggccctctg 368220
atgcccaggg ctcattcaag ggcatctgcc ctgtgtcctc atgcacctcc attcagggaa 368280
cctgggctcc ccactctcac aggggtggag acctgcacct ctttttcacc cccaaacccg 368340
cctgccgtca gtgcttggag caaatgcccc tcccccgcca tcttttcatg actctccccc 368400
ttcctcaacc ctgcgcctgg tcaccaagtc ctgacaacac ctccagcccc tgtctctatg 368460
gtcccctcct tgatctggag ccattcagcc acatggagta tgtcctctgt cgagggggca 368520
gggactcaaa ggatgagaga aggaacagag gggaggacca acatctcggc tgatcctggt 368580
ctatttttag ttggtggtgg gctgtcactc cggaggccag tgactgcgtc atcagtgcct 368640
tttgatcttg ttgccgcaag atacacagga ggcagctgct cactgcttgt ggaaagaatg 368700
agggcgggca cataggcctg gggtgtgggg agcattaatg agtgtgagtg agtggcggat 368760
gagtaggtag atggatgggg agctgcaggg agggagggtt gcagaaaggg atgcgtggaa 368820
ggatggttga tggatggatg gttagatgga tgaagagata gatgaatgga taaagaggtg 368880
aaaggatgaa tagagagatg gagggaagga gggctgaata aagaaatgga tggatggatg 368940
gatgatggat ggatgggtgt gtgggtatgt ggatggagag atggatgaat ggttaaagag 369000
gtggatggat gaatggagag atggagggaa ggagggatga ataaagggat gggtggataa 369060
tggatggatg aatgggtagg tgggtgaatg gatggataga tggttgagtg ggggggtaga 369120
tggagagatg catgaatgga tagaggtgga tggataaatg cagagataga gggaaggagg 369180
gctgaataaa ggatggatgg atggtgggat ggatggatgg atggatggat agatggatgg 369240
atggatcgat gggtgtgtgg gtgggtggag agatggatga atggataaag aggtggatag 369300
ataaatggag ggaaggagag ctgaataaaa ggatggtggg tgggtggatg gatggatggg 369360
gaaatgaaga gatgggtggg tggatggatg gatgagtggt gaatgaatgg atggatgggg 369420
agatggaggg aagggaaggc tggataaaga gacggctggg tgggtgagct gatggggaaa 369480
tgatggatag gtggatgggt agattgagaa atgatggata ggtggatggg tagatggatg 369540
gaaggagaca aggaaggaag gaaggaagga aggaaggaag ggtggaggta agggagggag 369600
ggagagggag caagcaggct tggatgagta gctaaagcac ctcaagcaag ggtgtctccc 369660
ttagaaatac atgtgcctcc aagtcctcga ggctggcatc ccctcctgct ccatctgcct 369720
ctgcctgctg ggcagaccag tctgctgtcc taccaaggcc taggtcttga ctctggactc 369780
ttccatgctc atcagagggt actgttggag cttcctggtc aggctgaccc agctgcctct 369840
ggagcctggc ctgggatctg gagagaaagc acctgtgcag acggccccag cgctatgccc 369900
ttctcaggcc tgctctgcac acacagcttt cctcatcccg gcctcatgca ctgtgggcag 369960
gagttgtcct agcaaccatc atccaggcac ctgctgcgtg ctgagcacca tgctgggtgc 370020
ttcctgtgct ctcaacagcc ttatgtggtc agtaccaatc cctccccaaa ttaccccccat 370080
gctcagggtg tcactgaggg tcccaagtct ggggtggcca ggtcacagct tgaacctggg 370140
cagcctttat tctctagggg ccttgggggt gtctaggctg ccaccacagc atccacactc 370200
cccactagag cccacatagg tcttatgggt gccacagcag ggaccccact ggacctctgt 370260
gctttctggt ggggggcttg tcagggagct catgggcacc tctgggttct aagaagctat 370320
gctgaggccc acagggtagt tctgagttcg ggggaccctc tcctggccct gtggggtcgg 370380
aggaggtcct gggagcccac ctcctgtaga tccaaacacc tgatctcagc tcaggatcgc 370440
cactccagtg ccccatccca gagcctttga gagtggggac agggtgtcct gttgtagttg 370500
ccaagcccaa gaaagatgag gcacccagga tgcctgacag tagagttgca ggggggcagg 370560
caccatcgcc cccagcccca ggctggcccc agtccctccc tatgcaggca gaggggcaat 370620
tggaagaggc tggagactat tcaggagagg gtgggagcag acacgggagt aggatggggg 370680
ccctggaggt actgggtgga gctgccccca gcccttcctg ctggcctccc cagagctcca 370740
ggctctgagg ccacaccctc acccaaggca agttgctcag gggtctccca ggctgtatct 370800
aacagctgcc tgtgccgaaa aattaagcac cgctgagtcg ccgcacacct gtcagggtgg 370860
aggggacttg gggggaccagc cagctggata tgttcccttg caggcgggca gggctctggg 370920
gagtccaagt gtgcacacag tcctgggtga gggctccgtt agatgaatgt ggacggctgg 370980
cggccggggc ttgggagatc aagaagtccc tgaggaagag gacagtagcc aggggcaaga 371040
cctcacacgc ctctgcccat cctgggaaac tcaccatggc attgtggttg aagggtcagt 371100
ggccaccaga gagttcctgc tgcagtgtgg aaaagacaaa caggcgagtg aagtggataa 371160
agattcaggt tgtgggaggg agacttgaag ggcaagttgg ccaagactaa aaagtggagt 371220
caagctcagt gctggtgacg atgttgggga gaggggcctc cagcgccgtg gggggagaatt 371280
tcaagagcct tttgtgaaaa tggtcaggct gctgaacgtg agaccacact caccctgtgg 371340
tccagtgatc tccttctgag aatccgccct ggagcagtaa caccccttggg actgagaatg 371400
gcttctgggt tgtgtgtcat cgctgtccag gagtggtgaa aagctggact ctgactgcct 371460
gtcatccaga gggagcaaac agccaccctg tggtgaagcc acaccacata tgatgagggg 371520
ctggaggcag cagaaagggg gctataggac cctttgactc aagggctaac catgatgttt 371580
cattaaggga gaaatgcact tgctgctcct ggaacattct ggctcactcc cgcctcaggc 371640
ccactgccct ggctggactc cctgcactga acgctcctcc cagctcatgc tttccaaagt 371700
cccctgctca ggaggccttc cctgagcccc tgccccctcc atttcagaca tctccatctg 371760
atgtctgagc cctgaacaga cacaggtgtc tgttcagggc tcctcaaatg cacaaataca 371820
tgtctgtgac cacagcccaa cccctgggca gtggctgccc ctctgcctct ggaggtcccc 371880
tccaaaacct tggtccctgt ccgcagaggg tgtcagggct tgaggtcaac agggaggtct 371940
cagggcaaca gagcccagtg gcactcctga ccccaggaga cagagggaac ccaccctcac 372000
cctagtccac atgcccgacc catgacccag gcctgtggcg ccagcctgca cccggctctg 372060
ctccacaggc caactctgcg cacgctcctt tcaagggtta acggtgcaag ctcctcacgg 372120
caccagtgcg cttgcctttg acatgaaaat gtttttgcag caggctcgga tgccagcatt 372180
tttgtggttg cagtcagatg tttttaacta cgttggacag aacccacggc ggccctttcc 372240
gtggcttcag ccagtttctg agcgctacct tgaacccctg ttgcacccca ggaggagaat 372300
cacaccagtg ccccctgacc cccagccttg tgcagacact gataccctta ggatgaagct 372360
gaccccagtc gtggcagcca ccccagcagt cagggaagga cctgctgggg catttcagat 372420
cctgagcagc atgtaccctg tgaaagaaca ggttccccaa ttttggttca tggtacctga 372480
gatgacggct tcagatgatg tccctggcca gggaggtgga ggacgctggg cagagccctg 372540
ggcattaact cagggccatc acagaggtgg tgagagctac cccgggtctg gggactgtta 372600
gcacagacct gagccgaggc cccccttctca caggggccta cccacttacg acccacctcc 372660
tctcctccat ggcaaaggtg atacattaga ctcaaagaga catgatatcc ccttgggctg 372720
caacttaaat tccaaggaga gatcctgaat ccagagtcac atgtatgtta gaaacctctg 372780
gcactctccc ctccccagcc agcacctacc agctttgcgc aaatgctcca catttgcatt 372840
ttaaaagccc tgagaaggcc tgcagtgaaa aaaactaact tcgtataacc caactattcc 372900
caaactctat ctacaaaata tttttctctt ttatcattaa agaatatgca ttaacaccta 372960
aaacccacta tcctggcaaa aaagtggcag gattgtctga aaaacacatg gccagccacc 373020
ctgcaccctg agttccacaa catctaaacc cagtgtctgc tggccctcag agtgggagcg 373080
cgtgccccaa cttccgagcc ctaggaaagg gtcttgtctg ctcttcccct cagtgtcagg 373140
tgacccaaga gtgtgggggt caggaatggc gtccttgtgc ccttgtcacc cactcctgtg 373200
ggtacacagc ttccctttct gcaaagtcac accccaagcc ctggcttgag catgtacaca 373260
ggctgcagcc cgtgttcctg gagccaccgt cccaggtgtg gctaaggccc ccacagagtg 373320
tgcatcctaa ggtggttcag aggtcctcag aaagtgccaa gaggccttcc tcagaggaag 373380
agcaagggta ggtgcctctg gcatgagcca gatgatggga gctgtcacag gactttgcca 373440
cccggggtga ggggcctaga aacccctctc caccagatgc cttacacccc ccatccccac 373500
acgcacacag cttggaggct ggaagccccc ggaatgcggc ccaccctgtc tccagttgtt 373560
ccctaccagc ccagctgctg gtccctaacc gggcccacct gttgggtcct tagcaccagc 373620
tgcccagagc ccccagcccc taccctagtc tgatgaccca ggcctttccc cctgcccagg 373680
ctagccttgt gctcagctgc cagcacagcc cccaccacac actccccaac aggtgtctcc 373740
acaactgcca ggagacagct cagcttagct gatcttcccc taacccctag gcccagcaga 373800
atcacatcta ggagagtggg ccacatgcct cttggaaggc aggtggcaca agaggttcat 373860
cccaccctcc agcattaccc agccccacag gacccacatc ctgctcccag ctccagcctg 373920
aaaggagcta gtcctctcca gccccttttga aaagaccagc tggacattct ccagggagat 373980
tctgccctac aggattaggg agtaccctca cctggccttt gttcattggt tcattcattc 374040
attcattcat tcaacaagta tttgccaagc atccctatgc tccaggcatc agtggtaggc 374100
cagacagcca aagtctctcc tcccaagggc tgtggcccac taggaggaca gacaatgaca 374160
gagcattgtg tgctctatgc ctgcccatgt gctgaggaag gagcaggaga ggaagacaaa 374220
ccagagttta agtgaggagt gggcaaggct tttatgaggc ccagcccacc ctcccctggg 374280
caagctgggg atttgggaat gggagacatc caacacgtgt cagcccatac atgagggtag 374340
aagtccagtt gaaaacacac ctgaaacagc agggtccaaa caccaggtgc cgagagcctt 374400
cctgacattg aaccttcctt gaattcctga ggtaaacctt atgtgatctt gactcaagtc 374460
cagctgctga tgcattttta ggttttagca tctgtgttca tacctgattt gggcctagaa 374520
ttttcttgtg tttgcttgag cagttatggt gcctggggtt ttaccttgtc agataagttg 374580
agcaacctcc ccttttggct agtgctctgg gatggatggg atggatgtcg tctgcttttt 374640
taggtaatta tagaaatcac ccccaaaaac tagactggaa accttttaga ggagggtagg 374700
taactggcat ttgtgtctcc ccaatgggtt tatgtttctt aggattttct accgcataag 374760
ccacttttgg tattttttgc cttgaaactt atccatcata ttgtgttttc aattttattg 374820
atatgaaagt atatatcata atcacttaca attattcaat tccctcggta gcagtagtat 374880
tcattcctaa ttcttatttg ttactttact tgcttaaggt ttatctactt tactggctct 374940
tcaaacaacc tgcatttggt tttattggtc aattcttttt cataaaatat ttttctattt 375000
tgctaatatc ttcctttgac tttgttcatt cttttcttg tatttgtttt ggtgttattt 375060
ttctagcttc ttgagttgaa agcttagcac atttattttc aatctttttt attttctaaa 375120
attgccatcg atacttctcc aaatacccta taggaagcat cccacactct tggcatgtaa 375180
tcagctcctt gtaaatccat cctaagattt tctctctgcc ttattttctc tttaatcaaa 375240
gagttattta gaagggtact ttttaaactt caagatgtat ccatctgttg ctatttttat 375300
taataatttt ctattttaca tcaaggtaca gatttttaga aatttatgga gttttccttt 375360
ggtgcctaat aggatcattt ctgtgacctt tttgtatatg tgtggaggcg gtggagtctt 375420
ttctgttaat tgtgttaaac ttgttagtgg agttctgcga ctcctccacc tcctgactta 375480
ccttgctgtt tgtttgtttg tttgtttgtt tgttagtttc acccactgtg gtttgtcagt 375540
ttctgagaga caggcactag gatggccaat aatattgtgg atttcttgat gtgttggttt 375600
tgttcatttg tttttcctgc cccatcctct gggcccttaa agcctgggca catgtgtcct 375660
ctccttacgt ctggggaaat ggtctccatt gagggtttga gtctgcgtgg cttccgcctc 375720
ccttccctcc tgctagagcc cctctggaag ctgctggaag ccatgtcctc cacatcccct 375780
ggctcttcct tcatcccata ctttcttctc cctgacagag ctgtcaaggg gagtgcctac 375840
accccacctc cattgctgct caccctcccc tggcccgtgc tgggcctcgg ccatctctgg 375900
ggctgtttct aggcccatct aagcgagggg ttccttaacc tgccttgctt ttgcagctgc 375960
ctgaacctcc ctctaaggac atcagcactc ttcggaggcc aggtccggcc tgctctgctg 376020
ccttggtggg aagctttcgt ccctgcaggg tggggtgggt ctgtcaagtg ttcggtggcc 376080
cctggctggt gctgtagcaa cacgggtgtc agagggcgga caccgaagcc tggtgctctg 376140
tgcgagtccc gtttcctcgc ctctcagctg tgtgactcca ggtgcagagg ccccgcgtgg 376200
ggcaggagca ctgcaagcga gaggatggga aggtggccgt gggcctggca agggttgggg 376260
aatgtggtga gaatggtgcc catggggtca cgccagccac acacactttc tcgagaagtt 376320
tcaagtggag ccacagggcc attgtgtgtc ctgaatcatt gctctggctg agggagtctg 376380
gggacccatg agggccagat ggatgggctc agatggagtg ggaggccatt gggaagtggc 376440
tggtaaaaag cctcatgagg gcagagcccc actgacccca cacagttacc catggtgtcc 376500
cyttccccac gtggtaattc tggactgttc acagtggctt ccaaggcctt tgggatgggc 376560
cttgcktkct rcccttctgc tggaaaccct cccagccatt tgaggtcctg ccctctgctc 376620
accttgttcc ctgtgcccat gacatctccc caccttttcc tggctgctat gtactggtcc 376680
tataggggtt ccttaaaggg tgcatcttcc aagccactcc tgttgccctc ctctgcakcc 376740
acatccctgc tctgcacacc cccaccccag caagtgtgtg tgagctctgt agtcgtgtca 376800
tggccccagt gatgtcctca ttctatccct gtcccttcat ggcagagtgg actttgcagg 376860
gtgactaagt gaaggatcca gagatgggga gatgatcctg ggttatccag gggccccgaa 376920
tgtgatcaca agggtccttc taagagggag gcaggagggt cagtcagcgg agaagacagg 376980
gggatggaag cagagctcag agaggctgaa ggtgctgtgc tgctggcttt gaagacggag 377040
gaggggccac agcccaggaa cgcaggcagc ttctagaaaa ccggagaagg tgaggaatga 377100
atcagcccta gagcctccag caggtatcag ccctgctgac accttgttag cccggtgaga 377160
ctcctgacct ccagtgctgc aagatgtcac acacgtgttg cgctatgctt gtggtaacat 377220
ggcaccacag tgcaggatgc tgacacaagc accagcacag cgccaggccc tggggtatag 377280
tgtggataag atggactgga ccctaccctc ctagggatgt ccctctagga ggtggaggtg 377340
gggaaatggg gacagatatt aggccattat ggcagaatgc aagtgtttag ttagaactgt 377400
gctaagtgcg taaagagagc taaaggctac ataataagtt gtgagcctac ctagggtatt 377460
agcagaggtg tcccaaggaa gctccctgtg agccaaaccc caaaggatgg gtggaaatta 377520
gctcaactaa gtggagaggt gggatagtca tgggccaasg ccccaaggca ggaargaata 377580
ggcctggtct gtgggtctga gaggatggag agggctgaac acgggccaaa ggagaaagtt 377640
agggagggaa ggtggagtcc ytggcagggg ctcagctcag aacaggggga gccccaaagg 377700
atgtgaggca agggagcaat gaacaaatct caccattgtg agatctgaaa ttcagaacgg 377760
tggcataggc cagagtagga cattgtgaaa aagaaacaat tagagaagca gaaagagtgc 377820
ttggaaatgt caattatgct gctgaattaa aaaaaaaaaa atcagtaaaa gatggaagta 377880
aatctccctg aaagtggaat gaagactgaa agacagaaaa tcagaacacc caagaaacat 377940
gcagactcaa tccaaggaca tccaatatcc tgctattgga agttccagaa agggagatga 378000
gaggaaatag agactaaaga aagggcccac tgagaacctc tagcagaaaa gagcagccac 378060
tgtgtcatca tgcccttcag gaacagcaga gataaagaca acattctaga atcttctcaa 378120
agaagtaaca ggcgattttc caaacatggg cctctgaaca gatcagtctt tggtagagaa 378180
aatttatgaa gagagatgcc ttcaaaattg tgaaggaaaa taaaattcta tacctagcca 378240
aagtatctat caagggtgag gatacagtaa agacattttc agatactcaa gaacttataa 378300
aatttttcca agtcactgca ggaaaaaagt atagaatttg ctttctatcc cttttcttag 378360
aaggttctgg agaatgcact ccagcaaaac gtgggaggaa accagggaaa aggaaggcac 378420
caacaacaag gaggcagaag accctacaca gacagaacag ggaggtccaa gcccagcagc 378480
tggctcaggg ctacaggcct ccagcccagg cagcccaggc aggagcagag gacaggatac 378540
tcctgaagag gccacccagg aagagaaaat aggtgggact gggaagaaaa tctgcaacgg 378600
agcttccaaa acagcggagg atctccctga gggaggtgtt gttagagaag agagcagaga 378660
agcaggagaa cccagaaagg aaatgtgagc acagtatacc ccctggctct gtgggggacc 378720
caggcagtgg gcatagattt catcaaaaca atggggaagc tgtgctggac agttagaggg 378780
tggacaaagc cgagggtggg gtgagagctt aagcctcacc ttcatacaag gaagattcta 378840
gtagctaaga ttgacaagtc gagaaaccat gtggccagca tgtcaccaaa agctgataag 378900
aggaccagtg atgggcttcc cgrgagtgga gmtgggcatg cacamtaagg cctggaggct 378960
krtgmttatc satmatatag caggcstgcc ctttccacag cacaaacacc ttgacacaca 379020
ccgtcacaca cacccatatt cgacacacac attcacacaa acacacccag acacatgcat 379080
gcacatggat aactaactct tccagcaaga gccacccccct ggctgaagtg tgaggctgtc 379140
catggagggg ccagagtaga ggggaggtgg gtgaggaggm tacgcagagg ccctgggagg 379200
agggaggcta ggcccagggg tggaaagaag acagatacga gaggggattt ggagacacaa 379260
tccccagact tggggacgag ctggatatgg tggygawgga ggkgagtctt caggamagac 379320
ccccwggttc tggcttggcc atatgttgga ggctgaaacg attcatccag acaggagcag 379380
ggaggaggac atgcagggcc tgaaagkttc tgaggtgtcc acgtggaggt gtttgcyygg 379440
cagtttaggc tgcaaggctc agcagggaga ttggagctga aaacagaggc tgcaacatgg 379500
aggtggtacc tgaagaaggg gtgtggatga ggttgcctgg caagagattg cagggagagg 379560
agagagtgag aatggggcca ctcaaggggt gaacagggcc ttgcagtaca ggaagcagct 379620
gggggtggcg ggaagaagac agtcaggagc ttgggcatcc tagaggcccc cgggacagct 379680
ttgaggaagg aacgtcccca caccacagag ccatagaatt ctgtacttgg cctgtctcag 379740
tgccgtgccg catccatcct gcccctggca ccggagggta cactgatcag ggacacgagt 379800
tcccctgccg ggcacagagc aggttcccag tgagttctgg ggcctcagtg actgggcaag 379860
gacaggggcg tttggacagg ggaggccggg tgtggatgga agctgtacga tggggcctgg 379920
gccagggatt gtgggccagc tccgagctca gacattggtc tgcacatgtg gctggtgcag 379980
gaggcgcagt gtgctgggcc tcagcctgga cacggctgtc ccatgcgcag agacagggtc 380040
acggtggaaa gagagtccag agaacatggg aggtgccgtt tccctgcggc gggactgggg 380100
ctggggcccg acttccccga ccctgctgtc gggcgtgtgc cttcatagcc caggaagcca 380160
gttcctggca gggtgggctc tgcagccagg ccgccagggt gcagacccag accaatggga 380220
ggccaaggga ggcccgcagc ccagaccttc cgagccctca gcctgctcag ctcagtgtcc 380280
ttccagggaa atgggcgttt cctgtgggaa ggtgccaggg gccccgggtg ctggaagagc 380340
aagcaccacg cggggggggta ggggcgcccc agccctctac tggccagtgt ccctccagtc 380400
gtccagccct tgctgccagg ggccccgccc atgtgcctgg aatcacaccc tggacgcttc 380460
cttctttggg ttagatgtcg tcgtcttcaa caaatatttt ctgaatgtct gctatgtact 380520
agactctggg aacacagggg aaagtatgtg gacctgccca tgaggaagtc agtacagtgg 380580
ggccatgaac aataaacaga caattaatta tccttcgcgg agctgcgcgg gggcagctct 380640
cccaaagcag tcagtcattc acacttcagt atgaatgagt ctccgggtac tttgctcagt 380700
aacggactgg accagcgcgg cctccacgcc agggactggg gcaagggtgg agtttggagt 380760
aaagagagag gcarggcaac ccctttccac agacacttta ccacctcccc acattgacaa 380820
gctggctccc cagggccacc cggagcccct tcctcagatc ctgtccccat tggcatggtc 380880
tcagcccctc ctgccccagt accctctccc cgaggcctcg tcctccccgc catcctggaa 380940
acgattttgt tgtctgcaga gattatgtgt aactgcctgt gagttataag cctccacagc 381000
aagcagcctg ttacctaacc aggcctggct catgccaatg tcttgagtaa ttattggggg 381060
gcgggggctg tccagcccgc agcagaacct ctccgaggga gtgctattgt ttttcatgtc 381120
agctgcattt taaggctaca tttcacgtca gctgtgactt ggaaggaaag agggcccggc 381180
ctttgaaaaa tgaagaaatt gagccggggt tgggggcggg gagggcargt taacccttcg 381240
ggctccagta ttccccagct tcccagggtc tcctggcagt aaccaggcca gctgggggtc 381300
agaacccgcg gccaggccca gcagccgcct cttggcagcg ctgatggaaa ccgccgtgcg 381360
gttccgcgca gacagtcacg gaaactcagg cagacccggc gttgggtgcg ccaggccggt 381420
gtgggagcac tttcccccgc cccctcctgc tgctgcttcc ccgaaggcct ccccagcaga 381480
cctgcagctg ggcacccaca gggtagaaat gccctggatt ggctgtggca caagagggmt 381540
ggcccagcac acccagccca ccactgtgct cccagaggga gaacagagag gggtgcagag 381600
ggccagagag gcacggggct cccctgggca cccctcgtct tggggcccct gccctgcctc 381660
cactcagaat cccactatgt gcttggagcc atgctgggtg ctggggagac acactaacca 381720
cttccccata tgctcacagc cagagagaca cacaggccag cagcctgtaa accactgggt 381780
gtggggtgtc tggtcctgga gtgacaagga cagggaggaa gaaagccagg caggtggccc 381840
atgagccgtg gagtaggtgg ggaaggggac atctccaagg aggtgacatc ggagcagtcc 381900
tctaaggagt ttggagtcat tttcagtcac tcacaagcca caggagggct tcagcctgaa 381960
gctcagaggt gatgtgctta gatgtcacag agccgggagg ggaacaggct gggctgcaga 382020
gaggaggcca ggcacagtca cctcgtgttg ctgtccccca ggtaggagat aagggaccag 382080
agtcagggca ggtgggagaa ggggaggttc ttggttcagc tgctgctgag acagtgaccc 382140
tggggacagc ccaaataaga gagaactttg ccacccgcag ggtcccagag tagcagaagc 382200
ttcagggctg atgtgtgcct ggtgaatcag cctggcccca gacctcctct ctctgcttgc 382260
tttcctgtcc acaatccagt gcttctgtcc tatggtcccc agcggctgct cctgcattca 382320
ccatcacatc tgcattccag cagcaggagg gaggtaaaag acatgaagga caggccccac 382380
tcctgtaaaa ccctacacag aagcggccca cgtcatcccc ctttctgtcc acccgccgga 382440
atgtgacgca cgcctgagtc gctgcaaggg cccctgggga cggagtctct attccaggca 382500
ggcaaacact cagcttaatt cagggttctg ttgattaaaa aaaaaaagtg gggtcggggg 382560
ggcgggggag agcggctatg gagacaagtg gctgttttgc cagagggaaa attccacatg 382620
tggcttggag gccagaccag aaggactcag ataggagttg ggcgcttgag ggaggaaatg 382680
ggggtacact tcagcggctc aggccagggt gtaagtagca ggtatgtggt ggtactgttt 382740
tccggaatga agaggaaggg gcgggcagaa ggcagcgaga gctttgtttg gggtgtgtcg 382800
aattcaagat gcctctgaga catggaagtg gtgaggtcag gggccgggaa ccctatggtg 382860
gtgttggccc tgagtccaag ccaggcacca ccgggcacat agaggtcttg aaagctcgaa 382920
tgtggggagg ccagcaacag agggaacact acctgcaaag gggcgagggc aggacaaagg 382980
ctggcagcac cacacaggag ccagcaggga aggggccaca gccgggactc agaggaggca 383040
gccacgtgca gaaaggcacc catgggaaca tggctcctgg gagctggagg acytcagcag 383100
gcakggacta gcacccaaga agamaactct gagaagtcag gacaggagat ggtgtcgtca 383160
gggggctgct ggaaggtttg gtgaccggag cagcaggtgc cagagctgaa agcactggtt 383220
aaacgtgatg ggtaaacaca tgtctatttc agcttctttg aatcccacta aggtgacagt 383280
aaaggcatga aaaacatgga aacatgtaaa tcaactaggg taaagtggtc aggagaaaag 383340
aggagaccaa aaatatgttg acaaaggttt ggaagctggg aagcaggagg acagatggag 383400
actggcctag gagactggag agggtagaca ccaagccctg caggaagaag agccaccaag 383460
aatgaggcag ttcccaaccc aggaccctga caggcaggtc tcaccccagc ccatgaagcc 383520
agatgctact gattctcaag ctcagctaga gacaggttga gtctccagaa aagctgagcc 383580
tgagaggttc tgaacttgga gccaccagga gcagttgtrg gtggggcagg agctctygtg 383640
atgaaaacaa cagggattca gtaaatgcat tcmakctaaa aaggaagamc tcctccccca 383700
cttccctcat caactcccag aatgcccggt ggggcacacc attgttttca gaacaccagc 383760
aataaagcag acactccaca tttccagaga gaaaaagtaa gtcacacaca agagaataga 383820
aaatcaaaac ggtatccaat ttcttaacag caattcagaa agctagcaca tagtagagaa 383880
atgccttcaa acatctgagg gaaaaaatga tttcccatcc agaattctat acctagtcaa 383940
actctcaggt atgagaatag aataaagaca tttccaaaca tgcacagtca aaaattgtat 384000
ctaccacatg ccttttctca gaaagttact tgaggacgtg ctctagcaaa atgagaggaa 384060
aaaacaaaga aagagaaaca caattcaaga accagggaga ctccaacacc aaaaacaaaa 384120
ggccaagaga attttcaaca tgagtgaaag aagttctagc attacagctg ctcagcatgc 384180
ctacagtgca aacagtcctg ctaagactcc aggaagaaat cccagaagaa aaaaaaaatg 384240
aaggtgatag actgccagta ttctcaatag gatgaaagaa gttttacaat tcttacagaa 384300
agttcaagaa tgaattagtg acagatgcag taaaaaacaa gcaaaaccta aggccatttg 384360
taacccaagg gaaaacaaga agatgtaatc ataacagacc acaggacaca gctaaaaaca 384420
gtgattacat agtgacataa agagttatat actgtttgtg taaaacgcaa acagtaagta 384480
cttatttagc ctagaattct aatttaactg tattggaaag ataagggagt ggggagggca 384540
ggggcatgag aacaaaatct tgatcacttc tcttccatgt taggcagtca ctagataatg 384600
tctaaagtga caaaatttca aggaacagca atgtaaatgt gtagtttgga aataccaagg 384660
taaagccaag agatagtcgg tagggttgaa gggctgcctc tgggaacaga aattagagat 384720
agaagatcta gcgcccaggg aaggctgttt aaagatggga gagcttcacg ggttttctca 384780
ctaagggtaa gaaaatctaa gaaggaagtg atggtgccag agaataggga attctgccaa 384840
taccctggtg gggaggggga gggggarggg gargaggatg agaaggaagg aggagggarg 384900
aggaaggaag agggaggagg aaggaggagg aargaggagg aaggaggagg gaggargaag 384960
gargagrgwk gagggaggaa gagagagaag gwagagattg gccaaaggag ctctgagagg 385020
ggaaggtggg tgcatgccac cctggctggg aacagcaggt gtgtggtgaa ggggaaagac 385080
cagcaggccc tttacaccgt gggcacaggc tcaggactgg ctgcggtgct acgcaggagc 385140
cctctgacta gctggggctg gggctktgca ggataaggcc agtgagagaa gaggaytcac 385200
tggtgggtgc ctcctcccca cctttagcaa gggttgacag agggatctgg gctcttccct 385260
gggcaggcat cccagagcta tgacctgaat gatatcttag atgatctcca aggccccggg 385320
atctaagtcc ctgttaagtc ccctgttaaa ggacctaggt cctcccaatg gcctgcaaac 385380
cacacccagt ctagtcagca tgtatcccca caccccagtc ccagtgtccc aagaacctct 385440
tcctccagcc ccgggagcag gaagggcggg ctgggagctg caggatgggg cctgaatctc 385500
tcatcaactc acagggtcag cctgggccag gcaggctggg ggccagccca ggacctcctt 385560
cctgggtgga gaccttccca cccttccact caccttccga gcattgtggg ccttcccagg 385620
aacccccaca tctccgtggc cctcagacct ctgacctccc aagggcaccc cacgtgtgtg 385680
ccctccagca ccctggccac agagccacac acctgggcct tcccctctcc ccatcatcag 385740
gtaacccagc acaggctggc ccaacccctc tctaggcctc agctttcctg tcaggaaaat 385800
gcagggttag gagctgacca gggagtcttt gaaaccgcaa gggtaccctt gggagacccc 385860
gtgcaggtct tgtcaaggca ggacaggaa gtggtgatga tgagaggcag ctggtctggg 385920
tgctcagccc caccccagca cccgcccaat gggccccctg agggaagctg cccatgctct 385980
ctgcgcccca ttttctggcc tctggcatgc agatggcagc cctgcctgct tcccagtatg 386040
gctgtgaagc caaaggcggc gatcaatggg atgttctcag aatgacaggt gctctgtgat 386100
cagcagcagc tgctacaggg atggccatcg ggtgcagggc aggatgtccc tgaggaggca 386160
cctcagcaga cgtgatgggt gcctgtgccc acagttgggc catgagaaga agtacgtggc 386220
ccggcctgcc ctacaccatc agggggtgct tggaccagtg gcggctggaa ataacccatg 386280
aacaggggag agaaggggtg aatgccttgt aggcctggaa cactgtgggg ctgtcgaagg 386340
tgcttctgcc tccaggaagc cctccctgac tgtggagaca caagaagctc tccaggtctc 386400
tgggtccctc tggtactctg tgccctgaac caccaccctt aggcccagat ctattcctga 386460
tccttctcta gacttcagtc agtttcctct tgatgtcctg gatggccaca accatagtgt 386520
cccctccgct cctctctccc ccacttcctt ccacattgcc cctcctcccc tctccccttc 386580
cccaccactg ctcccctcct tcctccagca cccttctccc cgctgccctc ccctcccctc 386640
cccgctgccc tcctctgcct ctctccgttg ccccctcctc cctcccccac cagagccctg 386700
gaaggctagg tacagcgagg aagtggccac tccatgaccc ccagtgattt cacttctctg 386760
agcctcaaga gtctcacctg tccagggtcc atgggatatg cctgactcag cccctggcac 386820
atggtcttgc agtggcctga gctggacatg cccctggtag gaagctggaa aggaggccct 386880
gcccgtgtac caggagcctc tgctccaggg gggtggcctg aggcccaggc agacctccac 386940
ctccaggcag ccctgcaggt ggacagctgg gcctcaggct taggacctgg gacaactgcc 387000
tagactaccc ccagccttcc tgacaggtga tagcttcatt gtccccagga cacacaccag 387060
cccggtcccc accctaccct ttcccascac ccctgaggga aggcctggcc cctcasgcac 387120
artkggggtt gcccggcatc ttggcagatg ggcagcgtta gagaagcctt ggacctgggc 387180
ccttgcaaac ggaggtacca gagggctgaa ctagatgagg gacttgaagg ctcagatgcc 387240
tgtgcgggac ctggcagggt gggggcttcc gggctgggag actaggacag ggtgcctgtg 387300
tcccctcctg ggagtggggc cgtcagagct ccgaccgcac agggtcatgg ggagcaagag 387360
gaaccaggat acccacaagc tgctcgctca gacgggctct gcgactccac aactcacctt 387420
cccctactgc aagatcaggg agatgggacg cagtccccgc ccatgcccag ggccttggca 387480
gggtcaggag agccagtgca ggcaaagcac caagcaccct gctgcctggg agaccacagt 387540
tgcagcagga agccctcctc aggtctgccc gcctccccgg agcatgttcc ctctgtagct 387600
cccggtaggg cctgtgtgga gaaggttgct gatggcatca ctgagcggcc cagctgtggg 387660
gtgaaaggca aggctggggc tgatgctccc caaggcagga ggagaccatg gtctggctgg 387720
ggctgcccca ggtgacaact gtagggtgtg gggaaggtgg ctgccaccgc cgtggtccac 387780
agggcctggc cagggctcca tggggcagaa gccatgccca gctcaggggg cttcactcca 387840
ctctcccact ttgacctggt ccctcccctc tcccccagag tgacctggac actagcctcc 387900
tcccagtggg agacagatgt gggcaatgca gctgctgttc cctgctcagg gcaggctggt 387960
gcccaaggac tgcccaccag accaggggat aagaggttgg cagcatcgtc catggttatc 388020
ccacagctag gaggctgtgg gtgtgggaga acatgctggg taggggtgcc tgtgtgcctc 388080
tggagtcgag gcaattagag gccctgtgga agcccctgca cgcaaggggc ccacgcgcca 388140
gggcagagga catagcccct tcttgcttcc ctgagggacg ggaggcctgt ggacttctgg 388200
agacaatggc agagtcaggg cagccaagcc gggccagtgc cctggagccg agtcctcccc 388260
ccacctgccc acatgcccca cccctctcca agcttctccc ctcataggat cccagagccc 388320
cttgggacct ctgtgaagac tgcatagatg tgagggagtc tcagccttag ggtgggcacc 388380
tgggcgcagc tgtcaggccc caagtcagcc ccaggcacgt ggacctggga gccagcctca 388440
agggcagggg tccccgagca tccccactgc tgccccgcca gcaaccgtgt cactgggagg 388500
caagaggctg ggttcctggg gtgggcaggc ttccccgctt cactccattt gcagcccctg 388560
tcttgcagag gcaaaatgga ggttcagaga ggtgagcaaa caccaggtcc catgtttgca 388620
cctggctgtg accgtgcagt ccactgggcc cagcagcagg aactggggca agtgccccga 388680
gacgggaccg agacaacagt ggggaaggtg ggacaggcag ctgggggaag gccagagtgt 388740
ccagcaccag cgccaggggc cgttccgaca ggctgaggar cggcggggag cggggcttgc 388800
caaatatgtc cagatggggc tggagcccca gcaacttcct gccctcccag cctgctcccc 388860
cacctcctca ccccccttccc aggctgtcag caggggctgg ggggcagcag aaccccactt 388920
agccacaagg agtgcagcca ggggctggct cccgggagga catgggcaga ggcttaggtc 388980
cccttacaca cacacactgc tgcattcgtg caggatgggc tcagcgcctg ctgtgcctgg 389040
cgtggctgtg tgcatggcat ggtggtggca tggtgggagt ggtgtggcac atggtgtggc 389100
acatggcatg gctggggctg gggctgggtt gtgtagcatg tggagtggca aggtgcgtga 389160
catggtgtat ggcatggtag tgtgcccctc gagccatgtg tccaggtggg gcagatcatg 389220
gagggcgccc aggtgcggtg ctgaggctga gcatgcactg gctggggagg gtgggcagag 389280
caggaggaaa tcccttgttc tccggagctg gagagccaga aagagccctg cagcctgggc 389340
ctcatcatca cacctcgccc tcaaggcctc caggcacagc atccactgcc agcctctgct 389400
cctgcctctg agggtctgtc tccaaggtct tttgggggct gccccagctc ccccaacaca 389460
gacagcacca gagctgggcc cacctgtgag gtgctgagtt ccccatctca gagactgtgc 389520
gagcagaggc agggaggcgc ttgatgtcgg atggagaaag gacaggggag gggtgtgggg 389580
ctmagggccc cgccaggtga aggaacaagc ttggaagggt gtcsttatgt mtgagagttg 389640
gggagacacc cccaagcccc agatgggcyt cgaatgccag gcagggccaa gctgggccca 389700
gaagtgggaa ggatcccttg gctgccccag gaatgcaggt tccggggcaa gaatccagcc 389760
ctggctggtt gaagtccatc ccaagtctcc ctccccacga ggctcctgca gatgccagga 389820
atggggctgg attccagatt ccaagcctgg ccgcccagcc cctatctggg accccagccc 389880
agagccccca ggcctggcct ccaacctggc cccagcctca ggggagctga attcagagaa 389940
tcctgtccta ggagccagaa gcgggggagg gagggaggsc gsccytstcy tgggtgcagg 390000
ccmgggggct gggggctgcc cgcccgtytk ggtyarccgs arstgccaam ccgsccctgg 390060
ckgagtyakk gggcctycat ytycmrgcct kgcttgaggt gggaatagca gtgaggttgg 390120
acatccaggc acctggargg tgggcagggc tccctgcggc tggggtggcc agtggcacct 390180
ggctgttgcc cccctgcacc ccagcccttt ggcccccaag tstctgccac ctccctgggg 390240
ttctgctccc atattcctca cacccagcac agaacccagc atgtctcctg tagacacctg 390300
catataaacc ctgactcaca cacacacaca cacacacaca cacacgcaca catgcaggcc 390360
aggctcctcg gccagtcacc ctaccggcag agctctagac atttctggcc tctggtgact 390420
attcttcagg cagctcaccc tgcaagtctt tattgagcac ctactgtgtg ccaggcagtg 390480
gtacagcaag ggcagaagcc ccacctccaa ggagctgacc ccctgccgtg gcagagacag 390540
aaaacaaagg cagcaccaca gcgacgaggg cctgagagga aagtggagca ggagcctgca 390600
gcatgctggg gcaggggtgt ctttagaaag ggtactggga gggccctggc aagggactta 390660
agtaattact taaaggaggg aaagggtggc ctggggctca cagaggaaaa gccttcctca 390720
tggaggcggc ggggcakcgg gctcasccctg caktgtccag gagcgacggg aagcctcgtg 390780
gggctgttgg gagacagcaa gacctgggtc agcagagcac cgtgtggggt aagcagatga 390840
cagggcagtg acagggtgat tcggscccgg tcagtggtcc caggggtcgg ggacaggtgg 390900
gaatcgaagt cataggaggc ggggcaaagg ccacggggaa agggacagag ctgctcccaa 390960
ggacgcacca ccatggggtg ccccatggcg tggcgggggt gggggtcagg acctttagca 391020
gaaggtaaag atgagaccaa gaggcagatg ggtggaagag ttgaaagcag ccaagtgtca 391080
ccaaggcatt tctgagggag agggacacga ctagtggctc aaatctttag aaatgagggg 391140

-continued atgggtctgg tagagcaccc cagattcaag gcgggtggct tggggaaagc agggagaagg 391200
gtctggaaac tgctgctgag caggagcccc cacacccaca gagcaggtgc agggaggccc 391260
atctgtccat ccgtctgtct gtggggaggc atggtgacgt ttcagcccgg aggtagaagt 391320
tttcacccag gaggtagagg gtgaggccgg actgcactcc aaggggagga ggtgggagag 391380
cacagcctgg ctgctgccac caagctcccc agaagagggg acccctcccc ccgaacacca 391440
gcacatgtag gcagaaagac ttggcstgtg gagccctcag cytccacgcc caccagcagg 391500
gactgggtgg tgatgtcagc aatccccaca gaaaggaggg ctgcacagcc gtcccaggag 391560
ccagcactgt ccccgtgatt ctacatgcag cctccacaag tgtgtcgcat ggaaacaagc 391620
agtggagagc cacatgtgtg tcacatcacg cctcgcctca ctcgtgctaa acctcgctga 391680
ccaggcagaa ccaggcacga gctgcgtatc aaagttgctg gaaggagaaa catcagatcc 391740
ctaagctggt tacctggcag gcaggggccc tagagggaaa tggggcaggt gaaatggaga 391800
tgtgtctttg aaatgtcttt atttggcggg agaacgtctt catagggtac ttataccatg 391860
aaaaaccctg tacacagact aattttgaag caaacatgtg aggcgttcac agaaagggtt 391920
caggaagaca agcaccccag ccgcagagag cccgtgggct gggggcacgg ggcatggcar 391980
ccctctcctg gggatgggca ggatggggca cgtagggcgg aggaagaggc tcacatggtg 392040
tgcgtgtttg ggagcaccct gggcagcctc tcgagtgtcc agagagagga caccgtcttg 392100
agccagcagg gacagccaag agcgcccggg gagaggcctg ggtggagaca gaacacagca 392160
ggctgtgggc gtggccaatg ttgagggacg gaggtggcca gaggcctctc agtggtgccc 392220
cagggagctg gggacgaggg gcctcatcct tcccctgagc ccctcccttc aggcccaggg 392280
agtggcctgg ggcccaggag agcccgctcc gcgctcacag cctccgttcc cagacacgcc 392340
cgggcctgag cccccaggct gcactgtgcc acagaacaga ctcccyggcc cctccctgct 392400
cgagaggtga ccaaggccca gggtctccca gcgagcaaga ggccattgaa ctgttgttgg 392460
ctgtgcagtg ccctgccctc ggggaggcsg cctctaagaa gcacacacca ccagcaggaa 392520
ccgggcagac agaggtgggg gatggaaagc aggggaagtg gccacagcca aaccaggagg 392580
gggaagggag ggggcctcac caaggagacc ctcacctggg gcctggagaa tgagaagggt 392640
ctggaggcta aggagagggg tggatgctcc aggaggcagg gccagcccat gtgagggtcc 392700
tgaggtagga accagaggaa accggctctg gggcgagaag ggcagcgccc agggggccac 392760
aggggccggc ggcgagggac cctcagccga ggctggtatc tcgagaacag cagggatgcc 392820
tcaaaggttc tcgcccagca agtggacatt gtggtgtggg agatcagcag gtgccggtgc 392880
tttctctgtc tgcaggaagg agaggggggts atgggcccca gaggcctctg tcttagagaa 392940
aaatggtggc aacgtgggac agactgagga agccagccca gaaacgtccc gtcccaaatt 393000
caggaatatt tagggtatac ctgctgcacg ccaagggcag tttcaggaag gggacctact 393060
tctgagaagc aaacaccacc agtagggacc aggcagacag aggtggggat ggaaggaagc 393120
cagactgacc tcacgtggct cacagccact ggcagggtcg ggggacaggt gccaaactat 393180
ccacatgccc gtcaggcacc tggaggagtg tgaaacggca tgcagaaagr aggaagcagg 393240
cttggggctg ggggccaggg accggcgcgc tgggaagcag gctgcagagt gaggccaggg 393300
atgggggctg ggccagacca cagggttgtg agcggactct ggcattgatc cggagccact 393360
gagggttaga gcctatgaca ggggtctgac ttccagtggt atggggccac cctgctgggc 393420
tggggaaggg aggcgagagg aagtatctaa ggtctgcttg tggacttccg gggacagcga 393480
ggggtattgc wggggtccta ggggctggtg caaytcagag gttccagatg gcccagcaag 393540
tggctgaggg cccagggtag gggaggatgt gggggcagca gggccgatgt gggcagacst 393600
ggagcaatga cacgagaacg gccaggcagc cctgggytty ccctgcccac ctgcccccgt 393660
ggccgggytg gggtttggct gaggcagcag agcgctcgct ggctgcccga acaaagtgtt 393720
ctgcctggtg tcccctggca mtccgggcyt ctgcgggctc gccagagggg gcagctcagg 393780
aggcagcggc agagaatcaa atgcaggtgg ggcstgtgcc caccgccagc acaaacacgg 393840
mtcmtgggcc cccagcctgc csgamgttcc tgcccgcctg gcccccaaac agaggccgat 393900
gggacgagcc ctgcccgggg ttgcactagg tgggcaggtg ggcaggtggg cagctgcctc 393960
gggytyttgg acagagccgc ccctgcctgg cgtctgccgg caggaagctc ctgaggccgg 394020
gctagggata ggccagccct tgggggaggc tcgagacccc atcccagcct ggggcttccc 394080
caccccytcc cacctgcctg gcagtgaggc agctccctgg cctctgggtg cacctgggcc 394140
tcctgcccag gccccttcca agggaagagg gcaaaggggc tccagtgcca cccagggagt 394200
gttgtgccac gtgggccccc ctggctctgc cactgactcc ctccatgacc tctgtcccca 394260
ccctgaagtt gacatgaatg tccgcacgga gcakcctctg caggtctgtg aggctgtgga 394320
tgtgacagct ctggctctgg cacaaacgtc agccccaacc casatgcagg gagggaggtg 394380
gctgcgtgtc caggagcacg gggccatgtg gcaccggctc atgtcagcag acacggcaca 394440
catagacccc ctgggggcta tgacgaggtg agggctgagc cgagggagaa tccaggaagg 394500
cgtgcgggcc gagaggaaga ggaagggagg ctstggtggc tggagccagc tgggggaggg 394560
aaggcagcag gggmtgggat ccctcagccc ccacagccgt ggtgcggact ttgttgtttg 394620
ctcagagtac aaagaagagg ccttctccgg gttcttagca gacgagcgcg acctctccga 394680
ccagggagac agacaagagg ggaggttatg aggtcacctg ggagaggtgt gggttccagc 394740
tcccgtcgcc actccccgac tggatgccag aacgagcctg tcgtctttca cctccagaca 394800
gcagggccct ggctcccagt atcaaagcat gtacaagagc ggtctctagg gcagttctgc 394860
gtagacgcca aagtacagga agacgtgcag gaactttgtg ccgtcgaccc ttgaacaatg 394920
cagggttggg gcaccgaccc ccgaactgcc cagtcaaaaa cccatgtata acttttgact 394980
ccccagaaac ttcactaata gcctcctgtt gactggaggc cctaccaata acataatcaa 395040
ttaacacatt ttgtatgctt catgtattac aataaagtaa agtaaggaag agaaaagata 395100
ttcattcagc ataagcagat cattgtaaag gtcttcatcc tcgtcatctt cacgttgagt 395160
cagctgggga ggaggagggg tggctcttac tgtctcgggt gacagaggag gaagaaaatc 395220
cacgtagaag tgcacccaca cggctcaaac ttgggttgtt cagggtcgat gatacacaaa 395280
aaggacattc taatccagtg gggaaaaggt ccatcattcc ataagtggtg gggtatcagc 395340
aggataacct gcaaaagtaa gtctgtaggt cagaaatcaa tcccaggcga ttcaaagatt 395400
tagggggtaa aacacaaatc aaaaaagtat taggaaaaaa gattttggcg ttggaatgga 395460
ggaggccctt ccaagcacgc acaggatgag aaggcataaa ggaaaagatg gatggctttg 395520
accacgtgaa aaagtgaaaa cataagtaag acctctgtgt ggcaaaacaa aaaaataata 395580
aatgccataa acccatacac gagacaaata gcacactagg gaaaaacatg tgtgatgtgt 395640
acttgacatc tttcttaaca tagagtcctt acaaatcaat gaacgtgaaa aggcccagtc 395700
ccagcctcag cttctctgct cagcacccac cctgggaagg agtgggcttg gggggcttct 395760 acccccctcac tccagccttg gggccccggg aaattggccg gggcctcact tactaattca 395820
acaaacattt gtgcagcgcc aactctaccc tccatgtatt tactgggcac cttctaggct 395880
ccaggctcca ggctctggga gactgtctag ggttaagacg gtgactgcct ggcctagagc 395940
tgggcctcca gctggtggca aaacaccaag caaggagatc aataaaccgg gacatttcag 396000
ggagtggtga aggcttacag gaacatgggg agagatgaga cgaggaggcc gcccaggatt 396060
ttgagctaag gttacaaagc agcagaggac agcgggtgca aaggccccag ggcccaactg 396120
agatgggcgc tcagatcaac acgggcatgc tcagtgccgg agaggggcca gcggagcctc 396180
tgggggcact gcaaaaggag actggatttt actcccagtc cagtgggaat tctgcagaag 396240
gatttggccc aggctgggag ggaaggctca gcctggctgt tgcctggaac aagcggggaa 396300
caggttgggg gcatagccag gcagtgaggt ggttgtgaca gtccaggcag aagatgctgc 396360
cagcctgggc aaggggcatg gggggcaggc tcagagcaca tgctccagac cagagagcca 396420
cagacaccag gtgcacacca gggaccctgg gtagttggtc gtgccctgtg gatacaggat 396480
tcgggccggc ttgggaggaa tctgagctcc cgctgggaca cgctgagctg tggggctgtt 396540
ggcctgcagg ccttggagcc cctggagaga gcaagtagct gacggggaca tcctagctag 396600
ccgaggtccc aggaagggaa cgagggtcgt gtggtgacga tcttgagata ttcccccaca 396660
gtcgtcagcc agggacatgg cgcccctgag gcccttgggg ggccaagcat ccgtcagtgg 396720
gcagaggctg gcaaaagtgg atgtcagcag caggggggaag ggtctttctt tcaccatctt 396780
gggcctctct cagagggagg caaccccgct cctggggggt ggtcagtgag ggccagccag 396840
gcagcggcag ccccaggaag ggtgttgggg tggagctgac caggcctctg ccgcatggtt 396900
gcgctgtgcc gaggacccgc tgaggacata accgaccatg agcggtgtgg gtccccagcc 396960
gcagcagagc ttcctctggc tgctcggcag acaacagaca ccagggacag agacaaggtt 397020
gaggatttgg tctgcagcct ctgagcggac acactcaccc tcagtgcgtg ccaattcagc 397080
cccaccacag gcgccagtcc cgagcctgag cacaggggct gccacgacgc tcgactctct 397140
gggccaagac tcacacacag cctggacact gcccgggtga agggctctgg gggacagggg 397200
gagcagctgg tatgtgtgtg accatgggtc ccagactcag tgccatctgt ctccccatta 397260
ggagatgacg cctggtacct gcccaagcac ccaagccatg ggagttgctg cttgctctcc 397320
acgcagcttt gtcccagcag cacccccaac tcctgtgatg ggttgcaggg ggtgctcacc 397380
tctgtggcac acacaaaggc ccaggggcct gggggtgcat gcaggtgcac tccaaccctt 397440
gggcagccca gagaacaacc taatggaaag tgaagggaat tgtacaagtg tgtacaaggg 397500
tgcagggtgg ttcctgcctt cttgcacgca cagtctccca cactcataca gccacaggtt 397560
cgtacgaggt acacatatgt gggctcacct agcatgcctc ccgtgtgcac agcagtgctc 397620
ctttggcctc aggccacagg catacatgtg caactgtacg tgcactctag gaatccctaa 397680
tgatcatggc catcgggtgg ctcgcagtgc actgagcacc atgctctgtc cctggtgtct 397740
tcatgcctca gtccacttga tcccctcagc atcctcctgg ggaaggtgct acagctgccc 397800
tgttttatag gcagggaaac tgaggttcag agaagcaaag tgacttgccc aaggtcaccc 397860
ggccaggaag cggcagaggc aggatctgac cccagacccg ctgcggcaca cacacgcctg 397920
cctgcacgct cccgtgagga ggtgctttgt gcccaaggcc ctgcagcagt gtgggggtt 397980 ctgaggccat ctcccactgg ccacagcaca gcaagctcca gcagggcagc tgccccaagg 398040
cctggcggta aaacctcagc agcgagaaac acggtcgact tttgtccaag aactgaagca 398100
ctaaagcaaa gtcaaacaca atcgctccat gccctgccac gaaccgcgac cttaccacgt 398160
gctgtgacct attgccactt gtgcccagct ccacacagga gccgggtctg acatccgatt 398220
gctcagagcc tggtatgaaa cattctaggt accgccctga gagtggctta gtaactgctg 398280
gttcctcagg acagacagga ggaaggccaa ggtgaccttt gccctgcgac cctacagagg 398340
gccctgggga ggccctgcct ggtctttaga cactgcccaa caaggatgct agaaggggca 398400
gtgagttttc tgcctcctgg ggaactgcag cccaggcaga gaacaggacc cccaccctgg 398460
gagcagcggg tgtgcccggc ctctcccgcc tgtccctggc cagtctgcca tccacgaggc 398520
cagggccttt ggcggtccta ggcggggatc aaggccgggc aggttctgca aaaatttccc 398580
ttgaaagact ctttttcaag attttctttt gaaaacaaat tcataaccac atcaaacagg 398640
aatccccgtt gccttgggtt tgatcgccgg ccgcccgggg ctctctaact agctgttatt 398700
ctaattgctt ttttctcttc cgagggctgc ataggtctct tatggttatt aatttggtga 398760
gtgcaggccg ggcacaaagc agcttttgtc tgccttgcct tttaatcact atcaaattgc 398820
aaataatggt ggaggctgag atccccaaaa ttgatctgtc ccagcagttc ttggggaacc 398880
ggccccagtg catagagcat gcactgcctt cccccagggc ggcagctccc cgatggcacc 398940
tgcccggatg cacctccgca tgggtggggt ctggcctcgg ccatgggagg tgcttctcag 399000
gctcctccat cgccaaaaaa aaccaaacgt gccagcgaga tgaaggcgcc ctgcccgcag 399060
agtggtgggg tgggactctt cagggacacg tgctgtgaca agtgcttgag tcagagctaa 399120
gactctgggg ctgccgagga gccacctgta gcccaggcct gggcccttct cacaaggggg 399180
cggcaccatg atgcatcaaa ctgtggaacc gccctgggca tccagcccac atcctggccc 399240
accccccgggg cctctgtcac cagcagctgg gatgatgaga gcatgtctct ggggccagag 399300
accctagcca gtccctcaaa gccccagttg gcacaggcag cagttgaggt gagcctggga 399360
ccagccagag ccaggcatgg gctgacgctg gcccaggcag cttcagggag cccttcagtg 399420
tccgtcggag gcaagctcgg ccctgtggct gcctcccgac cccaaaggtg gctgagtgcc 399480
tctctacacg gtgccgggac tccctgccgg gaggagctgt caccaaagtg gctcaggact 399540
gagcgctgat tccagccaca ccctcagcct gcactgcctg cctgcggccc tgacacccac 399600
tgtctctttc tgtcccaaga atcccctgtg aaggcctcca cacccattag cacatgtggg 399660
acttggacag atgttcgagt gccataatgt gaaaatttat gaaaccacaa atgttcatct 399720
gtgatgtatt tggtgcttta attaatgcca aaccaattga tacccaagct ggggcctgca 399780
cagttagtga cagtaagcca cgcggggcaa acctcgttcc acactaccag tatgcggggc 399840
ccagggagct gaggtgagcc ctaggacaca agcccaggct ttgccctcaa agacccacgc 399900
tggctgcacc tttgatctgt tacgctctcg taggtctctg ggcgtcagtt tcctcatgtg 399960
caccctgaag gctgagagac ctcccatgac ccctaccagg catgagcagg tcgtgggact 400020
gagagggctg gtcctgccgg cagcaggagc cacgggggtc agggtgtggc tgaacaagaa 400080
cgagacctca ggccgttccc cttcccagag gccccgcccc accctgcctt ttgctttcgc 400140
cggctcctaa cttgacacac tgtgtccccc catatggcag ctccgtggtc tcgagatgga 400200
gccttggggt gggagctgtg gggacaggat gggagacatg gcactttcag ccagtgactc 400260
tgaccttctt ttcctgggcc tcagtgtctg catctgtggg atggagtgtg ggcctctgtg 400320
gctcgtcccc aagtggcttt gcagagcact gaagtgctgg cgggtccttg ggtgtgagag 400380
accccggtgg atggccgtgg gcccttgccc gtgccaaacc acagaagtcc tgcacccctt 400440
tcttccatag tgtgggcctc acatcaggtt tatctgggaa aaataaaaca tggggctccc 400500
tctggcctgg accgtcagac ctcggatgta cacctgccct tgtgttcagg acagttgggt 400560
ctcagactca ccccatacct gcaaggcaga accacagggg agccagggag cctccacact 400620 gcagcccccca ccacccaggg ctggaagtgg gtcccctggg ctcctgctct gggcagggca 400680
cagtcccacc ctcccaggtg gaggctgccc acctagccct ctagacagac gctcggcccc 400740
actcaggcag gcgcccccct ctcatctcaa cctctcacag caccctgttg gccgcctctt 400800
ccttagcctg ctcagcctcc gtggtaggtg ctgtgggtga ccaccacagc acccaaccct 400860
tgaagctggc ccgggtccac ccagacccta gcaaactggt tggaccctct ctggccatcc 400920
cggggcttgt gcccaccttc acccagcagc atcttccctg gggttgttct cacccgcaca 400980
gaacccagcc ttggcccaca cctcacccca agcctatccg gctggatcag cagtggggcc 401040
gggcgcatga gggaccaggc ccgcccggcg cagcctaggg tgcagacccc tggagtgcac 401100
ggccaggtgg accgggccag ctcccgcctg ctgcctgtgc ttagggccag tggttgacgt 401160
tgctgtggct gagtcatctt cgtgcctctc tctggagcca tacgtttccc tgaagcagct 401220
ctgctgttca gcccttatcg cgtgctgatc tgtttgcccc tcccccacca cttctaggtc 401280
tttccaggcc tccaggtacc cacggtgggg gagggtctac ttcattctcc acagagcacg 401340
ctgaggggct ctcctgcaag aacaccgcag gctgaaggac cagccctgtc tcctgtggcc 401400
accaacagag ctgtgcgccc tccccgaacc ctcactcatg ctagggcccc caggtccaac 401460
ctcctaggga gaggggtccc caacctggac tccctcacct gccctagtct gcccctgggg 401520
ttggccctgc tccacccagc acctgctctg agggtgccag ggtgccggcc tgccggccag 401580
ggccttccag tctccccatc aaggctggat ggccacttcc cacccggggc gggctccagc 401640
ctcattcccc agcggtgctg tccttccaag gagctctcag atcacctggc tgtccactcg 401700
tttggggctt ctctgctgcc tccgcagcac tgcgaggcct ctgatcacct actctctgtg 401760
ctgggtgcat ttcgggttct gtcctgcctt gacctccctg ccagctttgc agggcagcca 401820
ccctggcaca tagctcactg cagaaccagc ccctgagaag gtggaggcca catggctagc 401880
cagagggcac gctctagggc actgctctga ccacagaatg tgggtgcaga tggtgtctgg 401940
gaaaatagtg gtgtccccgc taggttaaag acatggcata atggttcctg ggggatgaca 402000
aaaaaaccca cccccacccc cttgcagaaa gcatcacaga ggcacaagcc ctgtgccctg 402060
caagcccctc ctggaagtgg cccagcaggg gcatcccctg cacacccagg caaagcccaa 402120
gccctctgcc tcctcaacca ccccaggccc tgcccatgag ccagccttgc tgaactctgc 402180
cctctgtcca gttctcctcc agacacagta gacatagccc ccagcctttc ttgaccctta 402240
acccaaatgt ccccaagcct ggcctcaaga agccaaaggc tgccgcaaac ccaaatattt 402300
caggtccggg tccctggtgc agaccctgcc atgcggggat gtggcacaga aggccggcca 402360
gcctggggag cagagaagga ggagaggaga gctcctggcc ttgagcctga atgcctgtgg 402420
acacatatag ggactcccag cacgcacggg atggattcca atcggcacac atgcacattc 402480
cttgcacaca cacaggcgcg accgagggcc ttgcagacat agggtgcaca cgtgcgtgcc 402540
gcctgcatac agcatgcact tgcagagacg gttggcacct tcccttctct ggccccaaac 402600
ctgggccctg aggctgtctg cacacctggg tgcttcccac cactgactct ctcgtctgcc 402660
tttgtccccg caggtgacgc agctggacca gaggctggca ctcatcaccg acatgcttca 402720
ccagctgctc tccttgcacg gtggcagcac ccccggcagc ggcggccccc ccagagaggg 402780
cggggcccac atcacccagc cctgcggcag tggcggctcc gtcgaccctg agctcttcct 402840
gcccagcaac accctgccca cctacgagca gctgaccgtg cccaggaggg gccccgatga 402900
ggggtcctga ggaggggatg gggctggggg atgggcctga gtgagagggg aggccaagag 402960
tggccccacc tggccctctc tgaaggaggc cacctcctaa aaggcccaga gagaagagcc 403020

-continued

```
ccactctcag aggccccaat accccatgga ccatgctgtc tggcacagcc tgcacttggg 403080
ggctcagcaa ggccacctct tcctggccgg tgtgggggcc ccgtctcagg tctgagttgt 403140
taccccaagc gccctggccc ccacatggtg atgttgacat cactggcatg gtggttggga 403200
cccagtggca gggcacaggg cctggcccat gtatggccag gaagtagcac aggctgagtg 403260
caggcccacc ctgcttggcc caggggggctt cctgagggga gacagagcaa cccctggacc 403320
ccagcctcaa atccaggacc ctgccaggca caggcagggc aggaccagcc cacgctgact 403380
acagggccac cggcaataaa agcccaggag cccatttgga gggcctgggc ctggctccct 403440
cactctcagg aaatgctgac ccatgggcag gagactgtgg agactgctcc tgagccccca 403500
gcttccagca ggagggacag tctcaccatt tccccagggc acgtggttga gtggggggaa 403560
cgcccacttc cctgggttag actgccagct cttcctagct ggagaggagc cctgcctctc 403620
cgcccctgag cccactgtgc gtggggctcc cgcctccaac ccctcgccca gtcccagcag 403680
ccagccaaac acacagaagg ggactgccac ctccccttgc cagctgctga gccgcagaga 403740
agtgacggtt cctacacagg acaggggttc cttctgggca ttacatcgca tagaaatcaa 403800
taatttgtgg tgatttggat ctgtgtttta atgagtttca cagtgtgatt ttgattatta 403860
attgtgcaag cttttcctaa taaacgtgga gaatcacagg ctgggctggg cactgctctc 403920
accttggttc ctggggcatc catggggtct ctcacagaca ggacccctgc agttcccctg 403980
gaagcagtgc ccaggtggct gtggaatagg aacgctatgt ccgtgtactg aggagtaggt 404040
cagggttcag aggggctgca agatgccatc gaaggctcta gcttaaggac gtcgctcctg 404100
ttctgggccc tggggctggc cct                                         404123
```